United States Patent
Chambers et al.

(10) Patent No.: US 6,900,215 B2
(45) Date of Patent: May 31, 2005

(54) IMIDAZO-PYRIMIDINE DERIVATIVES AS LIGANDS FOR GABA RECEPTORS

(75) Inventors: Mark Stuart Chambers, Puckeridge (GB); Simon Charles Goodacre, Benington (GB); David James Hallett, Watford (GB); Andrew Jennings, Sawbridgworth (GB); Philip Jones, Bishops Stortford (GB); Richard Thomas Lewis, Bishops Stortford (GB); Kevin William Moore, Buntingford (GB); Michael Geoffrey Neil Russell, Welwyn Garden City (GB); Leslie Joseph Street, Little Hallingbury (GB); Helen Jane Szekeres, Roydon (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 527 days.

(21) Appl. No.: 10/100,797

(22) Filed: Mar. 19, 2002

(65) Prior Publication Data

US 2002/0193385 A1 Dec. 19, 2002

(30) Foreign Application Priority Data

Mar. 21, 2001 (GB) .............................................. 0107134
Nov. 21, 2001 (GB) .............................................. 0127938

(51) Int. Cl.$^7$ ...................... A61K 31/519; A61P 25/22; C07D 487/04
(52) U.S. Cl. ...................... 514/258; 544/117; 544/238; 544/281
(58) Field of Search .................. 544/117, 281; 514/258

(56) References Cited

FOREIGN PATENT DOCUMENTS

WO      2001090108    * 11/2001

* cited by examiner

Primary Examiner—Robert W. Ramsuer
(74) Attorney, Agent, or Firm—J. Eric Thies; Melvin Winokur

(57) ABSTRACT

A class of 3-phenylimidazo[1,2-α]pyrimidine derivatives, substituted at the meta position of the phenyl ring by an optionally substituted aryl or heteroaryl group which is directly attached or bridged by an oxygen atom or a —NH— linkage, and further substituted on the phenyl ring by alkyl, trifluoromethyl, alkoxy or one or two halogen atoms, especially fluoro, are selective ligands for $GABA_A$ receptors, in particular having good affinity for the α2 and/or α3 and/or α5 subunit thereof, and are accordingly of benefit in the treatment and/or prevention of adverse conditions of the central nervous system, including anxiety, convulsions and cognitive disorders.

28 Claims, No Drawings

US 6,900,215 B2

IMIDAZO-PYRIMIDINE DERIVATIVES AS LIGANDS FOR GABA RECEPTORS

CROSS REFERENCE TO RELATED APPLICATIONS

This application claims priority under 35 U.S.C. § 119 from GB Application No. 0107134.9, filed Mar. 21, 2001, and GB Application No. 0127938.9, filed Nov. 21, 2001.

The present invention relates to a class of substituted imidazo-pyrimidine derivatives and to their use in therapy. More particularly, this invention is concerned with imidazo [1,2-α]pyrimidine analogues which are substituted in the 3-position by a substituted phenyl ring. These compounds are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six α subunits, four β subunits, three γ subunits, one δ subunit, one ε subunit and two ρ subunits.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, δ, ε and ρ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, α1β2γ2, α2βγ1, α2β2/3γ2, α3βγ2/3, α4βδ, α5β3γ2/3, α6βγ2 and α6βδ. Subtype assemblies containing an α1 subunit are present in most areas of the brain and are thought to account for over 40% of $GABA_A$ receptors in the rat. Subtype assemblies containing α2 and α3 subunits respectively are thought to account for about 25% and 17% of $GABA_A$ receptors in the rat. Subtype assemblies containing an α5 subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with a β subunit and γ2. This is the most abundant $GABA_A$ receptor subtype, and is believed to represent almost half of all $GABA_A$ receptors in the brain.

Two other major populations are the α2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2 or α3βγ2 subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which interact more favourably with the α2 and/or α3 subunit than with α1 will be effective in the treatment of anxiety with a reduced propensity to cause sedation. Moreover, agents which are inverse agonists of the α5 subunit are likely to be beneficial in enhancing cognition, for example in subjects suffering from dementing conditions such as Alzheimer's disease. Also, agents which are antagonists or inverse agonists at α1 might be employed to reverse sedation or hypnosis caused by α1 agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; speech disorders, including stuttering; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse or dependency, including alcohol withdrawal. Selective ligands for $GABA_A$ receptors may be beneficial in enhancing cognition, for example in subjects suffering from dementing conditions such as Alzheimer's disease; and may also be effective as pre-medication prior to anaesthesia or minor procedures such as endoscopy, including gastric endoscopy.

In addition, the compounds in accordance with the present invention may be useful as radioligands in assays for detecting compounds capable of binding to the human $GABA_A$ receptor.

The present invention provides a class of imidazopyrimidine derivatives which possess desirable binding properties at various $GABA_A$ receptor subtypes. The compounds in accordance with the present invention have good affinity as ligands for the α2 and/or α3 and/or α5 subunit of the human $GABA_A$ receptor. The compounds of this invention may interact more favourably with the α2 and/or α3 subunit than with the α1 subunit; and/or may interact more favourably with the α5 subunit than with the α1 subunit.

The compounds of the present invention are $GABA_A$ receptor subtype ligands having a binding affinity ($K_i$) for the α2 and/or α3 and/or α5 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 and/or α5 subunit relative to the α1 subunit. However, compounds which are not selective in terms of their binding affinity for the α2 and/or α3 and/or α5 subunit relative to the α1 subunit are also encompassed within the scope of the present invention; such compounds will desirably exhibit functional selectivity in terms of zero or weak (positive or negative) efficacy at the α1 subunit and (i) a full or partial agonist profile at the α2 and/or α3 subunit, and/or (ii) an inverse agonist profile at the α5 subunit.

The present invention provides a compound of formula I, or a salt or prodrug thereof:

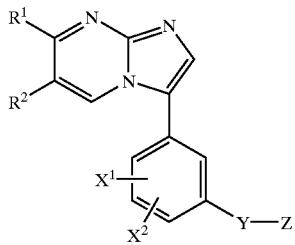

(I)

wherein $X^1$ represents halogen, $C_{1-6}$ alkyl, trifluoromethyl or $C_{1-6}$ alkoxy;

$X^2$ represents hydrogen or halogen;

Y represents a chemical bond, an oxygen atom, or a —NH— linkage;

Z represents an optionally substituted aryl or heteroaryl group;

$R^1$ represents hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$, —$CONR^aR^b$ or —$CR^a$=$NOR^b$;

$R^2$ represents hydrogen or halogen; and $R^a$ and $R^b$ independently represent hydrogen, hydrocarbon or a heterocyclic group.

The aryl or heteroaryl group Z in the compounds of formula I above may be unsubstituted, or substituted by one or more substituents. Typically, the group Z will be unsubstituted, or substituted by one or two substituents. Suitably, the group Z is unsubstituted or monosubstituted. Typical substituents on the group Z include halogen, cyano, nitro, $C_{1-6}$ alkyl, hydroxy, $C_{1-6}$ alkoxy, oxy, $C_{1-6}$ alkylsulphonyl, amino, aminocarbonyl, formyl, $C_{2-6}$ alkoxycarbonyl and —$CR^a$=$NOR^b$, wherein $R^a$ and $R^b$ are as defined above. Illustrative substituents on the group Z include halogen, cyano, nitro, $C_{1-6}$ alkyl, $C_{1-6}$ alkoxy, amino, formyl, $C_{2-6}$ alkoxycarbonyl and —$CR^a$=$NOR^b$, wherein $R^a$ and $R^b$ are as defined above.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, indanyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "$C_{1-6}$ alkoxy", "$C_{1-6}$ alkylamino" and "$C_{1-6}$ alkylsulphonyl" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of $C_{3-7}$ cycloalkyl($C_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl, preferably phenyl.

Particular aryl($C_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —$NR^vR^w$, —$NR^vCOR^w$, —$NR^vCO_2R^w$, —$NR^vSO_2R^w$, —$CH_2NR^vSO_2R^w$, —$NHCONR^vR^w$, —$CONR^vR^w$, —$SO_2NR^vR^w$ and —$CH_2SO_2NR^vR^w$, in which $R^v$ and $R^w$ independently represent hydrogen, $C_{1-6}$ alkyl, aryl or aryl($C_{1-6}$)alkyl.

The term "halogen" as used herein includes fluorine, chlorine, bromine and iodine, especially fluoro or chloro.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitable values for the $X^1$ substituent include fluoro, chloro, methyl, trifluoromethyl and methoxy, especially fluoro.

Typical values of $X^2$ include hydrogen and fluoro, especially hydrogen.

In a preferred embodiment, Y represents a chemical bond. In another embodiment, Y represents an oxygen atom. In a further embodiment, Y represents a —NH— linkage.

Selected values for the substituent Z include phenyl, pyridinyl, pyridazinyl, pyrimidinyl, pyrazinyl, thienyl, thiazolyl, isothiazolyl, pyrrolyl, pyrazolyl, imidazolyl, triazolyl and tetrazolyl, any of which groups may be optionally substituted by one or more substituents.

Individual values for the substituent Z include phenyl, pyridinyl, pyridazinyl, pyrimidinyl, pyrazinyl, thienyl, thiazolyl, isothiazolyl, pyrrolyl, imidazolyl, triazolyl and tetrazolyl, any of which groups may be optionally substituted by one or more substituents.

Representative values for the substituent Z include phenyl, pyridinyl, pyridazinyl, pyrimidinyl, pyrazinyl, thienyl, thiazolyl, imidazolyl and triazolyl, any of which groups may be optionally substituted. Typical values of Z include phenyl, pyridinyl, pyridazinyl, pyrimidinyl and pyrazinyl, any of which groups may be optionally substituted. In one favoured embodiment, Z represents an optionally substituted phenyl group, in particular monosubstituted or disubstituted phenyl. In another favoured embodiment, Z represents optionally substituted pyridinyl, especially unsubstituted or monosubstituted pyridin-2-yl, pyridin-3-yl or pyridin-4-yl.

Examples of suitable substituents on the group Z include fluoro, chloro, cyano, nitro, methyl, hydroxy, methoxy, oxy, methanesulphonyl, amino, aminocarbonyl, formyl, methoxycarbonyl and —CH=NOH. Examples of individual substituents on the group Z include fluoro, chloro, cyano, methyl, hydroxy, methoxy, oxy, methanesulphonyl and aminocarbonyl.

Examples of typical substituents on the group Z include fluoro, chloro, cyano, nitro, methyl, methoxy, amino, formyl, methoxycarbonyl and —CH=NOH. Examples of particular substituents on the group Z include fluoro, cyano and methyl; especially fluoro or cyano; and more especially cyano.

Detailed values of Z include cyanophenyl, (cyano)(fluoro)phenyl, (chloro)(cyano)phenyl, nitrophenyl, methoxyphenyl, methanesulphonylphenyl, pyridinyl, fluoro-pyridinyl, difluoro-pyridinyl, (amino)(chloro)pyridinyl, cyano-pyridinyl, methyl-pyridinyl, hydroxy-pyridinyl, methoxy-pyridinyl, oxy-pyridinyl, aminocarbonyl-pyridinyl, pyridazinyl, pyrimidinyl, pyrazinyl, cyano-thienyl, aminocarbonyl-thienyl, formyl-thienyl, methoxycarbonyl-thienyl, thienyl-CH=NOH, thiazolyl, isothiazolyl, pyrrolyl, pyrazolyl, imidazolyl, triazolyl and methyl-tetrazolyl.

Specific values of Z include cyanophenyl, (cyano)(fluoro)phenyl, (chloro)(cyano)phenyl, methanesulphonyl-phenyl, pyridinyl, fluoro-pyridinyl, difluoro-pyridinyl, cyano-pyridinyl, methyl-pyridinyl, hydroxy-pyridinyl, methoxy-pyridinyl, oxy-pyridinyl, aminocarbonyl-pyridinyl, pyridazinyl, pyrimidinyl, pyrazinyl, cyano-thienyl, aminocarbonyl-thienyl, thiazolyl, isothiazolyl, pyrrolyl, pyrazolyl, imidazolyl, triazolyl and methyl-tetrazolyl.

Suitable values of Z include cyanophenyl, (cyano)(fluoro)phenyl, (chloro)(cyano)phenyl, nitrophenyl, methoxyphenyl, methanesulphonyl-phenyl, pyridinyl, fluoro-pyridinyl, difluoro-pyridinyl, (amino)(chloro)pyridinyl, cyano-pyridinyl, methyl-pyridinyl, hydroxy-pyridinyl, methoxy-pyridinyl, oxy-pyridinyl, pyridazinyl, pyrimidinyl, pyrazinyl, cyano-thienyl, aminocarbonyl-thienyl, formyl-thienyl, methoxycarbonyl-thienyl, thienyl-CH=NOH, thiazolyl, isothiazolyl, pyrrolyl, imidazolyl, triazolyl and methyl-tetrazolyl.

Typical values of Z include cyanophenyl, (cyano)(fluoro)phenyl, (chloro)(cyano)phenyl, methanesulphonyl-phenyl, pyridinyl, fluoro-pyridinyl, difluoro-pyridinyl, cyano-pyridinyl, methyl-pyridinyl, hydroxy-pyridinyl, methoxy-pyridinyl, oxy-pyridinyl, pyridazinyl, pyrimidinyl, pyrazinyl, cyano-thienyl, aminocarbonyl-thienyl, isothiazolyl, pyrrolyl, imidazolyl and methyl-tetrazolyl.

Illustrative values of Z include cyanophenyl, (cyano)(fluoro)phenyl, nitrophenyl, methoxyphenyl, pyridinyl, fluoro-pyridinyl, (amino)(chloro)pyridinyl, cyano-pyridinyl, methyl-pyridinyl, pyridazinyl, pyrimidinyl, pyrazinyl, cyano-thienyl, formyl-thienyl, methoxycarbonyl-thienyl, thienyl-CH=NOH, thiazolyl, imidazolyl and triazolyl. Individual values of Z include cyanophenyl, (cyano)(fluoro) phenyl, pyridinyl, fluoro-pyridinyl, cyano-pyridinyl, methyl-pyridinyl, pyridazinyl, pyridimidinyl and pyrazinyl.

Particular values of Z include 2-cyanophenyl, 2-cyano-4-fluorophenyl, pyridinyl-2-yl, pyridin-3-yl and 3-cyanopyridin-2-yl.

In one embodiment, Z represents 2-cyano-4-fluorophenyl.
In another embodiment, Z represents pyridin-3-yl.

Typically, $R^1$ represents hydrogen, hydrocarbon, a heterocyclic group, halogen, cyano, trifluoromethyl, —$COR^a$, —$CO_2R^a$ or —$CR^a$=$NOR^b$.

Typical values of $R^a$ include hydrogen and $C_{1-6}$ alkyl. Suitably, $R^a$ represents hydrogen or methyl.

Typical values of $R^b$ include hydrogen, $C_{1-6}$ alkyl, hydroxy($C_{1-6}$)alkyl and di($C_{1-6}$)alkylamino($C_{1-6}$)alkyl. Suitably, $R^b$ represents hydrogen, methyl, ethyl, hydroxyethyl or dimethylaminoethyl. Particular values of $R^b$ include hydrogen, hydroxyethyl and dimethylaminoethyl, especially hydrogen or dimethylaminoethyl.

Suitable values of $R^1$ include hydrogen, $C_{1-6}$ alkyl, halo($C_{1-6}$)alkyl, dihalo($C_{1-6}$)alkyl, hydroxy($C_{1-6}$)alkyl, dihydroxy($C_{1-6}$)alkyl, $C_{1-6}$ alkoxy($C_{1-6}$)alkyl, di($C_{1-6}$)alkoxy($C_{1-6}$)alkyl, cyano($C_{1-6}$)alkyl, $C_{2-6}$ alkoxycarbonyl($C_{1-6}$)alkyl, heteroaryl, $C_{1-6}$ alkyl-heteroaryl, heteroaryl($C_{1-6}$)alkyl, halogen, cyano, trifluoromethyl, formyl, $C_{2-6}$ alkylcarbonyl, $C_{2-6}$ alkoxycarbonyl and —$CR^a$=$NOR^b$, in which $R^a$ and $R^b$ are as defined above.

Representative values of $R^1$ include hydrogen, $C_{1-6}$ alkyl, halo($C_{1-6}$)alkyl, dihalo($C_{1-6}$)alkyl, hydroxy($C_{1-6}$)alkyl, $C_{1-6}$ alkoxy($C_{1-6}$)alkyl, di($C_{1-6}$)alkoxy($C_{1-6}$)alkyl, heteroaryl, $C_{1-6}$ alkyl-heteroaryl, heteroaryl($C_{1-6}$)alkyl, halogen, cyano, trifluoromethyl, formyl, $C_{2-6}$ alkylcarbonyl, $C_{2-6}$ alkoxycarbonyl and —$CR^a$=$NOR^b$, in which $R^a$ and $R^b$ are as defined above.

Individual values of $R^1$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), dihydroxypropyl (especially 1,2-dihydroxyprop-2-yl), fluoropropyl (especially 2-fluoroprop-2-yl), cyanopropyl (especially 2-cyanoprop-2-yl), methoxycarbonylpropyl (especially 2-methoxycarbonylprop-2-yl), tert-butyl, hydroxybutyl (especially 1-hydroxy-2-methylprop-2-yl), pyridinyl, furyl, thienyl, oxazolyl, methylthiazolyl, methyloxadiazolyl, imidazolylmethyl, triazolylmethyl, chloro, cyano, trifluoromethyl, formyl, acetyl, methoxycarbonyl and —$CR^3$=$NOR^4$, in which $R^3$ represents hydrogen or methyl, and $R^4$ represents hydrogen, hydroxyethyl or dimethylaminoethyl.

Itemised values of $R^1$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), fluoropropyl (especially 2-fluoroprop-2-yl), tert-butyl, pyridinyl, furyl, thienyl, oxazolyl, methylthiazolyl, methyloxadiazolyl, imidazolylmethyl, triazolylmethyl, chloro, cyano, trifluoromethyl, formyl, acetyl, methoxycarbonyl and —$CR^3$=$NOR^4$, in which $R^3$ and $R^4$ are as defined above.

In one favoured embodiment, $R^1$ represents 2-hydroxyprop-2-yl. In another favoured embodiment, $R^1$ represents trifluoromethyl.

Typical values of $R^2$ include hydrogen and fluoro, especially hydrogen.

Suitably, $R^3$ is hydrogen.

Suitably, $R^4$ represents hydrogen or dimethylaminoethyl, especially hydrogen.

A particular sub-class of compounds according to the invention is represented by the compounds of formula IIA, and salts and prodrugs thereof:

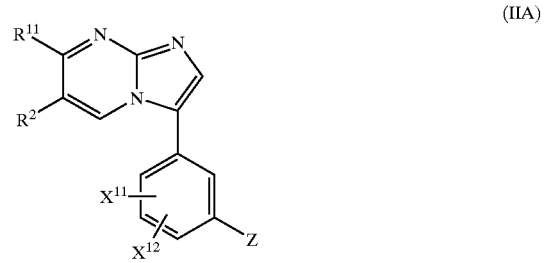

(IIA)

wherein
Z and $R^2$ are as defined above;
$X^{11}$ represents fluoro, chloro, methyl, trifluoromethyl or methoxy;
$X^{12}$ represents hydrogen or fluoro;
$R^{11}$ represents hydrogen, $C_{1-6}$ alkyl, halo($C_{1-6}$)alkyl, dihalo($C_{1-6}$)alkyl, hydroxy($C_{1-6}$)alkyl, dihydroxy($C_{1-6}$) alkyl, $C_{1-6}$ alkoxy($C_{1-6}$)alkyl, di($C_{1-6}$)alkoxy($C_{1-6}$)alkyl, cyano($C_{1-6}$)alkyl, $C_{2-6}$ alkoxycarbonyl($C_{1-6}$)alkyl, heteroaryl, $C_{1-6}$ alkyl-heteroaryl, heteroaryl($C_{1-6}$)alkyl, halogen, cyano, trifluoromethyl, formyl, $C_{2-6}$ alkylcarbonyl, $C_{2-6}$ alkoxycarbonyl or —$CR^5$=$NOR^6$;
$R^5$ represents hydrogen or $C_{1-6}$ alkyl; and
$R^6$ represents hydrogen, $C_{1-6}$ alkyl, hydroxy($C_{1-6}$)alkyl or di($C_{1-6}$)alkylamino($C_{1-6}$)alkyl.

The present invention also provides a compound of formula IIA as depicted above, or a salt thereof or a prodrug thereof, wherein
$R^{11}$ represents hydrogen, $C_{1-6}$ alkyl, halo($C_{1-6}$)alkyl, dihalo($C_{1-6}$)alkyl, hydroxy($C_{1-6}$)alkyl, $C_{1-6}$ alkoxy($C_{1-6}$) alkyl, di($C_{1-6}$)alkoxy($C_{1-6}$)alkyl, heteroaryl, $C_{1-6}$ alkyl-heteroaryl, heteroaryl($C_{1-6}$)alkyl, halogen, cyano, trifluoromethyl, formyl, $C_{2-6}$ alkylcarbonyl, $C_{2-6}$ alkoxycarbonyl or —$CR^5$=$NOR^6$; and
Z, $X^{11}$, $X^{12}$, $R^2$, $R^5$ and $R^6$ are as defined above.

A particular value of $X^{11}$ is fluoro.

In a favoured embodiment, $X^{12}$ represents hydrogen. In another embodiment, $X^{12}$ represents fluoro.

Suitably, $R^5$ represents hydrogen or methyl, especially hydrogen.

Suitably, $R^6$ represents hydrogen, methyl, ethyl, hydroxyethyl or dimethylaminoethyl. Particular values of $R^6$ include hydrogen, hydroxyethyl and dimethylaminoethyl. Typically, $R^6$ represents hydrogen or dimethylaminoethyl, especially hydrogen.

Where $R^{11}$ represents heteroaryl, this group is suitably pyridinyl, furyl, thienyl or oxazolyl.

Where $R^{11}$ represents $C_{1-6}$ alkyl-heteroaryl, this group is suitably methylthiazolyl (e.g. 2-methylthiazol-5-yl) or methyloxadiazolyl (e.g. 3-methyl-[1,2,4]oxadiazol-5-yl).

Where $R^{11}$ represents heteroaryl($C_{1-6}$)alkyl, this group is suitably imidazolylmethyl or triazolylmethyl.

Individual values of $R^{11}$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), dihydroxypropyl (especially 1,2-dihydroxyprop-2-yl), fluoropropyl (especially 2-fluoroprop-2-yl), cyanopropyl (especially 2-cyanoprop-2-yl), methoxycarbonylpropyl (especially 2-methoxycarbonylprop-2-yl), tert-butyl, hydroxybutyl (especially 1-hydroxy-2-methylprop-2-yl), pyridinyl, furyl, thienyl, oxazolyl, methylthiazolyl, methyloxadiazolyl, imidazolylmethyl, triazolylmethyl, chloro, cyano, trifluoromethyl, formyl, acetyl, methoxycarbonyl and —$CR^3$=$NOR^4$, in which $R^3$ and $R^4$ are as defined above.

Itemised values of $R^{11}$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), fluoropropyl (especially 2-fluoroprop-2-yl), tert-butyl, pyridinyl, furyl, thienyl, oxazolyl, methylthiazolyl, methyloxadiazolyl, imidazolylmethyl, triazolylmethyl, chloro, cyano, trifluoromethyl, formyl, acetyl, methoxycarbonyl and —$CR^3$=$NOR^4$, in which $R^3$ and $R^4$ are as defined above.

In one favoured embodiment, $R^{11}$ represents 2-hydroxyprop-2-yl. In another favoured embodiment, $R^{11}$ represents trifluoromethyl.

The present invention advantageously provides a compound of formula IIA as depicted above, or a pharmaceutically acceptable salt thereof, wherein Z represents (cyano)(fluoro)phenyl or pyridinyl; and $X^{11}$, $X^{12}$, $R^2$ and $R^{11}$ are as defined above.

One representative subset of the compounds of formula IIA above is represented by the compounds of formula IIB, and salts and prodrugs thereof:

(IIB)

wherein $X^{11}$, $X^{12}$ and $R^{11}$ are as defined above; and $R^7$ represents hydrogen, fluoro or chloro.

Suitably, $R^7$ represents hydrogen or fluoro.

In one embodiment, $R^7$ is hydrogen.

In another embodiment, $R^7$ is fluoro.

In a further embodiment, $R^7$ is chloro.

Another representative subset of the compounds of formula IIA above is represented by the compounds of formula IIC, and salts and prodrugs thereof:

(IIC)

wherein $X^{11}$, $X^{12}$ and $R^{11}$ are as defined with reference to formula IIA above; and $R^7$ is as defined with reference to formula IIB above.

An additional representative subset of the compounds of formula IIA above is represented by the compounds of formula IID, and salts and prodrugs thereof:

(IID)

wherein $X^{11}$, $X^{12}$ and $R^{11}$ are as defined with reference to formula IIA above; and $R^8$ represents hydrogen, fluoro, cyano or methyl.

Suitably, $R^8$ represents hydrogen or cyano, especially hydrogen.

In one embodiment, $R^8$ is hydrogen.

In an additional embodiment, $R^8$ is fluoro.

In another embodiment, $R^8$ is cyano.

In a further embodiment, $R^8$ is methyl.

A further representative subset of the compounds of formula IIA above is represented by the compounds of formula IIE, and salts and prodrugs thereof:

(IIE)

wherein $X^{11}$, $X^{12}$ and $R^{11}$ are as defined with reference to formula IIA above;

$R^8$ is as defined with reference to formula IID above; and $R^9$ represents hydrogen or fluoro.

Suitably, $R^9$ represents hydrogen.

In another embodiment, $R^9$ represents fluoro.

Specific compounds within the scope of the present invention include:

2'-fluoro-5'-(imidazo[1,2-α]pyrimidin-3-yl)biphenyl-2-carbonitrile;
2'-fluoro-5'-(7-methylimidazo[1,2-α]pyrimidin-3-yl)biphenyl-2-carbonitrile;
5'-(7-acetylimidazo[1,2-α]pyrimidin-3-yl)-2'-fluorobiphenyl-2-carbonitrile;
2'-fluoro-5'-(7-isopropylimidazo[1,2-α]pyrimidin-3-yl)biphenyl-2-carbonitrile;
2'-fluoro-5'-(7-tert-butylimidazo[1,2-α]pyrimidin-3-yl)biphenyl-2-carbonitrile;
2'-fluoro-5'-[7-(1-hydroxy-1-methylethyl)imidazo[1,2-α]pyrimidin-3-yl]biphenyl-2-carbonitrile;
2'-fluoro-5'-[7-(1-fluoro-1-methylethyl)imidazo[1,2-α]pyrimidin-3-yl]biphenyl-2-carbonitrile;
2'-fluoro-5'-(7-hydroxymethylimidazo[1,2-α]pyrimidin-3-yl)biphenyl-2-carbonitrile;
2'-fluoro-5'-[7-(1-hydroxyethyl)imidazo[1,2-α]pyrimidin-3-yl]biphenyl-2-carbonitrile;
2'-fluoro-5'-[7-(1-fluoroethyl)imidazo[1,2-α]pyrimidin-3-yl]biphenyl-2-carbonitrile;
2'-fluoro-5'-[7-(2-methylthiazol-5-yl)imidazo[1,2-α]pyrimidin-3-yl]biphenyl-2-carbonitrile;
2'-fluoro-5'-(7-trifluoromethylimidazo[1,2-α]pyrimidin-3-yl)biphenyl-2-carbonitrile;
5'-[7-(1,1-difluoroethyl)imidazo[1,2-α]pyrimidin-3-yl]-2'-fluorobiphenyl-2-carbonitrile;
5'-(7-chloroimidazo[1,2-α]pyrimidin-3-yl)-2'-fluorobiphenyl-2-carbonitrile;
5'-(7-difluoromethylimidazo[1,2-α]pyrimidin-3-yl)-2'-fluorobiphenyl-2-carbonitrile;
2'-fluoro-5'-(7-methoxymethylimidazo[1,2-α]pyrimidin-3-yl)biphenyl-2-carbonitrile;
3-(2'-cyano-6-fluorobiphenyl-3-yl)imidazo[1,2-α]pyrimidine-7-carbonitrile;
2'-fluoro-5'-[7-(3-methyl-[1,2,4]oxadiazol-5-yl)imidazo[1,2-α]pyrimidin-3-yl]biphenyl-2-carbonitrile;
2'-fluoro-5'-[7-(oxazol-5-yl)imidazo[1,2-α]pyrimidin-3-yl]biphenyl-2-carbonitrile;
2'-fluoro-5'-[7-(hydroxyiminomethyl)imidazo[1,2-α]pyrimidin-3-yl]biphenyl-2-carbonitrile;
5'-{7-[1-(2-dimethylaminoethoxyimino)methyl]imidazo[1,2-α]pyrimidin-3-yl}-2'-fluorobiphenyl-2-carbonitrile;
3'-(7-difluoromethylimidazo[1,2-α]pyrimidin-3-yl)-4'-fluorobiphenyl-2-carbonitrile;
2'-fluoro-5'-(7-fluoromethylimidazo[1,2-α]pyrimidin-3-yl)biphenyl-2-carbonitrile;
2'-fluoro-5'-[7-(furan-3-yl)imidazo[1,2-α]pyrimidin-3-yl]biphenyl-2-carbonitrile;
2'-fluoro-5'-[7-(thien-3-yl)imidazo[1,2-α]pyrimidin-3-yl]biphenyl-2-carbonitrile;
2'-fluoro-5'-[7-(pyridin-2-yl)imidazo[1,2-α]pyrimidin-3-yl]biphenyl-2-carbonitrile;
2'-fluoro-5'-(6-fluoro-7-methylimidazo[1,2-α]pyrimidin-3-yl)biphenyl-2-carbonitrile;
7-(1,1-difluoroethyl)-3-[4-fluoro-3-(pyridin-3-yl)phenyl]imidazo[1,2-α]pyrimidine;
2-[3-(4-fluoro-3-(pyridin-3-yl)phenyl)imidazo[1,2-α]pyrimidin-7-yl]propan-2-ol;
3'-fluoro-5'-(7-trifluoromethylimidazo[1,2-α]pyrimidin-3-yl)biphenyl-2-carbonitrile;
3'-fluoro-5'-(7-hydroxymethylimidazo[1,2-α]pyrimidin-3-yl)biphenyl-2-carbonitrile;
2'-fluoro-3'-(7-trifluoromethylimidazo[1,2-α]pyrimidin-3-yl)biphenyl-2-carbonitrile;
3-[4-fluoro-3-(pyridin-2-yl)phenyl]-7-trifluoromethylimidazo[1,2-α]pyrimidine;
3-[4-fluoro-3-(pyridin-3-yl)phenyl]-7-trifluoromethylimidazo[1,2-α]pyrimidine;
2'-fluoro-5'-[7-([1,2,4]triazol-1-ylmethyl)imidazo[1,2-α]pyrimidin-3-yl]biphenyl-2-carbonitrile;
2'-fluoro-5'-[7-(imidazol-1-ylmethyl)imidazo[1,2-α]pyrimidin-3-yl]biphenyl-2-carbonitrile;
2'-fluoro-5'-[7-([1,2,3]triazol-1-ylmethyl)imidazo[1,2-α]pyrimidin-3-yl]biphenyl-2-carbonitrile;
2'-fluoro-5'-[7-([1,2,3]triazol-2-ylmethyl)imidazo[1,2-α]pyrimidin-3-yl]biphenyl-2-carbonitrile;
3-[4-fluoro-3-(pyridin-4-yl)phenyl]-7-trifluoromethylimidazo[1,2-α]pyrimidine;
3-[2,4-difluoro-3-(pyridin-3-yl)phenyl]-7-trifluoromethylimidazo[1,2-α]pyrimidine;
3-[2,4-difluoro-3-(pyridin-2-yl)phenyl]-7-trifluoromethylimidazo[1,2-α]pyrimidine;
2-[3-(4-fluoro-3-(pyridin-4-yl)phenyl)imidazo[1,2-α]pyrimidin-7-yl]propan-2-ol;
3-[2-fluoro-3-(pyridin-3-yl)phenyl]-7-trifluoromethylimidazo[1,2-α]pyrimidine;
2-[3-(2-fluoro-3-(pyridin-3-yl)phenyl)imidazo[1,2-α]pyrimidin-7-yl]propan-2-ol;
3-[2-fluoro-3-(pyridin-4-yl)phenyl]-7-trifluoromethylimidazo[1,2-α]pyrimidine;
2-[3-(2-fluoro-3-(pyridin-4-yl)phenyl)imidazo[1,2-α]pyrimidin-7-yl]propan-2-ol;
3-[2-fluoro-3-(pyridin-2-yl)phenyl]-7-trifluoromethylimidazo[1,2-α]pyrimidine;
2-[3-(2-fluoro-3-(pyridin-2-yl)phenyl)imidazo[1,2-α]pyrimidin-7-yl]propan-2-ol;
3-[4-fluoro-3-(4-methylpyridin-2-yl)phenyl]-7-trifluoromethylimidazo[1,2-α]pyrimidine;
3-[4-fluoro-3-(pyridazin-3-yl)phenyl]-7-trifluoromethylimidazo[1,2-α]pyrimidine;
2-[2-fluoro-5-(7-trifluoromethylimidazo[1,2-α]pyrimidin-3-yl)phenyl]nicotinonitrile;
3-[4-fluoro-3-(pyridin-2-yl)phenyl]imidazo[1,2-α]pyrimidine;
3,2'-difluoro-5'-(7-trifluoromethylimidazo[1,2-α]pyrimidin-3-yl)biphenyl-2-carbonitrile;
6,2'-difluoro-5'-(7-trifluoromethylimidazo[1,2-α]pyrimidin-3-yl)biphenyl-2-carbonitrile;
5,2'-difluoro-5'-(7-trifluoromethylimidazo[1,2-α]pyrimidin-3-yl)biphenyl-2-carbonitrile;
4,2'-difluoro-5'-(7-trifluoromethylimidazo[1,2-α]pyrimidin-3-yl)biphenyl-2-carbonitrile;
2',6'-difluoro-3'-(7-trifluoromethylimidazo[1,2-α]pyrimidin-3-yl)biphenyl-2-carbonitrile;
3-[4-fluoro-3-(pyrazin-2-yl)phenyl]-7-trifluoromethylimidazo[1,2-α]pyrimidine;
3-[4-fluoro-3-(pyrimidin-2-yl)phenyl]-7-trifluoromethylimidazo[1,2-α]pyrimidine;
3-[2-fluoro-5-(7-trifluoromethylimidazo[1,2-α]pyrimidin-3-yl)phenyl]pyridine-2-carbonitrile;
3-[4-fluoro-3-(5-fluoropyridin-2-yl)phenyl]-7-trifluoromethylimidazo[1,2-α]pyrimidine;
7-(1,1-difluoroethyl)-3-[4-fluoro-3-(pyridin-4-yl)phenyl]imidazo[1,2-α]pyrimidine;
7-(1,1-difluoroethyl)-3-[2,4-difluoro-3-(pyridin-3-yl)phenyl]imidazo[1,2-α]pyrimidine;
3-[4-methyl-3-(pyridin-3-yl)phenyl]-7-trifluoromethylimidazo[1,2-α]pyrimidine;
3-[4-chloro-3-(pyridin-3-yl)phenyl]-7-trifluoromethylimidazo[1,2-α]pyrimidine;
3-[4-methoxy-3-(pyridin-3-yl)phenyl]-7-trifluoromethylimidazo[1,2-α]pyrimidine;
2-[3-(2,4-difluoro-3-(pyridin-3-yl)phenyl)imidazo[1,2-α]pyrimidin-7-yl]propan-2-ol;
1-[3-(4-fluoro-3-(pyridin-3-yl)phenyl)imidazo[1,2-α]pyrimidin-7-yl]ethanone;

3'-[7-(1-hydroxy-1-methylethyl)imidazo[1,2-α]pyrimidin-3-yl]-4,2',6'-trifluorobiphenyl-2-carbonitrile;
2-[3-(4-fluoro-3-(pyridin-3-yl)phenyl)imidazo[1,2-α]pyrimidin-7-yl]propane-1,2-diol;
3-[2-fluoro-5-(7-trifluoromethylimidazo[1,2-α]pyrimidin-3-yl)phenyl]thiophene-2-carbonitrile;
3-{2-fluoro-5-[7-(1-hydroxy-1-methylethyl)imidazo[1,2-α]pyrimidin-3-yl]phenyl}thiophene-2-carbonitrile;
2-{3-[4-fluoro-3-(1-oxypyridin-3-yl)phenyl]imidazo[1,2-α]pyrimidin-7-yl}propan-2-ol;
3-{2,6-difluoro-3-[7-(1-hydroxy-1-methylethyl)imidazo[1,2-α]pyrimidin-3-yl]phenyl}thiophene-2-carbonitrile;
3-{2,6-difluoro-3-[7-(1-hydroxy-1-methylethyl)imidazo[1,2-α]pyrimidin-3-yl]phenyl}thiophene-2-carboxylic acid amide;
3-[4-fluoro-3-(3-fluoropyridin-4-yl)phenyl]-7-trifluoromethylimidazo[1,2-α]pyrimidine;
4-chloro-2'-fluoro-5'-(7-trifluoromethylimidazo[1,2-α]pyrimidin-3-yl)biphenyl-2-carbonitrile;
3-[4-fluoro-3-(5-methylpyridin-3-yl)phenyl]-7-trifluoromethylimidazo[1,2-α]pyrimidine;
3-[2-fluoro-2'-(methanesulfonyl)biphenyl-5-yl]-7-trifluoromethylimidazo[1,2-α]pyrimidine;
2-[3-(4-fluoro-3-(pyrazin-2-yl)phenyl)imidazo[1,2-α]pyrimidin-7-yl]propan-2-ol;
2-[3-(4-fluoro-3-(5-fluoropyridin-2-yl)phenyl)imidazo[1,2-α]pyrimidin-7-yl]propan-2-ol;
3-[4-fluoro-3-(3-fluoropyridin-2-yl)phenyl]-7-trifluoromethylimidazo[1,2-α]pyrimidine;
2-[3-(4-fluoro-3-(3-fluoropyridin-2-yl)phenyl)imidazo[1,2-α]pyrimidin-7-yl]propan-2-ol;
3-[3-(3,5-difluoropyridin-2-yl)-4-fluorophenyl]-7-trifluoromethylimidazo[1,2-α]pyrimidine;
2-[3-(3-(3,5-difluoropyridin-2-yl)-4-fluorophenyl)imidazo[1,2-α]pyrimidin-7-yl]propan-2-ol;
3-[2,4-difluoro-3-(pyridin-4-yl)phenyl]-7-trifluoromethylimidazo[1,2-α]pyrimidine;
2-[3-(2,4-difluoro-3-(pyridin-4-yl)phenyl)imidazo[1,2-α]pyrimidin-7-yl]propan-2-ol;
4,2'-difluoro-5'-[7-(1-hydroxy-1-methylethyl)imidazo[1,2-α]pyrimidin-3-yl]biphenyl-2-carbonitrile;
2'-fluoro-5'-(7-trifluoromethylimidazo[1,2-α]pyrimidin-3-yl)biphenyl-3-carbonitrile;
2'-fluoro-5'-(7-trifluoromethylimidazo[1,2-α]pyrimidin-3-yl)biphenyl-4-carbonitrile;
4-fluoro-2'-methyl-3'-(7-trifluoromethylimidazo[1,2-α]pyrimidin-3-yl)biphenyl-2-carbonitrile;
3-[2,4-difluoro-3-(pyridin-3-yl)phenyl]-7-(1-fluoro-1-methylethyl)imidazo[1,2-α]pyrimidine;
7-(1-fluoro-1-methylethyl)-3-[4-fluoro-3-(pyridin-3-yl)phenyl]imidazo[1,2-α]pyrimidine;
2-[3-(2,4-difluoro-3-(pyridin-3-yl)phenyl)imidazo[1,2-α]pyrimidin-7-yl]-2-methylpropionic acid methyl ester;
2-[3-(4-fluoro-3-(pyridin-3-yl)phenyl)imidazo[1,2-α]pyrimidin-7-yl]-2-methylpropionitrile;
2-[3-(4-fluoro-3-(pyridin-3-yl)phenyl)imidazo[1,2-α]pyrimidin-7-yl]-2-methylpropan-1-ol;
3-[4-fluoro-3-(6-methoxypyridin-3-yl)phenyl]-7-trifluoromethylimidazo[1,2-α]pyrimidine;
5-[2-fluoro-5-(7-trifluoromethylimidazo[1,2-α]pyrimidin-3-yl)phenyl]pyridin-2-ol;
3-[4-fluoro-3-(4-fluoropyridin-3-yl)phenyl]-7-trifluoromethylimidazo[1,2-α]pyrimidine;
3-[4-fluoro-3-(pyrrol-1-yl)phenyl]-7-trifluoromethylimidazo[1,2-α]pyrimidine;
3-[4-fluoro-3-(pyridin-3-yl)phenyl]imidazo[1,2-α]pyrimidine;
3-[4-fluoro-3-(5-fluoropyridin-2-yl)phenyl]imidazo[1,2-α]pyrimidine;
3-[2,4-difluoro-3-(pyridin-3-yl)phenyl]imidazo[1,2-α]pyrimidine;
3-[4-chloro-3-(pyridin-3-yl)phenyl]imidazo[1,2-α]pyrimidine;
3-[5-fluoro-3-(pyridin-3-yl)phenyl]-7-trifluoromethylimidazo[1,2-α]pyrimidine;
3-[4-fluoro-3-(4-methylpyridin-3-yl)phenyl]-7-trifluoromethylimidazo[1,2-α]pyrimidine;
3-[2-fluoro-5-(pyridin-3-yl)phenyl]-7-trifluoromethylimidazo[1,2-α]pyrimidine;
3-[4-fluoro-3-(pyridazin-4-yl)phenyl]-7-trifluoromethylimidazo[1,2-α]pyrimidine;
3-[4-fluoro-3-(imidazol-1-yl)phenyl]-7-trifluoromethylimidazo[1,2-α]pyrimidine;
3-[4-fluoro-3-(isothiazol-4-yl)phenyl]-7-trifluoromethylimidazo[1,2-α]pyrimidine;
3-[4-fluoro-3-(pyrimidin-5-yl)phenyl]-7-trifluoromethylimidazo[1,2-α]pyrimidine;
3-[4-fluoro-3-(5-methoxypyridin-3-yl)phenyl]-7-trifluoromethylimidazo[1,2-α]pyrimidine;
3-[4-fluoro-3-(2-methylpyridin-3-yl)phenyl]-7-trifluoromethylimidazo[1,2-α]pyrimidine;
3-[4-fluoro-3-(2-methyltetrazol-5-yl)phenyl]-7-trifluoromethylimidazo[1,2-α]pyrimidine;
3-[4-fluoro-3-(1-methyltetrazol-5-yl)phenyl]-7-trifluoromethylimidazo[1,2-α]pyrimidine;
3-[4-fluoro-3-(6-methoxypyridin-2-yl)phenyl]-7-trifluoromethylimidazo[1,2-α]pyrimidine;
3-[4-fluoro-3-(4-methoxypyridin-2-yl)phenyl]-7-trifluoromethylimidazo[1,2-α]pyrimidine;
3-[4-fluoro-3-(thiazol-2-yl)phenyl]-7-trifluoromethylimidazo[1,2-α]pyrimidine;
2-{2-fluoro-5-[7-(1-hydroxy-1-methylethyl)imidazo[1,2-α]pyrimidin-3-yl]phenyl}nicotinonitrile;
4-[2-fluoro-5-(7-trifluoromethylimidazo[1,2-α]pyrimidin-3-yl)phenyl]nicotinonitrile;
4-{2-fluoro-5-[7-(1-hydroxy-1-methylethyl)imidazo[1,2-α]pyrimidin-3-yl]phenyl}nicotinonitrile;
3-[2-fluoro-5-(7-trifluoromethylimidazo[1,2-α]pyrimidin-3-yl)phenyl]isonicotinonitrile;
3-[2-fluoro-5-(7-trifluoromethylimidazo[1,2-α]pyrimidin-3-yl)phenyl]isonicotinamide;
3-{2-fluoro-5-[7-(1-hydroxy-1-methylethyl)imidazo[1,2-α]pyrimidin-3-yl]phenyl}isonicotinamide;
2-[3-(4-fluoro-3-(pyridazin-3-yl)phenyl)imidazo[1,2-α]pyrimidin-7-yl]propan-2-ol;
2-[3-(4-fluoro-3-(pyridazin-4-yl)phenyl)imidazo[1,2-α]pyrimidin-7-yl]propan-2-ol;
3-[4-fluoro-3-(pyrazol-1-yl)phenyl]-7-trifluoromethylimidazo[1,2-α]pyrimidine;
2-[3-(4-fluoro-3-(pyrazol-1-yl)phenyl)imidazo[1,2-α]pyrimidin-7-yl]propan-2-ol;
3-[4-fluoro-3-([1,2,4]triazol-1-yl)phenyl]-7-trifluoromethylimidazo[1,2-α]pyrimidine;
2-[3-(4-fluoro-3-([1,2,4]triazol-1-yl)phenyl)imidazo[1,2-α]pyrimidin-7-yl]propan-2-ol;
2-[2-fluoro-5-(7-trifluoromethylimidazo[1,2-α]pyrimidin-3-yl)phenyl]nicotinamide;
2-{3-[4-fluoro-3-(5-fluoropyridin-3-yl)phenyl]imidazo[1,2-α]pyrimidin-7-yl}propan-2-ol;
and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the α3 subunit of the human GABA$_A$ receptor is conveniently as measured in the assay described hereinbelow. The α3 subunit binding affinity ($K_i$) of the anxiolytic compounds of the invention is ideally 50 nM or less, preferably 10 nM or less, and more preferably 5 nM or less.

The anxiolytic compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human GABA$_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human GABA$_A$ receptor.

The potentiation of the GABA $EC_{20}$ response in stably transfected cell lines expressing the α3 and α1 subunits of the human GABA$_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk-fibroblast cells.

The compounds according to the present invention may exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are likely to be substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In another aspect, the present invention provides a method for the treatment and/or prevention of cognitive disorders, including dementing conditions such as Alzheimer's disease, which comprises administering to a patient in need of such treatment an effective amount of a compound of formula I as defined above or a pharmaceutically acceptable salt thereof.

Cognition enhancement can be shown by testing the compounds in the Morris watermaze as reported by McNamara and Skelton, *Psychobiology*, 1993, 21, 101–108. Further details of relevant methodology are described in WO 96/25948.

Cognitive disorders for which the compounds of the present invention may be of benefit include delirium, dementia, amnestic disorders, and cognition deficits, including age-related memory deficits, due to traumatic injury, stroke, Parkinson's disease and Down Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV disease, head trauma, Parkinson's disease or Creutzfeld-Jakob disease.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of neurological disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

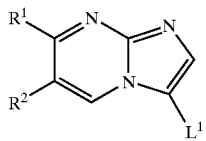

(III)

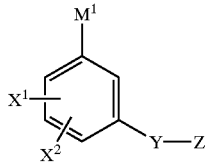

(IV)

wherein $X^1$, $X^2$, Y, Z, $R^1$ and $R^2$ are as defined above, $L^1$ represents a suitable leaving group, and $M^1$ represents a boronic acid moiety —$B(OH)_2$ or a cyclic ester thereof formed with an organic diol, e.g. pinacol, 1,3-propanediol or neopentyl glycol, or $M^1$ represents —$Sn(Alk)_3$ in which Alk represents a $C_{1-6}$ alkyl group, typically n-butyl; in the presence of a transition metal catalyst.

The leaving group $L^1$ is typically a halogen atom, e.g. bromo.

The transition metal catalyst of use in the reaction between compounds III and IV is suitably tetrakis (triphenylphosphine)palladium(0). The reaction is conveniently carried out at an elevated temperature in a solvent such as N,N-dimethylacetamide, 1,4-dioxane or tetrahydrofuran, advantageously in the presence of potassium phosphate, copper(I) iodide, sodium carbonate or cesium carbonate. Alternatively, the transition metal catalyst employed may be dichloro[1,1'-bis(diphenylphosphino) ferrocene]palladium(II), in which case the reaction is conveniently effected at an elevated temperature in a solvent such as N,N-dimethylformamide, advantageously in the presence of potassium phosphate.

In an alternative procedure, the compounds according to the present invention may be prepared by a process which comprises reacting a compound of formula V with a compound of formula VI:

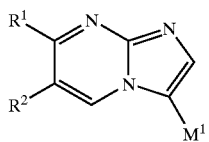

(V)

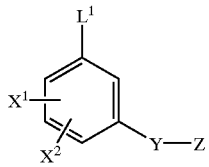

(VI)

wherein $X^1$, $X^2$, Y, Z, $R^1$, $R^2$, $L^1$ and $M^1$ are as defined above; in the presence of a transition metal catalyst; under conditions analogous to those described above for the reaction between compounds III and IV.

In another procedure, the compounds according to the present invention in which Y represents a chemical bond may be prepared by a process which comprises reacting a compound of formula VII with a compound of formula VIII, or a cyclic boroxine of formula VIIIA:

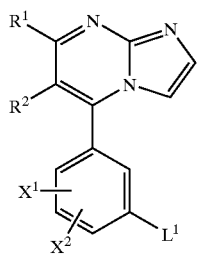

(VII)

$M^1$—Z (VIII)

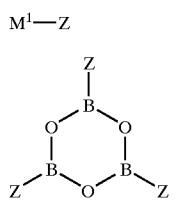

(VIIIA)

wherein $X^1$, $X^2$, Z, $R^1$, $R^2$, $L^1$ and $M^1$ are as defined above; in the presence of a transition metal catalyst; under conditions analogous to those described above for the reaction between compounds III and IV.

In the compounds of formula VII above, the leaving group $L^1$ is typically trifluoromethanesulfonyloxy (triflyloxy); or a halogen atom, e.g. bromo or chloro.

For the reaction between compounds VII and VIIIA, the transition metal catalyst employed may suitably be bis (dibenzylideneacetone)palladium(0), in which case the reaction is conveniently effected at an elevated temperature in a solvent such as aqueous 1,4-dioxane, advantageously in the presence of potassium phosphate and tri-tert-butylphosphine.

Alternatively, the compounds according to the present invention in which Y represents a chemical bond may be prepared by a process which comprises reacting a compound of formula IX with a compound of formula X:

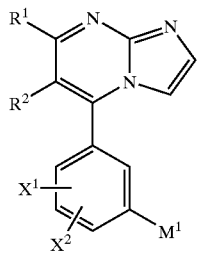

(IX)

$L^1$—Z (X)

wherein $X^1$, $X^2$, Z, $R^1$, $R^2$, $L^1$ and $M^1$ are as defined above; in the presence of a transition metal catalyst; under conditions analogous to those described above for the reaction between compounds III and IV.

In an additional procedure, the compounds according to the present invention in which Y represents an oxygen atom may be prepared by a process which comprises reacting a compound of formula X as defined above with a compound of formula XI:

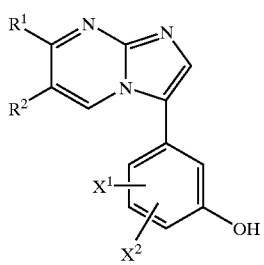

(XI)

wherein $X^1$, $X^2$, $R^1$ and $R^2$ are as defined above.

The reaction is conveniently carried out under basic conditions, e.g. using sodium hydride in a solvent such as N,N-dimethylformamide, typically at an elevated temperature which may be in the region of 120° C.

In a further procedure, the compounds according to the present invention in which Y represents a —NH— linkage may be prepared by a process which comprises reacting a compound of formula X as defined above with a compound of formula XII:

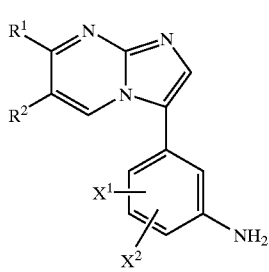

(XII)

wherein $X^1$, $X^2$, $R^1$ and $R^2$ are as defined above.

In relation to the reaction between compounds X and XII, the leaving group $L^1$ in the compounds of formula X may suitably represent fluoro.

The reaction between compounds X and XII is conveniently carried out by heating the reactants, typically at a temperature in the region of 120° C., in a solvent such as N,N-dimethylformamide.

Where $M^1$ in the intermediates of formula IV and IX above represents a boronic acid moiety —B(OH)$_2$ or a cyclic ester thereof formed with pinacol or neopentyl glycol, the relevant compound IV or IX may be prepared by reacting bis(pinacolato)diboron or bis(neopentyl glycolato)diborane respectively with a compound of formula VIA or VIIA:

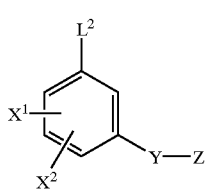

(VIA)

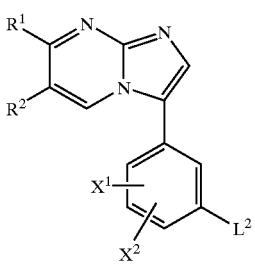

(VIIA)

wherein $X^1$, $X^2$, Y, Z, $R^1$ and $R^2$ are as defined above, and $L^2$ represents hydroxy or a suitable leaving group; in the presence of a transition metal catalyst.

Where $L^2$ represents a leaving group, this is typically triflyloxy; or a halogen atom such as bromo.

The transition metal catalyst of use in the reaction between bis(pinacolato)diboron or bis(neopentyl glycolato) diborane and compound VIA or VIIA is suitably dichloro[1,1'-bis(diphenylphosphino)ferrocene]palladium(II). The reaction is conveniently carried out at an elevated temperature in a solvent such as 1,4-dioxane, optionally in admixture with dimethylsulfoxide, typically in the presence of 1,1'-bis(diphenylphosphino)ferrocene and/or potassium acetate.

Where $L^1/L^2$ in the intermediates of formula VII/VIIA above represents triflyloxy, the relevant compound VII/VIIA may be prepared by reacting the appropriate compound of formula XI as defined above with triflic anhydride, typically in the presence of pyridine. Analogous conditions may be utilised for converting an intermediate of formula VIA above wherein $L^2$ represents hydroxy into the corresponding compound of formula VI/VIA wherein $L^1/L^2$ represents triflyloxy.

The intermediates of formula XI above may suitably be prepared from the appropriate methoxy-substituted precursor of formula XIII:

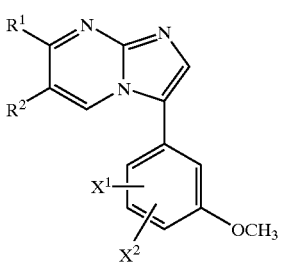

(XIII)

wherein $X^1$, $X^2$, $R^1$ and $R^2$ are as defined above; by treatment with hydrogen bromide, typically in acetic acid at reflux.

The intermediates of formula XII and XIII above may be prepared by reacting a compound of formula III as defined above with the appropriate compound of formula XIV:

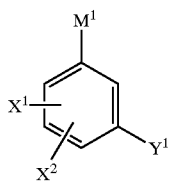

(XIV)

wherein X¹, X² and M¹ are as defined above, and Y¹ represents amino or methoxy; in the presence of a transition metal catalyst; under conditions analogous to those described above for the reaction between compounds III and IV. In particular, the transition metal catalyst of use in the reaction between compounds III and XIV is suitably tetrakis(triphenylphosphine)palladium(0), in which case the reaction is conveniently carried out at an elevated temperature in a solvent such as aqueous 1,2-dimethoxyethane, advantageously in the presence of sodium carbonate.

Where M¹ in the intermediates of formula V above represents —Sn(Alk)₃ and Alk is as defined above, this compound may be prepared by reacting a compound of formula III as defined above with a reagent of formula (Alk)₃Sn—Hal, in which Hal represents a halogen atom, typically chloro. The reaction is conveniently effected by treating compound III with isopropylmagnesium chloride, typically in a solvent such as tetrahydrofuran, with subsequent addition of the stannyl reagent (Alk)₃Sn-Hal.

Where L¹ in the intermediates of formula III above represents bromo, this compound may be prepared by bromination of the corresponding compound of formula XV:

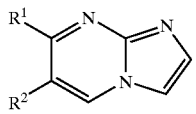

(XV)

wherein R¹ and R² are as defined above; typically by treatment with bromine in methanol, in the presence of sodium acetate and optionally also potassium bromide.

The intermediates of formula XV may be prepared by reacting chloroacetaldehyde or bromoacetaldehyde, or an acetal derivative thereof, e.g. the dimethyl or diethyl acetal thereof, with the requisite compound of formula XVI:

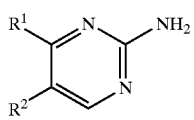

(XVI)

wherein R¹ and R² are as defined above.

Where chloroacetaldehyde or bromoacetaldehyde is utilised as one of the reactants, the reaction is conveniently carried out by heating the reactants under basic conditions in a suitable solvent, e.g. sodium methoxide or sodium hydrogencarbonate in a lower alkanol such as methanol and/or ethanol at the reflux temperature of the solvent. Where an acetal derivative of chloroacetaldehyde or bromoacetaldehyde, e.g. the dimethyl or diethyl acetal thereof, is utilised as one of the reactants, the reaction is conveniently effected by heating the reactants under acidic conditions in a suitable solvent, e.g. aqueous hydrobromic acid in a lower alkanol such as methanol or ethanol, typically at the reflux temperature of the solvent.

In a still further procedure, the compounds according to the present invention may be prepared by a process which comprises reacting a compound of formula XVI as defined above with a compound of formula XVII:

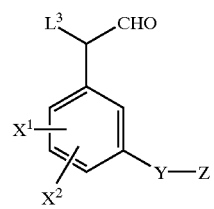

(XVII)

wherein X¹, X², Y and Z are as defined above, and L³ represents a suitable leaving group; under conditions analogous to those described above for the reaction between chloroacetaldehyde or bromoacetaldehyde, or an acetal derivative thereof, and compound XVI.

The leaving group L³ is suitably a halogen atom, e.g. bromo.

The intermediates of formula XV may also be prepared by reacting a compound of formula XVIII or XIX with the compound of formula XX, or with an acid addition salt of the latter compound, e.g. the hemisulfate salt:

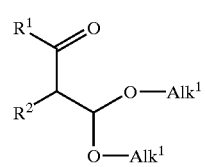

(XVIII)

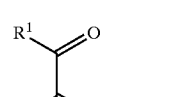

(XIX)

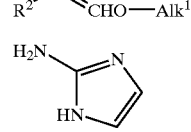

(XX)

wherein R¹ and R² are as defined above, and Alk¹ represents C₁₋₆ alkyl.

Typical values of Alk¹ include methyl and ethyl.

The reaction is conveniently effected by heating the reactants under basic conditions in a suitable solvent, e.g. a lower alkoxide such as sodium methoxide or ethoxide in a lower alkanol such as methanol or ethanol, typically at the reflux temperature of the solvent.

In a yet further procedure, the compounds according to the present invention wherein R¹ represents an aryl or heteroaryl moiety may be prepared by a process which comprises reacting a compound of formula XXI with a compound of formula XXII:

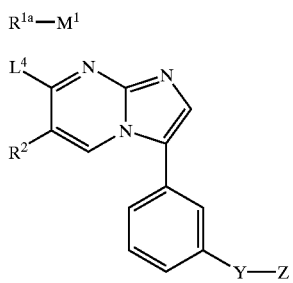

(XXI) R$^{1a}$—M$^1$ (XXII)

wherein Y, Z, R$^2$ and M$^1$ are as defined above, R$^{1a}$ represents an aryl or heteroaryl moiety, and L$^4$ represents a suitable leaving group; in the presence of a transition metal catalyst.

The leaving group L$^4$ is typically a halogen atom, e.g. chloro.

The transition metal catalyst of use in the reaction between compounds XXI and XXII is suitably tetrakis(triphenylphosphine)palladium(0), in which case the reaction is conveniently effected at an elevated temperature in a solvent such as N,N-dimethylacetamide, typically in the presence of potassium phosphate or in the presence of lithium chloride and copper(I) iodide. Alternatively, the transition metal catalyst may suitably be tris(dibenzylideneacetone)dipalladium(0), in which case the reaction is conveniently effected at an elevated temperature in a solvent such as 1,4-dioxane, typically in the presence of tri-tert-butylphosphine and cesium carbonate.

Where L$^4$ in the compounds of formula XXII above represents a halogen atom, these compounds correspond to compounds of formula I as defined above wherein R$^1$ represents halogen, and they may therefore be prepared by any of the methods described above for the preparation of the compounds according to the invention.

The compounds according to the invention in which Y represents a chemical bond and Z represents pyrrol-1-yl may be prepared by reacting a compound of formula XII as defined above with 2,5-dimethoxytetrahydrofuran. The reaction is conveniently accomplished at an elevated temperature in a solvent such as acetic acid.

The intermediates of formula VII above wherein L$^1$ represents chloro may, for example, be prepared by reacting a compound of formula XV as defined above with a compound of formula XXIII:

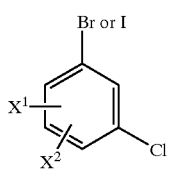

(XXIII)

wherein X$^1$ and X$^2$ are as defined above; in the presence of a transition metal catalyst.

The transition metal catalyst of use in the reaction between compounds XV and XXIII is suitably palladium acetate, in which case the reaction is conveniently effected at an elevated temperature in a solvent such as 1,4-dioxane, advantageously in the presence of cesium carbonate and triphenylphosphine.

The cyclic boroxine of formula VIIIA above may be prepared by treating a compound of formula X as defined above and a tri(C$_{1-6}$)alkyl borate, e.g. triisopropyl borate, with a C$_{1-6}$ alkyllithium, e.g. n-butyllithium.

The compound of formula XX above is commercially available from the Sigma-Aldrich Company Ltd., Dorset, United Kingdom.

Where they are not commercially available, the starting materials of formula VI, VIII, X, XIV, XVI, XVII, XVIII, XIX, XXI and XXIII may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I wherein R$^1$ represents —C(O—Alk$^1$)$_2$R$^a$ initially obtained, wherein Alk$^1$ is as defined above, may be converted into the corresponding compound of formula I wherein R$^1$ represents —COR$^a$ by hydrolysis with a mineral acid, typically aqueous hydrochloric acid. A compound wherein R$^1$ represents formyl may be reduced with sodium triacetoxyborohydride to the corresponding compound wherein R$^1$ represents hydroxymethyl. A compound of formula I wherein R$^1$ represents hydroxymethyl may be oxidised to the corresponding compound of formula I wherein R$^1$ represents formyl by treatment with manganese dioxide. The formyl derivative thereby obtained may be condensed with a hydroxylamine derivative of formula H$_2$N—OR$^b$ to provide a compound of formula I wherein R$^1$ represents —CH=NOR$^b$. Furthermore, a compound of formula I wherein R$^1$ represents —CH=NOH may be treated with triethylamine in the presence of 1,1'-carbonyldiimidazole to afford a corresponding compound of formula I wherein R$^1$ represents cyano. Alternatively, the compound of formula I wherein R$^1$ represents formyl may be reacted with a Grignard reagent of formula R$^a$MgBr to afford a compound of formula I wherein R$^1$ represents —CH(OH)R$^a$, and this compound may in turn be oxidised using manganese dioxide to the corresponding compound of formula I wherein R$^1$ represents —COR$^a$. The latter compound may then be condensed with a hydroxylamine derivative of formula H$_2$N—OR$^b$ to provide a compound of formula I wherein R$^1$ represents —CR$^a$=NOR$^b$. A compound of formula I wherein R$^1$ represents —CH(OH)R$^a$ may be converted into the corresponding compound of formula I wherein R$^1$ represents —CHFR$^a$ by treatment with (diethylamino)sulfur trifluoride (DAST). Similarly, a compound of formula I wherein R$^1$ represents —COR$^a$ may be converted into the corresponding compound of formula I wherein R$^1$ represents —CF$_2$R$^a$ by treatment with DAST. A compound of formula I wherein R$^1$ represents amino may be converted into the corresponding compound of formula I wherein R$^1$ represents chloro by diazotisation, using sodium nitrite, followed by treatment with copper(I) chloride. A compound of formula I wherein R$^1$ represents —COCH$_3$ may be treated with thioacetamide in the presence of pyridinium tribromide to furnish the corresponding compound of formula I wherein R$^1$ represents 2-methylthiazol-5-yl. Moreover, a compound of formula I wherein R$^1$ is formyl may be treated with (p-tolylsulfonyl)methyl isocyanide (TosMIC) in the presence of potassium carbonate to afford the corresponding compound of formula I wherein R$^1$ represents oxazol-5-yl. A compound of formula I wherein R$^1$ represents hydroxymethyl may be treated with carbon tetrabromide and triphenylphosphine to afford the corresponding compound of formula I wherein R$^1$ represents bromomethyl, which may then be reacted (typically in situ) with the sodium salt of imidazole or 1H-[1,2,4]triazole to provide a compound of formula I wherein R$^1$ represents imidazol-1-ylmethyl or [1,2,4]triazol-1-ylmethyl respectively; or with the sodium salt of 1H-[1,2,3]triazole to provide a mixture of compounds of formula I wherein $R^1$ represents [1,2,3]triazol-1-ylmethyl and [1,2,3]triazol-2-ylmethyl; or with morpholine to provide a compound of formula I wherein $R^1$ represents morpholin-4-ylmethyl. A compound of formula I wherein Z is substituted with methoxy may be converted to the corresponding compound wherein Z is substituted with hydroxy by treatment with boron tribromide.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 and/or α3 and/or α5 subunit stably expressed in Ltk$^-$ cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 and/or α5 subunit of the human $GABA_A$ receptor of 100 nM or less.

EXAMPLE 1

2'-Fluoro-5'-(imidazo[1,2-α]pyrimidin-3-yl) biphenyl-2-carbonitrile

A mixture of 2-bromo-1-fluoro-4-nitrobenzene (prepared according to the procedure of Groweiss in *Org. Proc. Res. Dev.*, 2000, 4(1), 30–33) (66 g, 300 mmol), potassium acetate (58.9 g, 600 mmol), bis(pinacolato)diboron (83.8 g, 330 mmol) and dichloro[1,1'-bis(diphenylphosphino) ferrocene]palladium(II) dichloromethane adduct (7.35 g, 9 mmol) in 1,4-dioxane (900 ml containing 18 ml dimethylsulfoxide) was degassed with nitrogen for 1 h then heated at 90° C. for 14 h. The reaction was cooled to ambient temperature and then concentrated in vacuo. The residue was stirred with 2N sodium hydroxide (1 l) for 10 min then filtered. The filtrate was extracted with diethyl ether (2×750 ml) and the organics discarded. The aqueous component was cooled to 0° C. then treated with 36% hydrochloric acid (ca. 175 ml) added dropwise over 15 min until pH 5. The resulting precipitate was allowed to stand at 0° C. for 2 h then filtered and washed with ice-cold water. The sand-coloured solid was dried under vacuum (300 mmHg) over phosphorus pentoxide to afford 2-(2-fluoro-5-nitrophenyl)-4,4,5,5-tetramethyl-[1,3,2]dioxaborolane (76.1 g, 95%): $δ_H$ (400 MHz, CDCl$_3$) 1.38 (12H, s), 7.17 (1H, dd, J 9 and 9), 8.32 (1H, ddd, J 9, 5 and 3) 8.64 (1H, dd, J 5 and 3).

A mixture of 2-bromobenzonitrile (34.6 g, 190 mmol), 2-(2-fluoro-5-nitrophenyl)-4,4,5,5-tetramethyl-[1,3,2] dioxaborolane (76.1 g, 285 mmol) and potassium fluoride (36.4 g, 627 mmol) in tetrahydrofuran (600 ml) was degassed with nitrogen for 30 min then treated with tris (dibenzylideneacetone)dipalladium(0) (1.74 g, 1.9 mmol) followed by tri-tert-butylphosphine (38 ml of a 0.1M solution in 1,4-dioxane, 3.8 mmol) and then the reaction was stirred at ambient temperature for 30 min before heating at 50° C. for 1 h to complete the coupling. The slurry-like reaction mixture was then diluted with water (3 l) and stirred at ambient temperature for 90 min. The resulting solid was collected by filtration, washed with water then with isohexane and finally dried under vacuum over phosphorus pentoxide to afford 2'-fluoro-5'-nitrobiphenyl-2-carbonitrile as a beige solid (46 g, 100%): $\delta_H$ (360 MHz, CDCl$_3$) 7.37–7.42 (1H, m), 7.53 (1H, d, J 8), 7.59 (1H, td, J 8 and 1), 7.75 (1H, td, J 8 and 1), 7.83 (1H, dd, J 8 and 1), 8.35–8.39 (2H, m).

A cooled (0° C.) suspension of 2'-fluoro-5'-nitrobiphenyl-2-carbonitrile (24.2 g, 100 mmol) in ethanol (150 ml) and tetrahydrofuran (150 ml) was treated with tin(II) chloride dihydrate (67.7 g, 300 mmol) and the mixture was stirred to ambient temperature over 12 h. The solvent was removed in vacuo and the residue treated with ice-cold 2N sodium hydroxide (750 ml). The resulting slurry was stirred for 60 min then extracted with dichloromethane (2×400 ml). The organics were combined, washed with water, brine, dried over anhydrous magnesium sulfate, filtered and concentrated to give a red solid. Crystallisation from toluene gave 5'-amino-2'-fluorobiphenyl-2-carbonitrile as a cream-coloured solid (16 g, 75%): $\delta_H$ (400 MHz, CDCl$_3$) 3.65 (2H, br), 6.67–6.73 (2H, m), 7.00 (1H, t, J 9), 7.44–7.49 (2H, m), 7.64 (1H, td, J 9 and 2), 7.75 (1H, dd, J 8 and 2); m/z (ES$^+$) 213 (M$^+$+H).

A solution of 5'-amino-2'-fluorobiphenyl-2-carbonitrile (7.85 g, 37 mmol) in 1,4-dioxane (25 ml) was treated with 48% hydrobromic acid (125 ml) and the resulting suspension stirred and cooled to 3° C. (internal temperature). A solution of sodium nitrite in water (5 ml) was then added dropwise over 20 min keeping the internal temperature <5° C. Stirring at <5° C. was continued for 2 h before pouring the reaction into a cooled (5° C.) solution of freshly purified copper(I) bromide (6.37 g, 44 mmol) in 48% hydrobromic acid (50 ml). The resulting purple reaction mixture was stirred at 5° C. for 10 min then warmed to 50° C. for 20 min. The reaction was diluted with ice-cold water (500 ml) and extracted with ethyl acetate (2×250 ml). The organics were combined, washed with 5% aqueous sodium sulfite, saturated aqueous ammonium chloride, dried over anhydrous magnesium sulfate, filtered and pre-adsorbed onto silica. Purification by chromatography on silica eluting with isohexane (containing 1% methanol) on a gradient of ethyl acetate (2–10%) afforded a colourless oil which crystallised on standing to give 5'-bromo-2'-fluorobiphenyl-2-carbonitrile as a white solid (6.5 g, 64%): $\delta_H$ (400 MHz, CDCl$_3$) 7.09–7.14 (1H, m), 7.45–7.57 (4H, m), 7.66 (1H, td, J 8 and 2), 7.77 (1H, dd, J 8 and 2).

A mixture of 5'-bromo-2'-fluorobiphenyl-2-carbonitrile (1.1 g, 4 mmol), potassium acetate (1.18 g, 12 mmol) and bis(pinacolato)diboron (1.17 g, 4.6 mmol) was dissolved in 1,4-dioxane containing 1% v/v dimethylsulfoxide (15 ml) and this solution was degassed with nitrogen for 5 min. Dichloro[1,1'-bis(diphenylphosphino)ferrocene]palladium (II) dichloromethane adduct (98 mg, 0.12 mmol) was then added and the mixture heated at 90° C. for 16 h. After cooling to ambient temperature the reaction was partitioned between ethyl acetate and water. The organic phase was washed with brine, dried over anhydrous magnesium sulfate, filtered and pre-adsorbed on to silica. Purification by chromatography on silica eluting with isohexane on a gradient of ethyl acetate (2–10%) gave a colourless oil that crystallised on standing to furnish 2'-fluoro-5'-(4,4,5,5-tetramethyl-[1,3,2]dioxaborolan-2-yl)biphenyl-2-carbonitrile as a white solid (1.3 g, 100%): $\delta_H$ (400 MHz, CDCl$_3$) 1.34 (12H, s), 7.21 (1H, dd, J 10 and 8), 7.45–7.52 (2H, m), 7.65 (1H, td, J 8 and 2), 7.74–7.78 (1H, m), 7.83 (1H, dd, J 8 and 2), 7.88 (1H, ddd, J 8, 5 and 2).

A solution of 2-aminopyrimidine (0.5 g, 5.26 mmol), bromoacetaldehyde diethyl acetal (2.07 g, 10.5 mmol) and 48% aqueous hydrobromic acid (0.5 ml) in ethanol (5 ml) was heated at reflux for 18 h. The reaction was cooled and pre-adsorbed directly onto silica gel. Purification by flash chromatography eluting with dichloromethane (containing 1% conc. ammonia) on a gradient of methanol (1–3%) gave a solid which was triturated with 5% diethyl ether in isohexane to afford imidazo[1,2-α]pyrimidine (0.51 g, 82%) as a tan solid: $\delta_H$ (400 MHz, CDCl$_3$) 6.92 (1H, dd, J 7 and 4), 7.59 (1H, d, J 1), 7.84 (1H, d, J 1), 8.49 (1H, dd, J 7 and 2), 8.58 (1H, dd, J 7 and 2).

Imidazo[1,2-α]pyrimidine (0.20 g, 1.68 mmol) and sodium acetate 207 mg, 2.52 mmol) were dissolved in methanol (2 ml) which had been saturated with potassium bromide and this mixture was cooled to −10° C. before dropwise addition of bromine (269 mg, 1.68 mmol) over 5 min. On complete addition the mixture was quenched by addition of 1M sodium sulfite solution (2 ml) and the solvent removed in vacuo. The residue was treated with water (15 ml) and saturated sodium hydrogencarbonate solution (15 ml) and extracted with ethyl acetate (2×50 ml). The organics were combined then washed with brine (40 ml), dried over anhydrous sodium sulfate and evaporated to give an off-white solid. This solid was purified by silica gel chromatography eluting with dichloromethane and 1% conc. ammonia on a gradient of methanol (1–2%) to give 3-bromoimidazo[1,2-α]pyrimidine (0.29 g, 87%) as a white solid: $\delta_H$ (400 MHz, CDCl$_3$) 7.02 (1H, dd, J 7 and 4), 7.83 (1H, s), 8.43 (1H, dd, J 7 and 2), 8.59 (1H, dd, J 7 and 2).

3-Bromoimidazo[1,2-α]pyrimidine (198 mg, 1.00 mmol) potassium phosphate (425 mg, 2.00 mmol) and 3'-(4,4,5,5-tetramethyl-[1,3,2]dioxaborolan-2-yl)biphenyl-2-carbonitrile (581 mg, 1.80 mmol) in N,N-dimethylacetamide (3 ml) was degassed with nitrogen for 15 min. Tetrakis (triphenylphosphine)palladium(0) (58 mg, 0.05 mmol) was added and the mixture heated at 80° C. for 18 h. The mixture was allowed to cool to ambient temperature, diluted with water (50 ml) and saturated sodium hydrogencarbonate solution (20 ml) then extracted with ethyl acetate (2×75 ml). The combined organic fractions were washed with brine (40 ml), dried over anhydrous sodium sulfate and evaporated to give a black oil. This oil was purified by silica gel chromatography eluting with dichloromethane (containing 1% conc. ammonia) on a gradient of methanol (1–3%). The solid obtained was triturated with diethyl ether to give 2'-fluoro-5'-(imidazo[1,2-α]pyrimidin-3-yl)biphenyl-2-carbonitrile as an off-white powder: $\delta_H$ (360 MHz, CDCl$_3$) 6.96 (1H, dd, J 7 and 4), 7.41 (1H, t, J 9), 7.55 (1H, td, J 8 and 1), 7.59–7.65 (3H, m), 7.71 (1H, td, J 8 and 1), 7.84 (1H, dd, J 8 and 1), 7.92 (1H, s), 8.61 (1H, dd, J 7 and 2), 8.86 (1H, d, J 7 and 2); m/z (ES$^+$) 315 (M$^+$+H).

EXAMPLE 2

2'-Fluoro-5'-(7-methylimidazo[1,2-α]pyrimidin-3-yl)biphenyl-2-carbonitrile

Sodium methoxide (1.62 g, 30 mmol) was added to a stirred solution of 2-aminoimidazole hemisulfate (2.64 g, 20 mmol) and 1,1-dimethoxy-3-butanone (2 ml) in ethanol (25 ml). The mixture was heated under reflux for 8 h, allowed to cool to room temperature then pre-adsorbed directly onto silica. Purification by silica gel chromatography eluting with dichloromethane and 1% conc. ammonia on a gradient of methanol (1–4%) gave a 95:5 mixture of 7-methylimidazo[1,2-α]pyrimidine and 5-methylimidazo[1,2-α]pyrimidine respectively (1.68 g, 64%) as a white crystalline solid: $\delta_H$ (400 MHz, CDCl$_3$, 7-methyl isomer) 2.64 (3H, s), 6.74 (1H, d, J 7), 7.45 (1H, d, J 1), 7.73 (1H, d, J 1), 8.29 (1H, d, J 7).

7-Methylimidazo[1,2-α]pyrimidine (100 mg, 0.75 mmol) was brominated as described in Example 1 to give 3-bromo-7-methylimidazo[1,2-α]pyrimidine (100 mg, 63%) as a white crystalline solid: δ$_H$ (400 MHz, CDCl$_3$) 2.67 (3H, s), 6.87 (1H, d, J 7), 7.71 (1H, s), 8.27 (1H, d, J 7).

3-Bromo-7-methylimidazo[1,2-α]pyrimidine was coupled with 2'-fluoro-5'-(4,4,5,5-tetramethyl-[1,3,2]dioxaborolan-2-yl)biphenyl-2-carbonitrile as described in Example 1 to give 2'-fluoro-5'-(7-methylimidazo[1,2-α]pyrimidin-3-yl)biphenyl-2-carbonitrile. Purification by high performance liquid chromatography afforded the trifluoroacetate salt as a white powder: δ$_H$ (400 MHz, DMSO) 2.60 (3H, s), 7.11 (1H, d, J 7), 7.59–7.70 (2H, m), 7.76 (1H, d, J 8), 7.84–7.89 (3H, m), 8.00–8.04 (2H, m), 9.00 (1H, d, J 7); m/z (ES$^+$) 329 (M$^+$+H).

EXAMPLE 3

5'-(7-Acetylimidazo[1,2-α]pyrimidin-3-yl)-2'-fluorobiphenyl-2-carbonitrile

Boron trifluoride etherate (17.03 g, 120.0 mmol) was added drop-wise over 15 min to a cooled (−40° C.) solution of triethyl orthoformate (14.82 g, 100.0 mmol) in dichloromethane (50 ml). Stirring was continued for 10 min then the solution was transferred to an ice-water bath and stirred at 0° C. for 20 min. The mixture was cooled to −78° C., and 3,3-dimethoxy-2-butanone (6.61 g, 50.0 mmol) added followed by dropwise addition of N,N-diisopropylethylamine (19.39 g, 150.0 mmol) over 15 min. Stirring was continued for 1 h then the solution was poured onto a vigorously stirred mixture of saturated sodium hydrogencarbonate solution (500 ml) and dichloromethane (200 ml). The organic phase was separated, washed with ice-cold 1M sulfuric acid solution (2×500 ml) and ice-cold water (2×500 ml), dried over anhydrous sodium sulfate solution and evaporated to give 1,1-diethoxy-4,4-dimethoxypentan-3-one (11.72 g, 100%) as an orange oil.

1,1-Diethoxy-4,4-dimethoxypentan-3-one was condensed with 2-aminoimidazole hemisulfate as described in Example 2 to give 7-(1,1-dimethoxyethyl)imidazo[1,2-α]pyrimidine (6.61 g, 64%) as a white solid: δ$_H$ (400 MHz, CDCl$_3$) 1.70 (3H, s), 3.28 (6H, s), 7.30 (1H, d, J 7), 7.55 (1H, d, J 1), 7.84 (1H, d, J 1), 8.43 (1H, d, J 7).

7-(1,1-Dimethoxyethyl)imidazo[1,2-α]pyrimidine (207 mg, 1.00 mmol) was brominated as described in Example 1 to give 3-bromo-7-(1,1-dimethoxyethyl)imidazo[1,2-α]pyrimidine (197 mg, 69%) as a white solid: δ$_H$ (360 MHz, CDCl$_3$) 1.70 (3H, s), 3.28 (6H, s), 7.43 (1H, d, J 7), 7.82 (1H, s), 8.39 (1H, d, J 7).

3-Bromo-7-(1,1-dimethoxyethyl)imidazo[1,2-α]pyrimidine (860 mg, 3 mmol) was coupled with 2'-fluoro-5'-(4,4,5,5-tetramethyl-[1,3,2]dioxaborolan-2-yl)biphenyl-2-carbonitrile (1.45 g, 4.5 mmol) as described in Example 1 to give crude 5'-[7-(1,1-dimethoxyethyl)imidazo[1,2-α]pyrimidin-3-yl]-2'-fluorobiphenyl-2-carbonitrile (1.21 g).

A suspension of crude 5'-[7-(1,1-dimethoxyethyl)imidazo[1,2-α]pyrimidin-3-yl]-2'-fluorobiphenyl-2-carbonitrile (1.21 g) in 2.5N hydrochloric acid (40 ml) was stirred at 50° C. for 15 h. After cooling to ambient temperature the mixture was made neutral with solid sodium hydrogencarbonate, added portionwise over 15 min. The aqueous was extracted with 2% methanol in dichloromethane (2×75 ml), the organics combined, dried over anhydrous magnesium sulfate, filtered and pre-adsorbed onto silica. Purification by chromatography on silica, eluting with dichloromethane (+0.5% triethylamine) on a gradient of methanol (1–5%) gave a solid. Trituration with diethyl ether afforded 5'-(7-acetylimidazo[1,2-α]pyrimidin-3-yl)-2'-fluorobiphenyl-2-carbonitrile (0.82 g, 77%) as a yellow solid: δ$_H$ (360 MHz, CDCl$_3$) 2.83 (3H, s), 7.44 (1H, t, J 9), 7.53–7.74 (6H, m), 7.87 (1H, dd, J 8 and 1), 8.12 (1H, s), 8.92 (1H, d, J 7); m/z (ES$^+$) 357 (M$^+$+H).

EXAMPLE 4

2'-Fluoro-5'-(7-isopropylimidazo[1,2-α]pyrimidin-3-yl)biphenyl-2-carbonitrile 3-Methylbutan-2-one was converted to 1,1-diethoxy-4-methylpentan-3-one as described in Example 3 and condensed with 2-aminoimidazole hemisulfate as described in Example 2 to give 7-isopropylimidazo[1,2-α]pyrimidine as an orange solid: δ$_H$ (400 MHz, CDCl$_3$) 1.36 (6H, d, J 7), 3.12 (1H, septet, J 7), 6.78 (1H, d, J 7), 7.45 (1H, d, J 1), 7.72 (1H, d, J 1), 8.33 (1H, d, J 7).

7-Isopropylimidazo[1,2-α]pyrimidine was brominated as described in Example 1 to give 3-bromo-7-isopropylimidazo[1,2-α]pyrimidine as a cream-coloured solid: δ$_H$ (400 MHz, CDCl$_3$) 1.37 (6H, d, J 7), 3.16 (1H, septet, J 7), 6.91 (1H, d, J 7), 7.71 (1H, s), 8.30 (1H, d, J 7).

3-Bromo-7-isopropylimidazo[1,2-α]pyrimidine was coupled with 2'-fluoro-5'-(4,4,5,5-tetramethyl-[1,3,2]dioxaborolan-2-yl)biphenyl-2-carbonitrile as described in Example 1 to give 2'-fluoro-5'-(7-isopropylimidazo[1,2-α]pyrimidin-3-yl)biphenyl-2-carbonitrile as an off-white powder: δ$_H$ (360 MHz, CDCl$_3$) 1.38 (6H, d, J 7), 3.15 (1H, septet, J 7), 6.87 (1H, d, J 7), 7.39 (1H, t, J 9), 7.52–7.63 (4H, m), 7.71 (1H, dd, J 8 and 1), 7.83 (2H, dd, J 8 and 7), 8.74 (1H, d, J 7); m/z (ES$^+$) 357 (M$^+$+H).

EXAMPLE 5

2'-Fluoro-5'-(7-tert-butylimidazo[1,2-α]pyrimidin-3-yl)biphenyl-2-carbonitrile 3,3-Dimethylbutan-2-one was converted to 1,1-diethoxy-4,4-dimethylpentan-3-one as described in Example 3 and condensed with 2-aminoimidazole hemisulfate as described in Example 2 to give 7-tert-butylimidazo[1,2-α]pyrimidine as a pale-orange solid: δ$_H$ (400 MHz, CDCl$_3$) 1.42 (9H, s), 6.96 (1H, d, J 7), 7.45 (1H, d, J 1), 7.72 (1H, d, J 1), 8.33 (1H, d, J 7).

7-tert-Butylimidazo[1,2-α]pyrimidine was brominated as described in Example 1 to give 3-bromo-7-tert-butylimidazo[1,2-α]pyrimidine as an off-white solid: δ$_H$ (400 MHz, CDCl$_3$) 1.43 (9H, s), 7.09 (1H, d, J 7), 7.71 (1H, s), 8.30 (1H, d, J 7).

3-Bromo-7-tert-butylimidazo[1,2-α]pyrimidine was coupled with 2'-fluoro-5'-(4,4,5,5-tetramethyl-[1,3,2]dioxaborolan-2-yl)biphenyl-2-carbonitrile as described in Example 1 to give 2'-fluoro-5'-(7-tert-butylimidazo[1,2-α]pyrimidin-3-yl)biphenyl-2-carbonitrile as an off-white powder: δ$_H$ (360 MHz, CDCl$_3$) 1.43 (9H, s), 7.05 (1H, d, J 7), 7.37–7.73 (6H, m), 7.81 (1H, s), 7.85 (1H, dd, J 8 and 1), 8.75 (1H, d, J 7); m/z (ES$^+$) 371 (M$^+$+H).

EXAMPLE 6

2'-Fluoro-5'-[7-(1-hydroxy-1-methylethyl)imidazo[1,2-α]pyrimidin-3-yl]biphenyl-2-carbonitrile A solution of 3-hydroxy-3-methyl-2-butanone (10.75 ml, 100 mmol) and triethylamine (21 ml, 150 mmol) in dichloromethane (125 ml) was treated with acetic anhydride (11.8 ml, 125 mmol) then with 4-dimethylaminopyridine (610 mg, 5 mmol) and the reaction was stirred at ambient temperature for 14 h. Methanol (10 ml) was added and stirring continued for 30 min before concentrating the reaction in vacuo. The residue was dissolved in ether (300 ml) and washed with 0.5N hydrochloric acid (2×300 ml), water, saturated aqueous sodium hydrogencarbonate, dried over anhydrous magnesium sulfate, filtered and evaporated to dryness to afford acetic acid 1,1-dimethyl-2-oxopropyl ester as a yellow liquid (13.5 g, 94%): $\delta_H$ (400 MHz, CDCl$_3$) 1.46 (6H, s), 2.09 (3H, s), 2.12 (3H, s).

Acetic acid 1,1-dimethyl-2-oxopropyl ester was converted to acetic acid 4,4-diethoxy-1,1-dimethyl-2-oxobutyl ester as described in Example 3 and condensed with 2-aminoimidazole hemisulfate as in Example 2 to give 2-(imidazo[1,2-α]pyrimidin-7-yl)propan-2-ol as an orange solid: $\delta_H$ (400 MHz, CDCl$_3$) 1.60 (6H, s), 5.31 (1H, s), 7.10 (1H, d, J 7), 7.54 (1H, d, J 1), 7.72 (1H, d, J 1), 8.49 (1H, d, J 7).

2-(Imidazo[1,2-α]pyrimidin-7-yl)propan-2-ol was brominated as described in Example 1 to give 2-(3-bromoimidazo[1,2-α]pyrimidin-7-yl)propan-2-ol as an off-white solid: $\delta_H$ (400 MHz, CDCl$_3$) 1.62 (6H, s), 4.20 (1H, s), 7.17 (1H, d, J 7), 7.76 (1H, s), 8.40 (1H, d, J 7).

2-(3-Bromoimidazo[1,2-α]pyrimidin-7-yl)propan-2-ol was coupled with 2'-fluoro-5'-(4,4,5,5-tetramethyl-[1,3,2]dioxaborolan-2-yl)biphenyl-2-carbonitrile as described in Example 1 to give 2'-fluoro-5'-[7-(1-hydroxy-1-methylethyl)imidazo[1,2-α]pyrimidin-3-yl]biphenyl-2-carbonitrile as an off-white solid: $\delta_H$ (360 MHz, CDCl$_3$) 1.62 (6H, s), 4.50 (1H, s), 7.08 (1H, d, J 7), 7.41 (1H, t, J 9), 7.53–7.64 (4H, m), 7.72 (1H, dd, J 8 and 1), 7.84 (1H, s), 7.86 (1H, s), 8.86 (1H, d, J 7); m/z (ES$^+$) 373 (M$^+$+H).

EXAMPLE 7

2'-Fluoro-5'-[7-(1-fluoro-1-methylethyl)imidazo[1,2-α]pyrimidin-3-yl]biphenyl-2-carbonitrile To a cooled (−78° C.) suspension of 2-(imidazo[1,2-α]pyrimidin-7-yl)propan-2-ol (1.02 mg, 5.8 mmol) in dichloromethane (25 ml) was added (diethylamino)sulfur trifluoride (1.22 mg, 7.5 mmol) dropwise over 5 min. The mixture was stirred at −78° C. for 40 min then quenched with methanol (1 ml). The mixture was warmed to ambient temperature, made basic with saturated sodium hydrogencarbonate solution (25 ml) and extracted with dichloromethane (2×25 ml). The combined organics were washed with brine (50 ml), dried over anhydrous sodium sulfate and evaporated to dryness. Purification of this material by chromatography on silica eluting with dichloromethane (containing 0.5% conc. ammonia) on a gradient of methanol (1–3%) gave 7-(1-fluoro-1-methylethyl)imidazo[1,2-α]pyrimidine (180 mg, 17%) as a yellow solid: $\delta_H$ (360 MHz, CDCl$_3$) 1.78 (6H, d, J 22), 7.21 (1H, dd, J 7 and 1), 7.54 (1H, d, J 1), 7.79 (1H, d, J 1), 8.45 (1H, d, J 7).

7-(1-Fluoro-1-methylethyl)imidazo[1,2-α]pyrimidine was brominated as described in Example 1 to give 3-bromo-7-(1-fluoro-1-methylethyl)imidazo[1,2-α]pyrimidine as an off-white solid: m/z (ES$^+$) 258/260 (M$^+$+H).

3-Bromo-7-(1-fluoro-1-methylethyl)imidazo[1,2-α]pyrimidine was coupled with 2'-fluoro-5'-(4,4,5,5-tetramethyl-[1,3,2]dioxaborolan-2-yl)biphenyl-2-carbonitrile in the same way as described for Example 1 to give 2'-fluoro-5'-[7-(1-fluoro-1-methylethyl)imidazo[1,2-α]pyrimidin-3-yl]biphenyl-2-carbonitrile as an off-white solid: $\delta_H$ (360 MHz, DMSO) 1.76 (6H, d, J 22), 7.27 (1H, dd, J 6 and 1), 7.64–7.72 (2H, m), 7.80 (1H, s), 7.89–7.92 (3H, m), 8.04 (1H, s), 8.06 (1H, s), 9.15 (1H, d, J 7); m/z (ES$^+$) 375 (M$^+$+H).

EXAMPLE 8

2'-Fluoro-5'-(7-hydroxymethylimidazo[1,2-α]pyrimidin-3-yl)biphenyl-2-carbonitrile Pyruvic aldehyde dimethyl acetal (8.43 g, 71.4 mmol) and N,N-dimethylformamide dimethyl acetal (8.51 g, 71.4 mmol) were heated at 100° C. for 18 h. The mixture was concentrated to give a brown oil and was then added dropwise over 10 min to a warm (60° C.) suspension of 2-aminoimidazole hemisulfate (9.43 g, 71.4 mmol) in water (50 ml). The mixture was heated at 50° C. for 36 h, cooled to ambient temperature and then pre-adsorbed directly onto silica. Purification by chromatography on silica gel eluting with dichloromethane (containing 1% conc. ammonia) on a gradient of methanol (1–2%) gave a 3:1 mixture of 7-dimethoxymethylimidazo[1,2-α]pyrimidine and 5-dimethoxymethylimidazo[1,2-α]pyrimidine respectively. Crystallisation from toluene gave 7-dimethoxymethylimidazo[1,2-α]pyrimidine (2.20 g, 16%) as a brown crystalline solid: $\delta_H$ (400 MHz, CDCl$_3$) 3.50 (6H, s), 5.26 (1H, s), 7.15 (1H, d, J 7), 7.56 (1H, d, J 1), 7.84 (1H, d, J 1), 8.47 (1H, d, J 7).

7-Dimethoxymethylimidazo[1,2-α]pyrimidine (1.00 g, 5.18 mmol) was dissolved in 3N hydrochloric acid and heated at 48° C. for 14 h. The solution was layered with ethyl acetate (30 ml) and solid sodium hydrogencarbonate (1.06 g, 12.6 mmol) was added in portions over 5 min. The mixture was diluted with water (6 ml) and extracted with dichloromethane (5×50 ml). The combined organics were dried over anhydrous sodium sulfate, filtered and evaporated to give imidazo[1,2-α]pyrimidine-7-carbaldehyde (749 mg, 99%) as a yellow solid: $\delta_H$ (360 MHz, CDCl$_3$) 7.53 (1H, d, J 7), 7.77 (1H, d, J 1), 8.10 (1H, d, J 1), 8.60 (1H, d, J 7), 10.05 (1H, s).

Sodium triacetoxyborohydride (21.5 g, 102 mmol) was added portionwise over 20 min to a stirred solution of imidazo[1,2-α]pyrimidine-7-carbaldehyde (5.00 g, 34.0 mmol) in methanol (100 ml) and the solution left to stir at ambient temperature for 18 h. The solvent was evaporated, the residue redissolved in methanol (150 ml) and pre-adsorbed onto silica. Purification by chromatography on silica gel eluting with dichloromethane (containing 1% conc. ammonia) on a gradient of methanol (1–10%) gave imidazo[1,2-α]pyrimidin-7-ylmethanol (5.06 g, 99%) as a white solid: $\delta_H$ (360 MHz, DMSO) 4.57 (2H, d, J 6), 5.62 (1H, t, J 6), 7.13 (1H, d, J 7), 7.64 (1H, d, J 1), 7.86 (1H, d, J 1), 8.94 (1H, d, J 7).

Imidazo[1,2-α]pyrimidin-7-ylmethanol (1.70 g, 11.4 mmol) was brominated as described in Example 1 to give 3-bromoimidazo[1,2-α]pyrimidin-7-ylmethanol (912 mg, 35%) as a white solid: $\delta_H$ (400 MHz, CDCl$_3$) 2.95 (1H, br), 4.88 (2H, s), 7.03 (1H, d, J 7), 7.73 (1H, s), 8.37 (1H, d, J 7).

3-Bromoimidazo[1,2-α]pyrimidin-7-ylmethanol (912 mg, 4.00 mmol) was dissolved in dichloromethane (10 ml) and treated with imidazole (0.70 g, 10.3 mmol) and tert-butyldimethylsilyl chloride (0.77 g, 5.1 mmol) and the mixture left to stir at ambient temperature for 1 h. The reaction was diluted with dichloromethane (75 ml) and washed with 0.01N hydrochloric acid (2×50 ml). The organic phase was washed with saturated sodium hydrogencarbonate solution (50 ml), water (50 ml) and brine (50 ml), dried over anhydrous magnesium sulfate, filtered and evaporated to give crude 3-bromo-7-(tert-butyldimethylsilanyloxymethyl)imidazo[1,2-α]pyrimidine (1.37 g, 100%) as a yellow solid.

3-Bromo-7-(tert-butyldimethylsilanyloxymethyl)imidazo [1,2-α]pyrimidine was coupled with 2'-fluoro-5'-(4,4,5,5-tetramethyl-[1,3,2]dioxaborolan-2-yl)biphenyl-2-carbonitrile as described in Example 1 to give 5'-[7-(tert-butyldimethylsilanyloxymethyl)imidazo[1,2-α]pyrimidin-3-yl]-2-fluorobiphenyl-2-carbonitrile. This solid was suspended in methanol (30 ml) and treated with conc. hydrochloric acid (5 ml) and left to stir at ambient temperature for 5 min. The solution was loaded onto a cartridge of strong cation-exchange resin, eluting with methanol then with 10% conc. ammonia in methanol. The basic fractions were concentrated in vacuo and the residue purified further by chromatography on silica gel. Elution with dichloromethane (containing 1% conc. ammonia) on a gradient of methanol (2–5%) afforded 2'-fluoro-5'-(7-hydroxymethylimidazo[1,2-α]pyrimidin-3-yl)-biphenyl-2-carbonitrile as a pale yellow solid: Found C, 65.74; H, 4.07; N, 15.07. $C_{20}H_{13}FN_4O.1.2(H_2O)$ requires C, 65.64; H, 4.24; N, 15.31; $\delta_H$ (400 MHz, DMSO) 4.61 (2H, d, J 6), 5.70 (1H, t, J 6), 7.20 (1H, d, J 7), 7.60 (1H, t, J 10), 7.68 (1H, ddd, J 8, 8 and 1), 7.76–7.79 (1H, m), 7.84–7.89 (3H, m), 7.96 (1H, s), 8.04 (1H, dd, J 8 and 1), 9.08 (1H, d, J 7); m/z (ES$^+$) 345 (M$^+$+H).

EXAMPLE 9

2'-Fluoro-5'-[7-(1-hydroxyethyl)imidazo[1,2-α] pyrimidin-3-yl]biphenyl-2-carbonitrile Acetic acid 1-methyl-2-oxopropyl ester was converted to acetic acid 4,4-diethoxy-1-methyl-2-oxobutyl ester as described in Example 3 and condensed with 2-aminoimidazole hemisulfate as described in Example 2. Flash column chromatography on silica gel, eluting with dichloromethane with 1% conc. ammonia on a gradient of methanol (1–8%), furnished (in order of elution) acetic acid 1-(imidazo[1,2-α]pyrimidin-7-yl)ethyl ester as a yellow solid (1.38 g): $\delta_H$ (360 MHz, CDCl$_3$) 1.64 (3H, d, J 7), 2.16 (3H, s), 5.90 (1H, q, J 7), 6.95 (1H, d, J 7), 7.57 (1H, d, J 1), 7.76 (1H, d, J 1), 8.51 (1H, d, J 7); followed by 1-(imidazo[1,2-α]pyrimidin-7-yl)ethanol (3.96 g) as an off-white solid: $\delta_H$ (360 MHz, CDCl$_3$) 1.52 (3H, d, J 7), 3.47 (1H, s), 7.11 (1H, d, J 7), 7.52 (1H, d, J 1), 7.63 (1H, d, J 1), 8.48 (1H, d, J 7).

1-(Imidazo[1,2-α]pyrimidin-7-yl)ethanol was converted to 7-[1-(tert-butyldimethylsilanyloxy)ethyl]imidazo[1,2-α] pyrimidine as described in Example 8. Bromination as described in Example 1 gave 3-bromo-7-[1-(tert-butyldimethylsilanyloxy)ethyl]imidazo[1,2-α]pyrimidine. This was coupled with 2'-fluoro-5'-(4,4,5,5-tetramethyl-[1,3,2]dioxaborolan-2-yl)biphenyl-2-carbonitrile as described in Example 1 to furnish 5'-{7-[1-(tert-butyldimethylsilanyloxy)ethyl]imidazol[1,2-α]pyrimidin-3-yl}-2'-fluorobiphenyl-2-carbonitrile. This was deprotected as described in Example 8 to afford 2'-fluoro-5'-[7-(1-hydroxyethyl)imidazo[1,2-α]pyrimidin-3-yl]biphenyl-2-carbonitrile as an off-white solid: $\delta_H$ (360 MHz, CDCl$_3$) 1.57 (3H, d, J 7), 1.66 (1H, s), 4.97 (1H, q, J 7), 6.98 (1H, d, J 7), 7.41 (1H, t, J 9), 7.53–7.64 (4H, m), 7.69–7.74 (1H, m), 7.84–7.86 (2H, m), 8.83 (1H, d, J 7); m/z (ES$^+$) 359 (M$^+$+H).

EXAMPLE 10

2'-Fluoro-5'-[7-(1-fluoroethyl)imidazo[1,2-α] pyrimidin-3-yl]biphenyl-2-carbonitrile 2'-Fluoro-5'-[7-(1-hydroxyethyl)imidazo[1,2-α] pyrimidin-3-yl]biphenyl-2-carbonitrile was converted to 2'-fluoro-5'-[7-(1-fluoroethyl)imidazo[1,2-α]pyrimidin-3-yl]biphenyl-2-carbonitrile using (diethylamino)sulfur trifluoride as described in Example 7 to give a pale yellow solid: $\delta_H$ (360 MHz, CDCl$_3$) 1.71 (3H, dd, J 25 and 7), 5.83 (1H, dq, J 48 and 7), 7.24 (1H, d, J 7), 7.64 (1H, s), 7.70 (1H, d, J 1), 7.80 (1H, s), 7.90 (2H, dd, J 7 and 2), 7.93 (1H, s), 8.06 (1H, dd, J 7 and 1), 8.07 (1H, s), 9.17 (1H, d, J 7); m/z (ES$^+$) 361 (M$^+$+H).

EXAMPLE 11

2'-Fluoro-5'-[7-(2-methylthiazol-5-yl)imidazo[1,2-α] pyrimidin-3-yl]biphenyl-2-carbonitrile 5'-(7-Acetylimidazo[1,2-α]pyrimidin-3-yl)-2'-fluorobiphenyl-2-carbonitrile (80 mg, 0.22 mmol) and pyridinium tribromide (110 mg, 0.34 mmol) in chloroform (5 ml) was stirred at 50° C. for 3 h. Thioacetamide (33 mg, 0.44 mmol) was then added and the reaction stirred at 50° C. for 16 h. The resulting mixture was partitioned between dichloromethane and saturated aqueous sodium hydrogencarbonate solution. The organic extracts were washed with brine, dried over anhydrous magnesium sulfate, filtered and evaporated to dryness. The residue was purified by preparative thin-layer chromatography eluting with dichloromethane containing 5% methanol and 1% conc. ammonia to give a foam. Trituration with diethyl ether afforded 2'-fluoro-5'-[7-(2-methylthiazol-5-yl)imidazo[1,2-α]pyrimidin-3-yl] biphenyl-2-carbonitrile as a yellow solid (10 mg, 11%): $\delta_H$ (400 MHz, DMSO) 2.75 (3H, s), 7.56–7.68 (5H, m), 7.81–7.92 (3H, m), 7.98–8.05 (2H, m), 8.40 (1H, s), 9.12 (1H, s); m/z (ES$^+$) 412 (M$^+$+H).

EXAMPLE 12

2'-Fluoro-5'-(7-trifluoromethylimidazo[1,2-α] pyrimidin-3-yl)biphenyl-2-carbonitrile A mixture of 2-amino-4-(trifluoromethyl)pyrimidine (prepared according to Zanatta et al. in *J. Heterocyclic Chem.*, 1997, 34(2), 509–513) (500 mg, 3.1 mmol) and bromoacetaldehyde diethyl acetal (1.38 ml, 9.2 mmol) in ethanol (10 ml) was treated with hydrobromic acid (0.5 ml of a 48% aqueous solution) and then heated at 70° C. for 12 h. The reaction was cooled to ambient temperature then pre-adsorbed onto silica. Purification by chromatography on silica eluting with dichloromethane (containing 1% conc. ammonia) on a gradient of methanol (1–5%) afforded 7-trifluoromethylimidazo[1,2-α]pyrimidine (500 mg, 87%) as a cream-coloured solid: $\delta_H$ (400 MHz, CDCl$_3$) 7.22 (1H, d, J 7), 7.74 (1H, d, J 1), 8.03 (1H, d, J 1), 8.67 (1H, d, J 7).

7-Trifluoromethylimidazo[1,2-α]pyrimidine (0.20 g, 1.07 mmol) was brominated as described in Example 1 to give 3-bromo-7-trifluoromethylimidazo[1,2-α]pyrimidine (0.28 g, 98%) as a white solid: $\delta_H$ (400 MHz, CDCl$_3$) 7.35 (1H, d, J 7), 8.02 (1H, s), 8.62 (1H, d, J 7).

3-Bromo-7-trifluoromethylimidazo[1,2-α]pyrimidine was coupled with 2'-fluoro-5'-(4,4,5,5-tetramethyl-[1,3,2] dioxaborolan-2-yl)biphenyl-2-carbonitrile as described in Example 1 to give 2'-fluoro-5'-(7-trifluoromethylimidazo[1, 2-α]pyrimidin-3-yl)biphenyl-2-carbonitrile as a yellow powder: $\delta_H$ (400 MHz, CDCl$_3$) 7.29 (1H, d, J 7), 7.45 (1H, t, J 8), 7.56 (1H, ddd, J 8, 8 and 1), 7.62–7.68 (3H, m), 7.70 (1H, ddd, J 8, 8 and 1), 7.85 (1H, dd, J 8 and 1), 8.10 (1H, s), 9.06 (1H, d, J 7); m/z (ES$^+$) 383 (M$^+$+H).

EXAMPLE 13

5'-[7-(1,1-Difluoroethyl)imidazo[1,2-α]pyrimidin-3-yl]-2'-fluorobiphenyl-2-carbonitrile To a cooled (0° C.) solution of 2,2-difluoropropionic acid (prepared according to the procedure described in U.S. Pat.

No. 5,859,051) (2.20 g, 20.0 mmol) in dichloromethane (15 ml) was added oxalyl chloride (2.79, 22.0 mmol) dropwise over 10 min. The mixture was stirred at 0° C. for 10 min then allowed to warm to ambient temperature overnight. The mixture was cooled to −10° C. and added via a cannula to a cooled (−10° C.) solution of ethyl vinyl ether (1.59 g, 22.0 mmol) and pyridine (1.74 g, 22.0 mmol) in dichloromethane (50 ml). The mixture was stirred at −10° C. for 10 min then at ambient temperature for 5 h. The brown solution was diluted with dichloromethane (30 ml) and washed with ice-cold 1M sulphuric acid (2×50 ml) and ice-cold water (2×50 ml), dried over anhydrous sodium sulfate and evaporated to give crude 1-ethoxy-4,4-difluoropent-1-en-3-one (3.28 g, 100%) as an orange oil: $\delta_H$ (400 MHz, CDCl$_3$) 1.38 (3H, t, J 7), 1.71 (3H, t, J 19), 4.05 (2H, q, J 7), 5.94 (1H, dt, J 12 and 1), 7.81 (1H, d, J 12).

1-Ethoxy-4,4-difluoropent-1-en-3-one (3.28 g, 20.0 mmol) in ethanol (10 ml) was added dropwise over 10 min to a warm (60° C.) suspension of 2-aminoimidazole hemisulfate (3.96 g, 30.0 mmol) and sodium methoxide (2.16 g, 40.0 mmol) in ethanol (40 ml). The mixture was heated under reflux for 18 h, cooled to ambient temperature and then pre-adsorbed directly onto silica. Purification by chromatography on silica gel eluting with dichloromethane (containing 1% conc. ammonia) on a gradient of methanol (1–3%) gave 7-(1,1-difluoroethyl)imidazo[1,2-α]pyrimidine (1.80 g, 49%) as an off-white solid: $\delta_H$ (400 MHz, CDCl$_3$) 2.14 (3H, t, J 19), 7.26 (1H, d, J 7), 7.64 (1H, d, J 1), 7.92 (1H, d, J 1), 8.56 (1H, d, J 7).

7-(1,1-Difluoroethyl)imidazo[1,2-α]pyrimidine (0.30 g, 1.64 mmol) was brominated as described in Example 1 to give 3-bromo-7-(1,1-difluoroethyl)imidazo[1,2-α]pyrimidine (0.25 g, 59%) as a white solid: $\delta_H$ (400 MHz, CDCl$_3$) 2.14 (3H, t, J 19), 7.39 (1H, d, J 7), 7.90 (1H, s), 8.53 (1H, d, J 7).

3-Bromo-7-(1,1-difluoroethyl)imidazo[1,2-α]pyrimidine (130 mg, 0.50 mmol) was coupled with 2'-fluoro-5'-(4,4,5,5-tetramethyl-[1,3,2]dioxaborolan-2-yl)biphenyl-2-carbonitrile as described in Example 1 to give 5'-[7-(1,1-difluoroethyl)imidazo[1,2-α]pyrimidin-3-yl]-2'-fluorobiphenyl-2-carbonitrile (45 mg, 24%) as a white powder: $\delta_H$ (400 MHz, CDCl$_3$) 2.15 (3H, t, J 21), 7.34 (1H, d, J 7), 7.43 (1H, t, J 9), 7.53–7.74 (5H, m), 7.86 (1H, dd, J 8 and 1), 7.99 (1H, s), 8.95 (1H, d, J 7); m/z (ES$^+$) 379 (M$^+$+H).

EXAMPLE 14

5'-(7-Chloroimidazo[1,2-α]pyrimidin-3-yl)-2'-fluorobiphenyl-2-carbonitrile

A suspension of 2-aminoimidazole hemisulfate (15.2 g, 115 mmol) and sodium methoxide (7.14 g, 132 mmol) in ethanol (75 ml) was heated at reflux for 10 min before adding a solution of 3,3-diethoxypropionitrile (17.3 ml, 115 mmol) in ethanol (25 ml). The reaction was heated under reflux for a further 16 h then cooled to ambient temperature and evaporated to dryness. The residue was suspended in dichloromethane (300 ml), filtered and the filtrate was pre-adsorbed onto silica. Purification on silica, eluting with dichloromethane (+1% conc. ammonia) on a gradient of methanol (3–11%) gave imidazo[1,2-α]pyrimidin-7-ylamine as a pale orange solid (10.06 g, 65%): $\delta_H$ (400 MHz, DMSO) 6.24 (1H, d, J 7), 6.72 (2H, br), 7.11 (1H, d, J 1.5), 7.35 (1H, d, J 1.5), 8.36 (1H, d, J 7).

A cooled (0° C.) suspension of imidazo[1,2-α]pyrimidin-7-ylamine (10.06 g, 75 mmol) in dichloromethane (250 ml) and triethylamine (31.4 ml, 225 mmol) was treated with di-tert-butyl dicarbonate (40.9 g, 188 mmol) then with 4-dimethylaminopyridine (10.1 g, 83 mmol) added portionwise over 1 h. The reaction was stirred at ambient temperature for 14 h giving an orange solution. The mixture was concentrated in vacuo and the residue stirred with water (1000 ml) for 2 h. The resulting solid was collected by filtration, washed with water and dried to furnish imidazo[1,2-α]pyrimidine-7-iminodicarboxylic acid di-tert-butyl ester as a cream-coloured powder (22.5 g, 90%): $\delta_H$ (400 MHz, DMSO) 1.45 (18H, s), 7.17 (1H, d, J 7), 7.69 (1H, d, J 1.5), 7.92 (1H, d, J 1.5), 8.99 (1H, d, J 7).

Imidazo[1,2-α]pyrimidine-7-iminodicarboxylic acid di-tert-butyl ester (3.34 g, 10 mmol) was brominated as described in Example 1 to give 3-bromoimidazo[1,2-α]pyrimidine-7-iminodicarboxylic acid di-tert-butyl ester (3.3 g, 80%) as a pale pink solid: $\delta_H$ (400 MHz, CDCl$_3$) 1.54 (18H, s), 7.36 (1H, d, J 7), 7.69 (1H, s), 8.32 (1H, d, J 7).

3-Bromoimidazo[1,2-α]pyrimidine-7-iminodicarboxylic acid di-tert-butyl ester (2.07 g, 5 mmol) was coupled with 2'-fluoro-5'-(4,4,5,5-tetramethyl-[1,3,2]dioxaborolan-2-yl)biphenyl-2-carbonitrile (2.42 g, 7.5 mmol) as described in Example 1 to give 3-(2'-cyano-6-fluorobiphenyl-3-yl)imidazo[1,2-α]pyrimidine-7-iminodicarboxylic acid di-tert-butyl ester as a yellow solid: $\delta_H$ (360 MHz, CDCl$_3$) 1.54 (18H, s), 7.27 (1H, d, J 7), 7.40 (1H, t, J 9), 7.52–7.62 (4H, m), 7.71 (1H, ddd, J 8, 8 and 1), 7.80–7.85 (2H, m), 8.76 (1H, d, J 8).

Hydrogen chloride gas was bubbled through a solution of 3-(2'-cyano-6-fluorobiphenyl-3-yl)imidazo[1,2-α]pyrimidine-7-iminodicarboxylic acid di-tert-butyl ester (1.72 g, 3.25 mmol) in methanol (50 ml). After 5 min the reaction mixture was evaporated to dryness to afford 5'-(7-aminoimidazo[1,2-α]pyrimidin-3-yl)-2'-fluorobiphenyl-2-carbonitrile as a yellow foam. This foam was treated with a mixture of 36% hydrochloric acid (70 ml) and 1,4-dioxane (10 ml) and the resulting suspension was stirred and cooled to 0° C. (internal temperature) then treated with a solution of sodium nitrite (673 mg, 9.8 mmol) in water (2 ml). Stirring at 0° C. was continued for 14 h before adding a pre-cooled (0° C.) solution of freshly purified copper(I) chloride (800 mg, 8.1 mmol) in 36% hydrochloric acid (10 ml). The resulting dark mixture was stirred at 0° C. for 10 min then warmed to 50° C. for 20 min. The reaction was diluted with ice-cold water (500 ml) and extracted with dichloromethane (2×200 ml). The organics were combined, washed with 5% aqueous sodium sulfite and saturated aqueous ammonium chloride, dried over anhydrous magnesium sulfate, filtered and pre-adsorbed onto silica. Purification by chromatography on silica gel eluting with dichloromethane on a gradient of methanol (1–4%) gave 5'-(7-chloroimidazo[1,2-α]pyrimidin-3-yl)-2'-fluorobiphenyl-2-carbonitrile as a yellow powder (690 mg, 61%): $\delta_H$ (400 MHz, DMSO) 7.21 (1H, d, J 7), 7.60–7.70 (2H, m), 7.76–7.78 (1H, m), 7.86–7.91 (3H, m), 8.02–8.04 (2H, m), 9.10 (1H, d, J 7); m/z (ES$^+$) 349/351 (M$^+$+H).

EXAMPLE 15

5'-(7-Difluoromethylimidazo[1,2-α]pyrimidin-3-yl)-2'-fluorobiphenyl-2-carbonitrile Difluoroacetyl chloride (25 g, 0.22 mol) was converted to 4-ethoxy-1,1-difluorobut-3-en-2-one and condensed with 2-aminoimidazole hemisulfate using the procedure described Example 13 to give 7-difluoromethylimidazo[1,2-α]pyrimidine (16.9 g, 46%) as a pale brown crystalline solid: δ$_H$ (400 MHz, CDCl$_3$) 6.64 (1H, t, J 55), 7.26 (1H, d, J 7), 7.67 (1H, d, J 1), 7.95 (1H, d, J 1), 8.60 (1H, d, J 7).

7-Difluoromethylimidazo[1,2-α]pyrimidine (1.00 g, 5.91 mmol) was brominated as described in Example 1 to give 3-bromo-7-difluoromethylimidazo[1,2-α]pyrimidine (0.95 g, 65%) as a white solid: δ$_H$ (400 MHz, CDCl$_3$) 6.67 (1H, t, J 55), 7.34 (1H, d, J 7), 7.94 (1H, s), 8.57 (1H, d, J 7).

3-Bromo-7-difluoromethylimidazo[1,2-α]pyrimidine (248 mg, 1.00 mmol) was coupled with 2'-fluoro-5'-(4,4,5,5-tetramethyl-[1,3,2]dioxaborolan-2-yl)biphenyl-2-carbonitrile as described in Example 1 to give 5'-(7-difluoromethylimidazo[1,2-α]pyrimidin-3-yl)-2'-fluorobiphenyl-2-carbonitrile (180 mg, 49%) as a yellow powder: δ$_H$ (400 MHz, CDCl$_3$) 6.66 (1H, t, J 55), 7.29 (1H, d, J 7), 7.44 (1H, t, J 9), 7.54–7.74 (5H, m), 7.87 (1H, dd, J 8 and 1), 8.02 (1H, s), 9.00 (1H, d, J 7); m/z (ES$^+$) 365 (M$^+$+H).

EXAMPLE 16

2'-Fluoro-5'-(7-methoxymethylimidazo[1,2-α]pyrimidin-3-yl)biphenyl-2-carbonitrile Methoxyacetone (4.41 g, 50 mmol) was converted to 4,4-diethoxy-1-methoxybutan-2-one as described in Example 3 and condensed with 2-aminoimidazole hemisulfate as described in Example 2 to give 7-methoxymethylimidazo[1,2-α]pyrimidine (3.30 g, 40%) as a yellow solid: δ$_H$ (360 MHz, CDCl$_3$) 3.49 (3H, s), 4.63 (2H, s), 7.10 (1H, d, J 7), 7.51 (1H, d, J 1), 7.79 (1H, d, J 1), 8.42 (1H, d, J 7).

7-Methoxymethylimidazo[1,2-α]pyrimidine (0.50 g, 3.06 mmol) was brominated as described in Example 1 to give 3-bromo-7-methoxymethylimidazo[1,2-α]pyrimidine (450 mg, 61%) as an off-white solid: δ$_H$ (400 MHz, CDCl$_3$) 3.50 (3H, s), 4.66 (2H, s), 7.24 (1H, d, J 7), 7.77 (1H, s), 8.40 (1H, d, J 7).

3-Bromo-7-methoxymethylimidazo[1,2-α]pyrimidine (121 mg, 0.50 mmol) was coupled with 2'-fluoro-5'-(4,4,5,5-tetramethyl-[1,3,2]dioxaborolan-2-yl)biphenyl-2-carbonitrile as described in Example 1 to give 2'-fluoro-5'-(7-methoxymethylimidazo[1,2-α]pyrimidin-3-yl)biphenyl-2-carbonitrile (108 mg, 60%) as a white powder: δ$_H$ (400 MHz, CDCl$_3$) 3.50 (3H, s), 4.66 (2H, s), 7.19 (1H, d, J 7), 7.39–7.41 (1H, m), 7.53–7.64 (4H, m), 7.69–7.73 (1H, m), 7.85 (1H, dd, J 8 and 1), 7.87 (1H, s), 8.82 (1H, d, J 7); m/z (ES$^+$) 359 (M$^+$+H).

EXAMPLE 17

3-(2'-Cyano-6-fluorobiphenyl-3-yl)imidazo[1,2-α]pyrimidine-7-carbonitrile

7-Dimethoxymethylimidazo[1,2-α]pyrimidine was brominated as described in Example 1 to give 3-bromo-7-dimethoxymethylimidazo[1,2-α]pyrimidine as an off-white solid: δ$_H$ (400 MHz, CDCl$_3$) 3.50 (6H, s), 5.28 (1H, s), 7.28 (1H, d, J 7), 7.81 (1H, s), 8.43 (1H, d, J 7); m/z (ES$^+$) 272/274 (M$^+$+H).

A mixture of 3-bromo-7-dimethoxymethylimidazo[1,2-α]pyrimidine (1.36 g, 5 mmol), potassium phosphate (2.12 g, 10 mmol), 2'-fluoro-5'-(4,4,5,5-tetramethyl-[1,3,2]dioxaborolan-2-yl)biphenyl-2-carbonitrile (2.42 g, 7.5 mmol) and tetrakis(triphenylphosphine)palladium(0) (230 mg, 0.2 mmol) in N,N-dimethylformamide (15 ml) was heated at 80° C. for 14 h. The reaction was cooled and partitioned between ethyl acetate and water. The organics were washed with water, brine, dried over anhydrous magnesium sulfate, filtered and evaporated to dryness to afford crude 5'-(7-dimethoxymethylimidazo[1,2-α]pyrimidin-3-yl)-2'-fluorobiphenyl-2-carbonitrile. The residue was suspended in 1,4-dioxane (30 ml) then treated with 3N hydrochloric acid (30 ml) and this mixture was heated at 60° C. for 14 h. The reaction was cooled and partitioned between dichloromethane and water. The organics were washed with water, brine, dried over anhydrous magnesium sulfate, filtered and pre-adsorbed onto silica. Purification by chromatography on silica gel eluting with dichloromethane (+1% triethylamine) on a gradient of methanol (1–4%) gave a solid. Trituration with ether afforded 2'-fluoro-5'-(7-formylimidazo[1,2-α]pyrimidin-3-yl)biphenyl-2-carbonitrile as a yellow powder (1.2 g, 70% over 2 steps): δ$_H$ (400 MHz, DMSO) 7.48 (1H, d, J 7), 7.65–7.72 (2H, m), 7.75–7.80 (1H, m), 7.87 (1H, ddd, J 8, 8 and 1), 7.95–7.99 (2H, m), 8.02–8.05 (1H, m), 8.40 (1H, s), 9.27 (1H, dd, J 7 and 1), 9.96 (1H, s); m/z (ES$^+$) 343 (M$^+$+H).

A suspension of 2'-fluoro-5'-(7-formylimidazo[1,2-α]pyrimidin-3-yl)biphenyl-2-carbonitrile (260 mg, 0.8 mmol) in methanol (3 ml) was treated with hydroxylamine (0.13 ml of a 50 wt. % solution in water) then heated at 60° C. for 3 h. The reaction was cooled to 0° C., the solid collected by filtration and washed with a little cold methanol to afford 2'-fluoro-5'-[7-(hydroxyiminomethyl)imidazo[1,2-α]pyrimidin-3-yl]biphenyl-2-carbonitrile as a yellow solid. This solid was suspended in dichloromethane (5 ml), treated with 1,1'-carbonyldiimidazole (180 mg, 1.1 mmol) and triethylamine (0.31 ml, 2.3 mmol) then heated at reflux for 2 h. The reaction was cooled, diluted with dichloromethane then washed with water, brine, dried over anhydrous sodium sulfate, filtered and pre-adsorbed onto silica. Purification by chromatography on silica gel eluting with dichloromethane/methanol/conc. ammonia (99:0.9:0.1) afforded a solid which was recrystallised from acetonitrile to furnish 3-(2'-cyano-6-fluorobiphenyl-3-yl)imidazo[1,2-α]pyrimidine-7-carbonitrile as a yellow powder (160 mg, 63% over 2 steps): δ$_H$ (400 MHz, DMSO) 7.64–7.72 (3H, m), 7.78–7.81 (1H, m), 7.89 (1H, ddd, J 7, 7 and 1), 7.94–7.99 (2H, m), 8.05 (1H dd, J 8 and 2), 8.43 (1H, s), 9.36 (1H, d, J 7); m/z (ES$^+$) 340 (M$^+$+H).

EXAMPLE 18

2'-Fluoro-5'-[7-(3-methyl-[1,2,4]oxadiazol-5-yl)imidazo[1,2-α]pyrimidin-3-yl]biphenyl-2-carbonitrile Methyl oxalyl chloride was converted to 4-ethoxy-2-oxobut-3-enoic acid methyl ester and condensed with 2-aminoimidazole hemisulfate as described in Example 13 to give imidazo[1,2-α]pyrimidine-7-carboxylic acid methyl ester as an orange solid: δ$_H$ (400 MHz, CDCl$_3$) 4.05 (3H, s), 7.68 (1H, d, J 7), 7.72 (1H, d, J 1), 8.06 (1H, d, J 1), 8.59 (1H, d, J 7).

A mixture of imidazo[1,2-α]pyrimidine-7-carboxylic acid methyl ester (580 mg) and 28% ammonium hydroxide was heated at 100° C. in a sealed tube for 2 h then cooled to ambient temperature. The resulting solid was filtered, washed with ice-cold water and dried under vacuum to give imidazo[1,2-α]pyrimidine-7-carboxylic acid amide (310 mg, 58%) as a white solid: δ$_H$ (360 MHz, DMSO) 7.61 (1H, d, J 7), 7.77 (1H, s), 7.92 (1H, d, J 1), 8.09 (1H, d, J 1), 8.32 (1H, s), 9.11 (1H, d, J 7).

A mixture of imidazo[1,2-α]pyrimidine-7-carboxylic acid amide (310 mg) and N,N-dimethylacetamide dimethylacetal (270 mg) was heated at reflux for 16 h then cooled to ambient temperature. The reaction was then partitioned between dichloromethane and water. The organic phase was dried over anhydrous magnesium sulfate, filtered and evaporated to dryness to give imidazo[1,2-α]pyrimidine-7-carboxylic acid [1-(N,N-dimethylamino)ethylidene]amide as a brown oil. This oil was dissolved in 70% aqueous acetic acid (120 ml) and 1,4-dioxane (60 ml). A solution of hydroxylamine in water (40 wt. %, 0.15 ml) was then added and the mixture heated at 100° C. for 2 h then cooled to ambient temperature. This reaction mixture was dissolved in 50% methanol in dichloromethane and pre-adsorbed onto silica. Purification on silica gel eluting with dichloromethane (+1% conc. ammonia) on a gradient of methanol (2–5%) gave 7-(3-methyl-[1,2,4]oxadiazol-5-yl)imidazo[1,2-α]pyrimidine as a yellow solid (110 mg, 29% over 2 steps): $\delta_H$ (360 MHz, DMSO) 2.43 (3H, s), 7.76 (1H, d, J 7), 8.02 (1H, d, J 1), 8.19 (1H, d, J 1), 9.22 (1H, d, J 7).

7-(3-Methyl-[1,2,4]oxadiazol-5-yl)imidazo[1,2-α]pyrimidine was brominated as described in Example 1 to give 3-bromo-7-(3-methyl-[1,2,4]oxadiazol-5-yl)imidazo[1,2-α]pyrimidine as a yellow solid: $\delta_H$ (400 MHz, CDCl$_3$) 2.54 (3H, s), 7.86 (1H, d, J 7), 8.05 (1H, s), 8.61 (1H, d, J 7).

3-Bromo-7-(3-methyl-[1,2,4]oxadiazol-5-yl)imidazo[1,2-α]pyrimidine was coupled with 2'-fluoro-5'-(4,4,5,5-tetramethyl-[1,3,2]dioxaborolan-2-yl)biphenyl-2-carbonitrile as described in Example 2 to give 2'-fluoro-5'-[7-(3-methyl-[1,2,4]oxadiazol-5-yl)imidazo[1,2-α]pyrimidin-3-yl]biphenyl-2-carbonitrile as a yellow solid: $\delta_H$ (400 MHz, CDCl$_3$) 2.55 (3H, s), 7.46 (1H, t, J 9), 7.56–7.59 (1H, m), 7.64 (2H, dd, J 7 and 2), 7.69–7.73 (2H, m), 7.81–7.87 (2H, m), 8.16 (1H, s), 9.05 (1H, s); m/z (ES$^+$) 397 (M$^+$+H).

EXAMPLE 19

2'-Fluoro-5'-[7-(oxazol-5-yl)imidazo[1,2-α]pyrimidin-3-yl]biphenyl-2-carbonitrile 2'-Fluoro-5'-(7-formylimidazo[1,2-α]pyrimidin-3-yl)biphenyl-2-carbonitrile (100 mg), tosylmethyl isocyanide (60 mg) and potassium carbonate (40 mg) were suspended in methanol (10 ml) and heated at reflux for 90 min. The reaction was cooled, diluted with dichloromethane and filtered. The filtrate was evaporated to dryness and the residue partitioned between dichloromethane and water. The organic phase was dried over anhydrous magnesium sulfate, filtered and pre-adsorbed onto silica. Purification by flash column chromatography on silica gel eluting with dichloromethane with 1% ammonia on a gradient of methanol (1–5%) gave a solid. Trituration with diethyl ether afforded 2'-fluoro-5'-[7-(oxazol-5-yl)imidazo[1,2-α]pyrimidin-3-yl]biphenyl-2-carbonitrile as a yellow solid (40 mg, 34%): $\delta_H$ (360 MHz, DMSO) 7.53 (1H, d, J 7), 7.65 (1H, s), 7.70 (1H, s), 7.81 (1H, s), 7.87–7.95 (3H, m), 8.06 (1H, d, J 8), 8.11 (1H, s), 8.20 (1H, s), 8.70 (1H, s), 9.19 (1H, d, J 7); m/z (ES$^+$) 382 (M$^+$+H).

EXAMPLE 20

2'-Fluoro-5'-[7-(hydroxyiminomethyl)imidazo[1,2-α]pyrimidin-3-yl]biphenyl-2-carbonitrile and 5'-{7-[1-(2-dimethylaminoethoxyimino)methyl]imidazo[1,2-α]pyrimidin-3-yl}-2'-fluorobiphenyl-2-carbonitrile A mixture of 2'-fluoro-5'-(7-formylimidazo[1,2-α]pyrimidin-3-yl)biphenyl-2-carbonitrile (100 mg) and O-(2-dimethylaminoethyl)hydroxylamine (150 mg) in ethanol (5 ml) was heated at 55° C. for 16 h then cooled to ambient temperature. The resulting solid was collected by filtration and washed with ice-cold ethanol to give 2'-fluoro-5'-[7-(hydroxyiminomethyl)imidazo[1,2-α]pyrimidin-3-yl]biphenyl-2-carbonitrile as a white solid (30 mg): $\delta_H$ (360 MHz, DMSO) 7.44 (1H, d, J 7), 7.62–7.73 (2H, m), 7.80 (1H, s), 7.89 (1H, dd, J 8 and 1), 7.90–7.93 (2H, m), 8.06 (1H, dd, J 8 and 1), 8.08 (1H, s), 8.13 (1H, s), 9.05 (1H, d, J 7), 12.25 (1H, s); m/z (ES$^+$) 358 (M$^+$+H).

The filtrate was evaporated to dryness and purified by preparative thin-layer chromatography. Elution with 5% methanol in dichloromethane (containing 1% conc. ammonia) gave 5'-{7-[1-(2-dimethylamino-ethoxyimino)methyl]imidazo[1,2-α]pyrimidin-3-yl}-2'-fluorobiphenyl-2-carbonitrile as a white solid (3 mg): $\delta_H$ (360 MHz, DMSO) 2.61 (6H, s), 3.24 (2H, t, J 5), 4.37 (2H, t, J 5), 7.23 (1H, d, J 7), 7.41–7.50 (2H, m), 7.57 (1H, s), 7.64–7.72 (3H, m), 7.83 (1H, d, J 8), 7.92 (1H, s), 8.08 (1H, s), 8.90 (1H, d, J 7); m/z (ES$^+$) 429 (M$^+$+H).

EXAMPLE 21

3'-(7-Difluoromethylimidazo[1,2-α]pyrimidin-3-yl)-4'-fluorobiphenyl-2-carbonitrile A mixture of 4-bromo-1-fluoro-2-nitrobenzene (9.68 g, 44 mmol) and tetrakis(triphenylphosphine)palladium(0) (1.53 g, 1.3 mmol) was treated with 2-cyanophenylzinc bromide (100 ml of a 0.5M solution in tetrahydrofuran, 50 mmol) then heated under reflux for 8 h. After cooling to ambient temperature the reaction mixture was poured into water (1000 ml). After stirring for 30 min the resulting solid was collected by filtration and dried under vacuum over phosphorus pentoxide to afford 4'-fluoro-3'-nitrobiphenyl-2-carbonitrile as a tan solid (10.7 g, 100%) which was used without further purification.

A cooled (0° C.) suspension of crude 4'-fluoro-3'-nitrobiphenyl-2-carbonitrile (10.7 g, 44 mmol) in ethanol (80 ml) and tetrahydrofuran (80 ml) was treated with tin(II) chloride dihydrate (29.8 g, 132 mmol) and this mixture was stirred at ambient temperature for 12 h. The solvent was removed in vacuo and the residue treated with ice-cold 2N sodium hydroxide (400 ml). The resulting slurry was stirred at ambient temperature for 60 min then extracted with dichloromethane (2×400 ml). The organics were combined, washed with water, brine, dried over anhydrous magnesium sulfate, filtered and pre-adsorbed onto silica. Purification by chromatography on silica gel eluting with isohexane on a gradient of ethyl acetate (5–40%) gave 3'-amino-4'-fluorobiphenyl-2-carbonitrile as a cream-coloured solid (4.3 g, 46% over 2 steps): $\delta_H$ (400 MHz, CDCl$_3$) 3.85 (2H, br), 6.84 (1H, ddd, J 8, 4 and 2), 6.95 (1H, dd, J 8 and 2), 7.07 (1H, dd, J 11 and 8), 7.40–7.46 (2H, m), 7.57–7.62 (1H, m), 7.72–7.74 (1H, m).

A warm solution of 3'-amino-4'-fluorobiphenyl-2-carbonitrile (4.24 g, 20 mmol) in 1,4-dioxane (30 ml) was treated with 48% hydrobromic acid (100 ml) and the resulting suspension stirred and cooled to 3° C. (internal temp). A solution of sodium nitrite (1.59 g, 23 mmol) in water (4 ml) was then added dropwise over 20 min keeping the internal temperature <5° C. Stirring at <5° C. was continued for 2 h before adding a cooled (5° C.) solution of copper(I) bromide in 48% hydrobromic acid (30 ml). The resulting purple reaction mixture was stirred at 5° C. for 10 min then warmed to 50° C. for 20 min. The reaction was diluted with ice-cold water (500 ml) and extracted with ethyl acetate (2×200 ml). The organics were combined, washed with 5% aqueous sodium sulfite and saturated aqueous ammonium chloride, dried over anhydrous magnesium sulfate, filtered and pre-adsorbed onto silica. Purification on silica, eluting with isohexane on a gradient of ethyl acetate (2–12%) afforded 3'-bromo-4'-fluorobiphenyl-2-carbonitrile as a white solid (2.5 g, 45%): $\delta_H$ (400 MHz, CDCl$_3$) 7.22–7.27 (1H, m), 7.45–7.53 (4H, m), 7.66 (1H, td, J 8 and 2), 7.73 (1H, dd, J 8 and 2), 7.77 (1H, dd, J 8 and 2).

A mixture of 3'-bromo-4'-fluorobiphenyl-2-carbonitrile (2.48 g, 9 mmol), potassium acetate (2.65 g, 27 mmol), bis(pinacolato)diboron (2.63 g, 10.4 mmol) and dichloro[1,1'-bis(diphenylphosphino)ferrocene]palladium(II) dichloromethane adduct (220 mg, 0.3 mmol) in 1,4-dioxane (20 ml) was heated at 90° C. for 16 h. The reaction was cooled, filtered (washing the filter cake with a small quantity of dichloromethane) and the filtrate concentrated in vacuo. The residue was partitioned between diethyl ether (50 ml) and 2N sodium hydroxide (50 ml) and the organic phase discarded. The aqueous was washed with more ether and then cooled in an ice-water bath. The pH was adjusted to approximately 6 with 36% hydrochloric acid and then extracted with ether. The organic layer was washed with water, brine, dried over anhydrous magnesium sulfate, filtered and evaporated to dryness to afford 4'-fluoro-3'-(4,4,5,5-tetramethyl-[1,3,2]dioxaborolan-2-yl)biphenyl-2-carbonitrile as a pale yellow solid (2.4 g, 83%): $\delta_H$ (400 MHz, CDCl$_3$) 1.38 (12H, s), 7.16 (1H, dd, J 9 and 9), 7.43 (1H, td, J 8 and 2), 7.49–7.53 (1H, m), 7.60–7.67 (2H, m), 7.75 (1H, dd, J 8 and 2), 7.87 (1H, dd, J 5 and 3).

3-Bromo-7-difluoromethylimidazo[1,2-α]pyrimidine (124 mg, 0.50 mmol) was coupled with 4'-fluoro-3'-(4,4,5,5-tetramethyl-[1,3,2]dioxaborolan-2-yl)biphenyl-2-carbonitrile as described in Example 1 to give 3'-(7-difluoromethylimidazo[1,2-α]pyrimidin-3-yl)-4'-fluorobiphenyl-2-carbonitrile (180 mg, 49%) as a yellow powder: $\delta_H$ (400 MHz, CDCl$_3$) 6.69 (1H, t, J 55), 7.32 (1H, d, J 7), 7.42–7.57 (3H, m), 7.64–7.76 (3H, m), 7.84 (1H, dd, J 8 and 1), 8.13 (1H, d, J 1), 8.79 (1H, dd, J 7 and 2); m/z (ES$^+$) 365 (M$^+$+H).

EXAMPLE 22

2'-Fluoro-5'-(7-fluoromethylimidazo[1,2-α]pyrimidin-3-yl)biphenyl-2-carbonitrile Fluoroacetone (5.00 g, 65.7 mmol) was converted to 4,4-diethoxy-1-fluorobutan-2-one as described in Example 3 and condensed with 2-aminoimidazole hemisulfate as described in Example 2 to give 7-fluoromethylimidazo[1,2-α]pyrimidine (2.84 g, 29%) as a white solid: $\delta_H$ (360 MHz, CDCl$_3$) 5.53 (2H, d, J 47), 7.11 (1H, dd, J 7 and 1), 7.57 (1H, d, J 1), 7.82 (1H, d, J 1), 8.50 (1H, d, J 7).

7-Fluoromethylimidazo[1,2-α]pyrimidine (0.50 g, 3.31 mmol) was brominated as described in Example 1 to give 3-bromo-7-fluoromethylimidazo[1,2-α]pyrimidine (550 mg, 72%) as a white solid: $\delta_H$ (360 MHz, CDCl$_3$) 5.56 (2H, d, J 47), 7.25 (1H, dd, J 7 and 1), 7.81 (1H, s), 8.47 (1H, d, J 7).

3-Bromo-7-fluoromethylimidazo[1,2-α]pyrimidine (115 mg, 0.50 mmol) was coupled with 2'-fluoro-5'-(4,4,5,5-tetramethyl-[1,3,2]dioxaborolan-2-yl)biphenyl-2-carbonitrile as described in Example 1 to give 2'-fluoro-5'-(7-fluoromethylimidazo[1,2-α]pyrimidin-3-yl)biphenyl-2-carbonitrile (116 mg, 67%) as a white powder: $\delta_H$ (400 MHz, CDCl$_3$) 5.57 (2H, d, J 47), 7.20 (1H, dd, J 7 and 1), 7.42 (1H, dt, J 9 and 1), 7.55 (1H, dt, J 8 and 1), 7.60–7.66 (3H, m), 7.70–7.74 (1H, m), 7.85 (1H, dd, J 8 and 1), 7.90 (1H, s), 8.91 (1H, d, J 7); m/z (ES$^+$) 347 (M$^+$+H).

EXAMPLE 23

2'-Fluoro-5'-[7-(furan-3-yl)imidazo[1,2-α]pyrimidin-3-yl]biphenyl-2-carbonitrile 5'-(7-Chloroimidazo[1,2-α]pyrimidin-3-yl)-2'-fluorobiphenyl-2-carbonitrile (50 mg, 0.143 mmol), 3-furylboronic acid (32 mg, 0.287 mmol) and potassium triphosphate (61 mg, 0.287 mmol) were dissolved in N,N-dimethylacetamide (1 ml) and degassed with nitrogen for 15 min, tetrakis(triphenylphosphine)palladium(0) (8 mg, 0.0072 mmol) was then added and the reaction mixture heated at 80° C. for 18 h. The mixture was cooled to ambient temperature and partitioned between ethyl acetate (75 ml) and water (50 ml). The organic phase was washed with brine (50 ml), dried over anhydrous magnesium sulfate, filtered and evaporated. Purification of this material by preparative thin-layer chromatography eluting with dichloromethane/methanol/conc. ammonia (97:3:0.3) gave a solid which was triturated with diethyl ether to give 2'-fluoro-5'-[7-(furan-3-yl)imidazo[1,2-α]pyrimidin-3-yl]biphenyl-2-carbonitrile (24 mg, 46%) as a yellow powder: $\delta_H$ (400 MHz, CDCl$_3$) 7.10–7.13 (2H, m), 7.41 (1H, dt, J 9 and 1), 7.53–7.65 (5H, m), 7.71 (1H, dt, J 8 and 1), 7.84–7.86 (2H, m), 8.17 (1H, s), 8.80 (1H, d, J 7); m/z (ES$^+$) 381 (M$^+$+H).

EXAMPLE 24

2'-Fluoro-5'-[7-(thien-3-yl)imidazo[1,2-α]pyrimidin-3-yl]biphenyl-2-carbonitrile 5'-(7-Chloroimidazo[1,2-α]pyrimidin-3-yl)-2'-fluorobiphenyl-2-carbonitrile (50 mg, 0.143 mmol) and 3-thiopheneboronic acid (346 mg, 0.287 mmol) were reacted using the procedure in Example 23 to give 2'-fluoro-5'-[7-(thien-3-yl)imidazo[1,2-α]pyrimidin-3-yl]biphenyl-2-carbonitrile (44 mg, 77%) as a yellow powder: $\delta_H$ (400 MHz, CDCl$_3$) 7.31 (1H, d, J 7), 7.39–7.45 (2H, m), 7.55 (1H, dt, J 9 and 1), 7.61–7.67 (3, m), 7.71 (1H, dt, J 8 and 1), 7.84–7.90 (3H, m), 8.11 (1H, s), 8.82 (1H, d, J 7); m/z (ES$^+$) 397 (M$^+$+H).

EXAMPLE 25

2'-Fluoro-5'-[7-(pyridin-2-yl)imidazo[1,2-α]pyrimidin-3-yl]biphenyl-2-carbonitrile 5'-(7-Chloroimidazo[1,2-α]pyrimidin-3-yl)-2'-fluorobiphenyl-2-carbonitrile (50 mg, 0.143 mmol), 2-(1,1,1-tributylstannyl)pyridine (105 mg, 0.286 mmol), lithium chloride (61 mg, 1.43 mmol) and copper(I) iodide (3 mg, 0.014 mmol) were suspended in N,N-dimethylacetamide (1.5 ml) and degassed with N$_2$ for 15 min, tetrakis(triphenylphosphine)palladium(0) (8 mg, 0.0072 mmol) was then added and the reaction mixture heated at 80° C. for 18 h. The mixture was cooled to ambient temperature, diluted with water (20 ml) and saturated sodium hydrogencarbonate solution (20 ml) and extracted with ethyl acetate (2×100 ml). The combined organic phase was washed with brine (50 ml), dried over anhydrous sodium sulfate, filtered and evaporated. Purification by flash column chromatography on silica eluting with dichloromethane/methanol/conc. ammonia (99:1:0.1) gave a solid which was triturated with diethyl ether to give 2'-fluoro-5'-[7-(pyridin-2-yl)imidazo[1,2-α]pyrimidin-3-yl]biphenyl-2-carbonitrile (30 mg, 54%) as a yellow powder: $\delta_H$ (400 MHz, CDCl$_3$) 7.37–7.45 (2H, m), 7.55 (1H, dt, J 9 and 1), 7.61–7.74 (4H, m), 7.84–7.92 (2H, m), 7.96 (1H, s), 8.22 (1H, d, J 8), 8.69–8.75 (2H, m), 8.91 (1H, d, J 7); m/z (ES$^+$) 392 (M$^+$+H).

EXAMPLE 26

2'-Fluoro-5'-(6-fluoro-7-methylimidazo[1,2-α]pyrimidin-3-yl)biphenyl-2-carbonitrile 3-Fluoro-4,4-dimethoxybutan-2-one (prepared according to Funabiki et al., *J. Chem Soc., Perkin Trans.* 1, 1997, 2679) (0.56 g, 3.75 mmol) was cyclized with 2-aminoimidazole hemisulfate as described in Example 2 to give 6-fluoro-7-methylimidazo[1,2-α]pyrimidine (62 mg, 11%) as an off-white solid: $\delta_H$ (360 MHz, CDCl$_3$) 2.64 (3H, d, J 3), 7.48 (1H, d, J 1), 7.78 (1H, d, J 1), 8.25 (1H, d, J 4).

6-Fluoro-7-methylimidazo[1,2-α]pyrimidine (60 mg, 0.40 mmol) was brominated as described in Example 1 to give 3-bromo-6-fluoro-7-methylimidazo[1,2-α]pyrimidine (24 mg, 26%) as a white solid: $\delta_H$ (360 MHz, CDCl$_3$) 2.66 (3H, d, J 3), 7.75 (1H, s), 8.23 (1H, d, J 4).

3-Bromo-6-fluoro-7-methylimidazo[1,2-α]pyrimidine (24 mg, 0.50 mmol) was coupled with 2'-fluoro-5'-(4,4,5,5-tetramethyl[1,3,2]dioxaborolan-2-yl)biphenyl-2-carbonitrile as described in Example 1 to give 2'-fluoro-5'-(6-fluoro-7-methylimidazo[1,2-α]pyrimidin-3-yl)biphenyl-2-carbonitrile (21 mg, 58%) as a white powder: $\delta_H$ (400 MHz, CDCl$_3$) 2.67 (3H, d, J 3), 7.39–7.43 (1H, m), 7.53–7.62 (4H, m), 7.69–7.74 (1H, m), 7.84 (1H, d, J 1), 7.86 (1H, s), 8.67 (1H, d, J 5); m/z (ES$^+$) 347 (M$^+$+H).

EXAMPLE 27

7-(1,1-Difluoroethyl)-3-[4-fluoro-3-(pyridin-3-yl)phenyl]imidazo[1,2-α]pyrimidine 2-Bromo-1-fluoro-4-nitrobenzene was dissolved in tetrahydrofuran (75 ml) and ethanol (75 ml) and tin(II) chloride dihydrate added and the mixture left to stir at ambient temperature for 4 h. The solvent was evaporated and the residue was treated with ice-cold 2N sodium hydroxide solution (200 ml). The resulting slurry was stirred for 30 min then extracted with dichloromethane (3×200 ml). The combined organic phase was washed with water (200 ml) and brine (200 ml), dried over anhydrous magnesium sulfate, filtered and evaporated to give 3-bromo-4-fluorophenylamine (7.92 g, 92%) as a yellow oil: $\delta_H$ (360 MHz, CDCl$_3$) 3.53 (2H, s), 6.53–6.57 (1H, m), 6.83–6.85 (1H, m), 6.90 (1H, dd, J 9 and 9).

A mixture of 3-bromo-4-fluorophenylamine (7.92 g, 41.7 mmol), diethyl(3-pyridyl)borane (6.74 g, 45.9 mmol), tetrakis(triphenylphosphine)palladium(0) (0.96 g, 0.83 mmol) and potassium carbonate (17.26 g, 125 mmol) in 1,2-dimethoxyethane (30 ml) and water (15 ml) was heated at 80° C. for 20 h. After cooling to ambient temperature the reaction was partitioned between ethyl acetate (500 ml) and water (500 ml). The organics were washed with brine (400 ml), dried over anhydrous sodium sulfate, filtered and concentrated in vacuo. Purification of the residue by flash chromatography on silica gel, eluting with dichloromethane on a gradient of ethyl acetate (0%–20%) gave 4-fluoro-3-(pyridin-3-yl)phenylamine (3.64 g, 46%) as a colourless oil that solidified on standing to afford a white solid: $\delta_H$ (360 MHz, CDCl$_3$) 3.65 (2H, s), 6.65–6.72 (2H, m), 6.99 (1H, dd, J 9 and 9), 7.33–7.37 (1H, m), 7.84–7.86 (1H, m), 8.58 (1H, d, J 4), 8.76 (1H, m).

A warm solution of 4-fluoro-3-(pyridin-3-yl)phenylamine (3.64 g, 19.3 mmol) in 1,4-dioxane (10 ml) was treated with a solution of 48% aqueous hydrobromic acid (100 ml). The resulting suspension was cooled to 0° C. before being treated dropwise over 20 min with a solution of sodium nitrite (1.53 g, 22.2 mmol) in water (4 ml). After stirring at 0° C. for 2 h, a cooled (0° C.) solution of copper(I) bromide (8.31 g, 57.9 mmol) in 48% aqueous hydrobromic acid (30 ml) was added to the reaction which was stirred at 0° C. for 10 min then heated at 50° C. for 20 min. The reaction was cooled to ambient temperature, poured onto ice-cold conc. ammonia (500 ml) and the product was extracted into ethyl acetate (500 ml). The organics were washed with water (300 ml) and brine (300 ml), dried over anhydrous sodium sulfate, filtered and concentrated in vacuo to give a dark oil. Purification by dry flash column chromatography on silica eluting with isohexane on a gradient of ethyl acetate (10%–30%) gave 3-(5-bromo-2-fluorophenyl)pyridine (3.1 g, 64%) as a white solid: $\delta_H$ (360 MHz, CDCl$_3$) 7.09 (1H, dd, J 9 and 1), 7.37–7.40 (1H, m), 7.46–7.51 (1H, m), 7.56–7.59 (1H, m), 7.83–7.86 (1H, m), 8.63–8.65 (1H, m), 8.77–8.79 (1H, m).

3-(5-Bromo-2-fluorophenyl)pyridine (3.1 g, 12.3 mmol), potassium acetate (3.62 g, 36.9 mmol) and bis(pinacolato)diboron (3.75 g, 14.8 mmol) were dissolved in 1,4-dioxane (40 ml) and dimethylsulfoxide (0.8 ml) and the mixture degassed with N$_2$ for 15 min. Dichloro[1,1'-bis(diphenylphosphino)ferrocene]palladium(II) dichloromethane adduct (300 mg, 0.37 mmol) was added and the mixture heated at 90° C. for 18 h. The mixture was cooled to ambient temperature and partitioned between diethyl ether (200 ml) and 2N hydrochloric acid (50 ml). The organics were discarded and the aqueous phase adjusted to pH 8 by the addition of 4N sodium hydroxide solution and extracted with diethyl ether (2×500 ml). The organic layer was washed with brine (50 ml), dried over anhydrous sodium sulfate, filtered and pre-adsorbed onto silica. Purification by flash column chromatography on silica eluting with 25% ethyl acetate in isohexane gave 3-[2-fluoro-5-(4,4,5,5-tetramethyl-[1,3,2]dioxaborolan-2-yl)phenyl]pyridine (2.64 g, 72%) as a yellow oil that crystallised on standing: $\delta_H$ (360 MHz, CDCl$_3$) 1.35 (12H, s), 7.20 (1H, dd, J 10 and 8), 7.35–7.39 (1H, m), 7.81–7.91 (3H, m), 8.61 (1H, dd, J 5 and 2), 8.82 (1H, s).

3-Bromo-7-(1,1-difluoroethyl)imidazo[1,2-α]pyrimidine (113 mg, 0.43 mmol) was coupled with 3-[2-fluoro-5-(4,4,5,5-tetramethyl-[1,3,2]dioxaborolan-2-yl)phenyl]pyridine as described in Example 1 to give 7-(1,1-difluoroethyl)-3-[4-fluoro-3-(pyridin-3-yl)phenyl]imidazo[1,2-α]pyrimidine as a white powder: $\delta_H$ (360 MHz, DMSO) 2.11 (3H, t, J 7), 7.36 (1H, d, J 7), 7.55–7.64 (2H, m), 7.83–7.87 (1H, m), 7.99–8.01 (1H, m), 8.11–8.13 (1H, m), 8.21 (1H, s), 8.66 (1H, dd, J 5 and 1), 8.91 (1H, s), 9.27 (1H, d, J 7).

EXAMPLE 28

2-[3-(4-Fluoro-3-(pyridin-3-yl)phenyl)imidazo[1,2-α]pyrimidin-7-yl]propan-2-ol 2-(3-Bromoimidazo[1,2-α]pyrimidin-7-yl)propan-2-ol was coupled with 3-[2-fluoro-5-(4,4,5,5-tetramethyl-[1,3,2]dioxaborolan-2-yl)phenyl]pyridine as described in Example 1 to give 2-[3-(4-fluoro-3-(pyridin-3-yl)phenyl)imidazo[1,2-α]pyrimidin-7-yl]propan-2-ol as a white solid. Bis-hydrochloride salt (from ethyl acetate/ethanol): $\delta_H$ (400 MHz, DMSO) 1.56 (6H, s), 7.73 (1H, dd, J 11 and 9), 7.81–7.90 (3H, m), 8.09 (1H, dd, J 7 and 2), 8.42 (1H, dd, J 7 and 1), 8.55 (1H, s), 8.81 (1H, dd, J 5 and 1), 9.06 (1H, s), 9.39 (1H, d, J 7).

Alternative Method:

A mechanically stirred 3 l round-bottomed flask under an atmosphere of nitrogen was charged with 3-hydroxy-3-methyl-2-butanone (100.0 g, 979 mmol) and CH$_2$Cl$_2$ (900 ml). A solution of acetic anhydride (92.4 ml, 979 mmol) and CH$_2$Cl$_2$ (50 ml) was added over 10 min and the resulting solution was cooled to 10° C. DMAP (5.98 g, 49 mmol) was added in one portion followed by Et$_3$N (205 ml, 1.47 mol) over 50 min while maintaining an internal temperature below 16° C. After the addition, the mixture was aged for 16 h at room temperature. The resulting solution was poured onto MeOH (200 ml) and after 15 min 2N HCl (400 ml) was added. The phases were separated and the organic phase was washed with water (500 ml) then saturated NaHCO$_3$ (500 ml) then dried over Na$_2$SO$_4$. The solvent was removed under diminished pressure to provide 3-acetoxy-3-methyl-2-butanone as a golden oil (132.5 g): $^1$H NMR (CDCl$_3$, 400 MHz) δ 2.12 (3H, s), 2.09 (3H, s), 1.47 (6H, s); $^{13}$C NMR (CDCl$_3$, 100.61 MHz) δ 206.6, 170.2, 83.5, 23.4, 23.2, 21.0.

A 3 l round-bottomed flask fitted with a mechanical stirrer under an atmosphere of N$_2$ was charged with triethyl orthoformate (304 ml, 1.83 mol) and CH$_2$Cl$_2$ (1.30 l). The solution was cooled to −65° C. and BF$_3$.Et$_2$O (255 ml, 2.01 mol) was added over 30 min to provide a yellow solution. After an additional 15 min, the cold bath was removed and the flask contents were allowed to warm to 0° C. After ageing at 0° C. for 45 min, the mixture was cooled to −60° C. to provide a thin white slurry. A solution of 3-acetoxy-3-methyl-2-butanone (131.55 g, 0.912 mol) and CH$_2$Cl$_2$ (100 ml) was added over 17 min. After a 40 min age at −65° C., diisopropylethylamine (404 ml, 2.32 mol) was added over 30 min maintaining an internal temperature below −63° C. After an additional 45 min at −65° C., the mixture was warmed to room temperature over 45 min and aged at that temperature for 5 h. The reaction mixture was poured onto saturated aqueous NaHCO$_3$ (800 ml) and stirred for 15 min. The layers were partitioned and the organic phase was washed with 1M H$_2$SO$_4$ at 5° C. (2×800 ml), water at 5° C. (2×800 ml) and then dried over Na$_2$SO$_4$. The solvent was removed under diminished pressure to provide 4-acetoxy-1,1-diethoxy-4-methyl-3-butanone as an oil (270 g, 57 wt % pure) which was used without further purification in the subsequent steps. An analytical sample was prepared by HPLC on a Zorbax C-8 preparative column with gradient elution from 30% acetonitrile, 70% 0.1% H$_3$PO$_4$/H$_2$O to 70% acetonitrile, 30% 0.1% H$_3$PO$_4$/H$_2$O over 20 min: $^1$H NMR (CDCl$_3$, 400 MHz) δ 4.95 (1H, t, J 5.6), 3.69 (2H, m), 3.53 (2H, m), 2.79 (2H, d, J 5.6), 2.07 (3H, s), 1.47 (6H, s), 1.18 (6H, t, J 6.8); $^{13}$C NMR (CDCl$_3$, 100.61 MHz) δ 205.7, 170.4, 100.8, 83.7, 63.2, 41.4, 22.9, 21.1, 15.1.

A 3 l round-bottomed flask equipped with a mechanical stirrer, thermocouple and nitrogen inlet adaptor was charged with 2-aminoimidazole hemisulfate (84.6 g, 641 mmol) and absolute EtOH (900 ml). The resulting slurry was stirred at 24° C. and solid NaOMe (69.2 g, 1.28 mol) was added in two portions over 15 min. After the addition was complete the reaction temperature was 46° C. The mixture was warmed to 60° C. and stirred for 45 min. The mixture was then cooled to 50° C. A solution of crude 4-acetoxy-1,1-diethoxy-4-methyl-3-butanone (253.5 g of 57 wt % material, 611 mmol) and absolute EtOH (150 ml) was added over 1 h maintaining a reaction temperature of about 45° C. After the addition, the reaction was maintained at 60° C. for 3 h and then cooled to 20° C. The pH was adjusted to 5.9 by addition of aqueous HCl (5N, 130 ml) in 10 ml portions. Darco G-60 (9.0 g) was added and the slurry was stirred for 30 min. The solids were removed by filtration through a pad of Solka-floc and the cake was rinsed with EtOH (200 ml). The filtrate was concentrated to about 200 ml by rotary evaporation, then 300 ml of EtOAc was added and the mixture was concentrated to about 300 ml. This was repeated three times with crystals forming during the process. The final slurry was diluted to 600 ml with EtOAc and then cooled to 5° C. with stirring. The solids were collected on a frit, rinsed with cold EtOAc (50 ml) and dried overnight under vacuum at 22° C. to provide 2-(imidazo[1,2-α]pyrimidin-7-yl)propan-2-ol (79 g) as a crystalline solid: $^1$H NMR (MeOH-d$_4$, 400 MHz) δ 8.80 (1H, d, J 7.2), 7.77 (1H, d, J 1.6), 7.66 (1H, d, J 1.6), 7.39 (1H, d, J 7.2), 1.60 (6H, s); $^{13}$C NMR (MeOH-d$_4$, 100.61 MHz) δ 169.7, 147.8, 134.7, 132.8, 111.1, 105.4, 72.8, 28.4.

A 500 ml round-bottomed flask equipped with a mechanical stirrer, thermocouple and nitrogen/vacuum inlet was charged with 2-(imidazo[1,2-α]pyrimidin-7-yl)propan-2-ol (10.62 g, 60.0 mmol), 4-bromo-2-chloro-1-fluorobenzene (8.00 ml, 66.0 mmol), palladium(II) acetate (270 mg, 1.20 mmol), triphenylphosphine (630 mg, 2.40 mmol), cesium carbonate (19.6 g, 60.2 mmol), and anhydrous 1,4-dioxane (120 ml). The slurry was degassed using five vacuum/nitrogen back-fill cycles, and then heated to 90° C. and aged for 12 hours. The mixture was cooled to 60° C. then water (150 ml) and EtOAc (150 ml) were added to the crude reaction mixture and the slurry was stirred at 45° C. until all of the solids were dissolved. The layers were partitioned and the aqueous phase was extracted again with EtOAc (50 ml). The organic phases were combined and extracted twice with 2N HCl (100 ml then 30 ml). The acidic aqueous phases were combined with EtOAc (250 ml) and NaOH (10.9 g, final pH=10) was added slowly with stirring and the mixture was warmed to 65° C. to dissolve the solids. The phases were separated and the organic phase was concentrated to about 200 ml to provide a slurry. Isopropyl acetate (110 ml) was added and the slurry was concentrated again to about 200 ml. The slurry was warmed to 90° C. then cooled over several hours to 0° C. The crystalline solids were collected on a frit, rinsed with isopropyl acetate/EtOAc (1:1) and air dried to provide 2-[3-(3-chloro-4-fluorophenyl)imidazo[1,2-α]pyrimidin-7-yl]propan-2-ol (16.19 g) as a cream-colored crystalline solid: m.p. 180–182° C.; $^1$H NMR (CDCl$_3$, 400 MHz) δ 8.53 (1H, d, J 7.2), 7.86 (1H, s), 7.59 (1H, dd, J 6.8, 2.0), 7.42 (1H, m), 7.34 (1H, m), 7.14 (1H, d, J 7.2), 1.63 (6H, s); $^{13}$C NMR (CDCl$_3$, 100.64 MHz) δ 167.8, 158.1 (d, J 252.2), 148.0, 133.8, 131.4, 130.0, 127.8 (d, J 7.2), 125.5 (d, J 4.0), 122.4 (d, J 18.5), 122.1, 117.8 (d, J 20.9), 105.7, 72.5, 29.9.

A mechanically stirred 3 l round-bottomed flask equipped with a thermocouple and nitrogen/vacuum inlet was charged with toluene (800 ml), THF (200 ml), 3-bromopyridine (80.61 g, 500 mmol), and triisopropyl borate (115.15 g, 600 mmol). The solution was cooled to −40° C. using a dry ice/acetone bath. n-Butyllithium (2.6 M in hexanes) (231 ml, 600 mmol) was added over 30 min using a syringe pump. The resulting yellow solution was aged for 30 min at −40° C. then warmed to −15° C. 2N HCl (400 ml) was added in one portion and the phases were partitioned. The aqueous phase was adjusted to pH 7 by slow addition of 5N NaOH (about 160 ml). The solid product precipitated as the pH approached 7. This neutral aqueous layer was extracted three times with THF (800 ml portions). The combined extracts were concentrated under vacuum to dryness. Acetonitrile (200 ml) was added and the resulting suspension was warmed to 70° C. After 30 min, the slurry was allowed to cool to room temperature. The flask was placed in an ice bath and the slurry was cooled to 0° C. The product was collected on a frit and rinsed with a small aliquot of cold acetonitrile. The solids were dried under a stream of air to provide the boroxine of 3-pyridineboronic acid (51 g) as a colorless crystalline solid.

A 5 l round-bottomed flask equipped with a mechanical stirrer, thermocouple, nitrogen/vacuum inlet adaptor and septum was charged with 2-[3-(3-chloro-4-fluorophenyl)imidazo[1,2-α]pyrimidin-7-yl]propan-2-ol (101.59 g, 333 mmol), 3-pyridineboronic acid in the form of its boroxine (42.98 g, 350 mmol), $K_3PO_4$ (111.69 g, 526 mmol), 1,4-dioxane (1.20 l), and water (406 ml). Cycling vacuum and then nitrogen three times degassed the stirred slurry. All solids dissolved on warming to 70° C. A 500 ml round-bottomed flask equipped with a magnetic stir bar, thermocouple, nitrogen/vacuum inlet adaptor and septum was charged with bis(dibenzylideneacetone)palladium(0) (9.57 g, 16.7 mmol) and 1,4-dioxane (130 ml). The resulting solution was degassed as above, then tri-tert-butylphosphine (49.8 ml of a 10 wt % solution in hexanes, 16.7 mmol) was added by syringe. The solution was degassed again and then warmed to 70° C. The warm catalyst solution was cannulated to the 5 l flask and the resulting mixture was stirred at 70° C. for 16 h. At the end of reaction, most of the product had crystallized out to provide a grey slurry. The reaction mixture was partitioned between 2N HCl (1.8 l) and toluene (0.9 l). The clear yellow aqueous phase was transferred to a stirred 4 l Erlenmeyer flask with a nitrogen sweep and borane-trimethylamine complex (1.87 g) was added. After 90 min the resulting black solids were removed by filtration through a 1.0μ filter. The filtrate was transferred to a mechanically stirred 5 l flask equipped with a pH probe. The pH was adjusted to 3.8 by slow addition of 50 wt % NaOH (about 130 ml). The mixture self-nucleated to provide a slurry. Additional 50 wt % NaOH (about 36 ml) was added over 30 min to pH 7.1 to provide a cream-colored slurry. The solids were collected on a frit, washed with water (250 ml) and air dried to give the free base 2-[3-(4-fluoro-3-(pyridin-3-yl)phenyl)imidazo[1,2-α]pyrimidin-7-yl]propan-2-ol as an off-white crystalline solid (117.38 g, 94.5 wt % pure): m.p. 234–236° C.; $^1$H NMR (DMSO-$d_6$, 400 MHz) δ 9.00 (1H, d, J 7.2), 8.85 (1H, bs), 8.60 (1H, dd, J 4.8, 1.6), 8.06 (1H, m), 7.92 (1H, s), 7.87 (1H, dd, J 7.2, 2.4), 7.74 (1H, m), 7.76–7.68 (2H, m), 7.37 (1H, d, J 7.2), 5.49 (1H, s), 1.47 (6H, s); $^{13}$C NMR (DMSO-$d_6$, 100.55 MHz) δ 169.6, 159.3 (d, J 248.2), 149.9 (d, J 3.2), 149.6, 148.5, 137.0 (d, J 3.2), 134.0, 133.5, 130.9, 130.3 (d, J 3.2), 130.0 (d, J 8.0), 126.6 (d, J 14.5), 126.1 (d, J 4.0), 124.1, 122.7, 117.7 (d, J 22.5), 106.3, 73.0, 30.3.

A magnetically stirred 2 l three-necked round-bottomed flask equipped with a condenser, thermocouple and drying tube was charged with free base 2-[3-(4-fluoro-3-(pyridin-3-yl)phenyl)imidazo[1,2-α]pyrimidin-7-yl]propan-2-ol (25.00 g, 71.8 mmol) and EtOH (950 ml). The suspension was warmed to 75° C. then HCl (47 ml of a 4.6M solution in isopropyl alcohol) was added to provide a clear solution. Powdered Darco G-60 (2.50 g) was added and the mixture refluxed for 2 h. The suspension was cooled to 60° C. and the solids were removed by filtration through a pad of Solka-floc. The resulting clear solution was transferred to a mechanically stirred 3 l round-bottomed flask equipped with a reflux condenser. The solution was warmed to 75° C. and isopropyl acetate (1.00 l) was added. During the isopropyl acetate addition, the solution self-nucleated to provide a white suspension which was cooled over several hours to room temperature. The solids were collected on a frit, rinsed with 1:1 EtOH/isopropyl acetate (100 ml) then dried in a 60° C. vacuum oven to provide the bis-HCl salt as colorless crystals (26.76 g): m.p. 241–250° C.; $^1$H NMR (CD$_3$OD, 400 MHz) δ 9.32 (1H, m), 9.30 (1H, d, J 7.2), 9.02 (1H, m), 8.97 (1H, m), 8.38 (1H, s), 8.28 (1H, m), 8.18 (1H, dd, J 7.2, 2.0), 8.03 (1H, d, J 7.2), 7.99 (1H, m), 7.68 (1H, dd, J 10.4, 8.4), 1.67 (6H, s); $^{13}$C NMR (CD$_3$OD, 100.61 MHz) δ 178.4, 160.5 (d, J 254.0), 146.9 (d, J 3.4), 143.5, 141.4 (d, J 4.0), 140.7, 135.8, 134.4, 133.3 (d, J 9.4), 131.9 (d, J 2.4), 127.5, 124.3, 123.1 (d, J 13.6), 122.4 (d, J 3.8), 120.8, 117.8 (d, J 23.2), 110.7, 73.2, 28.5.

EXAMPLE 29

3'-Fluoro-5'-(7-trifluoromethylimidazo[1,2-α]pyrimidin-3-yl)biphenyl-2-carbonitrile A solution of 4-fluoro-2-nitroaniline (39.03 g, 250 mmol) in water (900 ml) and 48% hydrobromic acid (1500 ml) was treated with bromine (15.26 ml, 46 g, 288 mmol) added dropwise over 20 min. The resulting precipitate was stirred at ambient temperature for a further 45 min then diluted with ice-water (2000 ml). The solid product was collected by filtration, washed with cold water and dried to afford 2-bromo-4-fluoro-6-nitrophenylamine as an orange powder (55 g, 94%): $\delta_H$ (360 MHz, CDCl$_3$) 6.49 (2H, br), 7.56 (1H, dd, J 7 and 3), 7.90 (1H, dd, J 9 and 3).

A mixture of 2-bromo-4-fluoro-6-nitrophenylamine (55 g, 234 mmol) in 50% sulphuric acid (500 ml) was cooled to 0° C. then treated dropwise with a solution of sodium nitrite (22.6 g, 328 mmol) in water (100 ml) keeping the internal temperature <5° C. Following the addition of the sodium nitrite the reaction was stirred at <5° C. for 1 h. Ethanol (75 ml) was then added followed by ferrous sulfate heptahydrate (32.5 g, 117 mmol) and the reaction stirred at ambient temperature for 2 h. The reaction was diluted with water (1 l) and extracted with dichloromethane (2×500 ml). The organics were combined, washed with saturated aqueous sodium hydrogencarbonate, water and brine, then dried for 1 h over anhydrous magnesium sulfate containing decolorizing charcoal (5 g). Filtration through glass micro-fibre filter paper (Whatman GF/A) and evaporation to dryness gave an oil which on standing furnished 1-bromo-3-fluoro-5-nitrobenzene as colourless crystals (50 g, 97%): $\delta_H$ (360 MHz, CDCl$_3$) 7.61 (1H, ddd, J 8, 2 and 2), 7.90 (1H, ddd, J 8, 2 and 2), 8.20–8.23 (1H, m).

A mixture of 1-bromo-3-fluoro-5-nitrobenzene (17.6 g, 80 mmol), potassium acetate (15.7 g, 160 mmol) and bis(neopentyl glycolato)diboron in 1,4-dioxane (200 ml) was degassed with nitrogen for 30 min before adding dichloro[1,1'-bis(diphenylphosphino)ferrocene]palladium(II) dichloromethane adduct (1.96 g, 2.4 mmol). The reaction was heated at 90° C. for 16 h, cooled to ambient temperature, filtered (washing the filter cake with a small quantity of dichloromethane) and the filtrate concentrated in vacuo. The residue was partitioned between diethyl ether (300 ml) and 2M sodium hydroxide (300 ml) and the organics discarded. The aqueous was washed with more ether and then cooled in an ice-water bath. The pH was adjusted to approximately 6 with 36% hydrochloric acid and allowed to stand overnight. The resulting solid was collected by filtration, washed with ice-cold water and dried under vacuum over phosphorus pentoxide to furnish 2-(3-fluoro-5-nitrophenyl)-5,5-dimethyl-[1,3,2]dioxaborinane as a buff-coloured solid (15 g, 74%): $\delta_H$ (400 MHz, DMSO) 0.97 (6H, s), 3.81 (4H, s), 7.81 (1H, dd, J 8 and 2), 8.17 (1H, ddd, J 8, 2 and 2), 8.67 (1H, s).

A mixture of 2-(3-fluoro-5-nitrophenyl)-5,5-dimethyl-[1,3,2]dioxaborinane (15 g, 59 mmol) and 2-bromobenzonitrile (12.4 g, 68.2 mmol) in 1,2-dimethoxyethane (125 ml) and 2M aqueous sodium carbonate (50 ml) was degassed with nitrogen for 30 min then treated with tetrakis(triphenylphosphine)palladium(0) (2.06 g, 1.8 mmol). The reaction was then heated at 90° C. for 16 h, cooled to ambient temperature and partitioned between ethyl acetate and water. The organics were washed with brine, dried over anhydrous magnesium sulfate, filtered and pre-adsorbed onto silica. Purification by dry flash chromatography on silica, eluting with isohexane (containing 1% methanol) on a gradient of ethyl acetate (10–40%) afforded 3'-fluoro-5'-nitrobiphenyl-2-carbonitrile as a cream-coloured solid (10.3 g, 72%): $\delta_H$ (400 MHz, CDCl$_3$) 7.54–7.61 (2H, m), 7.65 (1H, ddd, J 8, 2 and 2), 7.74 (1H, ddd, J 8, 8 and 2), 7.84 (1H, dd, J 8 and 2), 8.03 (1H, ddd, J 8, 8 and 2), 8.22–8.24 (1H, m).

A cooled (0° C.) suspension of 3'-fluoro-5'-nitrobiphenyl-2-carbonitrile (8.9 g, 37 mmol) in ethanol (70 ml) and tetrahydrofuran (70 ml) was treated with tin(II) chloride dihydrate (29 g, 129 mmol) and the mixture was stirred at ambient temperature for 4 h. The solvent was removed in vacuo and the residue treated with ice-cold 2N sodium hydroxide (400 ml). The resulting slurry was stirred for 30 min then extracted with dichloromethane (2×400 ml). The organics were combined, washed with water and brine, dried over anhydrous magnesium sulfate, filtered and pre-adsorbed onto silica. Purification by dry flash chromatography on silica, eluting with dichloromethane containing 0.5% triethylamine, afforded 5'-amino-3'-fluorobiphenyl-2-carbonitrile as a white solid (4.5 g, 58%): $\delta_H$ (400 MHz, CDCl$_3$) 3.90 (2H, br), 6.45 (1H, ddd, J 8, 2 and 2), 6.58–6.63 (2H, m), 7.44 (1H, ddd, J 8, 8 and 2), 7.48 (1H, dd, J 8 and 2), 7.62 (1H, ddd, J 8, 8 and 2), 7.74 (1H, dd, J 8 and 2).

A warm solution of 5'-amino-3'-fluorobiphenyl-2-carbonitrile (4.5 g, 21 mmol) in 1,4-dioxane (20 ml) was treated with 48% hydrobromic acid (100 ml) and the resulting suspension stirred and cooled to 3° C. (internal temperature). A solution of sodium nitrite (1.7 g, 24 mmol) in water (4 ml) was then added dropwise over 20 min keeping the internal temperature <5° C. Stirring at <5° C. was continued for 2 h before adding a cooled (5° C.) solution of copper(I) bromide (9.1 g, 3 mmol) in 48% hydrobromic acid (30 ml). The resulting purple reaction mixture was stirred at 5° C. for 10 min then warmed to 50° C. for 20 min. The reaction was diluted with ice-cold water (500 ml) and extracted with ethyl acetate (2×200 ml). The organics were combined, washed with 5% aqueous sodium sulphite and saturated aqueous ammonium chloride, dried over anhydrous magnesium sulfate, filtered and pre-adsorbed onto silica. Purification on silica, eluting with isohexane (containing 1% methanol) on a gradient of ethyl acetate (5–15%) afforded 5'-bromo-3'-fluorobiphenyl-2-carbonitrile as a white solid (5.52 g, 94%).

A mixture of 5'-bromo-3'-fluorobiphenyl-2-carbonitrile (5.52 g, 20 mmol), potassium acetate (5.9 g, 60 mmol) and bis(pinacolato)diboron (6.1 g, 24 mmol) in 1,4-dioxane (60 ml) was degassed with nitrogen for 20 min. Dichloro[1,1'-bis(diphenylphosphino)ferrocene]palladium(II) dichloromethane adduct (500 mg, 0.6 mmol) was then added and the reaction heated at 90° C. for 24 h. The mixture was cooled to ambient temperature then partitioned between 2N sodium hydroxide and diethyl ether. The aqueous layer was washed with a further portion of diethyl ether and the organics were discarded. The aqueous extract was made acidic (pH 6) with 36% hydrochloric acid and then extracted with diethyl ether. The organic extract was dried over anhydrous magnesium sulfate, filtered and pre-adsorbed onto silica. Purification by dry flash chromatography on silica, eluting with isohexane on a gradient of ethyl acetate (5–10%) afforded 3'-fluoro-5'-(4,4,5,5-tetramethyl-[1,3,2] dioxaborolan-2-yl)biphenyl-2-carbonitrile as a colourless viscous oil (4.2 g, 65%) which crystallised on standing: $\delta_H$ (400 MHz, CDCl$_3$) 1.35 (12H, s), 7.36 (1H, ddd, J 8, 2 and 2), 7.46 (1H, ddd, J 8, 8 and 2), 7.52 (1H, dd, J 8 and 2), 7.57 (1H, ddd, J 8, 2 and 2), 7.64 (1H, ddd, J 8, 8 and 2), 7.70–7.72 (1H, m), 7.76 (1H, dd, J 8 and 2).

3-Bromo-7-trifluoromethylimidazo[1,2-α]pyrimidine was coupled with 3'-fluoro-5'-(4,4,5,5-tetramethyl-[1,3,2] dioxaborolan-2-yl)biphenyl-2-carbonitrile as described in Example 1 to give 3'-fluoro-5'-(7-trifluoromethylimidazo[1,2-α]pyrimidin-3-yl)biphenyl-2-carbonitrile as a yellow solid: $\delta_H$ (360 MHz, DMSO) 7.55 (1H, d, J 7), 7.62–7.69 (2H, m), 7.80–7.87 (4H, m), 8.03 (1H, d, J 8), 8.40 (1H, s), 9.47 (1H, d, J 7); m/z (ES$^+$) 383 (M$^+$+H).

EXAMPLE 30

3'-Fluoro-5'-(7-hydroxymethylimidazo[1,2-α] pyrimidin-3-yl)biphenyl-2-carbonitrile 3-Bromoimidazo[1,2-α]pyrimidin-7-ylmethanol was coupled with 3'-fluoro-5'-(4,4,5,5-tetramethyl-[1,3,2] dioxaborolan-2-yl)biphenyl-2-carbonitrile as described in Example 1 to give 3'-fluoro-5'-(7-hydroxymethylimidazo[1,2-α]pyrimidin-3-yl)biphenyl-2-carbonitrile as a yellow solid: $\delta_H$ (360 MHz, DMSO) 4.71 (2H, d, J 6), 5.81 (1H, t, J 6), 7.31 (1H, d, J 7), 7.63 (1H, d, J 9), 7.74–7.95 (5H, m), 8.10 (1H, d, J 8), 8.14 (1H, s), 9.26 (1H, d, J 7); m/z (ES$^+$) 345 (M$^+$+H).

EXAMPLE 31

2'-Fluoro-3'-(7-trifluoromethylimidazo[1,2-α] pyrimidin-3-yl)biphenyl-2-carbonitrile A mixture of 2-bromobenzonitrile (5.1 g, 28 mmol), 2-fluorobenzeneboronic acid (4.9 g, 35 mmol) and potassium fluoride (5.37 g, 92 mmol) in tetrahydrofuran (50 ml) was degassed with nitrogen for 10 min. This mixture was then treated with tris(dibenzylideneacetone)dipalladium(0) (510 mg, 0.56 mmol) followed by tri-tert-butylphosphine (5.6 ml of a 0.2M solution in 1,4-dioxane, 1.12 mmol) and the reaction was stirred at ambient temperature for 15 min. The resulting slurry was then heated at 50° C. for 30 min in order to consume remaining starting materials and then cooled to ambient temperature. The reaction mixture was filtered, washing the filter-cake with tetrahydrofuran (50 ml). The filtrate was evaporated to dryness and the residue partitioned between ethyl acetate and water. The organics were washed with brine, dried over anhydrous magnesium sulfate, filtered and pre-adsorbed onto silica. Purification by chromatography on silica eluting with isohexane on a gradient of ethyl acetate (5–10%) gave 2'-fluorobiphenyl-2-carbonitrile as a pale yellow solid (5.5 g, 100%): $\delta_H$ (360 MHz, CDCl$_3$) 7.19–7.29 (2H, m), 7.40–7.52 (4H, m), 7.65 (1H, ddd, J 8, 8 and 1), 7.79 (1H, dd, J 8 and 1).

A cooled (−78° C.) solution of n-butyllithium (11.7 ml of a 2.5M solution in hexanes, 29.1 mmol) in tetrahydrofuran (100 ml) was treated with 2,2,6,6-tetramethylpiperidine (5.16 ml) and stirring at −78° C. was continued for 15 min. The reaction was then treated with a cooled (0° C.) solution of 2'-fluorobiphenyl-2-carbonitrile (5.50 g) in tetrahydrofuran (15 ml) added dropwise over 10 min. This mixture was stirred at −78° C. for 2 h and then treated with trimethyl borate (6.30 ml) added dropwise over 5 min. The reaction was stirred at −78° C. for 10 min then allowed to warm to ambient temperature. 2N Hydrochloric acid (5 ml) was added and the mixture evaporated to dryness. The residue was stirred with 2N hydrochloric acid (95 ml) for 30 min and then extracted with diethyl ether (2×100 ml). The organics were combined, extracted with 2N sodium hydroxide (100 ml) and the organics discarded. The aqueous was cooled to 0° C. and made just acidic (pH 6) with 36% hydrochloric acid. After stirring at 0° C. for 1 h the resulting solid was collected by filtration and dried. Crystallisation from diethyl ether/isohexane afforded 2'-cyano-2-fluorobiphenyl-3-boronic acid as a yellow solid (4.50 g, 67%): $\delta_H$ (360 MHz, CDCl$_3$) 5.23 (1H, s), 5.25 (1H, s), 7.33 (1H, m), 7.42–7.56 (3H, m), 7.65 (1H, m), 7.77 (1H, m), 7.93 (1H, m).

3-Bromo-7-trifluoromethylimidazo[1,2-α]pyrimidine was coupled with 2'-cyano-2-fluorobiphenyl-3-boronic acid as described in Example 1 to give 2'-fluoro-3'-(7-trifluoromethylimidazo[1,2-α]pyrimidin-3-yl)biphenyl-2-carbonitrile as an off-white solid (70 mg, 18%): $\delta_H$ (400 MHz, DMSO) 7.60–7.64 (2H, m), 7.70 (1H, d, J 1), 7.76 (1H, d, J 2), 7.83 (1H, s), 7.87–7.91 (2H, m), 8.05 (1H, dd, J 7 and 1), 8.35 (1H, s), 9.13 (1H, dd, J 7 and 3); m/z (ES$^+$) 383 (M$^+$+H).

EXAMPLE 32

3-[4-Fluoro-3-(pyridin-2-yl)phenyl]-7-trifluoromethylimidazo[1,2-α]pyrimidine

To a cooled (−78° C.) solution of 3-bromo-7-trifluoromethylimidazo[1,2-α]pyrimidine (1.0 g, 3.78 mmol) in tetrahydrofuran (20 ml) was added isopropylmagnesium chloride (2.08 ml of a 2M solution in tetrahydrofuran, 4.16 mmol). After stirring for 5 min tributyltin chloride (1.2 ml, 4.42 mmol) was added and the reaction stirred for 10 min at −78° C. then allowed to warm to ambient temperature to give a solution of 3-tributylstannyl-7-trifluoromethylimidazo[1,2-α]pyrimidine in tetrahydrofuran (ca. 0.15M): m/z (ES$^+$) 474, 476, 478 (M$^+$+H).

To 3-tributylstannyl-7-trifluoromethylimidazo[1,2-α]pyrimidine (73 ml of a 0.13M solution in tetrahydrofuran, 9.44 mmol) was added 5-bromo-2-fluoronitrobenzene (4.20 g, 19 mmol) followed by tetrakis(triphenylphosphine)palladium(0) (0.62 g). The resulting mixture was heated at reflux for 4 h. The solvent was evaporated at reduced pressure and the residue chromatographed on silica gel eluting with 30% ethyl acetate in dichloromethane to afford 3-(4-fluoro-3-nitrophenyl)-7-trifluoromethylimidazo[1,2-α]pyrimidine: $\delta_H$ (400 MHz, DMSO) 7.59 (1H, d, J 7), 7.83 (1H, dd, J 11 and 9), 8.18 (1H, m), 8.36 (1H, s), 8.53 (1H, dd, J 7 and 2), 9.36 (1H, d, J 7); m/z (ES$^+$) 327 (M$^+$+H).

To a suspension of 3-(4-fluoro-3-nitrophenyl)-7-trifluoromethylimidazo[1,2-α]pyrimidine (0.819 g, 2.51 mmol) in ethanol (10 ml) was added anhydrous tin(II) chloride (2.0 g). After stirring at ambient temperature for 2 h the resulting solution was treated with 30% ammonium hydroxide (40 ml). This mixture was stirred for 10 min then concentrated at reduced pressure. The residue was then treated with ethanol and evaporated at reduced pressure to remove residual water. This residue was then boiled with 10% methanol in dichloromethane and insoluble material removed by filtration. The filtrate was evaporated in vacuo, the residue treated with a hot solution of 50% toluene in ethyl acetate and insoluble material removed by filtration. The filtrate was evaporated at reduced pressure and the residue crystallised from hot toluene to furnish 2-fluoro-5-(7-trifluoromethylimidazo[1,2-α]pyrimidin-3-yl) phenylamine: $\delta_H$ (400 MHz, DMSO) 5.42 (2H, br), 6.87 (1H, m), 7.07 (1H, dd, J 9 and 2), 7.20 (1H, dd, J 12 and 8), 7.50 (1H, d, J 7), 8.13 (1H, s), 9.18 (1H, d, J 7); m/z (ES$^+$) 297 (M$^+$+H).

To a cooled (4° C.) mixture of copper(II) bromide (0.285 g) in anhydrous acetonitrile (4 ml) was added tert-butyl nitrite (0.20 ml) followed by a solution of 2-fluoro-5-(7-trifluoromethylimidazo[1,2-α]pyrimidin-3-yl)phenylamine (0.297 g, 1 mmol) in acetonitrile (8 ml) added dropwise over 5 min. The resulting mixture was then stirred at ambient temperature for 16 h. The reaction mixture was purified by chromatography on silica gel eluting with 10% ethyl acetate in dichloromethane to afford 3-(3-bromo-4-fluorophenyl)-7-trifluoromethylimidazo[1,2-α]pyrimidine: m/z (ES$^+$) 360, 362 (M$^+$+H).

To a solution of 3-(3-bromo-4-fluorophenyl)-7-trifluoromethylimidazo[1,2-α]pyrimidine (0.190 g, 0.528 mmol) in N,N-dimethylformamide (5 ml) was added 2-tri-n-butylstannylpyridine (0.265 g) followed by dichloro[1,1'-bis(diphenylphosphino)ferrocene]palladium(II) dichloromethane adduct (0.187 g). The mixture was heated at 100° C. for 9 h. The solvent was evaporated at reduced pressure and the residue chromatographed on silica gel eluting with 4% methanol in dichloromethane. The residue was then loaded onto a cartridge of strong cation-exchange resin. Elution with methanol gave non-basic impurities. Further elution with 2M ammonia in methanol gave crude product. Further purification by preparative thin-layer chromatography on silica gel using 4% methanol in dichloromethane as eluant and crystallisation of the residue from toluene/isohexane afforded 3-[4-fluoro-3-(pyridin-2-yl)phenyl]-7-trifluoromethylimidazo[1,2-α]pyrimidine as yellow needles: $\delta_H$ (400 MHz, DMSO) 7.46 (1H, m), 7.53 (1H, d, J 7), 7.61 (1H, dd, J 11 and 9), 7.86–7.91 (2H, m), 7.95–7.99 (1H, m), 8.24 (1H, dd, J 7 and 2), 8.30 (1H, s), 8.74–8.76 (1H, m), 9.27 (1H, d, J 7); m/z (ES$^+$) 359 (M$^+$+H).

EXAMPLE 33

3-[4-Fluoro-3-(pyridin-3-yl)phenyl]-7-trifluoromethylimidazo[1,2-α]pyrimidine 3-(3-Bromo-4-fluorophenyl)-7-trifluoromethylimidazo[1,2-α]pyrimidine was coupled with 3-tri-n-butylstannylpyridine as described in Example 32 to give 3-[4-fluoro-3-(pyridin-3-yl)phenyl]-7-trifluoromethylimidazo[1,2-α]pyrimidine: $\delta_H$ (400 MHz, DMSO) 7.51 (1H, d, J 7), 7.53–7.64 (2H, m), 7.85–7.89 (1H, m), 8.03 (1H, dd, J 7 and 2), 8.12 (1H, dd, J 8 and 2), 8.34 (1H, s), 8.66 (1H, dd, J 5 and 2), 8.90 (1H, t, J 2), 9.38 (1H, d, J 7); m/z (ES$^+$) 359 (M$^+$+H).

EXAMPLE 34

2'-Fluoro-5'-[7-([1,2,4]triazol-1-ylmethyl)imidazo[1,2-α]pyrimidin-3-yl]biphenyl-2-carbonitrile To a solution of 2'-fluoro-5'-(7-hydroxymethylimidazo[1,2-α]pyrimidin-3-yl)biphenyl-2-carbonitrile (100 mg, 0.291 mmol) in dichloromethane (5 ml) was added carbon tetrabromide (289 mg, 0.872 mmol) and polymer-supported triphenylphosphine (291 mg, 0.872 mmol). This mixture was stirred at ambient temperature for 1 h followed by removal of the polymer by filtration. N,N-Dimethylformamide (5 ml) was added to the reaction mixture and dichloromethane removed by evaporation under vacuum without heating to give 5'-(7-bromomethylimidazo[1,2-α]pyrimidin-3-yl)-2'-fluorobiphenyl-2-carbonitrile as a solution in N,N-dimethylformamide.

To a solution of 1H-[1,2,4]triazole (30 mg, 0.435 mmol) in N,N-dimethylformamide was added sodium hydride (17 mg, 0.435 mmol) as a 60% dispersion in oil and the reaction stirred at ambient temperature for 0.5 h. To this mixture was added the previously prepared solution of 5'-(7- bromomethylimidazo[1,2-α]pyrimidin-3-yl)-2'-fluorobiphenyl-2-carbonitrile in N,N-dimethylformamide in a dropwise manner. This mixture was allowed to stir at ambient temperature for 16 h before removal of the reaction solvent in vacuo. The residue was purified by silica gel chromatography eluting with a mixture of dichloromethane, methanol and ammonia (90:5:0.5) to give 2'-fluoro-5'-[7-([1,2,4]triazol-1-ylmethyl)imidazo[1,2-α]pyrimidin-3-yl]biphenyl-2-carbonitrile: $\delta_H$ (360 MHz, CDCl$_3$) 5.57 (2H, s), 6.89 (1H, d, J 7.1), 7.41 (3H, t, J 9.5 ), 7.52–7.62 (4H, m), 7.68–7.73 (1H, m), 7.82–7.85 (1H, m), 7.92 (1H, s), 8.01 (1H, s), 8.32 (1H, s), 8.80 (1H, s); m/z (ES$^+$) 396 (M$^+$+H).

EXAMPLE 35

2'-Fluoro-5'-[7-(imidazol-1-ylmethyl)imidazo[1,2-α]pyrimidin-3-yl]biphenyl-2-carbonitrile 5'-(7-Bromomethylimidazo[1,2-α]pyrimidin-3-yl)-2'-fluorobiphenyl-2-carbonitrile was reacted with the sodium salt of imidazole as described in Example 34 to give 2'-fluoro-5'-[7-(imidazol-1-ylmethyl)imidazo[1,2-α]pyrimidin-3-yl]biphenyl-2-carbonitrile: $\delta_H$ (360 MHz, CDCl$_3$) 5.33 (2H, s), 6.62 (1H, d, J 7), 7.05 (1H, s), 7.15 (1H, s), 7.38–7.43 (1H, m), 7.52–7.73 (6H, m), 7.83 (1H, d, J 7), 7.92 (1H, s), 8.80 (1H, s); m/z (ES$^+$) 395 (M$^+$+H).

EXAMPLE 36

2'-Fluoro-5'-[7-([1,2,3]triazol-1-ylmethyl)imidazo[1,2-α]pyrimidin-3-yl]biphenyl-2-carbonitrile and 2'-Fluoro-5'-[7-([1,2,3]triazol-2-ylmethyl)imidazo[1,2-α]pyrimidin-3-yl]biphenyl-2-carbonitrile 5'-(7-Bromomethylimidazo[1,2-α]pyrimidin-3-yl)-2'-fluorobiphenyl-2-carbonitrile was reacted with the sodium derivative of 1H-[1,2,3]triazole (0.58 mmol) as described in Example 34 to afford (in order of elution on silica gel) 2'-fluoro-5'-[7-([1,2,3]triazol-2-ylmethyl)imidazo[1,2-α]pyrimidin-3-yl]biphenyl-2-carbonitrile: $\delta_H$ (360 MHz, CDCl$_3$) 5.92 (2H, s), 6.74 (1H, d, J 6.4), 7.42–7.47 (1H, m), 7.54–7.64 (4H, m), 7.70–7.74 (3H, m), 7.83 (1H, dd, J 6.0 and 0.94), 8.08 (1H, s), 8.90 (1H, s); m/z (ES$^+$) 396 (M$^+$+H); and 2'-fluoro-5'-[7-([1,2,3]triazol-1-ylmethyl)imidazo[1,2-α]pyrimidin-3-yl]biphenyl-2-carbonitrile: $\delta_H$ (360 MHz, CDCl$_3$) 5.83 (2H, s), 7.04 (1H, d, J 6.4), 7.45 (1H, t, J 7.8), 7.54 (1H, m), 7.59–7.65 (3H, m), 7.70–7.72 (1H, m), 7.79 (1H, s), 7.79–7.83 (2H, m), 8.03 (1H, s), 8.94 (1H, s); m/z (ES$^+$) 396 (M$^+$+H).

EXAMPLE 37

3-[4-Fluoro-3-(pyridin-4-yl)phenyl]-7-trifluoromethylimidazo[1,2-α]primidine

A solution of 3-(3-bromo-4-fluorophenyl)-7-trifluoromethylimidazo[1,2-α]pyrimidine (70 mg, 0.19 mmol) and 4-(tri-n-butylstannyl)pyridine (107 mg, 0.29 mmol) in N,N-dimethylacetamide (3 ml) was degassed with N$_2$. Tetrakis(triphenylphosphine)palladium(0) (30 mg, 0.026 mmol) and copper(I) iodide (15 mg, 0.079 mmol) was added and the mixture heated at 80° C. for 6 h. The solvent was evaporated in vacuo and the residue partitioned between dichloromethane and water, separated and the aqueous re-extracted with dichloromethane. The combined organics were washed with brine, dried (MgSO$_4$) and evaporated. The residue was purified using preparative thin-layer chromatography on silica gel, using 30% ethyl acetate/dichloromethane as the eluent, to give a yellow solid. Further purification using preparative thin-layer chromatography on silica gel, eluting with 2% methanol/dichloromethane, afforded 3-[4-fluoro-3-(pyridin-4-yl)phenyl]-7-trifluoromethylimidazo[1,2-α]pyrimidine as a cream solid: $\delta_H$ (360 MHz, DMSO) 7.52 (1H, d, J 7), 7.63 (1H, dd, J 10 and 8), 7.71–7.73 (2H, m), 7.90 (1H, ddd, J 9, 5 and 2), 8.04 (1H, dd, J 7 and 2), 8.33 (1H, s), 8.72 (2H, m), 9.37 (1H, d, J 7); m/z (ES$^+$) 359 (M$^+$+H).

Alternative Method:

3-Bromo-7-trifluoromethylimidazo[1,2-α]pyrimidine was coupled with 4-[2-fluoro-5-(4,4,5,5-tetramethyl-[1,3,2]dioxaborolan-2-yl)phenyl]pyridine (cf. Example 40 below) as described in Example 1 to give 3-[4-fluoro-3-(pyridin-4-yl)phenyl]-7-trifluoromethylimidazo[1,2-α]pyrimidine as a cream solid.

EXAMPLE 38

3-[2,4-Difluoro-3-(pyridin-3-yl)phenyl]-7-trifluoromethylimidazo[1,2-α]pyrimidine A mixture of 3-bromo-2,4-difluorophenylamine (prepared according to the procedure described in EP-A-0184384) (12.5 g, 60 mmol), diethyl(3-pyridyl)borane (10.6 g, 72 mmol) and potassium carbonate (16.6 g, 120 mmol) in tetrahydrofuran (150 ml) and water (50 ml) was degassed with nitrogen for 15 min. To this mixture was added tetrakis(triphenylphosphine)palladium(0) (2.1 g, 1.8 mmol) and the reaction was heated at reflux for 4 days. The mixture was cooled to ambient temperature and the majority of the tetrahydrofuran removed on a rotary evaporator. The residue was diluted with water (250 ml), extracted with ethyl acetate (300 ml), the organics were washed with water, brine, dried over anhydrous magnesium sulfate, filtered and pre-adsorbed onto silica. Purification by chromatography on silica gel eluting with isohexane (containing 1% triethylamine) on a gradient of ethyl acetate (10–50%) afforded 2,4-difluoro-3-(pyridin-3-yl)phenylamine as a cream-coloured solid (5.8 g, 47%): $\delta_H$ (400 MHz, CDCl$_3$) 3.69 (2H, br), 6.72–6.88 (2H, m), 7.39 (1H, dd, J 8 and 5), 7.80 (1H, d, J 8), 8.62 (1H, dd, J 5 and 1), 8.72 (1H, s).

2,4-Difluoro-3-(pyridin-3-yl)phenylamine was bromodeaminated as described in Example 27 to afford 3-(3-bromo-2,6-difluorophenyl)pyridine as a white solid: $\delta_H$ (400 MHz, CDCl$_3$) 6.97 (1H, ddd, J 9, 9 and 2), 7.40–7.44 (1H, m), 7.55–7.60 (1H, m), 7.77–7.81 (1H, m), 8.66 (1H, dd, J 5 and 2), 8.71 (1H, s).

A mixture of 3-(3-bromo-2,6-difluorophenyl)pyridine (2.97 g, 11 mmol), potassium acetate (2.16 g, 22 mmol) and bis(neopentyl glycolato)diboron (2.86 g, 12.7 mmol) in 1,4-dioxane (30 ml) was heated at 90° C. for 16 h. The reaction was cooled, filtered (washing the filter cake with a small quantity of diethyl ether) and the filtrate concentrated in vacuo. The residue was partitioned between diethyl ether (100 ml) and 1M sodium hydroxide (100 ml) and the organics discarded. The aqueous was washed with more diethyl ether and then cooled in an ice-water bath. The pH was adjusted to approximately 6 with 36% hydrochloric acid, and allowed to stand for 1 h. The resulting solid was collected by filtration and dried under vacuum to afford 2,4-difluoro-3-(pyridin-3-yl)benzeneboronic acid (2.2 g, 85%) as a grey solid: m/z (ES$^+$) 236 (M$^+$+H).

3-Bromo-7-trifluoromethylimidazo[1,2-α]pyrimidine was coupled with 2,4-difluoro-3-(pyridin-3-yl)benzeneboronic acid as described in Example 1 to give 3-[2,4-difluoro-3-(pyridin-3-yl)phenyl]-7-trifluoromethylimidazo[1,2-α]pyrimidine as an off-white solid. Bis-hydrochloride salt (from ethyl acetate/ethanol): $\delta_H$ (400 MHz, DMSO) 7.60–7.65 (2H, m), 7.90–7.96 (2H, m), 8.34 (1H, s), 8.47 (1H, d, J 8), 8.87 (1H, dd, J 5 and 1), 9.08 (1H, s), 9.32 (1H, dd, J 7 and 3).

EXAMPLE 39

3-[2 4-Difluoro-3-(pyridin-2-yl)phenyl]-7-trifluoromethylimidazo[1,2-α]pyrimidine A mixture of 3-bromo-2,4-difluorophenylamine (5.2 g, 25 mmol), 2-tri-n-butylstannylpyridine (11.0 g, 30 mmol), lithium chloride (10.6 g, 250 mmol) and copper(I) iodide (476 mg, 2.5 mmol) in tetrahydrofuran (100 ml) was degassed with nitrogen for 20 min before adding tetrakis (triphenylphosphine)palladium(0). The reaction was then heated at reflux for 5 days. The mixture was cooled to ambient temperature then partitioned between ethyl acetate and 10% ammonium hydroxide. The organics were washed with water, brine, dried over anhydrous magnesium sulfate, filtered and pre-adsorbed onto silica. Purification by chromatography on silica eluting with isohexane (containing 0.5% triethylamine) on a gradient of ethyl acetate (20–50%) gave 2,4-difluoro-3-(pyridin-2-yl)phenylamine as a brown oil (550 mg, 11%): $\delta_H$ (400 MHz, CDCl$_3$) 3.65 (2H, br), 6.74–6.84 (2H, m), 7.31 (1H, ddd, J 7, 5 and 1), 7.46–7.51 (1H, m), 7.78 (1H, ddd, J 8, 8 and 2), 8.74–8.77 (1H, m); m/z (ES$^+$) 207 (M$^+$+H).

2,4-Difluoro-3-(pyridin-2-yl)phenylamine was bromo-deaminated as described in Example 27 to afford a 50:50 mixture of 2-(3-bromo-2,6-difluorophenyl)pyridine and 2-(2,6-difluorophenyl)pyridine as a colourless oil which was used without further purification: m/z (ES$^+$) 269/272 and 192 (M$^+$+H).

A mixture of crude 2-(3-bromo-2,6-difluorophenyl) pyridine (300 mg, 1.1 mmol), potassium acetate (220 mg, 2.2 mmol) and bis(pinacolato)diboron (350 mg, 1.4 mmol) in 1,4-dioxane (3 ml) was heated at 90° C. for 14 h. The reaction was cooled, filtered (washing the filter cake with a small quantity of diethyl ether) and the filtrate concentrated in vacuo. The residue was stirred with 2N sodium hydroxide (20 ml) for 10 min then filtered. The filtrate was washed with diethyl ether (2×20 ml) and the organics discarded. The aqueous phase was cooled in an ice-water bath, the pH was adjusted to approximately 8 with 5N hydrochloric acid then extracted with diethyl ether. The organics were dried over anhydrous magnesium sulfate, filtered and evaporated to dryness to furnish 2-[2,6-difluoro-3-(4,4,5,5-tetramethyl-[1,3,2]dioxaborolan-2-yl)phenyl]pyridine (170 mg, 48%) as a straw-coloured solid: m/z (ES$^+$) 318 (M$^+$+H).

3-Bromo-7-trifluoromethylimidazo[1,2-α]pyrimidine was coupled with 2-[2,6-difluoro-3-(4,4,5,5-tetramethyl-[1,3,2]dioxaborolan-2-yl)phenyl]pyridine as described in Example 1 to give 3-[2,4-difluoro-3-(pyridin-2-yl)phenyl]-7-trifluoromethylimidazo[1,2-α]pyrimidine as a pale yellow solid. Bis-hydrochloride salt (from ethyl acetate/ethanol): $\delta_H$ (360 MHz, DMSO) 7.55 (1H, dd, J 9 and 9), 7.62–7.68 (2H, m), 7.86–7.96 (2H, m), 8.14 (1H, ddd, J 8, 8 and 2), 8.38 (1H, s), 8.84 (1H, d, J 5), 9.30 (1H, dd, J 7 and 3); m/z (ES$^+$) 377 (M$^+$+H).

EXAMPLE 40

2-[3-(4-Fluoro-3-(pyridin-4-yl)phenyl)imidazo[1,2-α]pyrimidin-7-yl]propan-2-ol

To a degassed solution of 2-bromo-1-fluoro-4-nitrobenzene (6.44 g, 29.3 mmol), 4-tri-n-butylstannylpyridine (14.0 g, 38.0 mmol), lithium chloride (12.4 g, 293 mmol) and copper(I) iodide (0.56 g, 2.93 mmol) in N,N-dimethylacetamide (40 ml) was added tetrakis (triphenylphosphine)palladium(0) (1.69 g, 1.46 mmol) and the reaction heated at 80° C. for 18 h. After cooling to ambient temperature the solvent was evaporated and the residue was diluted with dichloromethane (800 ml) and the mixture stirred vigorously for 30 min then filtered. The organics were washed with water (500 ml) and brine (300 ml), dried over anhydrous magnesium sulfate, filtered and evaporated to give a black oil. The residue was purified by silica gel chromatography eluting with iso-hexane (containing 1% methanol and 1% triethylamine) on a gradient of ethyl acetate (20–50%) to give 4-(2-fluoro-5-nitrophenyl)pyridine as an off-white solid (5.60 g, 88%): $\delta_H$ (360 MHz, CDCl$_3$) 7.38 (1H, t, J 9), 7.50–7.53 (2H, m), 8.30–8.35 (1H, m), 8.41–8.44 (1H, m), 8.76–8.78 (2H, m).

To a solution of 4-(2-fluoro-5-nitrophenyl)pyridine (1.0 g, 5.58 mmol) in ethanol (30 ml) and ethyl acetate (10 ml) was added platinum(IV) oxide (52 mg) and the mixture stirred for 35 min under hydrogen (40 psi). The reaction was filtered through glass microfibre filter paper and the filtrate evaporated to dryness to give 4-fluoro-3-(pyridin-4-yl) phenylamine (862 mg, 100%) as a white solid: $\delta_H$ (360 MHz, CDCl$_3$) 3.49 (2H, s), 6.66–6.70 (1H, m), 6.71–6.76 (1H, m), 6.99 (1H, t, J 9), 7.44–7.46 (2H, m), 8.66 (2H, d, J 5).

4-Fluoro-3-(pyridin-4-yl)phenylamine (0.58 g, 3.08 mmol) was bromo-deaminated following the procedure given in Example 27 to give 4-(5-bromo-2-fluorophenyl) pyridine (464 mg, 60%) as a white solid: $\delta_H$ (360 MHz, CDCl$_3$) 7.38 (1H, t, J 9), 7.59–7.62 (2H, m), 7.68–7.73 (1H, m), 7.84 (1H, dd, J 7 and 3), 8.68 (2H, d, J 5 and 3).

A mixture of 4-(5-bromo-2-fluorophenyl)pyridine (3.8 g, 15.1 mmol), potassium acetate (2.96 g, 30.1 mmol) and bis(pinacolato)diboron (4.21 g, 16.6 mmol) in 1,4-dioxane (50 ml) and dimethylsulfoxide (1 ml) was degassed with nitrogen for 1 h. Dichloro[1,1'-bis(diphenylphosphino) ferrocene]palladium(II) dichloromethane adduct (370 mg, 0.5 mmol) was added and the mixture heated at 90° C. for 18 h. The reaction was cooled to ambient temperature, filtered and the filter-cake washed with diethyl ether. The filtrate was evaporated to dryness and the residue stirred with ice-cold 2N sodium hydroxide (100 ml) for 20 min. The aqueous mixture was filtered and the filtrate washed with diethyl ether (2×75 ml). The organics were discarded and the aqueous phase cooled to 0° C. before lowering the pH to 8 by addition of 36% hydrochloric acid. The resulting solid was collected by filtration and triturated with diethyl ether to afford 4-fluoro-3-(pyridin-4-yl)benzeneboronic acid as a buff-coloured solid (1.51 g, 46%): $\delta_H$ (360 MHz, DMSO) 7.34 (1H, dd, J 11 and 8), 7.61 (2H, d, J 5), 7.88–7.92 (1H, m), 8.05 (1H, dd, J 8 and 1), 8.26 (2H, s), 8.70 (2H, d, J 5); m/z (ES$^+$) 218 (M$^+$+H). The aqueous filtrate was extracted with diethyl ether. The organic phase was washed with water, brine, dried over anhydrous magnesium sulfate, filtered and evaporated to afford 4-[2-fluoro-5-(4,4,5,5-tetramethyl-[1,3,2]dioxaborolan-2-yl)phenyl]pyridine as a dark oil (1.28 g, 29%) that solidified on standing for a few days: $\delta_H$ (360 MHz, CDCl$_3$) 1.36 (12H, s), 7.19 (1H, dd, J 11 and 8), 7.50–7.53 (2H, m), 7.82–7.87 (1H, m), 7.93 (1H, dd, J 8 and 1), 8.67 (2H, dd, J 4 and 1); m/z (ES$^+$) 300 (M$^+$+H).

2-(3-Bromoimidazo[1,2-α]pyrimidin-7-yl)propan-2-ol was coupled with 4-fluoro-3-(pyridin-4-yl)benzeneboronic acid as described in Example 1 to give 2-[3-(4-fluoro-3-(pyridin-4-yl)phenyl)imidazo[1,2-α]pyrimidin-7-yl]propan- 2-ol as a white solid (240 mg, 58%). Bis-hydrochloride salt (from ethyl acetate/ethanol): $\delta_H$ (360 MHz, DMSO) 1.56 (6H, s), 7.77 (1H, dd, J 11 and 9), 7.85 (1H, d, J 7), 7.94–7.98 (1H, m), 8.12–8.15 (3H, m), 8.55 (1H, s), 8.95 (2H, d, J 6), 9.38 (1H, d, J 7); m/z (ES$^+$) 349 (M$^+$+H).

EXAMPLE 41

3-[2-Fluoro-3-(pyridin-3-yl)phenyl]-7-trifluoromethylimidazo[1,2-α]pyrimidine

3-Bromopyridine and 2-fluorobenzeneboronic acid were coupled using the procedure described in Example 31 to afford 3-(2-fluorophenyl)pyridine as a pale yellow oil which crystallised on standing: $\delta_H$ (360 MHz, DMSO) 7.33–7.40 (2H, m), 7.46–7.55 (2H, m), 7.61 (1H, ddd, J 8, 8 and 2), 7.96–8.01 (1H, m), 8.61 (1H, dd, J 5 and 2), 8.77 (1H, s).

3-(2-Fluorophenyl)pyridine was lithiated and reacted with trimethyl borate as described in Example 31 to give 2-fluoro-3-(pyridin-3-yl)benzeneboronic acid as a white solid: m/z (ES$^+$) 218 (M$^+$+H).

3-Bromo-7-trifluoromethylimidazo[1,2-α]pyrimidine was coupled with 2-fluoro-3-(pyridin-3-yl)benzeneboronic acid as described in Example 1 to give 3-[2-fluoro-3-(pyridin-3-yl)phenyl]-7-trifluoromethylimidazo[1,2-α]pyrimidine as an off-white solid. Bis-hydrochloride salt (from ethyl acetate/ethanol): $\delta_H$ (360 MHz, DMSO) 7.62 (2H, dd, J 7 and 7), 7.85–7.96 (3H, m), 8.36 (1H, s), 8.58 (1H, d, J 8), 8.86 (1H, dd, J 5 and 1), 9.14 (1H, s), 9.33 (1H, dd, J 7 and 3); m/z (ES$^+$) 359 (M$^+$+H).

EXAMPLE 42

2-[3-(2-Fluoro-3-(pyridin-3-yl)phenyl)imidazo[1,2-α]pyrimidin-7-yl]propan-2-ol 2-(3-Bromoimidazo[1,2-α]pyrimidin-7-yl)propan-2-ol was coupled with 2-fluoro-3-(pyridin-3-yl)benzeneboronic acid as described in Example 1 to give 2-[3-(2-fluoro-3-(pyridin-3-yl)phenyl)imidazo[1,2-α]pyrimidin-7-yl]propan-2-ol as a white solid. Bis-hydrochloride salt (from ethyl acetate/ethanol): $\delta_H$ (360 MHz, DMSO) 1.56 (6H, s), 7.65 (1H, dd, J 8 and 8), 7.79–7.83 (1H, m), 7.85–7.87 (2H, m), 7.92–7.97 (1H, m), 8.48 (1H, d, J 7), 8.55 (1H, s), 8.83 (1H, dd, J 5 and 1), 9.10 (1H, s), 9.29 (1H, dd, J 7 and 3); m/z (ES$^+$) 349 (M$^+$+H).

EXAMPLE 43

3-[2-Fluoro-3-(pyridin-4-yl)phenyl]-7-trifluoromethylimidazo[1,2-α]pyrimidine

A mixture of 4-bromopyridine hydrochloride (7.5 g, 38.6 mmol) and 2-fluorobenzeneboronic acid (6.75 g, 48 mmol) in tetrahydrofuran (80 ml) and 2M sodium carbonate (58 ml) was degassed with nitrogen for 20 min then tetrakis(triphenylphosphine)palladium(0) (1.34 g, 1.2 mmol) was added and the reaction heated at reflux for 24 h. The mixture was cooled to ambient temperature then partitioned between ethyl acetate and 10% sodium carbonate. The organics were washed with water, saturated sodium hydrogencarbonate, dried over anhydrous magnesium sulfate, filtered and pre-adsorbed onto silica. Purification by chromatography on silica eluting with isohexane (containing 0.5% triethylamine) on a gradient of ethyl acetate (20–40%) afforded 4-(2-fluorophenyl)pyridine as a yellow oil that crystallised on standing (6.26 g, 94%): $\delta_H$ (400 MHz, CDCl$_3$) 7.17–7.22 (1H, m), 7.26 (1H, ddd, J 8, 8 and 1), 7.38–7.44 (1H, m), 7.47–7.50 (3H, m), 8.68 (2H, d, J 4); m/z (ES$^+$) 174 (M$^+$+H).

4-(2-Fluorophenyl)pyridine was lithiated and reacted with trimethyl borate as described in Example 31 to afford 2-fluoro-3-(pyridin-4-yl)benzeneboronic acid as a white solid: m/z (ES$^+$) 218 (M$^+$+H).

3-Bromo-7-trifluoromethylimidazo[1,2-α]pyrimidine was coupled with 2-fluoro-3-(pyridin-4-yl)benzeneboronic acid as described in Example 1 to give 3-[2-fluoro-3-(pyridin-4-yl)phenyl]-7-trifluoromethylimidazo[1,2-α]pyrimidine as a white solid. Bis-hydrochloride salt (from ethyl acetate/ethanol): $\delta_H$ (400 MHz, DMSO) 7.64–7.70 (2H, m), 7.95–8.01 (2H, m), 8.37 (1H, s), 8.39 (2H, s), 9.05–9.07 (2H, m), 9.40 (1H, dd, J 7 and 3); m/z (ES$^+$) 359 (M$^+$+H).

EXAMPLE 44

2-[3-(2-Fluoro-3-(pyridin-4-yl)phenyl)imidazo[1,2-α]pyrimidin-7-yl]propan-2-ol 2-(3-Bromoimidazo[1,2-α]pyrimidin-7-yl)propan-2-ol was coupled with 2-fluoro-3-(pyridin-4-yl)benzeneboronic acid as described in Example 1 to give 2-[3-(2-fluoro-3-(pyridin-4-yl)phenyl)imidazo[1,2-α]pyrimidin-7-yl]propan-2-ol as a white solid. Bis-hydrochloride salt (from ethyl acetate/ethanol): $\delta_H$ (360 MHz, DMSO) 1.56 (6H, s), 7.69 (1H, dd, J 8 and 8), 7.84–7.92 (2H, m), 7.99–8.04 (1H, m), 8.21 (2H, d, J 6), 8.53 (1H, s), 8.98 (2H, d, J 6), 9.30 (1H, dd, J 7 and 3); m/z (ES$^+$) 349 (M$^+$+H).

EXAMPLE 45

3-[2-Fluoro-3-(pyridin-2-yl)phenyl]-7-trifluoromethylimidazo[1,2-α]pyrimidine

2-Bromopyridine and 2-fluorobenzeneboronic acid were coupled using the procedure described in Example 43 to afford 2-(2-fluorophenyl)pyridine as a pale yellow oil which crystallised on standing: $\delta_H$ (400 MHz, CDCl$_3$) 7.13–7.19 (1H, m), 7.24–7.28 (2H, m), 7.35–7.41 (1H, m), 7.73–7.81 (2H, m), 7.97 (1H, ddd, J 8, 8 and 2), 8.72–8.74 (1H, m); m/z (ES$^+$) 174 (M$^+$+H).

2-(2-Fluorophenyl)pyridine was lithiated and reacted with trimethyl borate as described in Example 31 to give 2-fluoro-3-(pyridin-2-yl)benzeneboronic acid as a white solid: m/z (ES$^+$) 218 (M$^+$+H).

3-Bromo-7-trifluoromethylimidazo[1,2-α]pyrimidine was coupled with 2-fluoro-3-(pyridin-2-yl)benzeneboronic acid as described in Example 1 to give 3-[2-fluoro-3-(pyridin-2-yl)phenyl]-7-trifluoromethylimidazo[1,2-α]pyrimidine as a white solid. Bis-hydrochloride salt (from ethyl acetate/ethanol): $\delta_H$ (360 MHz, DMSO) 7.61–7.71 (3H, m), 7.87–7.91 (1H, m), 8.07–8.11 (2H, m), 8.20–8.24 (1H, m), 8.42 (1H, s), 8.87 (1H, dd, J 5 and 1), 9.42 (1H, dd, J 7 and 3); m/z (ES$^+$) 359 (M$^+$+H).

EXAMPLE 46

2-[3-(2-Fluoro-3-(pyridin-2-yl)phenyl)imidazo[1,2-α]pyrimidin-7-yl]propan-2-ol 2-(3-Bromoimidazo[1,2-α]pyrimidin-7-yl)propan-2-ol was coupled with 2-fluoro-3-(pyridin-2-yl)benzeneboronic acid as described in Example 1 to give 2-[3-(2-fluoro-3-(pyridin-2-yl)phenyl)imidazo[1,2-α]pyrimidin-7-yl]propan-2-ol as a white solid. Bis-hydrochloride salt (from ethyl acetate/ethanol): $\delta_H$ (360 MHz, DMSO) 1.57 (6H, s), 7.62 (1H, dd, J 7 and 5), 7.64 (1H, s), 7.80–7.85 (1H, m), 7.89 (1H, d, J 7), 8.03 (1H, s), 8.10–8.19 (2H, m), 8.62 (1H, s), 8.83 (1H, d, J 5), 9.35 (1H, dd, J 7 and 3); m/z (ES$^+$) 349 (M$^+$+H).

EXAMPLE 47

3-[4-Fluoro-3-(4-methylpyridin-2-yl)phenyl]-7-trifluoromethylimidazo[1,2-α]primidine A degassed solution of 2-bromo-4-methylpyridine (1.17 g, 6.8 mmol) and 2-(2-fluoro-5-nitrophenyl)-4,4,5,5-tetramethyl-[1,3,2]dioxaborolane (2 g, 7.49 mmol) was formed in 1,4-dioxane (20 ml). Potassium phosphate (4.76 g, 22 mmol) and dichloro[1,1'-bis(diphenylphosphino)ferrocene]palladium(II) dichloromethane adduct (300 mg, 0.4 mmol) were added and the mixture stirred for 16 h at 80° C. The reaction was allowed to cool to ambient temperature and poured into water (100 ml) and extracted with ethyl acetate (4×50 ml). The combined organic phases were dried over anhydrous magnesium sulfate, filtered and evaporated to dryness. Purification by chromatography on silica gel eluting with dichloromethane gave 2-(2-fluoro-5-nitrophenyl)-4-methylpyridine as a yellow solid: $\delta_H$ (400 MHz, CDCl$_3$) 8.96 (1H, dd, J 7 and 3), 8.62 (1H, d, J 5), 8.24–8.28 (1H, m), 7.65 (1H, s), 7.31 (1H, dd, J 9 and 9), 7.17 (1H, d, J 5), 2.45 (3H, s).

To a solution of 2-(2-fluoro-5-nitrophenyl)-4-methylpyridine (0.6 g, 2.6 mmol) in ethanol (50 ml) was added platinum(IV) oxide (100 mg) and the mixture stirred for 35 min under hydrogen (40 psi). The catalyst was filtered off and the solution evaporated to dryness to give 4-fluoro-3-(4-methylpyridin-2-yl)phenylamine as a brown oil: $\delta_H$ (400 MHz, CDCl$_3$) 8.55 (1H, d, J 5), 7.59–7.62 (1H, m), 7.27 (1H, dd, J 6 and 3), 7.06–7.09 (1H, m), 6.95 (1H, dd, J 11 and 9), 6.64–6.68 (1H, m), 2.60–3.20 (2H, br), 2.41 (3H, s); m/z (ES$^+$) 203 (M$^+$+H).

4-Fluoro-3-(4-methylpyridin-2-yl)phenylamine was bromo-deaminated using the procedure described in Example 32 to furnish 2-(5-bromo-2-fluorophenyl)-4-methylpyridine as a yellow solid: m/z (ES$^+$) 266, 268 (M$^+$+H).

2-(5-Bromo-2-fluorophenyl)-4-methylpyridine was coupled to 3-tributylstannyl-7-trifluoromethylimidazo[1,2-α]pyrimidine by the method of Example 32. Purification by chromatography on silica gel eluting with dichloromethane containing 1% methanol, then crystallisation from ethyl acetate/isohexane, gave 3-[4-fluoro-3-(4-methylpyridin-2-yl)phenyl]-7-trifluoromethylimidazo[1,2-α]pyrimidine as a yellow powder: $\delta_H$ (400 MHz, CDCl$_3$) 8.87 (1H, d, J 7), 8.58 (1H, d, J 5), 8.24 (1H, dd, J 7 and 2), 8.12 (1H, s), 7.71 (1H, s), 7.53–7.58 (1H, m), 7.38 (1H, dd, J 11 and 8), 7.26 (1H, d, J 7), 7.16 (1H, d, J 5), 2.46 (3H, s); m/z (ES$^+$) 373 (M$^+$+H).

EXAMPLE 48

3-[4-Fluoro-3-(pyridazin-3-yl)phenyl]-7-trifluoromethylimidazo[1,2-α]pyrimidine A degassed solution of 3-chloropyridazine (1.96 g, 17 mmol) (prepared according to Wermuth et al., *J. Med. Chem.*, 1997, 30(2), 239–249) and 2-(2-fluoro-5-nitrophenyl)-4,4,5,5-tetramethyl-[1,3,2]dioxaborolane (6.86 g, 25 mmol) was formed in 1,4-dioxane (20 ml). Potassium phosphate (16 g, 76 mmol) and dichloro[1,1'-bis(diphenylphosphino)ferrocene]palladium(II) dichloromethane adduct (700 mg, 0.9 mmol) were added and the mixture stirred at 50° C. for 72 h. The reaction mixture was adsorbed onto silica gel and purified by chromatography over silica gel using ethyl acetate as eluent. Further purification by chromatography on silica gel eluting with dichloromethane, then crystallisation from toluene/isohexane, gave 3-(2-fluoro-5-nitrophenyl)pyridazine as a white solid: $\delta_H$ (400 MHz, CDCl$_3$) 9.27 (1H, dd, J 5 and 2), 9.18 (1H, dd, J 7 and 3), 8.36–8.41 (1H, m), 8.00–8.04 (1H, m), 7.63 (1H, dd, J 9 and 5), 7.39 (1H, dd, J 10 and 9).

3-(2-Fluoro-5-nitrophenyl)pyridazine (348 mg, 1.6 mmol) was reduced by the method described in Example 47 over 8 h to give 4-fluoro-3-(pyridazin-3-yl)phenylamine as an oil: m/z (ES$^+$) 301 (M$^+$+H).

4-Fluoro-3-(pyridazin-3-yl)phenylamine (226 mg, 1.2 mmol) was bromo-deaminated by the method described in Example 27 to give 3-(5-bromo-2-fluorophenyl)pyridazine as an off-white solid: $\delta_H$ (400 MHz, CDCl$_3$) 9.20 (1H, dd, J 5 and 1), 8.37 (1H, dd, J 7 and 3), 7.94–7.98 (1H, m), 7.54–7.60 (2H, m), 7.11 (1H, dd, J 11 and 9).

3-(5-Bromo-2-fluorophenyl)pyridazine (80.6 mg, 0.3 mmol) was coupled to 3-tributylstannyl-7-trifluoromethylimidazo[1,2-α]pyrimidine (0.45 mmol) by the method of Example 32. Purification by chromatography on silica gel eluting with dichloromethane containing 1% methanol, then crystallisation from methanol, gave 3-[4-fluoro-3-(pyridazin-3-yl)phenyl]-7-trifluoromethylimidazo[1,2-α]pyrimidine as a yellow solid: $\delta_H$ (400 MHz, CDCl$_3$) 9.24 (1H, dd, J 5 and 1), 8.92 (1H, d, J 7), 8.48 (1H, dd, J 7 and 2), 8.16 (1H, s), 8.07–8.11 (1H, m), 7.66–7.71 (1H, m), 7.63 (1H, dd, J 9 and 5), 7.45 (1H, dd, J 11 and 9), 7.30 (1H, d, J 7); m/z (ES$^+$) 359 (M$^+$+H).

EXAMPLE 49

2-[2-Fluoro-5-(7-trifluoromethylimidazo[1,2-α]pyrimidin-3-yl)phenyl]nicotinonitrile 2-Chloronicotinonitrile (0.80 g, 5.8 mmol) was coupled to 2-(2-fluoro-5-nitrophenyl)-4,4,5,5-tetramethyl-[1,3,2]dioxaborolane (2 g, 7.49 mmol) using the method in Example 48. Purification by chromatography on silica gel eluting with dichloromethane gave 2-(2-fluoro-5-nitrophenyl)nicotinonitrile as a yellow solid: $\delta_H$ (360 MHz, CDCl$_3$) 8.97 (1H, dd, J 5 and 2), 8.56 (1H, dd, J 6 and 3), 8.40–8.45 (1H, m), 8.15 (1H, dd, J 8 and 2), 7.55 (1H, dd, J 8 and 5), 7.43 (1H, dd, J 9 and 9); m/z (ES$^+$) 244 (M$^+$+H).

2-(2-Fluoro-5-nitrophenyl)nicotinonitrile (1.2 g, 4.9 mmol) was reduced by the method described in Example 47. Purification by chromatography on silica gel eluting with dichloromethane containing 1% methanol gave 2-(5-amino-2-fluorophenyl)nicotinonitrile as an orange oil: $\delta_H$ (360 MHz, CDCl$_3$) 8.88 (1H, dd, J 5 and 2), 8.07 (1H, dd, J 8 and 2), 7.42 (1H, dd, J 8 and 5), 7.04 (1H, dd, J 9 and 9), 6.85 (1H, dd, J 6 and 3), 6.76–6.81 (1H, m); m/z (ES$^+$) 214 (M$^+$+H).

2-(5-Amino-2-fluorophenyl)nicotinonitrile (1.0 g, 4.7 mmol) was bromo-deaminated by the method described in Example 27 to give 2-(5-bromo-2-fluorophenyl)nicotinonitrile as a white powder: $\delta_H$ (360 MHz, CDCl$_3$) 8.92 (1H, dd, J 5 and 1), 8.10 (1H, dd, J 8 and 2), 7.74 (1H, dd, J 6 and 2), 7.59–7.64 (1H, m), 7.48 (1H, dd, J 8 and 5), 7.15 (1H, dd, J 9 and 9).

2-(5-Bromo-2-fluorophenyl)nicotinonitrile (214 mg, 0.8 mmol) was coupled to 3-tributylstannyl-7-trifluoromethylimidazo[1,2-α]pyrimidine (1.1 mmol) by the method of Example 32. Purification by chromatography on silica gel eluting with dichloromethane containing 1% methanol, then crystallisation from toluene, gave 2-[2-fluoro-5-(7-trifluoromethylimidazo[1,2-α]pyrimidin-3-yl)phenyl]nicotinonitrile as a yellow solid: $\delta_H$ (400 MHz, CDCl$_3$) 8.95 (1H, dd, J 5 and 2), 8.91 (1H, d, J 7), 8.17 (1H, dd, J 8 and 2), 8.13 (1H, s), 7.80 (1H, dd, J 7 and 2), 7.69–7.73 (1H, m), 7.46–7.55 (2H, m), 7.29 (1H, d, J 7); m/z (ES$^+$) 383 (M$^+$+H).

Alternative Method:

A degassed solution of 2-(5-bromo-2-fluorophenyl) nicotinonitrile (1.53 g, 5.5 mmol) and bis(neopentyl glycolato)diboron (1.37 g, 6.1 mmol) was formed in 1,4-dioxane (50 ml) with dimethylsulfoxide (1 ml). Potassium acetate (1.08 g, 11.0 mmol) and dichloro[1,1'-bis (diphenylphosphino)ferrocene]palladium(II) dichloromethane adduct (60 mg, 0.1 mmol) were added and the mixture stirred at 80° C. for 18 h. The reaction was allowed to cool to ambient temperature and the solvent removed under reduced pressure. The residue was dissolved in 2N sodium hydroxide solution (50 ml) and filtered. The filtrate was washed with diethyl ether (3×50 ml) then cooled to 0° C. and made neutral with 36% hydrochloric acid. The resulting precipitate was filtered and dried over phosphorus pentoxide to give 4-fluoro-3-(3-cyanopyridin-2-yl) phenylboronic acid as a white solid: m/z (ES$^+$) 242 (M$^+$+H).

A degassed solution of 4-fluoro-3-(3-cyanopyridin-2-yl) phenylboronic acid (390 mg, 1.6 mmol) and 3-bromo-7-trifluoromethylimidazo[1,2-α]pyrimidine (390 mg, 1.5 mmol) was formed in tetrahydrofuran (6 ml) with sodium carbonate (3 ml of a 2M solution in water). Tetrakis (triphenylphosphine)palladium(0) (50 mg, 0.04 mmol) was added and the solution stirred at 60° C. for 10 h. The reaction was allowed to cool to ambient temperature then poured into water (50 ml) and extracted with ethyl acetate (2×50 ml). The combined organic phases were dried over anhydrous magnesium sulfate, filtered and evaporated to dryness. Purification by chromatography on silica gel eluting with dichloromethane containing 1% methanol, then crystallisation from toluene, gave 2-[2-fluoro-5-(7-trifluoromethylimidazo [1,2-α]pyrimidin-3-yl)phenyl]nicotinonitrile as a yellow solid.

EXAMPLE 50

3-[4-Fluoro-3-(pyridin-2-yl)phenyl]imidazo[1,2-α] primidine

To a cooled (−78° C.) solution of 3-bromoimidazo[1,2-α]pyrimidine (500 mg, 2.5 mmol) in tetrahydrofuran (20 ml) was added isopropylmagnesium chloride (1.39 ml of a 2.0M solution in tetrahydrofuran, 2.78 mmol). After stirring for 5 min tri-n-butyltin chloride (0.8 ml, 2.90 mmol) was added and the reaction stirred for 10 min at −78° C. then allowed to warm to ambient temperature to give a solution of 3-tributylstannylimidazo[1,2-α]pyrimidine in tetrahydrofuran: m/z (ES$^+$) 407, 409, 411 (M$^+$+H).

2-(5-Bromo-2-fluorophenyl)pyridine (100 mg, 0.4 mmol) and tetrakis(triphenylphosphine)palladium(0) (150 mg, 0.13 mmol) were added and the mixture heated at reflux for 2 h. The reaction was allowed to cool to ambient temperature and the solvent was removed. Purification by chromatography on silica gel eluting with dichloromethane containing 4% methanol, then crystallisation from toluene/diethyl ether, gave 3-[4-fluoro-3-(pyridin-2-yl)phenyl]imidazo[1,2-α] pyrimidine as a white solid: $\delta_H$ (400 MHz, CDCl$_3$) 8.73–8.75 (1H, m), 8.68 (1H, dd, J 7 and 2), 8.60 (1H, dd, J 4 and 2), 8.23 (1H, dd, J 7 and 2), 7.49 (1H, s), 7.87–7.90 (1H, m), 7.79–7.84 (1H, m), 7.53–7.58 (1H, m), 7.30–7.38 (2H, m), 6.94 (1H, dd, J 7 and 4); m/z (ES$^+$) 291 (M$^+$+H).

EXAMPLE 51

3,2'-Difluoro-5'-(7-trifluoromethylimidazo[1,2-α] pyrimidin-3-yl)biphenyl-2-carbonitrile A mixture of 2,6-difluorobenzonitrile (19.0 g, 137 mmol) and ethanol (200 ml) pre-saturated with ammonia gas was heated at 140° C. in an autoclave for 6 h (terminal pressure 200 psi). The mixture was allowed to cool to ambient temperature, evaporated to dryness and triturated with water (200 ml). The solid was filtered and left to air dry to afford 2-amino-6-fluorobenzonitrile (18.0 g, 97%) as an off-white solid: $\delta_H$ (360 MHz, CDCl$_3$) 4.53 (3H, s), 6.44–6.52 (2H, m), 7.24–7.30 (1H, m).

2-Amino-6-fluorobenzonitrile (18.0 g, 132 mmol) was dissolved in hot 1,4-dioxane (20 ml), 48% hydrobromic acid (200 ml) was added and the mixture cooled to 0° C. before dropwise addition of sodium nitrite (10.5 g, 152 mmol) in water (20 ml) over 1.5 h. The resulting mixture was stirred at 0° C. for 1.5 h then poured onto a cooled (0° C.) solution of copper(I) bromide (56.8 g, 396 mmol) in 48% hydrobromic acid (50 ml). The solution was stirred at 0° C. for 15 min then heated at 50° C. for 20 min. The mixture was cooled to ambient temperature, diluted with water (1200 ml) and extracted with ethyl acetate (2×400 ml). The combined organics were washed with 10% aqueous ammonia solution (400 ml), water (400 ml) and brine (500 ml), dried over anhydrous magnesium sulfate, filtered and evaporated to give an orange oil. Purification by chromatography on silica gel eluting with isohexane on a gradient of ethyl acetate (2–4%) gave 2-bromo-6-fluorobenzonitrile (18.5 g, 70%) as a white solid: $\delta_H$ (400 MHz, CDCl$_3$) 7.17–7.23 (1H, ddd, J 8, 8 and 1), 7.44–7.52 (2H, m).

A suspension of 2-bromo-6-fluorobenzonitrile (2.50 g, 12.5 mmol), potassium fluoride (2.40 g, 41.3 mmol) and 2-(2-fluoro-5-nitrophenyl)-4,4,5,5-tetramethyl-[1,3,2] dioxaborolane (4.67 g, 17.5 mmol) in tetrahydrofuran (50 ml) was degassed with nitrogen for 30 min. Tris (dibenzylideneacetone)dipalladium(0) and tri-tert-butylphosphine (0.2M solution in 1,4-dioxane, 3.7 ml) were added and the mixture stirred at ambient temperature for 15 min then at 50° C. for 18 h. After cooling to ambient temperature, the resulting dark suspension was poured onto 0.5M sodium hydroxide solution (500 ml) and stirred vigorously for 2 h. The dark solid was collected by filtration, washed with water (100 ml) and isohexane (50 ml) and left to air dry which gave 3,2'-difluoro-5'-nitrobiphenyl-2-carbonitrile as a brown/black solid (3.25 g, 100%): $\delta_H$ (360 MHz, CDCl$_3$) 7.32–7.44 (3H, m), 7.71–7.77 (1H, m), 8.35–8.41 (2H, m). 3,2'-Difluoro-5'-nitrobiphenyl-2-carbonitrile (3.25 g, 12.5 mmol) in tetrahydrofuran (20 ml) and ethanol (20 ml) was treated with tin(II) chloride dihydrate (9.86 g, 43.8 mmol) and the mixture left to stir at ambient temperature for 18 h. The solvent was evaporated and the residue stirred with 2N sodium hydroxide solution (40 ml) for 2 h. The resulting suspension was diluted with water (100 ml) and extracted with dichloromethane (3×200 ml). The combined organics were washed with water (200 ml), brine (200 ml), dried over anhydrous sodium sulfate, filtered and evaporated to give 5'-amino-3,2'-difluorobiphenyl-2-carbonitrile as a brown solid (2.87 g, 100%): $\delta_H$ (360 MHz, CDCl$_3$) 3.74 (2H, s), 6.66–6.75 (2H, m), 7.01 (1H, dd, J 9 and 9), 7.19–7.30 (2H, m), 7.59–7.65 (1H, m).

5'-Amino-3,2'-difluorobiphenyl-2-carbonitrile (2.87 g, 12.5 mmol) was dissolved in hot 1,4-dioxane (4 ml), 48% aqueous hydrobromic acid (40 ml) was added and the mixture cooled to 0° C. before dropwise addition of sodium nitrite (0.86 g, 12.5 mmol) in water (1.5 ml) over 20 min. The resulting mixture was stirred at 0° C. for 1.5 h then poured onto a cooled (0° C.) solution of copper(I) bromide (5.38 g, 37.5 mmol) in 48% hydrobromic acid (10 ml). The solution was stirred at 0° C. for 15 min then heated at 50° C. for 20 min. The mixture was cooled to ambient temperature, diluted with water (500 ml) and extracted with ethyl acetate (2×300 ml). The combined organics were washed with 10% aqueous ammonia solution (200 ml), water (200 ml) and brine (200 ml), dried over anhydrous magnesium sulfate, filtered and evaporated to give a black solid. Purification by chromatography on silica gel eluting with isohexane (containing 0.5% methanol) on a gradient of ethyl acetate (2–6%) gave 5'-bromo-3,2'-difluorobiphenyl-2-carbonitrile (2.48 g, 68%) as a yellow solid: $\delta_H$ (400 MHz, CDCl$_3$) 7.13 (1H, dd, J 9 and 9), 7.27–7.30 (2H, m), 7.53–7.59 (2H, m), 7.64–7.69 (1H, m).

A mixture of 5'-bromo-3,2'-difluorobiphenyl-2-carbonitrile (2.48 g, 8.43 mmol), potassium acetate (2.48 g, 25.3 mmol) and bis(neopentyl glycolato)diboron (2.48 g, 11.0 mmol) in 1,4-dioxane (40 ml) containing dimethylsulfoxide (0.8 ml) was degassed with nitrogen for 20 min. Dichloro[1,1'-bis(diphenylphosphino)ferrocene]palladium (II) dichloromethane adduct (200 mg, 0.25 mmol) was then added and the reaction heated at 90° C. for 24 h. The mixture was cooled to ambient temperature then partitioned between 2N sodium hydroxide (75 ml) and diethyl ether (100 ml) and the organics were discarded. The aqueous extract was made acidic (pH 5) with 36% hydrochloric acid and then extracted with diethyl ether (2×75 ml). The organic extract was washed with water (50 ml) and brine (75 ml), dried over anhydrous magnesium sulfate and evaporated to give 5'-(5,5-dimethyl-[1,3,2]dioxaborinan-2-yl)-3,2'-difluorobiphenyl-2-carbonitrile as a brown oil (2.5 g, 95%) that crystallised on standing: $\delta_H$ (360 MHz, CDCl$_3$) 1.03 (6H, s), 3.77 (4H, s), 7.17–7.25 (2H, m), 7.30 (1H, d, J 8), 7.59–7.65 (1H, m), 7.81–7.91 (2H, m).

3-Bromo-7-trifluoromethylimidazo[1,2-α]pyrimidine was coupled with 5'-(5,5-dimethyl-[1,3,2]dioxaborinan-2-yl)-3,2'-difluorobiphenyl-2-carbonitrile as described in Example 1 to give 3,2'-difluoro-5'-(7-trifluoromethylimidazo[1,2-α]pyrimidin-3-yl)biphenyl-2-carbonitrile as an off-white solid: $\delta_H$ (360 MHz, CDCl$_3$) 7.31 (2H, dd, J 7 and 3), 7.43–7.49 (2H, m), 7.64–7.75 (3H, m), 8.10 (1H, s), 9.04 (1H, d, J 7); m/z (ES$^+$) 401 (M$^+$+H).

EXAMPLE 52

6,2'-Difluoro-5'-(7-trifluoromethylimidazo[1,2-α] pyrimidin-3-yl)biphenyl-2-carbonitrile A mixture of 2,3-difluorobenzonitrile (19.0 g, 137 mmol) and ethanol (200 ml) pre-saturated with ammonia gas was heated at 140° C. in an autoclave for 8 h (terminal pressure 200 psi). The mixture was allowed to cool to ambient temperature and evaporated to dryness. The residue was dissolved in water (400 ml) and extracted with diethyl ether (2×300 ml). The combined organics were washed with water (300 ml) and brine (250 ml), dried over anhydrous magnesium sulfate, filtered and evaporated. Trituration with isohexane (150 ml) afforded 2-amino-3-fluorobenzonitrile (9.8 g, 50%) as an off-white solid: $\delta_H$ (360 MHz, CDCl$_3$) 4.47 (2H, s), 6.65–6.71 (1H, m), 7.14–7.20 (2H, m).

2-Amino-3-fluorobenzonitrile (9.8 g, 71.9 mmol) was bromo-deaminated as described in Example 51 to afford 2-bromo-3-fluorobenzonitrile as a pale brown solid: $\delta_H$ (360 MHz, CDCl$_3$) 7.62–7.68 (1H, m), 7.74–7.85 (1H, ddd, J 9, 9 and 1), 7.74–7.85 (1H, ddd, J 8, 1 and 1).

2-Bromo-3-fluorobenzonitrile (2.50 g, 12.5 mmol) was coupled to 2-(2-fluoro-5-nitrophenyl)-4,4,5,5-tetramethyl-[1,3,2]dioxaborolane as described in Example 51 to give 6,2'-difluoro-5'-nitrobiphenyl-2-carbonitrile as a black solid: $\delta_H$ (400 MHz, CDCl$_3$) 7.40–7.44 (1H, m), 7.47–7.52 (1H, m), 7.59–7.67 (2H, m), 8.37–8.44 (2H, m).

6,2'-Difluoro-5'-nitrobiphenyl-2-carbonitrile (3.25 g, 12.5 mmol) was reduced using the procedure described in Example 51 to give 5'-amino-6,2'-difluorobiphenyl-2-carbonitrile as a brown oil: $\delta_H$ (360 MHz, CDCl$_3$) 3.74 (2H, s), 6.68 (1H, m), 6.73–6.77 (1H, m), 7.02 (1H, dd, J 9 and 9), 7.37–7.49 (2H, m), 7.56–7.65 (1H, m).

5'-Amino-6,2'-difluorobiphenyl-2-carbonitrile was bromo-deaminated as described in Example 51 to furnish 5'-bromo-6,2'-difluorobiphenyl-2-carbonitrile as a pale brown solid: $\delta_H$ (360 MHz, CDCl$_3$) 7.13 (1H, dd, J 9 and 9), 7.37–7.49 (2H, ddd, J 9, 9 and 1), 7.57–7.62 (4H, m).

5'-Bromo-6,2'-difluorobiphenyl-2-carbonitrile was converted to 6,2'-difluoro-5'-(4,4,5,5-tetramethyl-[1,3,2] dioxaborolan-2-yl)biphenyl-2-carbonitrile using the procedure described in Example 1. This gave a brown oil that crystallised on standing: $\delta_H$ (360 MHz, CDCl$_3$) 1.34 (12H, s), 7.21 (1H, dd, J 8 and 2), 7.38–7.51 (2H, m), 7.57–7.59 (1H, m), 7.85 (1H, dd, J 8 and 2), 7.90–7.94 (1H, m).

3-Bromo-7-trifluoromethylimidazo[1,2-α]pyrimidine was coupled with 6,2'-difluoro-5'-(4,4,5,5-tetramethyl-[1,3,2]dioxaborolan-2-yl)biphenyl-2-carbonitrile as described in Example 1 to give 6,2'-difluoro-5'-(7-trifluoromethylimidazo[1,2-α]pyrimidin-3-yl)biphenyl-2-carbonitrile as an off-white solid: $\delta_H$ (400 MHz, CDCl$_3$) 7.29 (1H, d, J 7), 7.44–7.71 (6H, m), 8.11 (1H, s), 9.00 (1H, d, J 7); m/z (ES$^+$) 401 (M$^+$+H).

EXAMPLE 53

5,2'-Difluoro-5'-(7-trifluoromethylimidazo[1,2-α] pyrimidin-3-yl)biphenyl-2-carbonitrile 2-Bromo-4-fluorobenzonitrile was coupled to 2-(2-fluoro-5-nitrophenyl)-4,4,5,5-tetramethyl-[1,3,2] dioxaborolane as described in Example 51 to give 5,2'-difluoro-5'-nitrobiphenyl-2-carbonitrile as a black solid: $\delta_H$ (360 MHz, CDCl$_3$) 7.25–7.33 (2H, m), 7.40–7.44 (1H, m), 7.86 (1H, dd, J 9 and 6), 8.35–8.42 (2H, m).

5,2'-Difluoro-5'-nitrobiphenyl-2-carbonitrile was reduced using the protocol described in Example 51 to give 5'-amino-5,2'-difluorobiphenyl-2-carbonitrile: $\delta_H$ (360 MHz, CDCl$_3$) 3.68 (2H, s), 6.67–6.76 (2H, m), 7.02 (1H, dd, J 9 and 9), 7.12–7.27 (2H, m), 7.78 (1H, dd, J 9 and 6).

5'-Amino-5,2'-difluorobiphenyl-2-carbonitrile was bromo-deaminated as described in Example 51 to give 5'-bromo-5,2'-difluorobiphenyl-2-carbonitrile as a pale brown solid: $\delta_H$ (400 MHz, CDCl$_3$) 7.13 (1H, dd, J 9 and 9), 7.19–7.23 (2H, m), 7.52–7.60 (2H, m), 7.81 (1H, dd, J 8 and 5).

5'-Bromo-5,2'-difluorobiphenyl-2-carbonitrile was converted to 5'-(5,5-dimethyl-[1,3,2]dioxaborinan-2-yl)-5,2'-difluorobiphenyl-2-carbonitrile as described in Example 51. This produced a brown oil that crystallised on standing: $\delta_H$ (400 MHz, CDCl$_3$) 1.03 (6H, s), 3.77 (4H, s), 7.15–7.24 (3H, m), 7.77 (1H, dd, J 9 and 6), 7.83 (1H, dd, J 8 and 2), 7.87–7.91 (1H, m).

3-Bromo-7-trifluoromethylimidazo[1,2-α]pyrimidine was coupled with 5'-(5,5-dimethyl-[1,3,2]dioxaborinan-2-yl)-5,2'-difluorobiphenyl-2-carbonitrile as described in Example 1 to give 5,2'-difluoro-5'-(7-trifluoromethylimidazo[1,2-α]pyrimidin-3-yl)biphenyl-2-carbonitrile as an off-white solid: $\delta_H$ (360 MHz, CDCl$_3$) 7.25–7.31 (2H, m), 7.44–7.50 (1H, m), 7.67 (1H, ddd, J 9, 5 and 2), 7.67 (1H, s), 7.69 (1H, s), 7.88 (1H, dd, J 9 and 6), 8.11 (1H, s), 9.05 (1H, d, J 7); m/z (ES$^+$) 401 (M$^+$+H).

EXAMPLE 54

4,2'-Difluoro-5'-(7-trifluoromethylimidazo[1,2-α] pyrimidin-3-yl)biphenyl-2-carbonitrile 2-Bromo-5-fluorobenzonitrile was coupled to 2-(2-fluoro-5-nitrophenyl)-4,4,5,5-tetramethyl-[1,3,2]

dioxaborolane as described in Example 51 to give 4,2'-difluoro-5'-nitrobiphenyl-2-carbonitrile as a black solid: $\delta_H$ (360 MHz, CDCl$_3$) 7.38–7.56 (4H, m), 8.33–8.40 (2H, m).

4,2'-Difluoro-5'-nitrobiphenyl-2-carbonitrile was reduced using the procedure described in Example 51 to give 5'-amino-4,2'-difluorobiphenyl-2-carbonitrile: $\delta_H$ (360 MHz, CDCl$_3$) 3.66 (2H, s), 6.66–6.70 (1H, m), 6.71–6.74 (1H, m), 7.00 (1H, dd, J 9 and 9), 7.33–7.38 (1H, m), 7.44–7.49 (1H, m).

5'-Amino-4,2'-difluorobiphenyl-2-carbonitrile was bromo-deaminated using the procedure described in Example 51 to give 5'-bromo-4,2'-difluorobiphenyl-2-carbonitrile as a pale brown solid: $\delta_H$ (360 MHz, CDCl$_3$) 7.11 (1H, dd, J 9 and 9), 7.37–7.58 (5H, m).

5'-Bromo-4,2'-difluorobiphenyl-2-carbonitrile was converted to 5'-(5,5-dimethyl-[1,3,2]dioxaborinan-2-yl)-4,2'-difluorobiphenyl-2-carbonitrile using the procedure described in Example 51. This produced a brown oil that crystallised on standing: $\delta_H$ (360 MHz, CDCl$_3$) 1.03 (6H, s), 3.76 (4H, s), 7.20 (1H, dd, J 10 and 8), 7.33–7.38 (1H, m), 7.44–7.50 (2H, m), 7.81 (1H, dd, J 8 and 2), 7.85–7.90 (1H, m).

3-Bromo-7-trifluoromethylimidazo[1,2-α]pyrimidine was coupled with 5'-(5,5-dimethyl-[1,3,2]dioxaborinan-2-yl)-4,2'-difluorobiphenyl-2-carbonitrile as described in Example 1 to give 4,2'-difluoro-5'-(7-trifluoromethylimidazo[1,2-α]pyrimidin-3-yl)biphenyl-2-carbonitrile as an off-white solid: $\delta_H$ (400 MHz, CDCl$_3$) 7.29 (1H, d, J 7), 7.42–7.48 (2H, m), 7.57 (1H, dd, J 8 and 3), 7.61–7.66 (3H, m), 8.10 (1H, s), 9.02 (1H, d, J 7); m/z (ES$^+$) 401 (M$^+$+H).

EXAMPLE 55

2',6'-Difluoro-3'-(7-trifluoromethylimidazo[1,2-α]pyrimidin-3-yl)biphenyl-2-carbonitrile A mixture of 2-bromobenzonitrile (20 g, 110 mmol), bis-(pinacolato)diboron (30.4 g, 120 mmol) and potassium acetate (32.4 g, 330 mmol) in 1,4-dioxane (100 ml) and dimethylsulfoxide (20 ml) was degassed with nitrogen for 30 min. Dichloro[1,1'-bis(diphenylphosphino)ferrocene]palladium(II) dichloromethane adduct (2.00 g, 2.73 mmol) was added and the mixture heated at 90° C. for 18 h. The mixture was cooled to ambient temperature and partitioned between diethyl ether and 2N sodium hydroxide solution. The organics were discarded and the aqueous phase cooled to 0° C. and adjusted to pH 7 by the addition of 36% hydrochloric acid. The solid was collected by filtration, washed with water and left to air dry to give 2-(4,4,5,5-tetramethyl-[1,3,2]dioxaborolan-2-yl)benzonitrile (19 g, 76%) as an off-white solid: $\delta_H$ (360 MHz, CDCl$_3$) 1.39 (12H, s), 7.52–7.57 (2H, m), 7.68–7.71 (1H, m), 7.87–7.89 (1H, m).

2-Bromo-1,3-difluorobenzene (3.0 g, 15.5 mmol) was coupled to 2-(4,4,5,5-tetramethyl-[1,3,2]dioxaborolan-2-yl)benzonitrile (4.63 g, 20.2 mmol) as described in Example 51. The resulting black solid was purified by chromatography on silica gel eluting with isohexane on a gradient of ethyl acetate (10–15%). Trituration with isohexane (20 ml) gave 2',6'-difluorobiphenyl-2-carbonitrile as a pale yellow solid (3.34 g, 100%): $\delta_H$ (360 MHz, CDCl$_3$) 7.06 (2H, dd, J 8 and 7), 7.38–7.44 (1H, m), 7.47–7.56 (2H, m), 7.61–7.72 (1H, m), 7.82 (1H, dd, J 8 and 1).

2',6'-Difluorobiphenyl-2-carbonitrile was lithiated and reacted with trimethyl borate as described in Example 31 to give 2'-cyano-2,6-difluorobiphenyl-3-boronic acid as a white crystalline solid.

3-Bromo-7-trifluoromethylimidazo[1,2-α]pyrimidine and 2'-cyano-2,6-difluorobiphenyl-3-boronic acid were coupled using the procedure described in Example 1 to give 2',6'-difluoro-3'-(7-trifluoromethylimidazo[1,2-α]pyrimidin-3-yl)biphenyl-2-carbonitrile as a white solid: $\delta_H$ (360 MHz, CDCl$_3$) 7.30–7.34 (2H, m), 7.59–7.68 (3H, m), 7.75–7.79 (1H, m), 7.88 (1H, dd, J 7 and 1), 8.13 (1H, s), 8.78 (1H, dd, J 7 and 4).

EXAMPLE 56

3-[4-Fluoro-3-(pyrazin-2-yl)phenyl]-7-trifluoromethylimidazo[1,2-α]pyrimidine

To a degassed mixture of 2-chloropyrazine (1.01 g, 8 mmol), 2-(2-fluoro-5-nitrophenyl)-4,4,5,5-tetramethyl-[1,3,2]dioxaborolane (2.36 g, 8.84 mmol) and potassium phosphate (6.3 g, 30 mmol) in 1,4-dioxane (30 ml) was added dichloro[1,1'-bis(diphenylphosphino)ferrocene]palladium(II) dichloromethane adduct (0.11 g) and the mixture stirred for 15 h at 90° C. The reaction was cooled to ambient temperature, poured into water (100 ml) and extracted with ethyl acetate (4×50 ml). The combined organic phases were dried over anhydrous sodium sulfate, filtered and evaporated to dryness. Purification by chromatography on silica gel eluting with 50% dichloromethane in isohexane then ethyl acetate gave 2-(2-fluoro-5-nitrophenyl)pyrazine: m/z (ES$^+$) 220 (M$^+$+H).

To a solution of 2-(2-fluoro-5-nitrophenyl)pyrazine (0.72 g, 3.3 mmol) in ethanol (20 ml) was added tin(II) chloride (2.8 g) and the mixture stirred for 3 h at ambient temperature. 25% Ammonium hydroxide (25 ml) was added and the mixture evaporated to dryness. The residual solid was boiled with ethyl acetate, and filtered whilst hot. The filtrate was evaporated at reduced pressure to give 4-fluoro-3-(pyrazin-2-yl)phenylamine: $\delta_H$ (400 MHz, CDCl$_3$) 9.09 (1H, dd, J 2 and 1.5), 8.66 (1H, m), 8.51 (1H, d, J 2), 7.31 (1H, dd, J 6 and 3), 7.02 (1H, dd, J 11 and 9), 6.74 (1H, m), 3.60 (2H, br).

A solution of 4-fluoro-3-(pyrazin-2-yl)phenylamine (989 mg) in acetonitrile (5 ml) was added dropwise to a pre-formed mixture of copper(II) bromide (800 mg) and tert-butyl nitrite (0.66 ml) in acetonitrile (10 ml) at 4° C. The cooling bath was then removed, the mixture was allowed to warm to ambient temperature and stirred a further 3.5 h. The reaction was then diluted with dichloromethane (20 ml), applied to a pad of silica gel and eluted with dichloromethane/methanol/ammonia (98:2:0.2). The residue was purified further by chromatography on silica gel, eluting with 2% methanol in dichloromethane, to afford 2-(5-bromo-2-fluorophenyl)pyrazine: m/z (ES$^+$) 253, 255 (M$^+$+H).

2-(5-Bromo-2-fluorophenyl)pyrazine was coupled to 3-tributylstannyl-7-trifluoromethylimidazo[1,2-α]pyrimidine by the method of Example 32. Purification by chromatography on silica gel eluting with dichloromethane containing 4% methanol followed by crystallisation from hot toluene gave 3-[4-fluoro-3-(pyrazin-2-yl)phenyl]-7-trifluoromethylimidazo[1,2-α]pyrimidine: $\delta_H$ (400 MHz, DMSO) 9.31 (1H, d, J 7), 9.14 (1H, m), 8.85 (1H, dd, J 2 and 1.5), 8.73 (1H, d, J 2), 8.32 (1H, s), 8.27 (1H, dd, J 7 and 2), 7.96 (1H, m), 7.68 (1H, dd, J 11 and 9), 7.54 (1H, d, J 7); m/z (ES$^+$) 360 (M$^+$+H).

EXAMPLE 57

3-[4-Fluoro-3-(pyrimidin-2-yl)phenyl]-7-trifluoromethylimidazo[1,2-α]pyrimidine

By the method of Example 56, 2-bromopyrimidine was coupled with 2-(2-fluoro-5-nitrophenyl)-4,4,5,5- tetramethyl-[1,3,2]dioxaborolane to give, after crystallisation from dichloromethane/isohexane, 2-(2-fluoro-5-nitrophenyl)pyrazine: $\delta_H$ (400 MHz, CDCl$_3$) 9.09 (1H, dd, J 7 and 3), 8.93 (2H, d, J 5), 8.35 (1H, m), 7.36 (2H, m).

To a solution of 2-(2-fluoro-5-nitrophenyl)pyrazine (1.24 g) in ethanol (75 ml) and ethyl acetate (15 ml) was added platinum(IV) oxide (120 mg) and the mixture shaken on a Parr hydrogenation apparatus under an atmosphere of hydrogen at 40 psi for 0.5 h. Filtration and evaporation of the filtrate afforded 4-fluoro-3-(pyrimidin-2-yl)phenylamine as a yellow solid: $\delta_H$ (400 MHz, CDCl$_3$) 8.86 (2H, d, J 5), 7.37 (1H, dd, J 6 and 3), 7.24 (1H, m), 7.02 (1H, dd, J 11 and 9), 6.75 (1H, m), 3.65 (2H, br).

By the method of Example 56, 4-fluoro-3-(pyrimidin-2-yl)phenylamine was converted to 2-(5-bromo-2-fluorophenyl)pyrimidine: m/z (ES$^+$) 253, 255 (M$^+$+H).

2-(5-Bromo-2-fluorophenyl)pyrazine was coupled to 3-tributylstannyl-7-trifluoromethylimidazo[1,2-α]pyrimidine by the method of Example 32. Purification by chromatography on silica gel eluting with dichloromethane containing 4% methanol, then crystallisation from hot methanol, gave 3-[4-fluoro-3-(pyrimidin-2-yl)phenyl]-7-trifluoromethylimidazo[1,2-α]pyrimidine: $\delta_H$ (400 MHz, DMSO) 9.28 (1H, d, J 7), 9.00 (2H, d, J 5), 8.32 (1H, dd, J 5 and 2), 8.31 (1H, s), 7.95 (1H, m), 7.62 (1H, dd, J 9 and 2), 7.56 (2H, m).

EXAMPLE 58

3-[2-Fluoro-5-(7-trifluoromethylimidazo[1,2-α]pyrimidin-3-yl)phenyl]pyridine-2-carbonitrile By the method of Example 56, 3-bromo-2-cyanopyridine was coupled with 2-(2-fluoro-5-nitrophenyl)-4,4,5,5-tetramethyl-[1,3,2]dioxaborolane to give, after crystallisation from ethyl acetate/diethyl ether, 3-(2-fluoro-5-nitrophenyl)pyridine-2-carbonitrile: m/z (ES$^+$) 244.

By the method of Example 1, 3-(2-fluoro-5-nitrophenyl)pyridine-2-carbonitrile was reduced with tin(II) chloride to afford 3-(5-amino-2-fluorophenyl)pyridine-2-carbonitrile, which in turn was converted to 3-(5-bromo-2-fluorophenyl)pyridine-2-carbonitrile. Crystallisation from toluene/isohexane furnished off-white needles: $\delta_H$ (400 MHz, CDCl$_3$) 8.77 (1H, dd, J 5 and 2), 7.83 (1H, t, J 1.5), 7.59 (3H, m), 7.16 (1H, t, J 9); m/z (ES$^+$) 277, 279.

3-(5-Bromo-2-fluorophenyl)pyridine-2-carbonitrile was coupled to 3-tributylstannyl-7-trifluoromethylimidazo[1,2-α]pyrimidine by the method of Example 32. Purification by chromatography on silica gel eluting with dichloromethane containing 4% methanol, then crystallisation from hot toluene, gave 3-[2-fluoro-5-(7-trifluoromethylimidazo[1,2-α]pyrimidin-3-yl)phenyl]pyridine-2-carbonitrile: $\delta_H$ (400 MHz, DMSO) 9.39 (1H, d, J 7), 8.87 (1H, dd, J 5 and 1.5), 8.33 (1H, s), 8.30 (1H, dd, J 8 and 1), 8.09 (1H, dd, J 7 and 2), 8.00–8.03 (1H, m), 7.94 (1H, dd, J 8 and 5), 7.72 (1H, dd, J 10 and 9), 7.54 (1H, d, J 7); m/z (ES$^+$) 384.

EXAMPLE 59

3-[4-Fluoro-3-(5-fluoropyridin-2-yl)phenyl]-7-trifluoromethylimidazo[1,2-α]pyrimidine By the method of Example 56, 2-bromo-5-fluoropyridine was coupled with 2-(2-fluoro-5-nitrophenyl)-4,4,5,5-tetramethyl-[1,3,2]dioxaborolane to give, after crystallisation from isohexane, 5-fluoro-2-(2-fluoro-5-nitrophenyl)pyridine: m/z (ES$^+$) 237.

By the method of Example 57, 5-fluoro-2-(2-fluoro-5-nitrophenyl)pyridine was hydrogenated over platinum to afford 4-fluoro-3-(5-fluoropyridin-2-yl)phenylamine: m/z (ES$^+$) 207.

4-Fluoro-3-(5-fluoropyridin-2-yl)phenylamine (1.2 g) was dissolved in 1,4-dioxane (4 ml) and 48% aqueous hydrobromic acid (30 ml). The solution was cooled to 0° C. A solution of sodium nitrite (478 mg) in water (6 ml) was added dropwise with stirring to maintain an internal temperature below 4° C. The mixture was then aged a further 1 h at 4° C. A solution of copper(I) bromide (2.58 g) in 48% aqueous hydrobromic acid (10 ml) was then added slowly to retain a reaction temperature below 5° C. The resulting mixture was then stirred at 5–10° C. for 1 h, ambient temperature for 0.5 h and then heated at 50° C. for 0.5 h. The mixture was then cooled to 4° C., and made basic by addition of 4N aqueous sodium hydroxide (106 ml), followed by 30% aqueous ammonium hydroxide (40 ml). The mixture was extracted with ethyl acetate, the organic phase dried over anhydrous sodium sulfate, filtered and evaporated to dryness. The residue was chromatographed on silica gel eluting with dichloromethane containing 30% isohexane to afford 2-(5-bromo-2-fluorophenyl)-5-fluoropyridine: $\delta_H$ (400 MHz, DMSO) 8.74 (1H, dd, J 2 and 1), 8.05 (1H, dd, J 7 and 3), 7.90 (2H, m), 7.69 (1H, m), 7.38 (1H, dd, J 11 and 9); m/z (ES$^+$) 270, 272.

To 2-(5-bromo-2-fluorophenyl)-5-fluoropyridine (0.94 g, 3.48 mmol) and bis(neopentyl glycolato)diborane (0.943 g) in 1,4-dioxane (12 ml) and dimethylsulfoxide (1.5 ml) was added potassium acetate (0.725 g) and dichloro[1,1'-bis(diphenylphosphino)ferrocene]palladium(II) dichloromethane adduct (100 mg). The mixture was degassed with nitrogen and then stirred at 85° C. for 15 h. On cooling to ambient temperature, 1N aqueous sodium hydroxide (32 ml) was added and the mixture stirred for 20 min. Diethyl ether was added and the aqueous phase separated and washed with diethyl ether. The organic extracts were washed with water, and the combined aqueous phases filtered then acidified to pH 5 by addition of 2N aqueous hydrochloric acid (18 ml). The resulting white solid was collected by filtration, washed with water and dried in vacuo to afford 4-fluoro-3-(5-fluoropyridin-2-yl)phenylboronic acid: $\delta_H$ (400 MHz, DMSO) 8.73 (1H, dd, J 2 and 1), 8.33 (1H, dd, J 9 and 2), 8.17 (2H, s), 7.87 (3H, m), 7.31 (1H, dd, J 12 and 8).

4-Fluoro-3-(5-fluoropyridin-2-yl)phenylboronic acid was coupled with 3-bromo-7-trifluoromethylimidazo[1,2-α]pyrimidine by the method of Example 1. Purification by chromatography on silica gel eluting with dichloromethane containing 3.5% methanol, then crystallisation from hot toluene/isohexane and further crystallisation from hot methanol, gave 3-[4-fluoro-3-(5-fluoropyridin-2-yl)phenyl]-7-trifluoromethylimidazo[1,2-α]pyrimidine: $\delta_H$ (400 MHz, DMSO) 9.28 (1H, d, J 7), 8.76 (1H, d, J 3), 8.30 (1H, s), 8.20 (1H, dd, J 7 and 2), 7.88 (3H, m), 7.62 (1H, dd, J 11 and 9), 7.53 (1H, d, J 7).

EXAMPLE 60

7-(1,1-Difluoroethyl)-3-[4-fluoro-3-(pyridin-4-yl)phenyl]imidazo[1,2-α]pyrimidine 3-Bromo-7-(1,1-difluoroethyl)imidazo[1,2-α]pyrimidine was converted to 7-(1,1-difluoroethyl)-3-tributylstannylimidazo[1,2-α]pyrimidine following the procedure described in Example 32: m/z (ES$^+$) 470, 472, 474 (M$^+$+H).

7-(1,1-Difluoroethyl)-3-tributylstannylimidazo[1,2-α]pyrimidine was reacted with 4-(5-bromo-2-fluorophenyl)pyridine following the procedure described in Example 32 to give 7-(1,1-difluoroethyl)-3-[4-fluoro-3-(pyridin-4-yl)phenyl]imidazo[1,2-α]pyrimidine as a white solid: $\delta_H$ (360

MHz, CDCl$_3$) 2.16 (1H, t, J 19), 7.31 (1H, d, J 7), 7.43 (1H, dd, J 10 and 8), 7.54 (2H, dd, J 6 and 1), 7.57–7.66 (2H, m), 8.00 (1H, s), 8.67 (1H, d, J 7), 8.74 (2H, d, J 6); m/z (ES$^+$) 355 (M$^+$+H).

EXAMPLE 61

7-(1,1-Difluoroethyl)-3-[2,4-difluoro-3-(pyridin-3-yl)phenyl]imidazo[1,2-α]pyrimidine 7-(1,1-Difluoroethyl)-3-tributylstannylimidazo[1,2-α] pyrimidine was reacted with 3-(3-bromo-2,6-difluorophenyl)pyridine following the procedure described in Example 32 to give 7-(1,1-difluoroethyl)-3-[2,4-difluoro-3-(pyridin-3-yl)phenyl]imidazo[1,2-α]pyrimidine as a white solid: δ$_H$ (360 MHz, CDCl$_3$) 2.16 (1H, t, J 19), 7.22–7.78 (1H, m), 7.31 (1H, d, J 7), 7.59 (1H, ddd, J 8, 3 and 1), 7.52–7.59 (1H, m), 7.85 (1H, dd, J 8 and 1), 8.03 (1H, s), 8.39 (1H, dd, J 7 and 3), 8.69 (1H, d, J 5 and 3), 8.78 (1H, s); m/z (ES$^+$) 373 (M$^+$+H).

EXAMPLE 62

3-[4-Methyl-3-(pyridin-3-yl)phenyl]-7-trifluoromethylimidazo[1,2-α]pyrimidine A mixture of 2-bromo-4-nitrotoluene (3 g, 13.0 mmol) and pyridine-3-boronic acid-1,3-propanediol cyclic ester (2.72 g, 16.7 mmol) in EtOH (30 ml) and toluene (30 ml) together with 2N Na$_2$CO$_3$ solution (13.9 ml) was degassed with a stream of N$_2$ for 10 min. Tetrakis(triphenylphosphine) palladium(0) (0.3 g, 0.26 mmol) was added and the reaction heated at reflux for 4 h. The mixture was concentrated under reduced pressure to remove the organic solvents and water (100 ml) was added. The organics were extracted with EtOAc (200 ml) and then washed with brine (75 ml), dried (MgSO$_4$), and concentrated under reduced pressure while dry loading onto silica. The resulting crude residue was purified by column chromatography on silica, using 60% diethyl ether in hexane as the eluent, to yield 3-(2-methyl-5-nitrophenyl)pyridine (2.87 g, 99%): δ$_H$ (360 MHz, CDCl$_3$) 2.38 (3H, s), 7.36–7.50 (2H, m), 7.67 (1H, dt, J 7.9 and 1.9), 8.10 (1H, d, J 2.4), 8.61 (1H, d, J 1.8), 8.67 (1H, dd, J 4.8 and 1.5).

Tin(II) chloride (11.86 g, 62.6 mmol) was added portionwise over 5 min to a stirred mixture of 3-(2-methyl-5-nitrophenyl)pyridine (2.86 g, 15.0 mmol) in EtOH (100 ml) and 1,4-dioxane (100 ml) at 0° C. The mixture was then stirred overnight, gradually warming to room temperature, and then concentrated under reduced pressure. 20% Aqueous NH$_3$ solution (200 ml) and EtOH (300 ml) were added and again the mixture concentrated under reduced pressure. EtOAc (300 ml) was added and the mixture heated to reflux, the solids were filtered off and the process repeated twice more. The combined organic filtrates were concentrated under reduced pressure and the resulting crude residue was purified by column chromatography on silica, using 3% MeOH in dichloromethane as the eluent, to yield 4-methyl-3-(pyridin-3-yl)phenylamine (1.22 g, 44%): δ$_H$ (360 MHz, CDCl$_3$) 2.15 (3H, s), 6.56 (1H, d, J 2.4), 6.65 (1H, dd, J 8.0 and 2.4), 7.07 (1H, d, J 8.1), 7.31 (1H, dd, J 7.8 and 4.7), 7.62 (1H, dt, J 7.8 and 2.0), 8.53–8.60 (2H, m); m/z (ES$^+$) 185 (M$^+$+H).

tert-Butyl nitrite (1.97 ml, 16.5 mmol) was added dropwise to a stirred mixture of the foregoing aniline (1.22 g, 6.6 mmol) and copper(II) bromide (1.63 g, 7.3 mmol) in MeCN (150 ml) and dichloromethane (30 ml) at −10° C. Upon complete addition the reaction was warmed to room temperature and stirred overnight. The mixture was concentrated under reduced pressure while dry loading onto silica and the resulting crude residue was purified by column chromatography on silica using 2.5% MeOH in dichloromethane as the eluent. The combined fractions were washed with 10% aqueous ammonia solution (2×100 ml), H$_2$O (100 ml) and brine (100 ml), dried (MgSO$_4$) and concentrated to yield 3-(5-bromo-2-methylphenyl)pyridine (0.87 g, 53%): δ$_H$ (360 MHz, CDCl$_3$) 2.20 (3H, s), 7.12–7.68 (5H, m), 8.52–8.70 (2H, m); m/z (ES$^+$) 247, 249 (1:1) (M$^+$).

A mixture of 3-(5-bromo-2-methylphenyl)pyridine (0.87 g, 3.5 mmol), bis(neopentyl glycolato)diborane (0.79 g, 3.5 mmol), KOAc (1.03 g, 10.5 mmol) and Pd(dppf)Cl$_2$ (143 mg, 5 mol %) in 1,4-dioxane (30 ml) was degassed with a stream of N$_2$ for 10 min and then heated at 110° C. for 16 h. The reaction mixture was concentrated under reduced pressure and H$_2$O (100 ml) was added, and then was extracted with diethyl ether (2×75 ml). The combined ethereal extracts were extracted with 4N NaOH (3×50 ml). These combined basic extracts were neutralised with conc. HCl and then back-extracted with dichloromethane (3×100 ml). The combined organic filtrates were washed with brine (50 ml) and dried (MgSO$_4$) to give 3-[5-(5,5-dimethyl-[1,3,2]dioxaborinan-2-yl)-2-methylphenyl]pyridine (469 mg, 48%): δ$_H$ (360 MHz, CDCl$_3$) 1.04 (6H, s), 2.28 (3H, s), 3.77 (4H, s), 7.28–7.40 (2H, m), 7.63–7.80 (3H, m), 8.53–8.65 (2H, m).

A mixture of 3-bromo-7-trifluoromethylimidazo[1,2-α] pyrimidine (222 mg, 0.84 mmol), the foregoing boronate ester (469 mg, 1.67 mmol) and K$_3$PO$_4$ (769 mg, 3.34 mmol) in N,N-dimethylacetamide (5 ml) was degassed with a stream of N$_2$ for 5 min and then tetrakis(triphenylphosphine) palladium(0) (96 mg, 10 mol %) was added and the reaction was heated at 65° C. for 4 h. EtOAc (100 ml) was added and the mixture washed with H$_2$O (3×100 ml) and brine (100 ml), dried (MgSO$_4$) and concentrated under reduced pressure while dry loading onto silica. The residue was purified by column chromatography on silica using 70% EtOAc in hexanes containing 1% Et$_3$N and 1% MeOH as the eluent. The resulting material was taken up in MeOH and was poured onto a strong cation exchange cartridge and eluted with methanol. The product was then eluted with 2.0M NH$_3$ in MeOH and evaporated while dry loading onto silica. Subsequent purification by column chromatography on silica using 60% EtOAc in dichloromethane gave 3-[4-methyl-3-(pyridin-3-yl)phenyl]-7-trifluoromethylimidazo [1,2-α]pyrimidine (83 mg, 28%): δ$_H$ (400 MHz, d$^6$-DMSO) 2.35 (3H, s), 7.45–7.60 (3H, m), 7.65 (1H, d, J 1.9), 7.72 (1H, dd, J 7.9 and 1.9), 7.93 (1H, dt, J 7.8 and 1.9), 8.30 (1H, s), 8.60–8.66 (1H, m), 8.70 (1H, s), 9.35 (1H, d, J 7.2); m/z (ES$^+$) 354 (M$^+$).

EXAMPLE 63

3-[4-Chloro-3-(pyridin-3-yl)phenyl]-7-trifluoromethylimidazo[1,2-α]pyrimidine 3-Bromo-4-chloronitrobenzene (5.17 g, 21.9 mmol) was reacted with pyridine-3-boronic acid-1,3-propanediol cyclic ester (4.27 g, 26.2 mmol) over 24 h, as described in Example 62. The resulting crude residue was purified by column chromatography on silica, using 50% diethyl ether in dichloromethane as the eluent, to yield 3-(2-chloro-5-nitrophenyl) pyridine (3.53 g, 69%): δ$_H$ (360 MHz, CDCl$_3$) 7.42–7.48 (1H, m), 7.70 (1H, d, J 8.7), 7.81 (1H, dt, J 8.0 and 1.8), 8.17–8.27 (2H, m), 8.68–8.77 (2H, m).

Tin(II) chloride (11.87 g, 62.6 mmol) and 3-(2-chloro-5-nitrophenyl)pyridine (3.53 g, 15.1 mmol) were reacted as described in Example 62 to give 4-chloro-3-(pyridin-3-yl) phenylamine (2.69 g, 87%) which was used without purification on silica: $\delta_H$ (360 MHz, CDCl$_3$) 6.65–6.70 (2H, m), 7.26 (1H, dt, J 8.5 and 1.1), 7.33 (1H, dd, J 7.8 and 4.8), 7.77 (1H, dt, J 7.8 and 1.9), 8.59 (1H, dd, J 4.8 and 1.6), 8.66 (1H, d, J 1.8); m/z (ES$^+$) 205, 207 (3:1) (M$^+$+H).

tert-Butyl nitrite (3.9 ml, 32.9 mmol), the foregoing aniline (2.69 g, 13.2 mmol) and copper(II) bromide (3.23 g, 14.5 mmol) were reacted as described in Example 62 to yield 3-(5-bromo-2-chlorophenyl)pyridine (1.60 g, 45%) after chromatography on silica eluting with dichloromethane: $\delta_H$ (360 MHz, CDCl$_3$) 7.30–7.50 (4H, m), 7.77 (1H, dt, J 7.9 and 1.9), 8.60–8.70 (2H, m); m/z (ES$^+$) 268, 270 (1:1) (M$^+$).

3-(5-Bromo-2-chlorophenyl)pyridine (600 mg, 2.3 mmol) and bis(neopentyl glycolato)diborane (562 mg, 2.49 mmol) were reacted as described in Example 62 to yield 3-[2-chloro-5-(5,5-dimethyl-[1,3,2]dioxaborinan-2-yl)phenyl] pyridine (830 mg, 99%): $\delta_H$ (400 MHz, CDCl$_3$) 1.02 (6H, s), 3.79 (4H, s), 7.30–7.43 (2H, m), 7.48 (1H, d, J 7.8), 7.70–7.87 (2H, m), 8.56–8.63 (1H, m), 8.69 (1H, d, J 1.8); m/z (ES$^+$) 302, 304 (3:1) (M$^+$+H).

3-Bromo-7-trifluoromethylimidazo[1,2-α]pyrimidine (176 mg, 0.66 mmol) and the foregoing boronate ester (400 mg, 1.32 mmol) were reacted at 65° C. for 1 hour as described in Example 62 to yield 3-[4-chloro-3-(pyridin-3-yl)phenyl]-7-trifluoromethylimidazo[1,2-α]pyrimidine (125 mg, 50%): $\delta_H$ (400 MHz, d$^6$-DMSO) 7.52 (1H, d, J 7.1), 7.54–7.60 (1H, m), 7.76–7.84 (2H, m), 7.90 (1H, d, J 1.8), 8.02 (1H, dt, J 7.8 and 2.0), 8.36 (1H, s), 8.66 (1H, dd, J 4.8 and 1.6), 8.78 (1H, d, J 1.8), 9.39 (1H, d, J 7.0); m/z (ES$^+$) 375, 377 (3:1) (M$^+$+H).

EXAMPLE 64

3-[4-Methoxy-3-(pyridin-3-yl)phenyl]-7-trifluoromethylimidazo[1,2-α]primidine

2-Bromo-4-nitroanisole (3.0 g, 12.9 mmol) was reacted with pyridine-3-boronic acid-1,3-propanediol cyclic ester (2.53 g, 15.5 mmol) over 8 hours, as described in Example 62. The resulting crude residue was purified by column chromatography on silica, using 60–70% diethyl ether in dichloromethane as the eluent, to yield 3-(2-methoxy-5-nitrophenyl)pyridine (2.26 g, 85%): $\delta_H$ (360 MHz, d$^6$-DMSO) 3.94 (3H, s), 7.39 (1H, d, J 9.2), 7.50 (1H, dd, J 7.9 and 4.8), 7.97 (1H, dt, J 8.0 and 1.9), 8.19 (1H, d, J 2.8), 8.33 (1H, dd, J 9.2 and 2.8), 8.57–8.64 (1H, m), 8.74 (1H, d, J 1.9).

Tin(II) chloride (8.32 g, 43.9 mmol) and 3-(2-methoxy-5-nitrophenyl)pyridine (2.26 g, 11.0 mmol) were reacted as described in Example 62 to give, after purification by column chromatography on silica using 2.5% MeOH in dichloromethane as the eluent, 4-methoxy-3-(pyridin-3-yl) phenylamine (0.93 g, 42%): $\delta_H$ (360 MHz, CDCl$_3$) 3.73 (3H, s), 6.67–6.76 (2H, m), 6.84 (1H, d, J 8.5), 7.30 (1H, dd, J 8.5 and 4.7), 7.84 (1H, dt, J 7.9 and 1.9), 8.50–8.58 (1H, m), 8.74 (1H, d, J 2.0); m/z (ES$^+$) 201 (M$^+$+H).

tert-Butyl nitrite (1.38 ml, 11.6 mmol), the foregoing aniline (0.93 g, 4.65 mmol) and copper(II) bromide (1.14 g, 5.1 mmol) were reacted as described in Example 62 to yield 3-(5-bromo-2-methoxyphenyl)pyridine (630 mg, 52%) after chromatography on silica eluting with 2.5% MeOH in dichloromethane: $\delta_H$ (360 MHz, CDCl$_3$) 3.80 (1H, s), 6.88 (1H, d, J 8.7), 7.29–7.50 (3H, m), 7.70–7.87 (1H, m), 8.50–8.80 (2H, m); m/z (ES$^+$) 263, 265 (1:1) (M$^+$).

3-(5-Bromo-2-methoxyphenyl)pyridine (630 mg, 2.4 mmol) and bis(neopentyl glycolato)diborane (541 mg, 2.39 mmol) were reacted as described in Example 62 to yield 3-[5-(5,5-dimethyl-[1,3,2]dioxaborinan-2-yl)-2-methoxyphenyl]pyridine (932 mg, 99%): $\delta_H$ (400 MHz, CDCl$_3$) 1.02 (6H, s), 3.70 (4H, s), 3.76 (3H, s), 6.98 (1H, d, J 8.3 Hz), 7.28–7.37 (1H, m), 7.72–7.90 (3H, m), 8.52 (1H, dd, J 4.4 and 1.4), 8.78 (1H, d, J 1.5); m/z (ES$^+$) 297 (M$^+$+H).

3-Bromo-7-trifluoromethylimidazo[1,2-α]pyrimidine (224 mg, 0.84 mmol) and the foregoing boronate ester (500 mg, 1.69 mmol) were reacted at 65° C. for 80 min as described in Example 62 to yield 3-[4-methoxy-3-(pyridin-3-yl)phenyl]-7-trifluoromethylimidazo[1,2-α]pyrimidine (120 mg, 38%): $\delta_H$ (360 MHz, d$^6$-DMSO) 3.90 (3H, s), 7.39 (1H, d, J 8.5), 7.44–7.50 (2H, m), 7.72–7.81 (2H, m), 8.01 (1H, dt, J 8.0 and 1.9), 8.26 (1H, s), 8.55 (1H, dd, J 4.8 and 1.5), 8.85–8.92 (1H, m), 9.31 (1H, d, J 7.1); m/z (ES$^+$) 370 (M$^+$+H).

EXAMPLE 65

2-[3-(2,4-Difluoro-3-(pyridin-3-yl)phenyl)imidazo [1,2-α]pyrimidin-7-yl]propan-2-ol A mixture of 2-(3-bromoimidazo[1,2-α]pyrimidin-7-yl) propan-2-ol (256 mg, 1.0 mmol) and 2,4-difluoro-3-(pyridin-3-yl)benzeneboronic acid (352 mg, 1.5 mmol) in tetrahydrofuran (3 ml) and sodium carbonate (1.25 ml of a 2M solution in water, 2.5 mmol) was degassed with nitrogen for 10 min. Tetrakis(triphenylphosphine)palladium(0) (58 mg, 0.05 mmol) was added and this mixture was heated at 65° C. for 24 h. The reaction was cooled to ambient temperature then partitioned between dichloromethane and saturated aqueous sodium hydrogencarbonate. The organics were dried over anhydrous magnesium sulfate, filtered and pre-adsorbed onto silica. Purification by chromatography on silica gel eluting with dichloromethane (containing 1% conc. ammonia) on a gradient of methanol (1–5%) gave 2-[3-(2,4-difluoro-3-(pyridin-3-yl)phenyl)imidazo[1,2-α] pyrimidin-7-yl]propan-2-ol as a pale yellow oil which solidified on standing (200 mg, 44%). Bis-hydrochloride salt (from ethyl acetate/ethanol): $\delta_H$ (360 MHz, d$_6$-DMSO) 1.56 (6H, s), 7.62 (1H, t, J 9), 7.79–7.84 (1H, m), 7.86 (1H, s), 7.88 (1H, s), 8.32 (1H, d, J 8), 8.54 (1H, s), 8.80 (1H, d, J 5), 8.98 (1H, s), 9.27 (1H, dd, J 7 and 3).

EXAMPLE 66

1-[3-(4-Fluoro-3-(pyridin-3-yl)phenyl)imidazo[1,2-α]pyrimidin-7-yl]ethanone

3-Bromo-7-(1,1-dimethoxyethyl)imidazo[1,2-α] pyrimidine was coupled with 4-fluoro-3-(pyridin-3-yl) benzeneboronic acid as described in Example 65 to give 7-(1,1-dimethoxyethyl)-3-[4-fluoro-3-(pyridin-3-yl)phenyl] imidazo[1,2-α]pyrimidine as an orange foam. This was dissolved in 2.5N hydrochloric acid and stirred at 50° C. for 15 h. After cooling to ambient temperature the reaction was neutralised by addition of solid sodium hydrogencarbonate and the resulting solid collected by filtration. The solid was dissolved in dichloromethane/methanol (1:1) and pre-adsorbed onto silica. Flash column chromatography on silica gel eluting with dichloromethane containing 1% ammonia and 5% methanol furnished 1-[3-(4-fluoro-3-(pyridin-3-yl) phenyl)imidazo[1,2-α]pyrimidin-7-yl]ethanone as a yellow solid: $\delta_H$ (360 MHz, d$_6$-DMSO) 2.71 (3H, s), 7.54–7.63 (3H, m), 7.84–7.88 (1H, m), 8.01 (1H, dd, J 8 and 2), 8.10–8.13 (1H, m), 8.34 (1H, s), 8.66 (1H, dd, J 5 and 2), 8.90 (1H, s), 9.24 (1H, d, J 7).

EXAMPLE 67

3'-[7-(1-Hydroxy-1-methylethyl)imidazo[1,2-α]pyrimidin-3-yl]-4,2',6'-trifluorobiphenyl-2-carbonitrile A mixture of 2,6-difluorobromobenzene (125.5 g, 650 mmol) in 98% sulphuric acid (250 ml) was cooled in an ice-water bath and then treated with a 1:1 mixture of 98% sulphuric acid and fuming nitric acid (100 ml) added at such a rate that the internal temperature never exceeded 35° C. Once addition was complete the reaction was stirred at ambient temperature for 3 h then poured onto ice. This mixture was diluted with water (final volume 5 l), the resulting solid collected by filtration, washed with water, then dried under vacuum over phosphorus pentoxide, to afford 2-bromo-1,3-difluoro-4-nitrobenzene as a cream-coloured solid (145 g, 94%): $\delta_H$ (360 MHz, $CDCl_3$) 7.10–7.15 (1H, m), 8.09–8.16 (1H, m).

A mixture of 2-bromo-1,3-difluoro-4-nitrobenzene (30 g, 130 mmol) and tin(II) chloride dihydrate in 36% hydrochloric acid (150 ml) was heated to 40° C. Diethyl ether (20 ml) was slowly added to bring about solution. Once in solution the reaction proceeded rapidly and the ether boiled away. After heating at 60° C. for 1 h the reaction was cooled and then poured onto ice-water (1.5 l). The solution was made basic (pH 13) with 30% aq. sodium hydroxide keeping the internal temperature below 20° C. The resulting grey slurry was swirled with chloroform (2×500 ml), the organic extracts were combined, washed with water, dried over anhydrous magnesium sulfate containing 2 g decolourising charcoal, filtered and evaporated to dryness. Trituration with isohexane afforded 3-bromo-2,4-difluorophenylamine as a buff-coloured solid (23 g, 85%): $\delta_H$ (360 MHz, $CDCl_3$) 3.51 (2H, br), 6.65–6.70 (1H, m), 6.75–6.80 (1H, m).

2-Bromo-5-fluorobenzonitrile was converted to 5-fluoro-2-(4,4,5,5-tetramethyl-[1,3,2]dioxaborolan-2-yl)benzonitrile as described in Example 55 to give a straw-coloured solid: $\delta_H$ (360 MHz, $CDCl_3$) 1.38 (12H, s), 7.27 (1H, ddd, J 8, 8 and 2), 7.39 (1H, dd, J 9 and 2), 7.90 (1H, dd, J 8 and 6).

A solution of 3-bromo-2,4-difluorophenylamine (5.2 g, 25 mmol) and 5-fluoro-2-(4,4,5,5-tetramethyl-[1,3,2]dioxaborolan-2-yl)benzonitrile (7.10 g, 28.8 mmol) in tetrahydrofuran (95 ml) and water (5 ml) was treated with potassium fluoride (4.8 g, 82.5 mmol) and this mixture was degassed with nitrogen for 10 min before adding tris(dibenzylideneacetone)dipalladium(0) (460 mg, 0.5 mmol) and tri-tert-butylphosphine (2.5 ml of a 0.2M solution in 1,4-dioxane, 0.5 mmol). The reaction was then heated at 50° C. for 2 h then cooled to ambient temperature. The mixture was poured into ice-cold 0.5N sodium hydroxide (750 ml), stirred for 10 min and the solid collected by filtration. This was triturated with water and dried to afford 3'-amino-4,2',6'-trifluorobiphenyl-2-carbonitrile as a grey powder (6.6 g). Used without further purification: $\delta_H$ (360 MHz, $CDCl_3$) 3.74 (2H, br), 6.79–6.89 (2H, m), 7.36–7.42 (1H, m), 7.45–7.51 (2H, m).

3'-Amino-4,2',6'-trifluorobiphenyl-2-carbonitrile was bromo-deaminated as described in Example 1 to give 3'-bromo-4,2',6'-trifluorobiphenyl-2-carbonitrile as an orange solid: $\delta_H$ (360 MHz, $CDCl_3$) 6.97–7.03 (1H, m), 7.39–7.54 (3H, m), 7.62–7.68 (1H, m).

3'-Bromo-4,2',6'-trifluorobiphenyl-2-carbonitrile was reacted with bis(pinacolato)diboron as described in Example 1 to give 3'-(4,4,5,5-tetramethyl-[1,3,2]dioxaborolan-2-yl)-4,2',6'-trifluorobiphenyl-2-carbonitrile as a buff-coloured solid: m/z ($ES^+$) 360 ($M^+$+H).

2-(3-Bromoimidazo[1,2-α]pyrimidin-7-yl)propan-2-ol was coupled with 3'-(4,4,5,5-tetramethyl-[1,3,2]dioxaborolan-2-yl)-4,2',6'-trifluorobiphenyl-2-carbonitrile as described in Example 65 to give 3'-[7-(1-hydroxy-1-methylethyl)imidazo[1,2-α]pyrimidin-3-yl]-4,2',6'-trifluorobiphenyl-2-carbonitrile as an off-white solid: $\delta_H$ (400 MHz, $d_6$-DMSO) 1.51 (6H, s), 7.42 (1H, d, J 7), 7.54–7.58 (1H, m), 7.80–7.85 (1H, m), 7.89–7.96 (3H, m), 8.14 (1H, dd, J 9 and 2), 8.78 (1H, dd, J 7 and 3).

EXAMPLE 68

2-[3-(4-Fluoro-3-(pyridin-3-yl)phenyl)imidazo[1,2-α]pyrimidin-7-yl]propane-1,2-diol A cooled (−10° C.) solution of methyl isopropenyl ketone (42 g, 500 mmol) in acetone (200 ml) was treated simultaneously but independently (do not pre-mix) with solutions of hydrogen peroxide (27.5 wt % in water, 61.9 g, 500 mmol) and aqueous sodium hydroxide (10 ml, 4N) added drop-wise at such a rate that the internal temperature did not exceed −5° C. Once addition was complete the reaction was stirred at −10° C. for 12 h. NMR indicated that the reaction was ~50% complete and so further portions of hydrogen peroxide (27.5 wt % in water, 61.9 g) and aqueous sodium hydroxide (10 ml, 4N) were added and stirring at −10° C. continued for 16 h. The reaction was made neutral with 4N sulphuric acid (20 ml) and then added drop-wise over 15 min to a flask containing manganese(IV) oxide (10 g). This mixture was filtered through glass microfibre filter paper (GF/A) and the acetone removed by distillation at atmospheric pressure to give crude 1-(2-methyloxiranyl)ethanone as a colourless liquid. Used without further purification: $\delta_H$ (360 MHz, $d_6$-DMSO) 1.36 (3H, s), 1.97 (3H, s), 2.91 (1H, d, J 5), 3.12 (1H, d, J 5).

The crude sample of 1-(2-methyloxiranyl)ethanone prepared above was diluted to 300 ml with water and treated with 70% perchloric acid (10 ml). This mixture was then heated at reflux for 6 h before cooling to ambient temperature. The mixture was filtered to remove black solids and the filtrate made neutral with solid sodium hydrogencarbonate. The aqueous filtrate was then saturated with solid sodium chloride, filtered (to remove excess) and continuously extracted with dichloromethane for 3 days. The organic phase was dried over anhydrous magnesium sulfate, filtered and evaporated to dryness. The residue was purified by dry flash chromatography, eluting with isohexane on a gradient of ether (20–100%) to afford 3,4-dihydroxy-3-methylbutan-2-one as a pale yellow oil (30 g, 51% over 2 steps): $\delta_H$ (360 MHz, $CDCl_3$) 1.29 (3H, s), 2.29 (3H, s), 2.50 (1H, br), 3.64 (1H, d, J 12), 3.85 (1H, d, J 12), 4.15 (1H, br).

A mixture of 3,4-dihydroxy-3-methylbutan-2-one (4.13 g, 35 mmol), acetone (25 ml) and p-toluenesulfonic acid monohydrate (33 mg, 0.18 mmol) in isohexane (75 ml) was heated in a Dean-Stark apparatus for 10 h. The solvent was removed by distillation at atmospheric pressure and the residue purified by chromatography on silica gel. Elution with 50% ether in isohexane afforded 1-(2,2,4-trimethyl-[1,3]dioxolan-4-yl)ethanone as a pale yellow liquid (5.1 g, 92%): $\delta_H$ (360 MHz, $d_6$-DMSO) 1.29 (3H, s), 1.34 (3H, s), 1.36 (3H, s), 2.20 (3H, s), 3.69 (1H, d, J 9), 4.18 (1H, d, J 9).

1-(2,2,4-Trimethyl-[1,3]dioxolan-4-yl)ethanone was converted to 3,3-diethoxy-1-(2,2,4-trimethyl-[1,3]dioxolan-4-yl)propan-1-one as described in Example 3 then condensed with 2-aminoimidazole sulfate as in Example 2 to give 7-(2,2,4-trimethyl-[1,3]dioxolan-4-yl)imidazo[1,2-α]

pyrimidine as a pale orange solid (7.10 g, 96%): $\delta_H$ (360 MHz, $d_6$-DMSO) 1.31 (3H, s), 1.47 (3H, s), 1.57 (3H, s), 4.05 (1H, d, J 9), 4.49 (1H, d, J 9), 7.27 (1H, d, J 7), 7.71 (1H, d, J 1), 7.92 (1H, d, J 1), 8.98 (1H, d, J 7).

7-(2,2,4-Trimethyl-[1,3]dioxolan-4-yl)imidazo[1,2-α]pyrimidine was brominated as described in Example 1 to give 3-bromo-7-(2,2,4-trimethyl-[1,3]dioxolan-4-yl)imidazo[1,2-α]pyrimidine as an off-white solid: $\delta_H$ (400 MHz, $d_6$-DMSO) 1.31 (3H, s), 1.47 (3H, s), 1.57 (3H, s), 4.06 (1H, d, J 9), 4.47 (1H, d, J 9), 7.40 (1H, d, J 7), 7.88 (1H, s), 8.81 (1H, d, J 7).

3-Bromo-7-(2,2,4-trimethyl-[1,3]dioxolan-4-yl)imidazo[1,2-α]pyrimidine was coupled with 3-[2-fluoro-5-(4,4,5,5-tetramethyl-[1,3,2]dioxaborolan-2-yl)phenyl]pyridine as described in Example 65 to give 3-[4-fluoro-3-(pyridin-3-yl)phenyl]-7-(2,2,4-trimethyl-[1,3]dioxolan-4-yl)imidazo[1,2-α]pyrimidine as an orange oil: $\delta_H$ (400 MHz, $d_6$-DMSO) 1.33 (3H, s), 1.47 (3H, s), 1.59 (3H, s), 4.08 (1H, d, J 9), 4.49 (1H, d, J 9), 7.31 (1H, d, J 7), 7.54–7.59 (2H, m), 7.77–7.81 (1H, m), 7.94 (1H, dd, J 7 and 2), 8.01 (1H, s), 8.09–8.12 (1H, m), 8.65 (1H, dd, J 5 and 2), 8.89 (1H, s), 9.08 (1H, d, J 7).

3-[4-Fluoro-3-(pyridin-3-yl)phenyl]-7-(2,2,4-trimethyl-[1,3]dioxolan-4-yl)imidazo[1,2-α]pyrimidine (1.00 g, 2.47 mmol) was stirred in 2N hydrochloric acid (20 ml) at 70° C. for 10 min. The reaction mixture was allowed to cool and was then loaded onto a strong cation-exchange cartridge. Non-basic impurities were removed by elution with methanol. Elution with 10% ammonia in methanol gave 2-[3-(4-fluoro-3-(pyridin-3-yl)phenyl)imidazo[1,2-α]pyrimidin-7-yl]propane-1,2-diol as an oil (450 mg) which solidified on standing. Bis-hydrochloride salt (from ethyl acetate/ethanol): $\delta_H$ (360 MHz, $d_6$-DMSO) 1.50 (3H, s), 3.67 (2H, m), 7.74 (1H, dd, J 11 and 8), 7.89 (3H, m), 8.13 (1H, dd, J 7 and 2), 8.51 (1H, d, J 8), 8.58 (1H, s), 8.85 (1H, dd, J 5 and 1), 9.12 (1H, s), 9.40 (1H, d, J 7).

EXAMPLE 69

3-[2-Fluoro-5-(7-trifluoromethylimidazo[1,2-α]pyrimidin-3-yl)phenyl]thiophene-2-carbonitrile 3-Bromothiophene-2-carbonitrile was coupled with 2-(2-fluoro-5-nitrophenyl)-4,4,5,5-tetramethyl-[1,3,2]dioxaborolane using the conditions described in Example 1 to give 3-(2-fluoro-5-nitrophenyl)thiophene-2-carbonitrile as an off-white solid. This in turn was reduced using the conditions outlined in Example 1 to give 3-(5-amino-2-fluorophenyl)thiophene-2-carbonitrile: $\delta_H$ (400 MHz, CDCl$_3$) 3.67 (2H, s), 6.68–6.72 (1H, m), 6.90 (1H, dd, J 6 and 3), 7.00 (1H, dd, J 9 and 1), 7.30 (1H, dd, J 5 and 2), 7.60 (1H, d, J 5).

3-(5-Amino-2-fluorophenyl)thiophene-2-carbonitrile was bromo-deaminated by the method of Example 32 to give 3-(5-bromo-2-fluorophenyl)thiophene-2-carbonitrile: $\delta_H$ (360 MHz, CDCl$_3$) 7.08–7.18 (1H, m), 7.27–7.44 (1H, m), 7.51–7.56 (1H, m), 7.61–7.74 (2H, m).

3-(5-Bromo-2-fluorophenyl)thiophene-2-carbonitrile was reacted as described in Example 1 to give 3-[2-fluoro-5-(4,4,5,5-tetramethyl-[1,3,2]dioxaborolan-2-yl)phenyl]thiophene-2-carbonitrile as a buff-coloured solid: m/z (ES$^+$) 330 (M$^+$+H).

3-Bromo-7-trifluoromethylimidazo[1,2-α]pyrimidine was coupled with 3-[2-fluoro-5-(4,4,5,5-tetramethyl-[1,3,2]dioxaborolan-2-yl)phenyl]thiophene-2-carbonitrile as described in Example 65 to give 3-[2-fluoro-5-(7-trifluoromethylimidazo[1,2-α]pyrimidin-3-yl)phenyl]thiophene-2-carbonitrile as a yellow solid: $\delta_H$ (400 MHz, CDCl$_3$) 7.32 (1H, d, J 7), 7.44–7.47 (2H, m), 7.63–7.66 (1H, m), 7.72 (1H, d, J 5), 7.88 (1H, dd, J 7 and 2), 8.12 (1H, s), 9.09 (1H, d, J 7).

EXAMPLE 70

3-{2-Fluoro-5-[7-(1-hydroxy-1-methylethyl)imidazo[1,2-α]pyrimidin-3-yl]phenyl}thiophene-2-carbonitrile 2-(3-Bromoimidazo[1,2-α]pyrimidin-7-yl)propan-2-ol was coupled with 3-[2-fluoro-5-(4,4,5,5-tetramethyl-[1,3,2]dioxaborolan-2-yl)phenyl]thiophene-2-carbonitrile as described in Example 65 to give 3-{2-fluoro-5-[7-(1-hydroxy-1-methylethyl)imidazo[1,2-α]pyrimidin-3-yl]phenyl}thiophene-2-carbonitrile as a buff-coloured solid: $\delta_H$ (400 MHz, CDCl$_3$) 1.57 (6H, s), 7.10 (1H, d, J 7), 7.41–7.44 (2H, m), 7.60–7.64 (1H, m), 7.71 (1H, d J 5), 7.84 (1H, dd, J 7 and 2), 7.87 (1H, s), 8.88 (1H, d, J 7).

EXAMPLE 71

2-{3-[4-Fluoro-3-(1-oxypyridin-3-yl)phenyl]imidazo[1,2-α]pyrimidin-7-yl}propan-2-ol A mixture of 3-(5-bromo-2-fluorophenyl)pyridine (2.52 g, 10.0 mmol) and peracetic acid (3.37 ml of a 36–40 wt % solution in acetic acid) in tetrahydrofuran (40 ml) was stirred at ambient temperature for 1 h and then heated at 50° C. for 2 h. Hydrogen peroxide (35 wt % solution in water, 1 ml) was added and the mixture heated at 50° C. for a further hour. The solvent was removed in vacuo and the residue diluted with water and layered with ethyl acetate. Solid sodium hydrogencarbonate was added to pH 8. The layers were separated and the organic layer washed with water, brine, dried over anhydrous magnesium sulfate, filtered and pre-adsorbed onto silica. Purification by flash column chromatography on silica gel eluting with dichloromethane (containing 1% ammonia) on a gradient of methanol (2–5%) gave 3-(5-bromo-2-fluorophenyl)pyridine-1-oxide as a white solid (2.00 g, 75%): $\delta_H$ (400 MHz, CDCl$_3$) 7.09–7.14 (1H, m), 7.35–7.43 (2H, m), 7.52–7.57 (2H, m), 8.22–8.25 (1H, m), 8.42 (1H, t, J 1).

Triethylsilyl trifluoromethanesulfonate (4.85 ml, 21.5 mmol) was added dropwise over 15 min to a cooled (−50° C.) solution of 2-(3-bromoimidazo[1,2-α]pyrimidin-7-yl)propan-2-ol (5.0 g, 19.5 mmol) and N,N-diisopropylethylamine (4.76 ml, 27.5 mmol) in dichloromethane (150 ml). The mixture was stirred at −50° C. for 20 min then allowed to warm to ambient temperature over 10 h. The reaction mixture was diluted with dichloromethane (100 ml) and washed with 1N hydrochloric acid (100 ml) and water (100 ml), dried over anhydrous magnesium sulfate, filtered and evaporated. The resulting red oil was purified by dry flash column chromatography on silica eluting with dichloromethane on a gradient of methanol (0–3%) to give 3-bromo-7-(1-methyl-1-triethylsilanyloxyethyl)imidazo[1,2-α]pyrimidine as a pale yellow oil which crystallised on standing (6.21 g, 86%): $\delta_H$ (400 MHz, CDCl$_3$) 0.64 (6H, q, J 8), 0.97 (9H, t, J 8), 7.50 (1H, d, J 7), 7.72 (1H, s), 8.35 (1H, d, J 7), 10.36 (1H, d, J 7); m/z (ES$^+$) 358 (M$^+$+H).

To a cooled (−78° C.) solution of 3-bromo-7-(1-methyl-1-triethylsilanyloxyethyl)imidazo[1,2-α]pyrimidine (440 mg, 1.20 mmol) in tetrahydrofuran (4 ml) was added isopropylmagnesium chloride (0.63 ml of a 2M solution in tetrahydrofuran, 1.26 mmol). After stirring at −78° C. for 5 min tributyltin chloride (0.36 ml, 1.32 mmol) was added, the reaction stirred for 10 min at −78° C., then allowed to warm to ambient temperature, to give a solution of 7-(1-methyl-1-triethylsilanyloxyethyl)-3-tributylstannanylimidazo[1,2-α]pyrimidine: m/z (ES$^+$) 581 (M$^+$+H).

To a degassed solution of 7-(1-methyl-1-triethylsilanyloxyethyl)-3-tributylstannanylimidazo[1,2-α]pyrimidine was added 3-(5-bromo-2-fluorophenyl)pyridine-1-oxide (480 mg, 1.8 mmol) and tetrakis(triphenylphosphine)palladium(0) (140 mg, 0.12 mmol) and the mixture heated at reflux for 7 h. The crude reaction was adsorbed onto silica and purified by chromatography on silica gel eluting with dichloromethane (containing 1% ammonia) on a gradient of methanol (0.5–2%) to give an orange solid. This was dissolved in methanol (4 ml) and 36% hydrochloric acid (1 ml) was added. This was stirred at 50° C. for 5 h and then at ambient temperature for 12 h. The mixture was evaporated to dryness and the residue dissolved in dichloromethane. Saturated sodium hydrogencarbonate solution was added until pH 8. The organic phase was washed with water, brine, dried over anhydrous magnesium sulfate, filtered and evaporated to dryness. Purification by preparative thin layer chromatography eluting with 10% methanol in dichloromethane led to 2-{3-[4-fluoro-3-(1-oxypyridin-3-yl)phenyl]imidazo[1,2-α]pyrimidin-7-yl}propan-2-ol as a white solid (40 mg, 10%): $\delta_H$ (360 MHz, d$_6$-DMSO) 1.51 (6H, s), 7.40 (1H, d, J 7), 7.53–7.60 (2H, m), 7.65 (1H, dd, J 7 and 1), 7.79–7.84 (1H, m), 7.95 (1H, dd, J 5 and 3), 7.97 (1H, s), 8.30 (1H, d, J 6), 8.62 (1H, d, J 1), 9.08 (1H, d, J 7).

EXAMPLES 72 AND 73

3-{2,6-Difluoro-3-[7-(1-hydroxy-1-methylethyl)imidazo[1,2-α]pyrimidin-3-yl]phenyl}thiophene-2-carbonitrile and 3-{2,6-difluoro-3-[7-(1-hydroxy-1-methylethyl)imidazo[1,2-α]pyrimidin-3-yl]phenyl}thiophene-2-carboxylic acid amide 3-Bromothiophene-2-carbonitrile was reacted with bis(pinacolato)diboron as described in Example 1 to give 3-(4,4,5,5-tetramethyl-[1,3,2]dioxaborolan-2-yl)thiophene-2-carbonitrile. This was coupled with 3-bromo-2,4-difluorophenylamine as outlined in Example 67 to give 3-(3-amino-2,6-difluorophenyl)thiophene-2-carbonitrile as an orange solid (3.00 g, 59%): $\delta_H$ (360 MHz, CDCl$_3$) 3.71 (2H, s), 6.84 (1H, q, J 3), 6.86 (1H, s), 7.21–7.23 (1H, m), 7.64 (1H, d, J 5).

3-(3-Amino-2,6-difluorophenyl)thiophene-2-carbonitrile was bromo-deaminated as described in Example 32 to give 3-(3-bromo-2,6-difluorophenyl)thiophene-2-carbonitrile as a pale yellow solid: $\delta_H$ (360 MHz, CDCl$_3$) 6.97–7.02 (1H, m), 7.21–7.22 (1H, m), 7.60–7.69 (2H, m).

3-(3-Bromo-2,6-difluorophenyl)thiophene-2-carbonitrile was reacted with bis(pinacolato)diboron as described in Example 1 to give 3-[2,6-difluoro-3-(4,4,5,5-tetramethyl-[1,3,2]dioxaborolan-2-yl)phenyl]thiophene-2-carbonitrile as a buff-coloured solid: m/z (ES$^+$) 348 (M$^+$+H).

2-(3-Bromoimidazo[1,2-α]pyrimidin-7-yl)propan-2-ol was coupled with 3-[2,6-difluoro-3-(4,4,5,5-tetramethyl-[1,3,2]dioxaborolan-2-yl)phenyl]thiophene-2-carbonitrile as in Example 65 to give (in order of elution on silica) 3-{2,6-difluoro-3-[7-(1-hydroxy-1-methylethyl)imidazo[1,2-α]pyrimidin-3-yl]phenyl}thiophene-2-carbonitrile (68 mg, 18%): $\delta_H$ (400 MHz, CDCl$_3$) 1.58 (6H, s), 7.11 (1H, d, J 7), 7.28–7.33 (2H, m), 7.58–7.64 (1H, m), 7.74 (1H, d, J 5), 7.89 (1H, s), 8.48 (1H, dd, J 7 and 4); followed by 3-{2,6-difluoro-3-[7-(1-hydroxy-1-methylethyl)imidazo[1,2-α]pyrimidin-3-yl]phenyl}thiophene-2-carboxylic acid amide (53 mg, 14%): $\delta_H$ (400 MHz, CDCl$_3$) 1.58 (6H, s), 5.65 (2H, s), 7.07 (1H, d, J 7), 7.15–7.22 (2H, m), 7.51 (1H, dd, J 6 and 2), 7.55 (1H, d, J 5), 7.86 (1H, s), 8.51 (1H, q, J 4).

EXAMPLE 74

3-[4-Fluoro-3-(3-fluoropyridin-4-yl)phenyl]-7-trifluoromethylimidazo[1,2-α]pyrimidine 3-Fluoro-4-bromopyridine (isolated as its hydrobromide salt) was prepared as described by Queguiner et al. in *Tetrahedron*, 1983, 39, 2009–2021. This was coupled with 2-(2-fluoro-5-nitrophenyl)-4,4,5,5-tetramethyl-[1,3,2]dioxaborolane using the Suzuki conditions described in Example 65 to give 4-(2-fluoro-5-nitrophenyl)-3-fluoropyridine: $\delta_H$ (360 MHz, CDCl$_3$) 7.37–7.42 (2H, m), 8.36–8.37 (1H, m), 8.38 (1H, s), 8.58 (1H, d, J 5), 8.65 (1H, d, J 1).

4-(2-Fluoro-5-nitrophenyl)-3-fluoropyridine was reduced using the procedure described in Example 40 to give 4-(5-amino-2-fluorophenyl)-3-fluoropyridine as an off-white solid: m/z (ES$^+$) 207 (M$^+$+H).

4-(5-Amino-2-fluorophenyl)-3-fluoropyridine was bromo-deaminated as described in Example 1 to give 4-(5-bromo-2-fluorophenyl)-3-fluoropyridine as a white solid: $\delta_H$ (360 MHz, CDCl$_3$) 7.11 (1H, t, J 10), 7.35 (1H, t, J 5), 7.55–7.58 (2H, m), 8.51 (1H, d, J 5), 8.59 (1H, d, J 1).

4-(5-Bromo-2-fluorophenyl)-3-fluoropyridine was reacted with bis(pinacolato)diboron by the method of Example 1 to give 4-[2-fluoro-5-(4,4,5,5-tetramethyl-[1,3,2]dioxaborolan-2-yl)phenyl]-3-fluoropyridine as a buff-coloured solid: m/z (ES$^+$) 235 (M$^+$+H).

3-Bromo-7-trifluoromethylimidazo[1,2-α]pyrimidine was coupled to 4-[2-fluoro-5-(4,4,5,5-tetramethyl-[1,3,2]dioxaborolan-2-yl)phenyl]-3-fluoropyridine using the method of Example 65 to give 3-[4-fluoro-3-(3-fluoropyridin-4-yl)phenyl]-7-trifluoromethylimidazo[1,2-α]pyrimidine as a yellow solid (130 mg, 35%): $\delta_H$ (400 MHz, CDCl$_3$) 7.28 (1H, d, J 7), 7.43–7.48 (2H, m), 7.63–7.68 (2H, m), 8.11 (1H, s), 8.55 (1H, d, J 5), 8.64 (1H, d, J 1), 8.77 (1H, d, J 7).

EXAMPLE 75

4-Chloro-2'-fluoro-5'-(7-trifluoromethylimidazo[1,2-α]pyrimidin-3-yl)biphenyl-2-carbonitrile 2-Amino-5-chlorobenzonitrile was bromo-deaminated as described in Example 1 to give 2-bromo-5-chlorobenzonitrile as a white solid: $\delta_H$ (400 MHz, CDCl$_3$) 7.45 (1H, dd, J 9 and 3), 7.61–7.64 (2H, m).

2-Bromo-5-chlorobenzonitrile was coupled with 2-(2-fluoro-5-nitrophenyl)-4,4,5,5-tetramethyl-[1,3,2]dioxaborolane in the same way as Example 1 to give 4-chloro-2'-fluoro-5'-nitrobiphenyl-2-carbonitrile as a grey solid: $\delta_H$ (360 MHz, CDCl$_3$) 7.39–7.43 (1H, m), 7.47–7.64 (1H, m), 7.73 (1H, dd, J 8 and 2), 7.82 (1H, d, J 2), 8.26–8.45 (2H, m).

4-Chloro-2'-fluoro-5'-nitrobiphenyl-2-carbonitrile was reduced in the same manner described in Example 40 to give 5'-amino-4-chloro-2'-fluorobiphenyl-2-carbonitrile as an off-white solid: $\delta_H$ (400 MHz, CDCl$_3$) 3.36–3.96 (2H, s), 6.64–6.74 (2H, m), 7.00 (1H, t, J 9), 7.42–7.55 (1H, m), 7.62 (1H, dd, J 8 and 2), 7.73 (1H, d, J 2).

5'-Amino-4-chloro-2'-fluorobiphenyl-2-carbonitrile was bromo-deaminated using the procedure outlined in Example 1 to give 5'-bromo-4-chloro-2'-fluorobiphenyl-2-carbonitrile: δ$_H$ (360 MHz, CDCl$_3$) 7.03–7.15 (1H, m), 7.41–7.66 (4H, m), 7.76 (1H, d, J 2).

5'-Bromo-4-chloro-2'-fluorobiphenyl-2-carbonitrile was reacted with bis(pinacolato)diboron as in Example 1 to give 4-chloro-2'-fluoro-5'-(4,4,5,5-tetramethyl-[1,3,2]dioxaborolan-2-yl)biphenyl-2-carbonitrile as a brown oil: m/z (ES$^+$) 358 (M$^+$+H).

3-Bromo-7-trifluoromethylimidazo[1,2-α]pyrimidine was coupled with 4-chloro-2'-fluoro-5'-(4,4,5,5-tetramethyl-[1,3,2]dioxaborolan-2-yl)biphenyl-2-carbonitrile by the method of Example 65 to give 4-chloro-2'-fluoro-5'-(7-trifluoromethylimidazo[1,2-α]pyrimidin-3-yl)biphenyl-2-carbonitrile as an off-white solid: δ$_H$ (360 MHz, CDCl$_3$) 7.29 (1H, d, J 7), 7.43–7.48 (1H, t, J 9), 7.54–7.71 (4H, m), 7.83 (1H, d, J 2), 8.10 (1H, s), 9.02 (1H, d, J 7).

EXAMPLE 76

3-[4-Fluoro-3-(5-methylpyridin-3-yl)phenyl]-7-trifluoromethylimidazo[1,2-α]pyrimidine A mixture of 3-bromo-5-methylpyridine (0.5 g, 2.91 mmol), bis(neopentyl glycolato)diboron (0.72 g, 3.19 mmol) and potassium acetate (0.86 g, 8.76 mmol) in 1,4-dioxane (10 ml) was degassed with nitrogen for 10 min. [1,1'-Bis(diphenylphosphino)ferrocene]palladium(II) dichloride 1:1 dichloromethane adduct (237 mg, 0.29 mmol) was added and the mixture heated at 100° C. for 1 h. The solvent was evaporated in vacuo and the residue partitioned between dichloromethane and water. The aqueous phase was re-extracted with dichloromethane and the combined organic layers were extracted with 4N sodium hydroxide (×3). The combined aqueous layers were extracted with diethyl ether (×2) and the organic layers discarded. The aqueous phase was neutralised with 5N hydrochloric acid and extracted with dichloromethane (×3). The combined organic layers were washed with brine, dried over anhydrous magnesium sulphate and evaporated to give 3-(5,5-dimethyl-[1,3,2]dioxaborinan-2-yl)-5-methylpyridine as a beige solid (150 mg, 25%): δ$_H$ (360 MHz, d$_6$-DMSO) 0.96 (6H, s), 2.28 (3H, s), 3.77 (4H, s), 7.79–7–82 (1H, m), 8.43–8.46 (1H, m), 8.56–8.59 (1H, m).

To a mixture of 3-(3-bromo-4-fluorophenyl)-7-trifluoromethylimidazo[1,2-α]pyrimidine (150 mg, 0.42 mmol) and 3-(5,5-dimethyl-[1,3,2]dioxaborinan-2-yl)-5-methylpyridine in 1,4-dioxane (5 ml) was added a solution of caesium carbonate (340 mg, 1.04 mmol) in water (0.5 ml). The reaction was degassed with nitrogen and tetrakis(triphenylphosphine)palladium(0) (48 mg, 0.04 mmol) was added and the mixture heated at 70° C. for 1 h. The solvent was evaporated in vacuo and the residue was partitioned between dichloromethane and water. The aqueous phase was re-extracted with dichloromethane and the combined organic layers dried over anhydrous magnesium sulphate, filtered and evaporated. The residue was purified using a short silica gel column eluting with 2% diethyl ether in dichloromethane followed by 15% diethyl ether in dichloromethane to give a yellow solid. This was purified further by loading as a solution in methanol onto a cartridge of strong cation-exchange resin, eluting with methanol then with 2M ammonia in methanol. The basic fractions were concentrated in vacuo to give a dark cream solid. The solid was triturated with diethyl ether to give 3-[4-fluoro-3-(5-methylpyridin-3-yl)phenyl]-7-trifluoromethylimidazo[1,2-α]pyrimidine as a cream solid (55 mg, 35%): δ$_H$ (360 MHz, d$_6$-DMSO) 2.39 (3H, s), 7.51 (1H, d, J 7), 7.60 (1H, dd, J 11 and 9), 7.85 (1H, ddd, J 9, 5 and 2), 7.91–7.94 (1H, m), 8.00 (1H, dd, J 7 and 2), 8.33 (1H, s), 8.49 (2H, d, J 2), 8.68–8.71 (1H, m), 9.36 (1H, d, J 7); m/z (ES$^+$) 373 (M$^+$+H).

EXAMPLE 77

3-[2-Fluoro-2'-(methanesulfonyl)biphenyl-5-yl]-7-trifluoromethylimidazo[1,2-α]pyrimidine A mixture of 2-bromo-1-fluoro-4-nitrobenzene (5.89 g, 26.8 mmol), 2-(methylthio)benzeneboronic acid (5.62 g, 33.5 mmol) and potassium fluoride (5.13 g, 88.3 mmol) in tetrahydrofuran (70 ml) was degassed with nitrogen for 30 min. This mixture was then treated with tris(dibenzylideneacetone)dipalladium(0) (496 mg, 0.541 mmol) followed by tri-tert-butylphosphine (5.35 ml of a 0.2M solution in 1,4-dioxane, 1.07 mmol) and the reaction was degassed for a further 10 min. The resulting slurry was then heated at 50° C. for 16 h under nitrogen. After cooling, the reaction mixture was partitioned between ethyl acetate (300 ml) and water (300 ml). The organic layer was washed with brine (200 ml), dried over anhydrous sodium sulphate, filtered and evaporated. Purification by chromatography on silica gel eluting with isohexane on a gradient of ethyl acetate (5–10%) gave 2-fluoro-2'-methylthio-5-nitrobiphenyl as a pale yellow solid (6.95 g, 99%): δ$_H$ (360 MHz, CDCl$_3$) 2.42 (3H, s), 7.21–7.32 (3H, m), 7.37 (1H, d, J 7), 7.44 (1H, td, J 8 and 2), 8.27–8.31 (2H, m).

A solution of 2-fluoro-2'-methylthio-5-nitrobiphenyl (6.00 g, 22.8 mmol) in tetrahydrofuran (50 ml) and ethanol (50 ml) was treated with tin(II) chloride dihydrate (25.70 g, 113.9 mmol) and the mixture was stirred at ambient temperature for 25 h. The solvent was evaporated and the residue stirred with 2N sodium hydroxide solution (240 ml) for 18 h. The resulting suspension was extracted with dichloromethane (3×200 ml). The combined organic extracts were dried over anhydrous magnesium sulphate and evaporated. The residue was purified by flash chromatography on silica gel eluting with 35% ethyl acetate in isohexane to afford 2-fluoro-2'-(methylthio)biphenyl-5-ylamine as a white solid (5.20 g, 98%): δ$_H$ (360 MHz, CDCl$_3$) 2.39 (3H, s), 6.60 (1H, dd, J 6 and 3), 6.64–6.68 (1H, m), 6.94 (1H, t, J 9), 7.19–7.20 (2H, m), 7.30 (1H, d, J 8), 7.33–7.37 (1H, m).

To a solution of 2-fluoro-2'-(methylthio)biphenyl-5-ylamine (397 mg, 1.70 mmol) in 1,4-dioxane (2.1 ml) was added 48% aqueous hydrobromic acid (8 ml) and the mixture was cooled to 3° C. before the dropwise addition of sodium nitrite (137 mg, 1.98 mmol) in water (0.5 ml) over 5 min, while the temperature was kept below 5° C. The resulting mixture was stirred at 4±1° C. for 2 h 40 min then more sodium nitrite (26 mg, 0.37 mmol) in water (0.1 ml) was added dropwise and the mixture was stirred at 3° C. for 50 min. A cooled (3° C.) solution of copper(I) bromide (744 mg, 5.19 mmol) in 48% hydrobromic acid (2.4 ml) was added and the mixture was stirred at 3° C. for 15 min then heated to 50° C. for 1 h. The mixture was cooled to ambient temperature, diluted with water (50 ml) and extracted with ethyl acetate (4×35 ml). The combined organics were washed with 1M aqueous sodium sulphite solution (30 ml), then saturated aqueous ammonium chloride solution (30 ml), dried over anhydrous magnesium sulphate and evaporated to give a brown oil. Purification by chromatography on silica gel eluting with isohexane on a gradient of ethyl acetate (0–2%) gave 5-bromo-2-fluoro-2'-(methylthio)biphenyl as a white solid (287 mg, 57%): δ$_H$ (360 MHz, CDCl$_3$) 2.40 (3H, s), 7.04 (1H, t, J 9), 7.16–7.24 (2H, m), 7.32 (1H, d, J 8), 7.36–7.51 (4H, m).

To a cooled (0° C.) solution of 5-bromo-2-fluoro-2'-(methylthio)biphenyl (117 mg, 0.392 mmol) in anhydrous dichloromethane (7 ml) was added 3-chloroperoxybenzoic acid (55%, 309 mg, 0.984 mmol) portionwise over 5 min. The mixture was stirred for 30 min, the cooling bath was removed and stirring was continued for a further 6 h. The mixture was diluted with dichloromethane (20 ml) and washed with 5% aqueous sodium hydrogencarbonate (2×20 ml), brine (10 ml), dried over anhydrous magnesium sulphate and evaporated. The residue was purified by flash chromatography on silica gel, eluting with 30% ethyl acetate in isohexane, to afford 5-bromo-2-fluoro-2'-(methanesulfonyl)biphenyl as a colourless oil (100 mg, 77%): $\delta_H$ (360 MHz, CDCl$_3$) 2.90 (3H, s), 7.05 (1H, t, J 9), 7.37 (1H, dd, J 7 and 1), 7.49 (1H, dd, J 7 and 3), 7.51–7.55 (1H, m), 7.64 (1H, td, J 8 and 2), 7.69 (1H, td, J 8 and 2), 8.21 (1H, dd, J 8 and 1).

A mixture of 5-bromo-2-fluoro-2'-(methanesulfonyl) biphenyl (701 mg, 2.13 mmol), dried potassium acetate (418 mg, 4.26 mmol) and bis(pinacolato)diboron (622 mg, 2.45 mmol) in 1,4-dioxane (4.9 ml) and dimethylsulfoxide (0.1 ml) was degassed by bubbling nitrogen through the mixture for 45 min. Dichloro[1,1'-bis(diphenylphosphino)ferrocene] palladium(II) dichloromethane adduct (52.2 mg, 0.0639 mmol) was added and the mixture was stirred at 90° C. under nitrogen for 16 h. After allowing to cool, the mixture was filtered through glass fibre paper (GF/A) and the solid was washed with a little dichloromethane. The combined filtrates were evaporated in vacuo and the residue was partitioned between 2M aqueous sodium hydroxide (10 ml) and diethyl ether (10 ml). The aqueous layer was washed with more diethyl ether (10 ml), cooled in an ice-water bath then acidified to pH 6 with 36% hydrochloric acid causing a solid to precipitate. This precipitate was aged at 4° C. for 10 h, the solid was collected by filtration, washed with water and dried under vacuum to leave 2-(2-fluoro-2'-(methanesulfonyl)biphenyl-5-yl)-4,4,5,5-tetramethyl-[1,3,2]dioxaborolane as a pale grey solid (809 mg, 100%): $\delta_H$ (360 MHz, CDCl$_3$) 1.33 (12H, s), 2.87 (3H, s), 7.16 (1H, dd, J 10 and 8), 7.38 (1H, dd, J 7 and 1), 7.60 (1H, m), 7.66 (1H, m), 7.78 (1H, dd, J 8 and 1), 7.85–7.89 (1H, m), 8.20 (1H, dd, J 8 and 1).

A stirred mixture of 3-bromo-7-trifluoromethylimidazo[1,2-α]pyrimidine (0.1073 g, 0.403 mmol) and 2-(2-fluoro-2'-(methanesulfonyl)biphenyl-5-yl)-4,4,5,5-tetramethyl-[1,3,2]dioxaborolane (228 mg, 0.607 mmol) in tetrahydrofuran (5 ml) and 2M aqueous sodium carbonate (containing 1 ml/l of 40 wt % tetrabutylammonium hydroxide in water) (0.605 ml, 1.21 mmol) was degassed by bubbling nitrogen through the mixture for 15 min. Tetrakis(triphenylphosphine) palladium(0) (24.6 mg, 0.0213 mmol) was then added and the mixture was heated at 65° C. under nitrogen for 6 h. After cooling, the mixture was partitioned between ethyl acetate (25 ml) and water (15 ml). The aqueous layer was extracted further with ethyl acetate (2×25 ml) and the combined organic extracts were dried over anhydrous sodium sulphate and evaporated in vacuo. The residue was purified by flash chromatography on silica gel, eluting with isohexane on a gradient of ethyl acetate (40–50%), to afford 3-[2-fluoro-2'-(methanesulfonyl)biphenyl-5-yl]-7-trifluoromethylimidazo[1,2-α]pyrimidine as a yellow solid (139 mg, 79%): mp 211–213° C. (ethyl acetate/isohexane); $\delta_H$ (360 MHz, CDCl$_3$) 2.89 (3H, s), 7.27 (1H, d, J 6.9), 7.40 (1H, td, J 1.2, 9.0), 7.46 (1H, dd, J 1.2, 7.4), 7.62–7.66 (2H, m), 7.68 (1H, td, J 1.6, 7.4), 7.74 (1H, td, J 1.6, 7.4), 8.10 (1H, s), 8.29 (1H, dd, J 1.4, 8.0), 9.22 (1H, d, J 7.0); MS (ES$^+$) m/z 436 [M+H]$^+$. Anal. Found: C, 55.02; H, 3.02; N, 9.23%. Required for C$_{20}$H$_{13}$F$_4$N$_3$O$_2$S.0.1H$_2$O: C, 54.94; H, 3.04; N, 9.61%.

EXAMPLE 78

2-[3-(4-Fluoro-3-(pyrazin-2-yl)phenyl)imidazo[1,2-α]pyrimidin-7-yl]propan-2-ol

To 2-(5-bromo-2-fluorophenyl)pyrazine (0.252 g, 1 mmol) and bis(neopentyl glycolato)diboron (0.292 g) was added dry 1,4-dioxane (4 ml) and dry dimethylsulfoxide (0.4 ml), followed by dry potassium acetate (0.225 g) and dichloro[1,1'-bis(diphenylphosphino)ferrocene]palladium (II) dichloromethane adduct (0.050 g). The mixture was thoroughly degassed with nitrogen and then stirred at 85° C. for 15 h. On cooling to ambient temperature 1N aqueous sodium hydroxide (20 ml) was added and the mixture stirred for 20 min. Diethyl ether was added and the aqueous phase separated and washed with more diethyl ether. The organic extracts were discarded. The aqueous phase was filtered then acidified to pH 5 by addition of 2N aqueous hydrochloric acid (15 ml). The acidic aqueous phase was extracted with dichloromethane. The organic extract was dried over anhydrous sodium sulphate, filtered and evaporated to give 2-[5-(5,5-dimethyl-[1,3,2]dioxaborinan-2-yl)-2-fluorophenyl]pyrazine. This was used without further purification: $\delta_F$ (400 MHz, CDCl$_3$) –113.66.

To 2-[5-(5,5-dimethyl-[1,3,2]dioxaborinan-2-yl)-2-fluorophenyl]pyrazine prepared above was added 2-(3-bromoimidazo[1,2-α]pyrimidin-7-yl)propan-2-ol (0.266 g, 1.04 mmol) followed by dry potassium phosphate (0.065 g), dichloro[1,1'-bis(diphenylphosphino)ferrocene]palladium (II) dichloromethane adduct (0.06 g) and dry N,N-dimethylformamide (5 ml). The mixture was degassed with nitrogen then stirred for 16 h at 65° C. under an atmosphere of dry nitrogen. The reaction was cooled to ambient temperature, silica gel added, and the solvent stripped at reduced pressure. The residue was subjected to chromatography on silica gel eluting with dichloromethane on a gradient of methanol (3.5–5%). The appropriate fractions were combined, concentrated in vacuo and the residue crystallised from toluene to afford 2-[3-(4-fluoro-3-(pyrazin-2-yl)phenyl)imidazo[1,2-α]pyrimidin-7-yl]propan-2-ol: $\delta_H$ (400 MHz, DMSO) 1.51 (6H, s), 5.51 (1H, s), 7.41 (1H, d, J 7), 7.62 (1H, dd, J 11 and 9), 7.88 (1H, m), 7.95 (1H, s), 8.18 (1H, dd, J 7 and 2), 8.72 (1H, d, J 2), 8.84 (1H, dd, J 1 and 2), 8.99 (1H, d, J 7), 9.14 (1H, dd, J 2 and 2); m/z (ES$^+$) 350 (MH$^+$).

EXAMPLE 79

2-[3-(4-Fluoro-3-(5-fluoropyridin-2-yl)phenyl) imidazo[1,2-α]pyrimidin-7-yl]propan-2-ol 3-(5-Fluoropyridin-2-yl)phenylboronic acid (0.24 g, 1.02 mmol) prepared according to the method of Example 59 was reacted with 2-(3-bromoimidazo[1,2-α]pyrimidin-7-yl) propan-2-ol (0.258 g, 1.01 mmol) according to the method of Example 78 to afford 2-[3-(4-fluoro-3-(5-fluoropyridin-2-yl)phenyl)imidazo[1,2-α]pyrimidin-7-yl]propan-2-ol which was converted to its hydrochloride salt by treatment with methanolic hydrogen chloride, evaporation and crystallisation of the residue from methanol/ethyl acetate: $\delta_H$ (400 MHz, DMSO) 1.56 (6H, s), 7.68 (1H, dd, J 11 and 9), 7.84–8.02 (4H, m), 8.24 (1H, dd, J 7 and 2), 8.55 (1H, s), 8.77 (1H, d, J 3), 9.25 (1H, d, J 7); m/z (ES$^+$) 367 (MH$^+$).

EXAMPLE 80

3-[4-Fluoro-3-(3-fluoropyridin-2-yl)phenyl]-7-trifluoromethylimidazo[1,2-α]pyrimidine 2-Bromo-3-fluoropyridine, prepared according to the procedure of Queguiner et al. in *Tetrahedron*, 1983, 39, 2009–21, was coupled with 2-(2-fluoro-5-nitrophenyl)-4,4,5,5-tetramethyl-[1,3,2]dioxaborolane by the method of Example 56 and then transformed into 4-fluoro-3-(3-fluoropyridin-2-yl)phenylboronic acid by the method of Example 59: $\delta_H$ (400 MHz, DMSO) 8.58 (1H, m), 8.19 (2H, s), 8.04 (1H, dd, J 8 and 2), 7.95 (1H, m), 7.86 (1H, m), 7.57 (1H, m), 7.31 (1H, dd, J 11 and 8).

4-Fluoro-3-(3-fluoropyridin-2-yl)phenylboronic acid was coupled with 3-bromo-7-trifluoromethylimidazo[1,2-α]pyrimidine by the method of Example 78. Purification by chromatography on silica gel eluting with dichloromethane containing 3.5% methanol and crystallisation from methanol gave 3-[4-fluoro-3-(3-fluoropyridin-2-yl)phenyl]-7-trifluoromethylimidazo[1,2-α]pyrimidine: $\delta_H$ (400 MHz, DMSO) 9.28 (1H, d, J 7), 8.61 (1H, m), 8.31 (1H, s), 7.90–7.99 (3H, m), 7.62 (2H, m), 7.52 (1H, d, J 7); m/z (ES$^+$) 377 (MH$^+$).

EXAMPLE 81

2-[3-(4-Fluoro-3-(3-fluoropyrydin-2-yl)phenyl)imidazo[1,2-α]pyrimidin-7-yl]propan-2-ol 4-Fluoro-3-(3-fluoropyridin-2-yl)phenylboronic acid (prepared according to Example 80) was coupled with 2-(3-bromoimidazo[1,2-α]pyrimidin-7-yl)propan-2-ol by the method of Example 78. Purification by chromatography on silica gel, eluting with dichloromethane containing 3.5% methanol, gave 2-[3-(4-fluoro-3-(3-fluoropyridin-2-yl)phenyl)imidazo[1,2-α]pyrimidin-7-yl]propan-2-ol which was converted to its hydrochloride salt by treatment with methanolic hydrogen chloride, evaporation, and crystallisation of the residue from isopropanol/ethyl acetate: $\delta_H$ (400 MHz, DMSO) 1.56 (6H, s), 7.62–7.71 (1H, m), 7.70 (1H, dd, J 9 and 2), 7.87 (1H, d, J 7.4), 7.92–8.00 (3H, m), 8.54 (1H, s), 8.61 (1H, m), 9.25 (1H, d, J 7); m/z (ES$^+$) 367 (MH$^+$).

EXAMPLE 82

3-[3-(3,5-Difluoropyridin-2-yl)-4-fluorophenyl]-7-trifluoromethylimidazo[1,2-α]pyrimidine To a degassed mixture of 3,5-difluoro-2,4,6-tribromopyridine (4.26 g, 12.1 mmol), 2-(2-fluoro-5-nitrophenyl)-4,4,5,5-tetramethyl-[1,3,2]dioxaborolane (2.80 g, 10.4 mmol), aqueous sodium carbonate (10 ml of a 2M solution) and tetrahydrofuran (40 ml) was added tetrakis(triphenylphosphine)palladium(0) (0.67 g). The mixture was then stirred at 55° C. for 48 h under an atmosphere of nitrogen. The reaction mixture was then partitioned between water and ethyl acetate. The organic layer was separated and evaporated and the residue chromatographed on silica gel eluting with isohexane on a gradient of dichloromethane (20–40%) to afford 2,4-dibromo-3,5-difluoro-6-(2-fluoro-5-nitrophenyl)pyridine as a solid (1.21 g): $\delta_H$ (400 MHz, CDCl$_3$) 7.37 (1H, t, J 9), 8.38 (1H, m), 8.55 (1H, dd, J 6 and 3).

To 2,4-dibromo-3,5-difluoro-6-(2-fluoro-5-nitrophenyl)pyridine (1.20 g, 2.91 mmol) dissolved in dichloromethane (30 ml) was added triethylamine (3 ml) and ethanol (80 ml) followed by 10% palladium on carbon (0.536 g). The mixture was then shaken under an atmosphere of hydrogen gas at 45 psi until complete reaction was indicated by TLC (0.25 to 3.5 h). The catalyst was then removed by filtration through glass microfibre filter paper (GF/A) and the solvent stripped at reduced pressure to afford 3-(3,5-difluoropyridin-2-yl)-4-fluorophenylamine which was used subsequently without further purification: m/z (ES$^+$) 225 (MH$^+$).

To the 3-(3,5-difluoropyridin-2-yl)-4-fluorophenylamine prepared above was added 1,4-dioxane (5 ml) and 48% aqueous hydrogen bromide (15 ml). The solution was cooled to −10° C. and a solution of sodium nitrite (0.252 g) in water (1 ml) was added dropwise with stirring at such a rate as to maintain an internal temperature below −5° C. The mixture was then stirred for a further 1 h at <0° C. before a solution of copper(I) bromide (1.283 g) in 48% aqueous hydrogen bromide (5 ml) was added slowly with stirring to maintain a reaction temperature below 10° C. This mixture was then stirred at 10° C. for 1 h, ambient temperature a further 1 h and then heated at 35° C. for 30 min. The reaction mixture was then cooled in an ice-water bath and 4N aqueous sodium hydroxide (41 ml) was added slowly with stirring, followed by 30% aqueous ammonia (15 ml). The resulting mixture was extracted with ethyl acetate. The organic extract was evaporated and the residue subjected to chromatography on silica gel, eluting with 10% diethyl ether in isohexane, to afford 2-(5-bromo-2-fluorophenyl)-3,5-difluoropyridine (0.48 g) as a colourless solid: m/z (ES$^+$) 288, 290 (MH$^+$).

To 2-(5-bromo-2-fluorophenyl)-3,5-difluoropyridine (0.746 g, 2.59 mmol), and bis(neopentyl glycolato)diborane (0.704 g) was added dry 1,4-dioxane (9 ml) and dry dimethylsulfoxide (1.1 ml) followed by potassium acetate (0.542 g) and dichloro[1,1′-bis(diphenylphosphino)ferrocene]palladium(II) dichloromethane adduct (0.080 g). The mixture was thoroughly degassed with nitrogen and then stirred at 85° C. for 24 h. On cooling to ambient temperature 1N aqueous sodium hydroxide (24 ml) was added and the mixture stirred for 30 min. Diethyl ether was added and the aqueous phase separated and washed with diethyl ether. The organics were discarded. The aqueous phase was filtered then acidified to pH 5 by addition of 2N aqueous hydrochloric acid (12 ml). The resulting solid was collected by filtration, washed with water and dried in vacuo at 60° C. to afford 4-fluoro-3-(3,5-difluoropyridin-2-yl)phenylboronic acid (0.618 g) as a colourless solid: $\delta_H$ (400 MHz, DMSO) 8.69 (1H, d, J 2), 8.21 (2H, s), 7.94–8.14 (3H, m), 7.34 (1H, dd, J 11 and 8).

4-Fluoro-3-(3,5-difluoropyridin-2-yl)phenylboronic acid was coupled with 3-bromo-7-trifluoromethylimidazo[1,2-α]pyrimidine by the method of Example 78. Purification by chromatography on silica gel eluting with dichloromethane containing 2% methanol and crystallisation from toluene/isohexane gave 3-[3-(3,5-difluoropyridin-2-yl)-4-fluorophenyl]-7-trifluoromethylimidazo[1,2-α]pyrimidine: $\delta_H$ (400 MHz, CDCl$_3$) 8.80 (1H, d, J 7), 8.50 (1H, d, J 2), 8.12 (1H, s), 7.79 (1H, dd, J 7 and 2), 7.64 (1H, m), 7.36–7.43 (2H, m), 7.26 (1H, d, J 7); m/z (ES$^+$) 395 (MH$^+$).

EXAMPLE 83

2-[3-(3-(3,5-Difluoropyridin-2-yl)-4-fluorophenyl)imidazo[1,2-α]pyrimidin-7-yl]propan-2-ol 4-Fluoro-3-(3,5-difluoropyridin-2-yl)phenylboronic acid was coupled with 2-(3-bromoimidazo[1,2-α]pyrimidin-7-yl)propan-2-ol by the method of Example 78. Purification by chromatography on silica gel eluting with dichloromethane containing 4% methanol and crystallisation from toluene/isohexane gave 2-[3-(3-(3,5-difluoropyridin-2-yl)-4-fluorophenyl)imidazo[1,2-α]pyrimidin-7-yl]propan-2-ol: $\delta_H$ (400 MHz, DMSO) 8.96 (1H, d, J 7), 8.72 (1H, d, J 2), 8.17 (1H, dd, J 2 and 1), 7.93 (1H, s), 7.85–7.91 (2H, m), 7.59 (1H, dd, J 10 and 8), 7.40 (1H, d, J 7), 5.51 (1H, s), 1.51 (6H, s); m/z (ES$^+$) 385 (MH$^+$).

EXAMPLE 84

3-[2,4-Difluoro-3-(pyridin-4-yl)phenyl]-7-trifluoromethylimidazo[1,2-α]pyrimidine A suspension of 4-bromopyridine hydrochloride (6.81 g, 35 mmol) in tetrahydrofuran (100 ml) was treated with sodium hydroxide (8.75 ml of a 4N solution in water) and this mixture was stirred at ambient temperature for 5 min. 2,6-Difluorobenzeneboronic acid (6.36 g, 40 mmol) and potassium fluoride (6.71 g, 116 mmol) were added and this mixture was degassed with nitrogen for 10 min before adding tris(dibenzylideneacetone)dipalladium(0) (640 mg, 0.7 mmol) followed by tri-tert-butylphosphine (7 ml of a 0.2M solution in 1,4-dioxane, 1.4 mmol). This mixture was stirred at ambient temperature for 15 min then heated at 50° C. for 30 min. The reaction mixture was diluted with dichloromethane then extracted with ice-cold 1N sodium hydroxide solution (×2). The organics were dried over anhydrous magnesium sulphate, filtered and pre-adsorbed onto silica. Purification by chromatography on silica eluting with isohexane (containing 0.5% methanol and 0.5% triethylamine) on a gradient of ethyl acetate (20–30%) gave 4-(2,6-difluorophenyl)pyridine as a white solid (3.2 g, 48%): $\delta_H$ (400 MHz, CDCl$_3$) 6.99–7.06 (2H, m), 7.32–7.39 (1H, m), 7.40–7.42 (2H, m), 8.71 (2H, d, J 6).

4-(2,6-Difluorophenyl)pyridine was converted to 2,4-difluoro-3-(pyridin-4-yl)benzeneboronic acid using the procedure described in Example 31: m/z (ES$^+$) 235 (M$^+$+H).

3-Bromo-7-trifluoromethylimidazo[1,2-α]pyrimidine was coupled with 2,4-difluoro-3-(pyridin-4-yl)benzeneboronic acid as described in Example 65 to give 3-[2,4-difluoro-3-(pyridin-4-yl)phenyl]-7-trifluoromethylimidazo[1,2-α]pyrimidine as a white solid. Bis-hydrochloride (from ethanol/ethyl acetate): $\delta_H$ (400 MHz, DMSO) 7.60–7.65 (2H, m), 7.96–8.01 (1H, m), 8.16 (2H, d, J 6), 8.34 (1H, s), 9.00–9.02 (2H, m), 9.34 (1H, dd, J 7 and 3); m/z (ES$^+$) 377 (M$^+$+H).

EXAMPLE 85

2-[3-(2,4-Difluoro-3-(pyridin-4-yl)phenyl)imidazo [1,2-α]pyrimidin-7-yl]propan-2-ol 2-(3-Bromoimidazo[1,2-α]pyrimidin-7-yl)propan-2-ol was coupled with 2,4-difluoro-3-(pyridin-4-yl)benzeneboronic acid as described in Example 65 to give 2-[3-(2,4-difluoro-3-(pyridin-4-yl)phenyl)imidazo[1,2-α]pyrimidin-7-yl]propan-2-ol as an off-white solid. Bis-hydrochloride (from ethanol/ethyl acetate): $\delta_H$ (360 MHz, DMSO) 1.56 (6H, s), 7.62–7.67 (1H, m), 7.85 (1H, d, J 7), 7.88–7.94 (1H, m), 7.99 (2H, d, J 6), 8.50 (1H, s), 8.94 (2H, d, J 6), 9.26 (1H, dd, J 7 and 3); m/z (ES$^+$) 367 (M$^+$+H).

EXAMPLE 86

4,2'-Difluoro-5'-[7-(1-hydroxy-1-methylethyl) imidazo[1,2-α]pyrimidin-3-yl]biphenyl-2-carbonitrile 2-(3-Bromoimidazo[1,2-α]pyrimidin-7-yl)propan-2-ol was coupled with 5'-(5,5-dimethyl-[1,3,2]dioxaborinan-2-yl)-4,2'-difluorobiphenyl-2-carbonitrile as described in Example 65 to give 4,2'-difluoro-5'-[7-(1-hydroxy-1-methylethyl)imidazo[1,2-α]pyrimidin-3-yl]biphenyl-2-carbonitrile as a white solid: $\delta_H$ (400 MHz, CDCl$_3$) 1.62 (6H, s), 4.47 (1H, s), 7.08 (1H, d, J 7), 7.39–7.46 (2H, m), 7.55 (1H, dd, J 8 and 3), 7.60–7.64 (3H, m), 7.85 (1H, s), 8.81 (1H, d, J 7); m/z (ES$^+$) 391 (M$^+$+H).

EXAMPLE 87

2'-Fluoro-5'-(7-trifluoromethylimidazo[1,2-α] pyrimidin-3-yl)biphenyl-3-carbonitrile 3-Bromobenzonitrile and 2-(2-fluoro-5-nitrophenyl)-4,4,5,5-tetramethyl-[1,3,2]dioxaborolane were coupled using the procedure described in Example 1 to afford 2'-fluoro-5'-nitrobiphenyl-3-carbonitrile as a brown solid: $\delta_H$ (360 MHz, DMSO) 7.33–7.40 (2H, m), 7.46–7.55 (2H, m), 7.61 (1H, ddd, J 8, 8 and 2), 7.96–8.01 (1H, m), 8.61 (1H, dd, J 5 and 2), 8.77 (1H, s).

2'-Fluoro-5'-nitrobiphenyl-3-carbonitrile was reduced using the procedure described in Example 1 to give 5'-amino-2'-fluorobiphenyl-3-carbonitrile as a brown solid: $\delta_H$ (360 MHz, CDCl$_3$) 3.66 (2H, s), 6.66–6.70 (1H, m), 6.71–6.74 (1H, m), 7.00 (1H, dd, J 9 and 9), 7.33–7.38 (1H, m), 7.44–7.49 (1H, m).

5'-Amino-2'-fluorobiphenyl-3-carbonitrile was bromo-deaminated using the procedure described in Example 51 to give 5'-bromo-2'-fluorobiphenyl-3-carbonitrile as a pale brown solid: $\delta_H$ (360 MHz, CDCl$_3$) 7.09 (1H, dd, J 9 and 9), 7.47–7.52 (1H, m), 7.53–7.59 (2H, m), 7.68 (1H, ddd, J 8, 1 and 1), 7.75 (1H, ddd, J 8, 1 and 1).

5'-Bromo-2'-fluorobiphenyl-3-carbonitrile was converted to 5'-(5,5-dimethyl-[1,3,2]dioxaborinan-2-yl)-2'-fluorobiphenyl-3-carbonitrile using the procedure described in Example 51. This produced a brown oil that crystallised on standing: $\delta_H$ (360 MHz, CDCl$_3$) 1.04 (6H, s), 3.78 (4H, s), 7.15 (1H, dd, J 8 and 8), 7.53 (1H, dd, J 8 and 8), 7.62–7.65 (1H, m), 7.79–7.88 (4H, m).

3-Bromo-7-trifluoromethylimidazo[1,2-α]pyrimidine was coupled with 5'-(5,5-dimethyl-[1,3,2]dioxaborinan-2-yl)-2'-fluorobiphenyl-3-carbonitrile as described in Example 65 to give 2'-fluoro-5'-(7-trifluoromethylimidazo[1,2-α] pyrimidin-3-yl)biphenyl-3-carbonitrile as a yellow solid: $\delta_H$ (360 MHz, CDCl$_3$) 7.28 (1H, d, J 7), 7.40–7.46 (1H, m), 7.55–7.64 (3H, m), 7.72–7.75 (1H, m), 7.83 (1H, dd, J 7 and 1), 7.89 (1H, d, J 1), 8.11 (1H, s), 8.75 (1H, d, J 7); m/z (ES$^+$) 383 (M$^+$+H).

EXAMPLE 88

2'-Fluoro-5'-(7-trifluoromethylimidazo[1,2-α] pyrimidin-3-yl)biphenyl-4-carbonitrile 4-Bromobenzonitrile and 2-(2-fluoro-5-nitrophenyl)-4,4,5,5-tetramethyl-[1,3,2]dioxaborolane were coupled using the procedure described in Example 1 to afford 2'-fluoro-5'-nitrobiphenyl-4-carbonitrile as a brown solid: $\delta_H$ (400 MHz, CDCl$_3$) 7.37 (1H, dd, J 9 and 9), 7.70 (2H, dd, J 8 and 1), 7.80 (1H, dd, J 8 and 1), 8.29–8.33 (1H, m), 8.37–8.40 (1H, m).

2'-Fluoro-5'-nitrobiphenyl-4-carbonitrile (3.03 g, 12.5 mmol) was reduced using the procedure described in Example 51 to give crude 5'-amino-2'-fluorobiphenyl-4-carbonitrile as a brown solid.

5'-Amino-2'-fluorobiphenyl-4-carbonitrile was bromo-deaminated following the procedure in Example 1 to give 5'-bromo-2'-fluorobiphenyl-4-carbonitrile as a white solid: $\delta_H$ (360 MHz, CDCl$_3$) 7.08 (1H, dd, J 9 and 9), 7.47–7.52 (1H, m), 7.54–7.58 (1H, m), 7.63 (2H, dd, J 8 and 1), 7.75 (2H, dd, J 8 and 1).

5'-Bromo-2'-fluorobiphenyl-4-carbonitrile was converted to 5'-(5,5-dimethyl-[1,3,2]dioxaborinan-2-yl)-2'-fluorobiphenyl-4-carbonitrile using the procedure described in Example 51. This produced a brown solid: $\delta_H$ (360 MHz, CDCl$_3$) 1.03 (6H, s), 3.77 (4H, s), 7.15 (1H, dd, J 8 and 8), 7.67–7.71 (4H, m), 7.80–7.83 (1H, m), 7.81 (1H, dd, J 8 and 2).

3-Bromo-7-trifluoromethylimidazo[1,2-α]pyrimidine was coupled with 5'-(5,5-dimethyl-[1,3,2]dioxaborinan-2-yl)-2'-fluorobiphenyl-4-carbonitrile as described in Example 65 to give 2'-fluoro-5'-(7-trifluoromethylimidazo[1,2-α] pyrimidin-3-yl)biphenyl-4-carbonitrile as a yellow solid: $\delta_H$ (360 MHz, CDCl$_3$) 7.26 (1H, d, J 7), 7.44 (1H, dd, J 8 and 8), 7.55–7.63 (2H, m), 7.70 (2H, dd, J 7 and 1), 7.79 (2H, dd, J 7 and 1), 8.11 (1H, s), 8.74 (1H, d, J 7); m/z (ES$^+$) 383 (M$^+$+H).

EXAMPLE 89

4-Fluoro-2'-methyl-3'-(7-trifluoromethylimidazo[1,2-α]pyrimidin-3-yl)biphenyl-2-carbonitrile 2-Bromo-6-nitrotoluene and 5-fluoro-2-(4,4,5,5-tetramethyl-[1,3,2]dioxaborolan-2-yl)benzonitrile were coupled using the procedure described in Example 1 to afford crude 4-fluoro-2'-methyl-3'-nitrobiphenyl-2-carbonitrile as a black solid: $\delta_H$ (360 MHz, CDCl$_3$) 2.32 (3H, s), 7.34–7.46 (5H, m), 7.95 (1H, m).

4-Fluoro-2'-methyl-3'-nitrobiphenyl-2-carbonitrile was reduced using the procedure described in Example 51 to give crude 3'-amino-4-fluoro-2'-methylbiphenyl-2-carbonitrile as a brown solid: $\delta_H$ (360 MHz, CDCl$_3$) 1.97 (3H, s), 3.73 (2H, s), 6.62 (1H, d, J 8), 6.77 (1H, d, J 8), 7.11 (1H, dd, J 9 and 9), 7.32–7.35 (2H, m), 7.41–7.44 (1H, m).

3'-Amino-4-fluoro-2'-methylbiphenyl-2-carbonitrile was bromo-deaminated following the procedure in Example 1 to give 3'-bromo-4-fluoro-2'-methylbiphenyl-2-carbonitrile as a white solid: $\delta_H$ (400 MHz, CDCl$_3$) 2.23 (3H, s), 7.14 (2H, dd, J 4 and 1), 7.31–7.39 (2H, m), 7.45 (1H, dd, J 8 and 2), 7.63–7.66 (1H, m).

3'-Bromo-4-fluoro-2'-methylbiphenyl-2-carbonitrile was converted to 3'-(5,5-dimethyl-[1,3,2]dioxaborinan-2-yl)-4-fluoro-2'-methylbiphenyl-2-carbonitrile using the procedure described in Example 51. This produced a brown oil which crystallised on standing: $\delta_H$ (360 MHz, CDCl$_3$) 1.05 (6H, s), 2.30 (3H, s), 3.76 (4H, s), 7.17–7.26 (2H, m), 7.31–7.33 (2H, dd, J 5 and 2), 7.41–7.45 (1H, m), 7.80 (1H, dd, J 7 and 2).

3-Bromo-7-trifluoromethylimidazo[1,2-α]pyrimidine was coupled with 3'-(5,5-dimethyl-[1,3,2]dioxaborinan-2-yl)-4-fluoro-2'-methylbiphenyl-2-carbonitrile as described in Example 65 to give 4-fluoro-2'-methyl-3'-(7-trifluoromethylimidazo[1,2-α]pyrimidin-3-yl)biphenyl-2-carbonitrile as a white solid: $\delta_H$ (360 MHz, CDCl$_3$) 1.94 (3H, s), 7.26 (1H, d, J 7), 7.40–7.51 (6H, m), 8.08 (1H, s), 8.35 (1H, d, J 7); m/z (ES$^+$) 397 (M$^+$+H).

EXAMPLE 90

3-[2,4-Difluoro-3-(pyridin-3-yl)phenyl]-7-(1-fluoro-1-methylethyl)imidazo[1,2-α]pyrimidine 3-Fluoro-3-methylbutan-2-one was prepared from 3-bromo-3-methylbutan-2-one as described by Fry and Migron in *Tetrahedron Lett.*, 1979, 3357–3360, to give, after distillation using a Vigreux column, a 47% yield of a 94:6 mixture of the desired fluoro compound and 3-methyl-3-buten-2-one as a colourless oil: bp 74–76° C.; $\delta_H$ (360 MHz, CDCl$_3$) 1.45 (6H, d, J 22), 2.28 (3H, d, J 5).

3-Fluoro-3-methylbutan-2-one was converted to 1,1-diethoxy-4-fluoro-4-methylpentan-3-one as described in Example 3, and condensed with 2-aminoimidazole hemisulfate as in Example 2, to give 7-(1-fluoro-1-methylethyl)imidazo[1,2-α]pyrimidine as an orange oil which crystallised on standing: $\delta_H$ (400 MHz, CDCl$_3$) 1.77 (6H, d, J 22), 7.21 (1H, dd, J 7 and 2), 7.54 (1H, d, J 1), 7.79 (1H, d, J 1), 8.45 (1H, d, J 7).

7-(1-Fluoro-1-methylethyl)imidazo[1,2-α]pyrimidine was brominated as described in Example 1 to give 3-bromo-7-(1-fluoro-1-methylethyl)imidazo[1,2-α]pyrimidine as an off-white solid: $\delta_H$ (360 MHz, CDCl$_3$) 1.78 (6H, d, J 22), 7.35 (1H, d, J 7 and 2), 7.77 (1H, s), 8.42 (1H, d, J 7).

3-Bromo-7-(1-fluoro-1-methylethyl)imidazo[1,2-α]pyrimidine was coupled to 2,4-difluoro-3-(pyridin-3-yl)phenylboronic acid as described in Example 65 to afford 3-[2,4-difluoro-3-(pyridin-3-yl)phenyl]-7-(1-fluoro-1-methylethyl)imidazo[1,2-α]pyrimidine as a white solid: $\delta_H$ (360 MHz, CDCl$_3$) 1.80 (6H, d, J 22), 7.21–7.29 (2H, m), 7.46 (1H, dd, J 8 and 5), 7.50–7.57 (1H, m), 7.85 (1H, d, J 8), 7.92 (1H, s), 8.31 (1H, dd, J 7 and 3), 8.70 (1H, dd, J 5 and 1), 8.79 (1H, s); m/z (ES$^+$) 369 (M$^+$+H).

EXAMPLE 91

7-(1-Fluoro-1-methylethyl)-3-[4-fluoro-3-(pyridin-3-yl)phenyl]imidazo[1,2-α]pyrimidine 3-Bromo-7-(1-fluoro-1-methylethyl)imidazo[1,2-α]pyrimidine was coupled with 3-[2-fluoro-5-(4,4,5,5-tetramethyl-[1,3,2]dioxaborolan-2-yl)phenyl]pyridine as described in Example 65 to afford 7-(1-fluoro-1-methylethyl)-3-[4-fluoro-3-(pyridin-3-yl)phenyl]imidazo[1,2-α]pyrimidine as a white solid after crystallisation from ethyl acetate/isohexane: $\delta_H$ (360 MHz, CDCl$_3$) 1.74 (6H, d, J 22), 7.26 (1H, dd, J 7 and 2), 7.53–7.60 (2H, m), 7.80 (1H, ddd, J 8, 5 and 2), 7.94 (1H, dd, J 8 and 2), 8.05 (1H, s), 8.10 (1H, ddd, J 8, 4 and 2), 8.65 (1H, dd, J 5 and 1.5), 8.89 (1H, s), 9.13 (1H, d, J 7); m/z (ES$^+$) 351 (M$^+$+H).

EXAMPLE 92

2-[3-(2,4-Difluoro-3-(pyridin-3-yl)phenyl)imidazo[1,2-α]pyrimidin-7-yl]-2-methylpropionic acid methyl ester Methyl 2,2-dimethylacetoacetate was converted to 5,5-diethoxy-2,2-dimethyl-3-oxopentanoic acid methyl ester as outlined in Example 3, then condensed with 2-aminoimidazole hemisulfate following the procedure in Example 2, to give 2-(imidazo[1,2-α]pyrimidin-7-yl)-2-methylpropionic acid methyl ester as a brown oil: $\delta_H$ (360 MHz, CDCl$_3$) 1.67 (6H, s), 3.70 (3H, s), 6.85 (1H, d, J 7), 7.48 (1H, d, J 1), 7.76 (1H, d, J 1), 8.34 (1H, d, J 7).

2-(Imidazo[1,2-α]pyrimidin-7-yl)-2-methylpropionic acid methyl ester was brominated in the same way as described in Example 1 to give 2-(3-bromoimidazo[1,2-α]pyrimidin-7-yl)-2-methylpropionic acid methyl ester as an off-white solid: $\delta_H$ (400 MHz, CDCl$_3$) 1.68 (6H, s), 3.69 (3H, s), 6.98 (1H, d, J 7), 7.75 (1H, s), 8.32 (1H, d, J 7).

2-(3-Bromoimidazo[1,2-α]pyrimidin-7-yl)-2-methylpropionic acid methyl ester and 2,4-difluoro-3-(pyridin-3-yl)benzeneboronic acid were coupled in the same way as described in Example 65 to give 2-[3-(2,4-difluoro-3-(pyridin-3-yl)phenyl)imidazo[1,2-α]pyrimidin-7-yl]-2-methylpropionic acid methyl ester as a white solid: $\delta_H$ (360 MHz, CDCl$_3$) 1.69 (6H, s), 3.70 (3H, s), 6.91 (1H, d, J 7), 7.20–7.25 (1H, m), 7.43–7.47 (1H, m), 7.50–7.57 (1H, m), 7.84–7.87 (1H, m), 7.89 (1H, s), 8.21 (1H, dd, J 7 and 3), 8.69 (1H, dd, J 5 and 2), 8.78 (1H, d, J 1); m/z (ES$^+$) 409 (M$^+$+H).

EXAMPLE 93

2-[3-(4-Fluoro-3-(pyridin-3-yl)phenyl)imidazo[1,2-α]pyrimidin-7-yl]-2-methylpropionitrile 2,2-Dimethyl-3-oxobutyronitrile was prepared from 3-methyl-2-butanone as described by Rasmussen (*Synthesis*, 1973, 682) to give, after distillation under reduced pressure, the desired nitrile as a colourless oil: bp 74–76° C. (30 mmHg); $\delta_H$ (360 MHz, CDCl$_3$) 1.51 (6H, s), 2.43 (3H, s).

2,2-Dimethyl-3-oxobutyronitrile was converted to 5,5-diethoxy-2,2-dimethyl-3-oxopentanenitrile as described in Example 3, then condensed with 2-aminoimidazole hemisulfate following the procedure in Example 2, to give 2-(imidazo[1,2-α]pyrimidin-7-yl)-2-methylpropionitrile as a white solid: $\delta_H$ (400 MHz, CDCl$_3$) 1.84 (6H, s), 7.27 (1H, d, J 7), 7.58 (1H, d, J 1), 7.84 (1H, d, J 1), 8.49 (1H, d, J 7).

2-(Imidazo[1,2-α]pyrimidin-7-yl)-2-methylpropionitrile was brominated in the same way as described in Example 1 to give 2-(3-bromoimidazo[1,2-α]pyrimidin-7-yl)-2-methylpropionitrile as an off-white solid: $\delta_H$ (400 MHz, CDCl$_3$) 1.84 (6H, s), 7.39 (1H, d, J 7), 7.82 (1H, s), 8.46 (1H, d, J 7).

2-(3-Bromoimidazo[1,2-α]pyrimidin-7-yl)-2-methylpropionitrile and 4-fluoro-3-(pyridin-3-yl)benzeneboronic acid were coupled following the procedure in Example 65 to give 2-[3-(4-fluoro-3-(pyridin-3-yl)phenyl)imidazo[1,2-α]pyrimidin-7-yl)-2-methylpropionitrile as a white solid: $\delta_H$ (360 MHz, CDCl$_3$) 1.86 (6H, s), 7.32 (1H, d, J 7), 7.38–7.45 (2H, m), 7.53–7.62 (2H, m), 7.86–7.97 (1H, m), 7.91 (1H, d, J 3), 8.62 (1H, d, J 7), 8.67 (1H, dd, J 8 and 3), 8.84 (1H, s); m/z (ES$^+$) 358 (M$^+$+H).

EXAMPLE 94

2–3-(4-Fluoro-3-(pyridin-3-yl)phenyl)imidazo[1,2-α]pyrimidin-7-yl]-2-methylpropan-1-ol 4-Hydroxy-3,3-dimethylbutan-2-one (prepared according to the procedure described in U.S. Pat. No. 4,255,434) (5.00 g, 43.0 mmol) was protected as the acetate following the procedure in Example 6, then converted to the diethyl acetal as described in Example 3, and condensed with 2-aminoimidazole hemisulfate as described in Example 2, to give 2-(imidazo[1,2-α]pyrimidin-7-yl)-2-methylpropan-1-ol (1.43 g, 17%) as a white solid: $\delta_H$ (360 MHz, CDCl$_3$) 1.37 (6H, s), 3.87 (2H, s), 5.29 (1H, s), 6.93 (1H, d, J 7), 7.47 (1H, d, J 1), 7.74 (1H, d, J 1), 8.37 (1H, d, J 7).

2-(Imidazo[1,2-α]pyrimidin-7-yl)-2-methylpropan-1-ol was brominated as described in Example 1 to give 2-(3-bromoimidazo[1,2-α]pyrimidin-7-yl)-2-methylpropan-1-ol as an off-white solid: $\delta_H$ (360 MHz, CDCl$_3$) 1.38 (6H, s), 3.88 (2H, s), 7.07 (1H, d, J 7), 7.72 (1H, s), 8.35 (1H, d, J 7).

2-(3-Bromoimidazo[1,2-α]pyrimidin-7-yl)-2-methylpropan-1-ol was converted to 3-bromo-7-(1,1-dimethyl-2-triethylsilanyloxyethyl)imidazo[1,2-α]pyrimidine following the procedure in Example 71 giving a colourless oil which crystallised on standing: $\delta_H$ (360 MHz, CDCl$_3$) 0.55 (6H, q, J 8), 0.88 (9H, t, J 8), 1.40 (6H, s), 3.77 (2H, s), 7.17 (1H, d, J 7), 7.71 (1H, s), 8.27 (1H, d, J 7).

3-Bromo-7-(1,1-dimethyl-2-triethylsilanyloxyethyl)imidazo[1,2-α]pyrimidine was coupled to 4-fluoro-3-(pyridin-3-yl)benzeneboronic acid (323 mg, 1.28 mmol) following the procedure in Example 65 and deprotected as described in Example 8 to give 2-[3-(4-fluoro-3-(pyridin-3-yl)phenyl)imidazo[1,2-α]pyrimidin-7-yl]-2-methylpropan-1-ol as a white powder: $\delta_H$ (360 MHz, CDCl$_3$) 1.39 (6H, s), 3.54 (1H, t, J 7), 3.89 (1H, d, J 7), 6.99 (1H, d, J 7), 7.35–7.45 (2H, m), 7.51–7.60 (2H, m), 7.83 (1H, s), 7.90–7.94 (1H, m), 8.53 (1H, d, J 7), 8.68 (1H, dd, J 5 and 2), 8.83 (1H, s); m/z (ES$^+$) 363 (M$^+$+H).

EXAMPLE 95

3-[4-Fluoro-3-(6-methoxypyridin-3-yl)phenyl]-7-trifluoromethylimidazo[1,2-α]pyrimidine A mixture of 3-bromo-7-trifluoromethylimidazo[1,2-α]pyrimidine (101 mg, 0.38 mmol) and 5-[5-(5,5-dimethyl-[1,3,2]dioxaborinan-2-yl)-2-fluorophenyl]-2-methoxypyridine (prepared in an analogous manner to 2'-fluoro-5'-(4,4,5,5-tetramethyl-[1,3,2]dioxaborolan-2-yl)biphenyl-2-carbonitrile in Example 1, using bis(neopentyl glycolato)diboron instead of bis(pinacolato)diboron in the final palladium coupling) (100 mg, 0.32 mmol) in tetrahydrofuran (2 ml) and 2N sodium carbonate solution (0.48 ml, 0.96 mmol) was degassed with nitrogen.

Tetrakis(triphenylphosphine)palladium(0) (37 mg, 0.032 mmol) was added and the reaction heated at 65° C. for 2 h. Further palladium catalyst (25 mg, 0.022 mmol) was added and heating continued for 2 h. The mixture was evaporated in vacuo and the residue partitioned between dichloromethane and water. The organic layer was separated, washed twice with 4N sodium hydroxide then brine, dried over anhydrous magnesium sulphate, filtered and concentrated in vacuo. Purification by chromatography on silica gel eluting with dichloromethane on a gradient of diethyl ether (1–3%) gave 3-[4-fluoro-3-(6-methoxypyridin-3-yl)phenyl]-7-trifluoromethylimidazo[1,2-α]pyrimidine as a yellow solid (73 mg, 59%): $\delta_H$ (400 MHz, DMSO) 3.92 (3H, s), 6.98 (1H, d, J 9), 7.51 (1H, d, J 7), 7.57 (1H, dd, J 11 and 9), 7.78–7.83 (1H, m), 7.96 (1H, dd, J 8 and 2), 8.02–8.06 (1H, m), 8.32 (1H, s), 8.49–8.51 (1H, m), 9.36 (1H, d, J 7); m/z (ES$^+$) 389 (M$^+$+H).

EXAMPLE 96

5-[2-Fluoro-5-(7-trifluoromethylimidazo[1,2-α]pyrimidin-3-yl)phenyl]pyridin-2-ol A solution of 3-[4-fluoro-3-(6-methoxypyridin-3-yl)phenyl]-7-trifluoromethylimidazo[1,2-α]pyrimidine (30 mg, 0.077 mmol) in 1,4-dioxane (2 ml) was treated with a 1M solution of boron tribromide in dichloromethane (0.77 ml, 0.77 mmol) and heated at reflux for 72 h. The mixture was partitioned between dichloromethane and water and the aqueous layer adjusted to pH 7. The organic layer was separated, washed with brine, dried (MgSO$_4$), and concentrated in vacuo. 5-[2-Fluoro-5-(7-trifluoromethylimidazo[1,2-α]pyrimidin-3-yl)phenyl]pyridin-2-ol was obtained in 31% yield after purification on silica gel: $\delta_H$ (400 MHz, DMSO) 6.46 (1H, d, J 9), 7.48–7.55 (2H, m), 7.72 (1H, ddd, J 8, 5 and 2), 7.76–7.82 (1H, m), 7.90 (1H, dd, J 8 and 2), 8.30 (1H, s), 9.35 (1H, d, J 7), 11.97 (1H, br); m/z (ES$^+$) 375 (M$^+$+H).

EXAMPLE 97

3-[4-Fluoro-3-(4-fluoropyridin-3-yl)phenyl]-7-trifluoromethylimidazo[1,2-α]pyrimidine 3-Bromo-7-trifluoromethylimidazo[1,2-α]pyrimidine was coupled to 3-[5-(5,5-dimethyl-[1,3,2]dioxaborinan-2-yl)-2-fluorophenyl]-4-fluoropyridine (prepared in an analogous manner to 2'-fluoro-5'-(4,4,5,5-tetramethyl-[1,3,2]dioxaborolan-2-yl)biphenyl-2-carbonitrile in Example 1, using bis(neopentyl glycolato)diboron instead of bis(pinacolato)diboron in the final palladium coupling) using the procedure described in Example 65. 3-[4-Fluoro-3-(4-fluoropyridin-3-yl)phenyl]-7-trifluoromethylimidazo[1,2-α]pyrimidine was isolated as a yellow solid in 36% yield after purification on silica gel eluting with dichloromethane on a gradient of diethyl ether (2–15%): $\delta_H$ (400 MHz, DMSO) 7.48–7.55 (2H, m), 7.63 (1H, dd, J 10 and 9), 7.94 (1H, ddd, J 9, 5 and 2), 7.99 (1H, dd, J 7 and 2), 8.33 (1H, s), 8.73 (1H, dd, J 8 and 5.5), 8.85 (1H, d, J 10), 9.38 (1H, d, J 7); m/z (ES$^+$) 377 (M$^+$+H).

EXAMPLE 98

3-[4-Fluoro-3-(pyrrol-1-yl)phenyl]-7-trifluoromethylimidazo[1,2-α]pyrimidine A mixture of 5-bromo-2-fluoroaniline (prepared according to the procedure of Roe et al. in *J. Org. Chem.*, 1956, 21, 28–29) (200 mg, 1.05 mmol) and 2,5-dimethoxytetrahydrofuran (171 μl, 1.32 mmol) in glacial acetic acid (1.5 ml) was heated at 130° C. for 20 min and then concentrated under reduced pressure. The residue was dissolved in dichloromethane and pre-adsorbed onto silica. Purification by chromatography on silica gel eluting with 10% diethyl ether in isohexane yielded 1-(5-bromo-2-fluorophenyl)-1H-pyrrole (335 mg, 99%): δ$_H$ (360 MHz, CDCl$_3$) 7.53 (1H, dd, J 7 and 3), 7.33 (1H, ddd, J 9, 4 and 3), 7.10 (1H, dd, J 11 and 9), 7.04–6.95 (2H, m), 6.36 (2H, t, J 2).

1-(5-Bromo-2-fluorophenyl)-1H-pyrrole was converted to 1-[5-(5,5-dimethyl-[1,3,2]dioxaborinan-2-yl)-2-fluorophenyl]-1H-pyrrole using bis(neopentyl glycolato)diboron and the procedure described in Example 1 to yield the desired boronate ester: δ$_H$ (400 MHz, CDCl$_3$) 7.83 (1H, dd, J 8 and 1.5), 7.70–7.63 (1H, m), 7.18 (1H, dd, J 11 and 8), 7.07 (2H, q, J 2), 6.33 (2H, t, J 2), 3.77 (4H, s), 1.02 (6H, s).

3-Bromo-7-trifluoromethylimidazo[1,2-α]pyrimidine was coupled to 1-[5-(5,5-dimethyl-[1,3,2]dioxaborinan-2-yl)-2-fluorophenyl]-1H-pyrrole by the method of Example 65 to furnish 3-[4-fluoro-3-(pyrrol-1-yl)phenyl]-7-trifluoromethylimidazo[1,2-α]pyrimidine: δ$_H$ (400 MHz, DMSO) 9.37 (1H, d, J 7), 8.33 (1H, s), 7.97 (1H, d, J 8 and 2), 7.75–7.62 (2H, m), 7.52 (1H, d, J 7), 7.30 (2H, q, J 2), 6.32 (2H, t, J 2); m/z (ES$^+$) 347 (M+H$^+$).

EXAMPLES 99 TO 113

The following compounds were all prepared using methodology analogous to that described above.

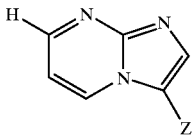

| Example No. | Z |
|---|---|
| 99 | |
| 100 | |
| 101 | |
| 102 | |
| 103 | |
| 104 | |
| 105 | |

-continued

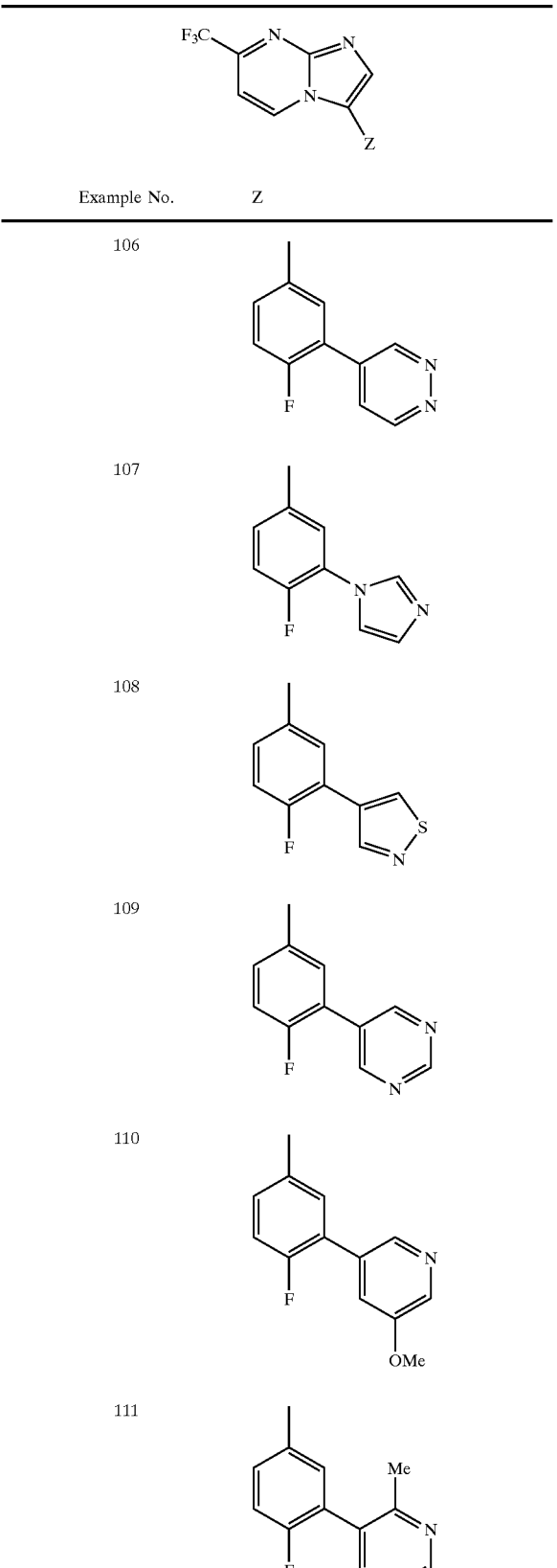

| Example No. | Z |
|---|---|
| 106 | |
| 107 | |
| 108 | |
| 109 | |
| 110 | |
| 111 | |

-continued

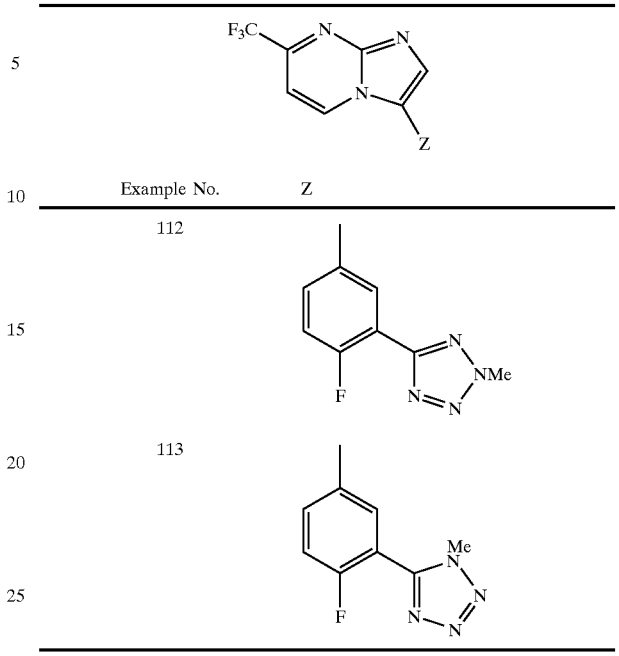

| Example No. | Z |
|---|---|
| 112 | |
| 113 | |

EXAMPLE 114

3-[4-Fluoro-3-(6-methoxypyridin-2-yl)phenyl]-7-trifluoromethylimidazo[1,2-α]pyrimidine 2-Chloro-6-methoxypyridine (1.26 g, 8.81 mmol) was coupled to 2-(2-fluoro-5-nitrophenyl)-4,4,5,5-tetramethyl-[1,3,2]dioxaborolane (3 g, 11.45 mmol) using the method in Example 47. Purification by chromatography on silica gel eluting with dichloromethane containing 20% isohexane then recrystallisation from toluene/isohexane gave 2-(2-fluoro-5-nitrophenyl)-6-methoxypyridine as a white solid: $\delta_H$ (400 MHz, CDCl$_3$) 4.05 (3H, s), 6.81 (1H, d, J 8), 7.30 (1H, dd, J 10 and 9), 7.48–7.51 (1H, m), 7.69 (1H, t, J 8), 8.22–8.26 (1H, m), 9.08 (1H, dd, J 7 and 3).

2-(2-Fluoro-5-nitrophenyl)-6-methoxypyridine (857 mg, 3.45 mmol) was reduced using the method in Example 47 to give 4-fluoro-3-(6-methoxypyridin-2-yl)phenylamine as an orange oil: $\delta_H$ (360 MHz, CDCl$_3$) 3.50 (2H, br s), 4.00 (3H, s), 6.62–6.71 (2H, m), 6.94 (1H, dd, J 11 and 9), 7.40–7.45 (2H, m), 7.61 (1H, t, J 8).

4-Fluoro-3-(6-methoxypyridin-2-yl)phenylamine (710 mg, 3.25 mmol) was bromo-deaminated using the method in Example 27 to give 2-(5-bromo-2-fluorophenyl)-6-methoxypyridine as a yellow solid: $\delta_H$ (400 MHz, CDCl$_3$) 4.02 (3H, s), 6.74 (1H, dd, J 8 and 1), 7.03 (1H, dd, J 11 and 9), 7.42–7.46 (2H, m), 7.64 (1H, t, J 8), 8.24 (1H, dd, J 7 and 3).

2-(5-Bromo-2-fluorophenyl)-6-methoxypyridine (595 mg, 2.1 mmol) was coupled to 3-tributylstannyl-7-trifluoromethylimidazol[1,2-α]pyrimidine (3.2 mmol) by the method of Example 32. Purification by chromatography on silica gel eluting with dichloromethane containing 1% methanol, then crystallisation from methanol, gave 3-[4-fluoro-3-(6-methoxypyridin-2-yl)phenyl]-7-trifluoromethylimidazo[1,2-α]pyrimidine as a yellow solid: $\delta_H$ (400 MHz, CDCl$_3$) 3.98 (3H, s), 6.79 (1H, d, J 8), 7.26 (1H, d, J 10), 7.38 (1H, dd, J 11 and 9), 7.52–7.56 (2H, m), 7.70 (1H, t, J 8), 8.12 (1H, s), 8.36 (1H, dd, J 7 and 2), 8.85 (1H, d, J 7).

EXAMPLE 115

3-[4-Fluoro-3-(4-methoxypyridin-2-yl)phenyl]-7-trifluoromethylimidazo[1,2-α]pyrimidine 2-Chloro-4-methoxypyridine (2.0 g, 13.9 mmol) was coupled to 2-(2-fluoro-5-nitrophenyl)-4,4,5,5-tetramethyl-[1,3,2]dioxaborolane (4.75 g, 17.8 mmol) using the method in Example 47. Purification by chromatography on silica gel eluting with dichloromethane containing 20% isohexane then recrystallisation from toluene/isohexane gave 2-(2-fluoro-5-nitrophenyl)-4-methoxypyridine as a white solid: $\delta_H$(400 MHz, CDCl$_3$) 3.93 (3H, s), 6.88 (1H, dd, J 6 and 2), 7.31 (1H, t, J 10), 7.35–7.37 (1H, m), 8.24–8.29 (1H, m), 8.59 (1H, d, J 6), 8.98 (1H, dd, J 7 and 3).

2-(2-Fluoro-5-nitrophenyl)-4-methoxypyridine (316 mg, 1.3 mmol) was reduced using the method in Example 47 to give 4-fluoro-3-(4-methoxypyridin-2-yl)phenylamine as an orange oil: $\delta_H$(400 MHz, CDCl$_3$) 3.59 (2H, br s), 3.88 (3H, s), 6.64–6.68 (1H, m), 6.78 (1H, d, J 6 and 3), 6.94 (1H, dd, J 11 and 9), 7.28 (1H, dd, J 6 and 3), 7.32 (1H, t, J 2), 8.50 (1H, d, J 5).

4-Fluoro-3-(4-methoxypyridin-2-yl)phenylamine (237 mg, 1.1 mmol) was bromo-deaminated using the method in Example 27 to give 2-(5-bromo-2-fluorophenyl)-4-methoxypyridine as a white solid: $\delta_H$ (400 MHz, CDCl$_3$) 3.90 (3H, s), 6.82 (1H, dd, J 6 and 2), 7.05 (1H, dd, 11 and 9), 7.31 (1H, t, J 2), 7.45–7.49 (1H, m), 8.15 (1H, dd, J 7 and 3), 8.54 (1H, d, J 6).

2-(5-Bromo-2-fluorophenyl)-4-methoxypyridine (50 mg, 0.2 mmol) was coupled to 3-tributylstannyl-7-trifluoromethylimidazo[1,2-α]pyrimidine (0.3 mmol) by the method of Example 32. Purification by chromatography on silica gel eluting with dichloromethane containing 1% methanol gave 3-[4-fluoro-3-(4-methoxypyridin-2-yl)phenyl]-7-trifluoromethylimidazo[1,2-α]pyrimidine as a yellow solid: $\delta_H$(400 MHz, CDCl$_3$) 3.93 (3H, s), 6.86 (1H, dd, J 5 and 2), 7.26 (1H, d, J 7), 7.38 (1H, dd, J 11 and 9), 7.42 (1H, s), 7.54–7.58 (1H, m), 8.12 (1H, s), 8.26 (1H, dd, J 7 and 2), 8.54 (1H, d, J 5), 8.86 (1H, d, J 7); m/z (ES$^+$) 388 (M$^+$+H).

EXAMPLE 116

3-[4-Fluoro-3-(thiazol-2-yl)phenyl]-7-trifluoromethylimidazo[1,2-α]pyrimidine 2-Bromothiazole (2.1 ml, 22.9 mmol) was coupled to 2-(2-fluoro-5-nitrophenyl)-4,4,5,5-tetramethyl-[1,3,2]dioxaborolane (3.0 g, 11.6 mmol) using the method in Example 47. Purification by chromatography on silica gel eluting with dichloromethane then recrystallisation from toluene/isohexane gave 2-(2-fluoro-5-nitrophenyl)thiazole as a brown solid: $\delta_H$ (360 MHz, CDCl$_3$) 7.38 (1H, t, J 9), 7.58 (1H, d, J 3), 8.03 (1H, t, J 3), 8.26–8.31 (1H, m), 9.26 (1H, d, J 6 and 3).

2-(2-Fluoro-5-nitrophenyl)thiazole (170 mg, 0.76 mmol) was reduced using the method in Example 51 to give 4-fluoro-3-(thiazol-2-yl)phenylamine as a yellow solid: m/z (ES$^+$) 195 (M$^+$+H).

4-Fluoro-3-(thiazol-2-yl)phenylamine (125 mg, 0.65 mmol) was bromo-deaminated using the method in Example 27 to give 2-(5-bromo-2-fluorophenyl)thiazole as a white solid: $\delta_H$ (400 MHz, CDCl$_3$) 7.10 (1H, dd, J 11 and 9), 7.47–7.51 (2H, m), 7.96 (1H, dd, J 3 and 2), 8.47 (1H, dd, J 6 and 2).

2-(5-Bromo-2-fluorophenyl)thiazole (50 mg, 0.2 mmol) was coupled to 3-tributylstannyl-7-trifluoromethylimidazo[1,2-α]pyrimidine (0.3 mmol) by the method of Example 32. Purification by chromatography on silica gel eluting with dichloromethane containing 1% methanol gave 3-[4-fluoro-3-(thiazol-2-yl)phenyl]-7-trifluoromethylimidazo[1,2-α]pyrimidine as a yellow solid: $\delta_H$ (400 MHz, CDCl$_3$) 7.29 (1H, d, J 7), 7.44 (1H, dd, J 11 and 9), 7.56–7.62 (2H, m), 7.97 (1H, dd, J 3 and 2), 8.15 (1H, s), 8.57 (1H, dd, J 7 and 2), 8.86 (1H, d, J 7); m/z (ES$^+$) 364 (M$^+$+H).

EXAMPLE 117

2-{2-Fluoro-5-[7-(1-hydroxy-1-methylethyl)imidazo[1,2-α]pyrimidin-3-yl]-phenyl}nicotinonitrile 4-Fluoro-3-(2-nicotinonitrile)phenylboronic acid (100 mg, 0.39 mmol) was coupled to 2-(3-bromoimidazo[1,2-α]pyrimidin-7-yl)propan-2-ol (100 mg, 0.41 mmol) by the method used in Example 1. Purification by chromatography on silica gel eluting with dichloromethane containing 3% methanol gave 2-{2-fluoro-5-[7-(1-hydroxy-1-methylethyl)imidazo[1,2-α]pyrimidin-3-yl]phenyl}nicotinonitrile as a white solid: $\delta_H$ (400 MHz, CDCl$_3$) 1.62 (6H, s), 4.43 (1H, br s), 7.08 (1H, d, J 7), 7.45 (1H, dd, J 9 and 9), 7.51 (1H, dd, J 8 and 5), 7.65–7.70 (1H, m), 7.77 (1H, dd, J 7 and 2), 7.88 (1H, s), 8.15 (1H, dd, J 8 and 2), 8.70 (1H, d, J 7), 8.95 (1H, dd, J 5 and 2); m/z (ES$^+$) 373 (M$^+$+H).

EXAMPLE 118

4-[2-Fluoro-5-(7-trifluoromethylimidazo[1,2-α]pyrimidin-3-yl)phenyl]nicotinonitrile 4-Bromonicotinaldehyde was prepared using the method of Kelly et al., *Tetrahedron Lett.*, 1993, 34, 6173–6176.

4-Bromonicotinonitrile was prepared from 4-bromonicotinaldehyde by the method of Reitz et al., *Bioorg. Med. Chem. Lett.*, 1994, 4(1), 99–104.

4-Bromonicotinonitrile (1.0 g, 5.5 mmol) was coupled to 2-(2-fluoro-5-nitrophenyl)-4,4,5,5-tetramethyl-[1,3,2]dioxaborolane (1.9 g, 7.1 mmol) using the method in Example 51. Purification by chromatography on silica gel eluting with dichloromethane gave 4-(2-fluoro-5-nitrophenyl)nicotinonitrile as a white solid: $\delta_H$ (400 MHz, CDCl$_3$) 7.44–7.52 (2H, m), 8.38–8.47 (2H, m), 8.95 (1H, d, J 5), 9.06 (1H, s).

4-(2-Fluoro-5-nitrophenyl)nicotinonitrile (489 mg, 2.0 mmol) was reduced using the method in Example 47 to give 4-(5-amino-2-fluorophenyl)nicotinonitrile as a yellow solid: $\delta_H$ (400 MHz, CDCl$_3$) 3.70 (2H, br s), 6.70 (1H, dd, J 6 and 3), 6.75–6.80 (1H, m), 7.04 (1H, t, J 9), 7.45–7.47 (1H, m), 8.81 (1H, d, J 5), 8.96 (1H, s).

4-(5-Amino-2-fluorophenyl)nicotinonitrile (337 mg, 1.6 mmol) was bromo-deaminated using the method in Example 27 to give 4-(5-bromo-2-fluorophenyl)nicotinonitrile as a white solid: $\delta_H$ (400 MHz, CDCl$_3$) 7.17 (1H, t, J 9), 7.44–7.46 (1H, m), 7.57 (1H, dd, J 6 and 2), 7.61–7.66 (1H, m), 8.87 (1H, d, J 5), 9.00 (1H, d, J 1).

4-(5-Bromo-2-fluorophenyl)nicotinonitrile (252 mg, 0.91 mmol) was reacted with bis(neopentyl glycolato)diboron (226 mg, 1.0 mmol) using the method in Example 51 to give 4-fluoro-3-(4-nicotinonitrile)phenylboronic acid as a white solid: $\delta_H$ (400 MHz, d$^6$-DMSO) 7.43 (1H, dd, J 8 and 10), 7.72 (1H, d, J 5), 7.95 (1H, d, J 8), 8.00–8.04 (1H, m), 8.29 (2H, s), 8.96 (1H, d, J 5), 9.16 (1H, s).

4-Fluoro-3-(4-nicotinonitrile)phenylboronic acid (50 mg, 0.21 mmol) was coupled to 3-bromo-7-trifluoromethylimidazo[1,2-α]pyrimidine (60 mg, 0.23 mmol) using the method in Example 1. Purification by chromatography on silica gel eluting with dichloromethane containing 1% methanol, then recrystallisation from toluene/isohexane, gave 4-[2-fluoro-5-(7-trifluoromethylimidazo[1,2-α]pyrimidin-3-yl)phenyl]nicotinonitrile as a yellow solid: δ$_H$ (400 MHz, CDCl$_3$) 7.32 (1H, d, J 7), 7.51 (1H, t, J 9), 7.60–7.63 (1H, m), 7.71–7.75 (2H, m), 8.12 (1H, s), 8.92 (1H, d, J 5), 9.03 (1H, d, J 7), 9.07 (1H, s); m/z (ES$^+$) 384 (M$^+$+H).

EXAMPLE 119

4-{2-Fluoro-5-[7-(1-hydroxy-1-methylethyl)imidazo[1,2-α]pyrimidin-3-yl]phenyl}nicotinonitrile 4-Fluoro-3-(4-nicotinonitrile)phenylboronic acid (70 mg, 0.29 mmol) was coupled to 2-(3-bromoimidazo[1,2-α]pyrimidin-7-yl)propan-2-ol (74 mg, 0.29 mmol) using the method in Example 1. Purification by chromatography on silica gel eluting with dichloromethane containing 3% methanol then trituration with diethyl ether gave 4-{2-fluoro-5-[7-(1-hydroxy-1-methylethyl)imidazo[1,2-α]pyrimidin-3-yl]phenyl}nicotinonitrile as a white solid: δ$_H$ (400 MHz, CDCl$_3$) 1.62 (6H, s), 4.42 (1H, br s), 7.11 (1H, d, J 7), 7.47 (1H, t, J 9), 7.59–7.62 (1H, m), 7.67–7.72 (2H, m), 7.87 (1H, s), 8.82 (1H, d, J 7), 8.90 (1H, d, J 5), 9.06 (1H, d, J 1); m/z (ES$^+$) 374 (M$^+$+H).

EXAMPLE 120

3-[2-Fluoro-5-(7-trifluoromethylimidazo[1,2-α]pyrimidin-3-yl)phenyl]isonicotinonitrile 3-Bromoisonicotinonitrile was formed by the methods of Reitz et al., *Bioorg. Med. Chem. Lett.*, 1994, 4(1), 99–104; and Dunn, *Org. Prep. Proced. Int.*, 1997, 29(5), 577–579.

3-Bromoisonicotinonitrile (2.0 g, 10.9 mmol) was coupled to 2-(2-fluoro-5-nitrophenyl)-4,4,5,5-tetramethyl-[1,3,2]dioxaborolane (3.8 g, 14.2 mmol) using the method in Example 51. Purification by chromatography on silica gel eluting with dichloromethane containing 10% isohexane gave 3-(2-fluoro-5-nitrophenyl)isonicotinonitrile as a white solid: δ$_H$ (400 MHz, CDCl$_3$) 7.46 (1H, t, J 9), 7.71 (1H, dd, J 5 and 1), 8.38–8.46 (2H, m), 8.87 (1H, s), 8.91 (1H, d, J 5).

3-(2-Fluoro-5-nitrophenyl)isonicotinonitrile (500 mg, 2.1 mmol) was reduced using the method in Example 47 to give 3-(5-amino-2-fluorophenyl)isonicotinonitrile as a yellow oil: m/z (ES$^+$) 214 (M$^+$+H).

3-(5-Amino-2-fluorophenyl)isonicotinonitrile (500 mg, 2.1 mmol) was bromo-deaminated using the method in Example 27 to give 3-(5-bromo-2-fluorophenyl)isonicotinonitrile as a white solid: δ$_H$ (400 MHz, CDCl$_3$) 7.17 (1H, t, J 9), 7.56 (1H, dd, J 6 and 3), 7.60–7.67 (2H, m), 8.81–8.84 (2H, m).

3-(5-Bromo-2-fluorophenyl)isonicotinonitrile (40 mg, 0.14 mmol) was coupled to 3-tributylstannyl-7-trifluoromethylimidazo[1,2-α]pyrimidine (0.18 mmol) by the method of Example 32. Purification by chromatography on silica gel eluting with dichloromethane containing 3% methanol, then recrystallisation from toluene/isohexane, gave 3-[2-fluoro-5-(7-trifluoromethylimidazo[1,2-α]pyrimidin-3-yl)phenyl]isonicotinonitrile as a yellow solid: δ$_H$ (400 MHz, CDCl$_3$) 7.30 (1H, d, J 7), 7.51 (1H, t, J 9), 7.67–7.73 (3H, m), 8.13 (1H, s), 8.87 (1H, d, J 5), 8.96–8.98 (2H, m); m/z (ES$^+$) 384 (M$^+$+H).

EXAMPLE 121

3-[2-Fluoro-5-(7-trifluoromethylimidazo[1,2-α]pyrimidin-3-yl)phenyl]isonicotinamide 3-(5-Bromo-2-fluorophenyl)isonicotinonitrile (242 mg, 0.87 mmol) was reacted with bis(neopentyl glycolato) diboron (217 mg, 0.96 mmol) using the method in Example 51. Extraction of the neutralised aqueous phase gave 3-[5-(5,5-dimethyl-[1,3,2]dioxaborinan-2-yl)-2-fluorophenyl]isonicotinamide as a brown oil: m/z (ES$^+$) 261 ((M—CH$_2$C(Me)$_2$CH$_2$)$^+$+3H).

3-[5-(5,5-Dimethyl-[1,3,2]dioxaborinan-2-yl)-2-fluorophenyl]isonicotinamide (100 mg, 0.41 mmol) was coupled to 3-bromo-7-trifluoromethylimidazo[1,2-α]pyrimidine (121 mg, 0.46 mmol) using the method in Example 1. Purification by chromatography on silica gel eluting with dichloromethane containing 4% methanol, then recrystallisation from toluene, gave 3-[2-fluoro-5-(7-trifluoromethylimidazo[1,2-α]pyrimidin-3-yl)phenyl]isonicotinamide as a yellow solid: δ$_H$ (400 MHz, d$^6$-DMSO) 7.50–7.60 (3H, m), 7.65 (1H, s), 7.80–7.86 (2H, m), 8.02 (1H, s), 8.30 (1H, s), 8.73–8.76 (2H, m), 9.33 (1H, d, J 7); m/z (ES$^+$) 402 (M$^+$+H).

EXAMPLE 122

3-{2-Fluoro-5-[7-(1-hydroxy-1-methylethyl)imidazo[1,2-α]pyrimidin-3-yl]phenyl}isonicotinamide 3-[5-(5,5-Dimethyl-[1,3,2]dioxaborinan-2-yl)-2-fluorophenyl]isonicotinamide (100 mg, 0.41 mmol) was coupled to 2-(3-bromoimidazo[1,2-α]pyrimidin-7-yl)propan-2-ol (106 mg, 0.41 mmol) using the method in Example 1. Purification by chromatography on silica gel eluting with dichloromethane containing 8% methanol then trituration with diethyl ether gave 3-{2-fluoro-5-[7-(1-hydroxy-1-methylethyl)imidazo[1,2-α]pyrimidin-3-yl]phenyl}isonicotinamide as a white solid: δ$_H$ (400 MHz, CDCl$_3$) 1.58 (6H, s), 4.42 (1H, s), 5.68 (1H, s), 5.82 (1H, s), 7.08 (1H, d, J 7), 7.36 (1H, t, J 7), 7.57–7.61 (3H, m), 7.86 (1H, s), 8.71 (1H, d, J 7), 8.74 (1H, s), 8.78 (1H, d, J 5); m/z (ES$^+$) 392 (M$^+$+H).

EXAMPLE 123

2-[3-(4-Fluoro-3-(pyridazin-3-yl)phenyl)imidazo[1,2-α]pyrimidin-7-yl]propan-2-ol 3-(5-Bromo-2-fluorophenyl)pyridazine (304 mg, 1.20 mmol) was reacted with bis(neopentyl glycolato)diboron (298 mg, 1.32 mmol) using the method in Example 51 to give 4-fluoro-3-(pyridazin-3-yl)phenylboronic acid as a white solid: m/z (ES$^+$) 219 (M$^+$+H).

4-Fluoro-3-(pyridazin-3-yl)phenylboronic acid (80 mg, 0.37 mmol) was coupled to 2-(3-bromoimidazo[1,2-α]pyrimidin-7-yl)propan-2-ol (94 mg, 0.37 mmol) using the method in Example 1. Purification by chromatography on silica gel eluting with dichloromethane containing 2% methanol then trituration with diethyl ether gave 2-[3-(4-fluoro-3-(pyridazin-3-yl)phenyl)imidazo[1,2-α]pyrimidin-7-yl]propan-2-ol as a white solid: δ$_H$ (400 MHz, CDCl$_3$) 1.62 (6H, s), 4.46 (1H, s), 7.09 (1H, d, J 7), 7.41 (1H, dd, J 11 and 9), 7.61 (1H, dd, J 9 and 5), 7.64–7.68 (1H, m), 7.90 (1H, s), 8.07 (1H, dt, J 9 and 2), 8.43 (1H, dd, J 7 and 2), 8.72 (1H, d, J 7), 9.22 (1H, dd, J 5 and 2); m/z (ES$^+$) 350 (M$^+$+H).

EXAMPLE 124

2-[3-(4-Fluoro-3-(pyridazin-4-yl)phenyl)imidazo[12-α]pyrimidin-7-yl]propan-2-ol

To a solution of 3-bromo-4-fluoronitrobenzene (2 g, 9.1 mmol) in tetrahydrofuran (30 ml) was added triethylamine (1.9 ml, 13.6 mmol), trimethylsilylacetylene (1.9 ml, 13.6 mmol), triphenylphosphine (60 mg, 0.23 mmol) and dichlorobis(triphenylphosphine)palladium(II) (319 mg, 0.46 mmol). After stirring at room temperature for 20 minutes copper(I) iodide (17 mg, 0.09 mmol) was added and the mixture left to stir for 18 hours at room temperature. The reaction mixture was quenched into isohexane (150 ml) and filtered through a plug of silica using isohexane as eluent. The solvent was removed ex vacuo to leave (2-fluoro-5-nitrophenylethynyl)trimethylsilane as a brown solid: $\delta_H$ (360 MHz, CDCl$_3$) 0.10 (9H, s), 7.02 (1H, dd, J 8 and 1), 7.97–8.02 (1H, m), 8.17 (1H, dd, J 6 and 3).

A solution of 1,2,4,5-tetrazine (0.53 M in dichloromethane), was prepared by the method of van der Plas et al., *J. Heterocycl. Chem.*, 1987, 24, 545–548.

(2-Fluoro-5-nitrophenylethynyl)trimethylsilane (8.8 g, 37.1 mmol) and 1,4-dioxane were added to a solution of 1,2,4,5-tetrazine (35 ml, 18.6 mmol, 0.53 M in dichloromethane). The dichloromethane was distilled off and the dioxane solution was stirred at reflux for 36 hours. The solvent was removed to leave a brown oil. Purification by chromatography on silica gel eluting with dichloromethane, then with dichloromethane containing 1% methanol, gave 4-(2-fluoro-5-nitrophenyl)-5-trimethylsilanylpyridazine as a brown oil: m/z (ES$^+$) 292 (M$^+$+H) and 249 (M$^+$-3CH$_2$).

A solution of 4-(2-fluoro-5-nitrophenyl)-5-trimethylsilanylpyridazine (5.25 g, 18.0 mmol) was formed in N,N-dimethylformamide (50 ml) with water (1 ml). Potassium fluoride (2.10 g, 36.1 mmol) was added and the mixture stirred at room temperature for 18 h. The reaction mixture was added to ethyl acetate (100 ml) and washed with water (4×100 ml) then brine (50 ml). The organic phase was dried over magnesium sulphate, filtered and the solvent removed to leave an orange-brown solid. Purification by chromatography on silica gel eluting with 1:1 ethyl acetate:isohexane, then recrystallisation from dichloromethane with isohexane, gave 4-(2-fluoro-5-nitrophenyl)pyridazine as light brown crystals: $\delta_H$ (360 MHz, CDCl$_3$) 7.45 (1H, t, J 9), 7.70–7.74 (1H, m), 8.38–8.43 (1H, m), 8.49 (1H, dd, J 6 and 3), 9.37 (1H, dd, J 5 and 1), 9.46–9.48 (1H, m).

4-(2-Fluoro-5-nitrophenyl)pyridazine (1.67 g, 7.62 mmol) was reduced using the method in Example 47 to give 4-fluoro-3-(pyridazin-4-yl)phenylamine as an orange solid: m/z (ES$^+$) 190 (M$^+$+H).

4-Fluoro-3-(pyridazin-4-yl)phenylamine (500 mg, 2.64 mmol) was bromo-deaminated using the method in Example 27 to give 4-(5-bromo-2-fluorophenyl)pyridazine as a white solid: $\delta_H$ (360 MHz, CDCl$_3$) 7.16 (1H, dd, J 9 and 1), 7.57–7.62 (1H, m), 7.63–7.66 (2H, m), 9.29 (1H, dd, J 5 and 1), 9.39–9.41 (1H, m).

4-(5-Bromo-2-fluorophenyl)pyridazine (1.0 g, 3.95 mmol) was reacted with bis(neopentyl glycolato)diboron (982 mg, 4.35 mmol) using the method in Example 51 to give 4-fluoro-3-(pyridazin-4-yl)phenylboronic acid: m/z (ES$^+$) 219 (M$^+$+H).

4-Fluoro-3-(pyridazin-4-yl)phenylboronic acid (100 mg, 0.46 mmol) was coupled to 2-(3-bromoimidazo[1,2-α]pyrimidin-7-yl)propan-2-ol (117 mg, 0.46 mmol) using the method in Example 1. Purification by chromatography on silica gel eluting with dichloromethane containing 5% methanol then trituration with diethyl ether gave 2-[3-(4-fluoro-3-(pyridazin-4-yl)phenyl)imidazo[1,2-α]pyrimidin-7-yl]propan-2-ol as a white solid: $\delta_H$ (400 MHz, CDCl$_3$) 1.63 (6H, s), 7.11 (1H, d, J 7), 7.43–7.48 (1H, m), 7.64–7.69 (2H, m), 7.71–7.74 (1H, m), 7.88 (1H, s), 8.54 (1H, d, J 7), 9.33 (1H, dd, J 5 and 1), 9.46–9.47 (1H, m); m/z (ES$^+$) 350 (M$^+$+H).

EXAMPLE 125

3-[4-Fluoro-3-(pyrazol-1-yl)phenyl]-7-trifluoromethylimidazo[1,2-α]pyrimidine

A solution of pyrazole (6.8 g, 100 mmol) was formed in N,N-dimethylformamide (80 ml) and cooled to 0° C. Sufficient sodium hydride (4.36 g, 182 mmol) was added until hydrogen evolution ceased. With the temperature maintained at 0° C., 3,4-difluoronitrobenzene (10 ml, 95 mmol) was added dropwise. The mixture was stirred at room temperature for 18 hours. The mixture was added to water (1 l) and the resulting yellow precipitate was filtered and sucked dry. Purification of the filter by chromatography on silica gel eluting with dichloromethane, then recrystallisation from dichloromethane with isohexane, gave 1-(2-fluoro-4-nitrophenyl)-1H-pyrazole as a yellow solid: $\delta_H$ (400 MHz, CDCl$_3$) 6.57 (1H, dd, J 3 and 2), 7.82 (1H, d, J 2), 8.14–8.20 (3H, m), 8.25–8.30 (1H, m).

1-(2-Fluoro-4-nitrophenyl)-1H-pyrazole was reduced using the method in Example 47 to give 3-fluoro-4-(pyrazol-1-yl)phenylamine as a colourless oil: m/z (ES$^+$) 178 (M$^+$+H).

To a solution of 3-fluoro-4-(pyrazol-1-yl)phenylamine (2.56 g, 14.5 mmol) in tetrahydrofuran (50 ml) was added dropwise a solution of pyridinium tribromide (5.09 g, 15.9 mmol) in tetrahydrofuran (50 ml). The mixture was stirred for 1 h at room temperature then diluted with ether (250 ml). After stirring for a further 30 min the precipitate was filtered and washed with ether (50 ml×2). The white solid was dissolved in water (200 ml) and extracted with ethyl acetate (100 ml×3). The combined organic phases were dried over magnesium sulphate, filtered and the solvent removed to leave an orange oil. Purification by chromatography on silica gel eluting with dichloromethane gave 2-bromo-5-fluoro-4-(pyrazol-1-yl)phenylamine as a white solid: m/z (ES$^+$) 256 and 258 (M$^+$+H).

A solution of 2-bromo-5-fluoro-4-(pyrazol-1-yl) phenylamine (1.94 g, 7.58 mmol) was formed in sulphuric acid (50%, 40 ml), and cooled to 0° C. Sodium nitrite (732 mg, 10.6 mmol) was added dropwise as a solution in water (5 ml) maintaining internal temperature <5° C. The mixture was stirred at 0° C. for 1 h. Ethanol (5 ml) and then iron sulphate heptahydrate (1.05 g, 3.79 mmol) were added and the mixture allowed to warm to room temperature for 2 h. The mixture was then cooled to 0° C. and neutralised with sodium hydroxide solution (4N) then extracted with ethyl acetate (4×50 ml). The combined organic phases were dried over magnesium sulphate, filtered and the solvent removed to leave an orange oil. Purification by chromatography on silica gel eluting with dichloromethane gave 1-(5-bromo-2-fluorophenyl)-1H-pyrazole as an orange solid: $\delta_H$ (400 MHz, CDCl$_3$) 6.49 (1H, dd, J 3 and 2), 7.12 (1H, dd, J 11 and 9), 7.34–7.39 (1H, m), 7.75 (1H, d, J 2), 8.02 (1H, t, J 3), 8.13 (1H, dd, J 7 and 2).

1-(5-Bromo-2-fluorophenyl)-1H-pyrazole (1 g, 4.15 mmol) was reacted with bis(neopentyl glycolato)diboron (1.03 g, 4.56 mmol) using the method in Example 51 to give 1-[5-(5,5-dimethyl-[1,3,2]dioxaborinan-2-yl)-2-fluorophenyl]-1H-pyrazole as a white solid: $\delta_H$ (400 MHz, d$^6$-DMSO) 0.96 (6H, s), 3.78 (4H, s), 6.57 (1H, t, J 2), 7.44 (1H, dd, J 12 and 8), 7.67–7.71 (1H, m), 7.79 (1H, d, J 2), 8.08 (1H, dd, J 9 and 2), 8.21 (1H, t, J 3).

1-[5-(5,5-Dimethyl-[1,3,2]dioxaborinan-2-yl)-2-fluorophenyl]-1H-pyrazole (300 mg, 1.0 mmol) was coupled to 3-bromo-7-trifluoromethylimidazo[1,2-α]pyrimidine (266 mg, 1.0 mmol) using the method in Example 1.

Purification by chromatography on silica gel eluting with dichloromethane containing 1% methanol, then recrystallisation from toluene/isohexane, gave 3-[4-fluoro-3-(pyrazol-1-yl)phenyl]-7-trifluoromethylimidazo[1,2-α]pyrimidine as a yellow solid: $\delta_H$ (400 MHz, CDCl$_3$) 6.55 (1H, dd, J 3 and 2), 7.28 (1H, d, J 7), 7.44–7.47 (2H, m), 7.77 (1H, d, J 2), 8.13–8.15 (2H, m), 8.21–8.24 (1H, m), 8.85 (1H, d, J 7); m/z (ES$^+$) 348 (M$^+$+H).

EXAMPLE 126

2-[3-(4-Fluoro-3-(pyrazol-1-yl)phenyl)imidazo[1,2-α]pyrimidin-7-yl]propan-2-ol

1-[5-(5,5-Dimethyl-[1,3,2]dioxaborinan-2-yl)-2-fluorophenyl]-1H-pyrazole (300 mg, 1.0 mmol) was coupled to 2-(3-bromoimidazo[1,2-α]pyrimidin-7-yl)propan-2-ol (256 mg, 1.0 mmol) using the method in Example 1. Purification by chromatography on silica gel eluting with dichloromethane containing 5% methanol then trituration with diethyl ether gave 2-[3-(4-fluoro-3-(pyrazol-1-yl)phenyl)imidazo[1,2-α]pyrimidin-7-yl]propan-2-ol as a white solid: $\delta_H$ (400 MHz, CDCl$_3$) 1.63 (6H, s), 4.40 (1H, br s), 6.54 (1H, t, J 2), 7.09 (1H, d, J 7), 7.40–7.44 (2H, m), 7.77 (1H, d, J 2), 7.89 (1H, s), 8.13 (1H, t, J 3), 8.16–8.19 (1H, m), 8.65 (1H, d, J 7); m/z (ES$^+$) 338 (M$^+$+H).

EXAMPLE 127

3-[4-Fluoro-3-([1,2,4]triazol-1-yl)phenyl]-7-trifluoromethylimidazo[1,2-α]pyrimidine 1H-[1,2,4]Triazole (6.91 g, 100 mmol) was reacted with sodium hydride (4.3 g, 180 mmol) then with 3,4-difluoronitrobenzene (10 ml, 95 mmol) as in Example 125 to give 1-(2-fluoro-4-nitrophenyl)-1H-[1,2,4]triazole as a yellow solid: $\delta_H$ (400 MHz, CDCl$_3$) 8.19–8.28 (4H, m), 8.85 (1H, d, J 3).

1-(2-Fluoro-4-nitrophenyl)-1H-[1,2,4]triazole (3 g, 14 mmol) was reduced using the method in Example 47 to give 3-fluoro-4-([1,2,4]triazol-1-yl)phenylamine as a white solid: $\delta_H$ (400 MHz, CDCl$_3$) 3.99 (2H, s), 6.51–6.56 (2H, m), 7.50 (1H, t, J 9), 8.07 (1H, s), 8.45 (1H, d, J 3).

3-Fluoro-4-([1,2,4]triazol-1-yl)phenylamine (2.2 g, 12 mmol) was brominated using the method in Example 125 to give 2-bromo-5-fluoro-4-([1,2,4]triazol-1-yl)phenylamine as a white solid: $\delta_H$ (360 MHz, CDCl$_3$) 4.40 (2H, br s), 6.65 (1H, d, J 12), 7.86 (1H, d, J 7), 8.08 (1H, s), 8.47 (1H, d, J 3).

2-Bromo-5-fluoro-4-([1,2,4]triazol-1-yl)phenylamine (1.35 g, 5.24 mmol) was deaminated using the method in Example 125 to give 1-(5-bromo-2-fluorophenyl)-1H-[1,2,4]triazole as a brown solid: $\delta_H$ (400 MHz, CDCl$_3$) 7.19 (1H, dd, J 11 and 9), 7.46–7.50 (1H, m), 8.11–8.13 (2H, m), 8.69 (1H, d, J 3).

1-(5-Bromo-2-fluorophenyl)-1H-[1,2,4]triazole (1.1 g, 4.5 mmol) was reacted with bis(neopentyl glycolato)diboron (1.13 g, 5.0 mmol) using the method in Example 51 to give 4-fluoro-3-([1,2,4]triazol-1-yl)phenylboronic acid as a white solid: m/z (ES$^+$) 208 (M$^+$+H).

4-Fluoro-3-([1,2,4]triazol-1-yl)phenylboronic acid (100 mg, 0.48 mmol) was coupled to 3-bromo-7-trifluoromethylimidazo[1,2-α]pyrimidine (117 mg, 0.44 mmol) using the method in Example 1. Purification by chromatography on silica gel eluting with dichloromethane containing 2% methanol, then recrystallisation from dichloromethane/isohexane, gave 3-[4-fluoro-3-([1,2,4]triazol-1-yl)phenyl]-7-trifluoromethylimidazo[1,2-α]pyrimidine as a yellow solid: $\delta_H$ (360 MHz, CDCl$_3$) 7.31 (1H, d, J 7), 7.51–7.60 (2H, m), 8.16 (2H, m), 8.21 (1H, dd, J 7 and 2), 8.80–8.83 (2H, m); m/z (ES$^+$) 349 (M$^+$+H).

EXAMPLE 128

2-[3-(4-Fluoro-3-([1,2,4]triazol-1-yl)phenyl)imidazo[1,2-α]pyrimidin-7-yl]propan-2-ol 4-Fluoro-3-([1,2,4]triazol-1-yl)phenylboronic acid (100 mg, 0.48 mmol) was coupled to 2-(3-bromoimidazo[1,2-α]pyrimidin-7-yl)propan-2-ol (113 mg, 0.44 mmol) using the method in Example 1. Purification by chromatography on silica gel eluting with dichloromethane containing 5% methanol then trituration with diethyl ether gave 2-[3-(4-fluoro-3-([1,2,4]triazol-1-yl)phenyl)imidazo[1,2-α]pyrimidin-7-yl]propan-2-ol as a pink solid: $\delta_H$ (400 MHz, CDCl$_3$) 1.63 (6H, s), 4.31 (1H, s), 7.12 (1H, d, J 7), 7.47–7.57 (2H, m), 7.91 (1H, s), 8.14–8.18 (2H, m), 8.61 (1H, d, J 7), 8.79 (1H, d, J 3); m/z (ES$^+$) 339 (M$^+$+H).

EXAMPLE 129

2-[2-Fluoro-5-(7-trifluoromethylimidazo[1,2-α]pyrimidin-3-yl)phenyl]nicotinamide During the work-up of 4-fluoro-3-(2-nicotinonitrile)phenylboronic acid, leaving the product in aqueous solution at pH 5 for extended periods of time resulted in hydrolysis of the product to give 4-fluoro-3-(2-nicotinamide)phenylboronic acid as a white solid: m/z (ES$^+$) 261 (M$^+$+H).

4-Fluoro-3-(2-nicotinamide)phenylboronic acid (100 mg, 0.38 mmol) was coupled to 3-bromo-7-trifluoromethylimidazo[1,2-α]pyrimidine (93 mg, 0.35 mmol) using the method in Example 1. Purification by chromatography on silica gel eluting with dichloromethane containing 5% methanol, then recrystallisation from dichloromethane with isohexane, gave 2-[2-fluoro-5-(7-trifluoromethylimidazo[1,2-α]pyrimidin-3-yl)phenyl]nicotinamide as a yellow solid: $\delta_H$ (400 MHz, d$^6$-DMSO) 7.48 (1H, dd, J 10 and 8), 7.52–7.58 (3H, m), 7.81–7.85 (1H, m), 7.88 (1H, dd, J 7 and 2), 7.94 (1H, s), 8.03 (1H, dd, J 8 and 2), 8.28 (1H, s), 8.76 (1H, dd, J 5 and 2), 9.26 (1H, d, J 7); m/z (ES$^+$) 402 (M$^+$+H).

EXAMPLE 130

2-{3-[4-Fluoro-3-(5-fluoropyridin-3-yl)phenyl]imidazo[1,2-α]pyrimidin-7-yl}propan-2-ol A solution of 5-fluoropyridin-3-ol (1.70 g, 15.0 mmol) in dry pyridine (10 ml) at 0° C. was treated with trifluoromethanesulfonic anhydride (4.23 g, 15 mmol). The solution was allowed to stir to room temperature over 12 hours under nitrogen. The resulting solution was diluted with water (10 ml) and then extracted with ethyl acetate (50 ml). The organic layer was washed with 1N citric acid (2×50 ml) followed by a brine wash (50 ml). The organic layer was dried over anhydrous magnesium sulfate, filtered and evaporated to dryness. The crude product was filtered through a plug of silica gel, eluting with isohexane containing 10% ether, and concentrated to give trifluoromethanesulfonic acid 5-fluoropyridin-3-yl ester as a clear oil (3.10 g, 84%), which was used without further purification: $\delta_H$ (360 MHz, d$_6$-DMSO) 8.36 (1H, m), 8.76 (1H, d, J 3), 8.83 (1H, d, J 3).

Trifluoromethanesulfonic acid 5-fluoropyridin-3-yl ester was coupled with 2-(2-fluoro-5-nitrophenyl)-4,4,5,5-tetramethyl-[1,3,2]dioxaborolane as described in Example 1 to give 3-fluoro-5-(2-fluoro-5-nitrophenyl)pyridine as a white solid: $\delta_H$ (360 MHz, CDCl$_3$) 7.39 (1H, t, J 9), 7.65 (1H, m), 8.31–8.36 (1H, m), 8.42 (1H, dd, J 7 and 3), 8.58 (1H, d, J 3), 8.67 (1H, d, J 1).

3-Fluoro-5-(2-fluoro-5-nitrophenyl)pyridine was reduced as described in Example 57 to give 4-fluoro-3-(5-fluoropyridin-3-yl)phenylamine as a brown oil: $\delta_H$ (400 MHz, CDCl$_3$) 6.67–6.75 (2H, m), 7.01 (1H, dd, J 10 and 9), 7.57–7.61 (1H, m), 8.46 (1H, d, J 3), 8.59 (1H, q, J 1).

4-Fluoro-3-(5-fluoropyridin-3-yl)phenylamine was bromo-deaminated as described in Example 59 to give 3-(5-bromo-2-fluorophenyl)-5-fluoropyridine as a white solid (1.2 g, 90%): $\delta_H$ (360 MHz, CDCl$_3$) 7.10 (1H, dd, J 9 and 1), 7.50–7.53 (1H, m), 7.57–7.62 (2H, m), 8.51 (1H, d, J 3), 8.60 (1H, d, J 1).

3-(5-Bromo-2-fluorophenyl)-5-fluoropyridine was reacted with bis(pinacolato)diboron as described in Example 1 to give 3-fluoro-5-[2-fluoro-5-(4,4,5,5-tetramethyl-[1,3,2]dioxaborolan-2-yl)phenyl]pyridine (300 mg, 22%) as a brown oil which solidified on standing: m/z (ES$^+$) 318 (M$^+$+H).

2-(3-Bromoimidazo[1,2-α]pyrimidin-7-yl)propan-2-ol was coupled with 3-fluoro-5-[2-fluoro-5-(4,4,5,5-tetramethyl-[1,3,2]dioxaborolan-2-yl)phenyl]pyridine as described in Example 65 to give 2-{3-[4-fluoro-3-(5-fluoropyridin-3-yl)phenyl]imidazo[1,2-α]pyrimidin-7-yl}propan-2-ol as an off-white solid (30 mg, 21%). Bis-hydrochloride salt (from ethyl acetate: ethanol (1:1)): $\delta_H$ (360 MHz, d$_6$-DMSO) 1.56 (6H, s), 7.67–7.73 (1H, m), 7.83–7.89 (2H, m), 8.05–8.07 (1H, m), 8.11–8.15 (1H, m), 8.51 (1H, s), 8.71 (1H, s), 8.80 (1H, s), 9.36 (1H, d, J 7).

What is claimed is:

1. A compound of formula I, or a pharmaceutically acceptable salt thereof:

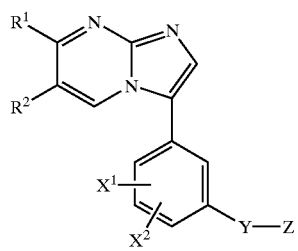

(I)

wherein

X$^1$ represents halogen, trifluoromethyl or C$_{1-6}$ alkoxy;

X$^2$ represents hydrogen or halogen;

Y represents a chemical bond, an oxygen atom, or a —NH— linkage;

Z represents an optionally substituted aryl or heteroaryl group;

R$^1$ represents hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$ or —CR$^a$=NOR$^b$;

R$^2$ represents hydrogen or halogen; and

R$^a$ and R$^b$ independently represent hydrogen, hydrocarbon or a heterocyclic group.

2. A compound as claimed in claim 1 represented by formula IIA, or a pharmaceutically acceptable salt thereof:

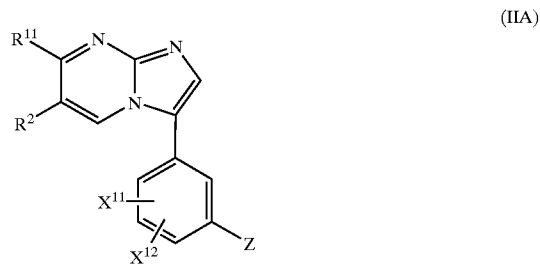

(IIA)

wherein

Z and R$^2$ are as defined in claim 1;

X$^{11}$ represents fluoro, chloro, trifluoromethyl or methoxy;

X$^{12}$ represents hydrogen or fluoro;

R$^{11}$ represents hydrogen, C$_{1-6}$ alkyl, halo(C$_{1-6}$)alkyl, dihalo(C$_{1-6}$)alkyl, hydroxy(C$_{1-6}$)alkyl, dihydroxy(C$_{1-6}$)alkyl, C$_{1-6}$alkoxy(C$_{1-6}$)alkyl, di(C$_{1-6}$)alkoxy(C$_{1-6}$)alkyl, cyano(C$_{1-6}$)alkyl, C$_{2-6}$ alkoxycarbonyl(C$_{1-6}$)alkyl, heteroaryl, C$_{1-6}$ alkyl-heteroaryl, heteroaryl(C$_{1-6}$)alkyl, halogen, cyano, trifluoromethyl, formyl, C$_{2-6}$ alkylcarbonyl, C$_{2-6}$ alkoxycarbonyl or —CR$^5$=NOR$^6$;

R$^5$ represents hydrogen or C$_{1-6}$ alkyl; and

R$^6$ represents hydrogen, C$_{1-6}$ alkyl, hydroxy(C$_{1-6}$)alkyl or di(C$_{1-6}$)alkylamino(C$_{1-6}$)alkyl.

3. A compound as claimed in claim 2 represented by formula IIB, or a pharmaceutically acceptable salt thereof:

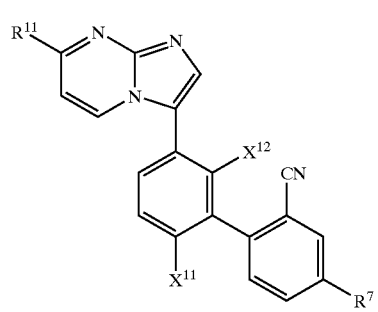

(IIB)

wherein X$^{11}$, X$^{12}$ and R$^{11}$ are as defined in claim 2; and

R$^7$ represents hydrogen, fluoro or chloro.

4. A compound as claimed in claim 3 wherein R$^7$ represents fluoro.

5. A compound as claimed in claim 4 wherein R$^{11}$ represents trifluoromethyl.

6. A compound as claimed in claim 2 represented by formula IIC, or a pharmaceutically acceptable salt thereof:

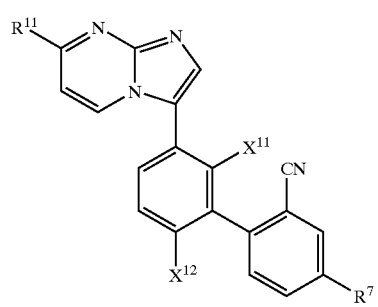

(IIC)

wherein X$^{11}$, X$^{12}$ and R$^{11}$ are as defined in claim 2; and

R$^7$ represents hydrogen, fluoro or chloro.

7. A compound as claimed in claim 2 represented by formula IID, or a pharmaceutically acceptable salt thereof:

(IID)

wherein $X^{11}$, $X^{12}$ and $R^{11}$ are as defined in claim 2; and $R^8$ represents hydrogen, fluoro, cyano or methyl.

8. A compound as claimed in claim 7 wherein $R^8$ represents hydrogen.

9. A compound as claimed in claim 8 wherein $R^{11}$ represents 2-hydroxyprop-2-yl.

10. A compound as claimed in claim 2 represented by formula IIE, or a pharmaceutically acceptable salt thereof:

(IIE)

wherein $X^{11}$, $X^{12}$ and $R^{11}$ are as defined in claim 2;
$R^8$ represents hydrogen, fluoro, cyano or methyl; and
$R^9$ represents hydrogen or fluoro.

11. A compound as claimed in claim 5 wherein $X^{11}$ represents fluoro.

12. A compound as claimed in claim 9 wherein $X^{11}$ represents fluoro.

13. A compound as claimed in claim 11 wherein $X^{12}$ represents hydrogen.

14. A compound as claimed in claim 12 wherein $X^{12}$ represents hydrogen.

15. A compound selected from:
2'-fluoro-5'-(imidazo[1,2-α]pyrimidin-3-yl)biphenyl-2-carbonitrile;
2'-fluoro-5'-(7-methylimidazo[1,2-α]pyrimidin-3-yl)biphenyl-2-carbonitrile;
5'-(7-acetylimidazo[1,2-α]pyrimidin-3-yl)-2'-fluorobiphenyl-2-carbonitrile;
2'-fluoro-5'-(7-isopropylimidazo[1,2-α]pyrimidin-3-yl)biphenyl-2-carbonitrile;
2'-fluoro-5'-(7-tert-butylimidazo[1,2-α]pyrimidin-3-yl)biphenyl-2-carbonitrile;
2'-fluoro-5'-[7-(1-hydroxy-1-methylethyl)imidazo[1,2-α]pyrimidin-3-yl]biphenyl-2-carbonitrile;
2'-fluoro-5'-[7-(1-fluoro-1-methylethyl)imidazo[1,2-α]pyrimidin-3-yl]biphenyl-2-carbonitrile;
2'-fluoro-5'-(7-hydroxymethylimidazo[1,2-α]pyrimidin-3-yl)biphenyl-2-carbonitrile;
2'-fluoro-5'-[7-(1-hydroxyethyl)imidazo[1,2-α]pyrimidin-3-yl]biphenyl-2-carbonitrile;
2'-fluoro-5'-[7-(1-fluoroethyl)imidazo[1,2-α]pyrimidin-3-yl]biphenyl-2-carbonitrile;
2'-fluoro-5'-[7-(2-methylthiazol-5-yl)imidazo[1,2-α]pyrimidin-3-yl]biphenyl-2-carbonitrile;
2'-fluoro-5'-(7-trifluoromethylimidazo[1,2-α]pyrimidin-3-yl)biphenyl-2-carbonitrile;
5'-[7-(1,1-difluoroethyl)imidazo[1,2-α]pyrimidin-3-yl]-2'-fluorobiphenyl-2-carbonitrile;
5'-(7-chloroimidazo[1,2-α]pyrimidin-3-yl)-2'-fluorobiphenyl-2-carbonitrile;
5'-(7-difluoromethylimidazo[1,2-α]pyrimidin-3-yl)-2'-fluorobiphenyl-2-carbonitrile;
2'-fluoro-5'-(7-methoxymethylimidazo[1,2-α]pyrimidin-3-yl)biphenyl-2-carbonitrile;
3-(2'-cyano-6-fluorobiphenyl-3-yl)imidazo[1,2-α]pyrimidine-7-carbonitrile;
2'-fluoro-5'-[7-(3-methyl-[1,2,4]oxadiazol-5-yl)imidazo[1,2-α]pyrimidin-3-yl]biphenyl-2-carbonitrile;
2'-fluoro-5'-[7-(oxazol-5-yl)imidazo[1,2-α]pyrimidin-3-yl]biphenyl-2-carbonitrile;
2'-fluoro-5'-[7-(hydroxyiminomethyl)imidazo[1,2-α]pyrimidin-3-yl]biphenyl-2-carbonitrile;
5'-{7-[1-(2-dimethylaminoethoxyimino)methyl]imidazo[1,2-α]pyrimidin-3-yl}-2'-fluorobiphenyl-2-carbonitrile;
3'-(7-difluoromethylimidazo[1,2-α]pyrimidin-3-yl)-4'-fluorobiphenyl-2-carbonitrile;
2'-fluoro-5'-(7-fluoromethylimidazo[1,2-α]pyrimidin-3-yl)biphenyl-2-carbonitrile;
2'-fluoro-5'-[7-(furan-3-yl)imidazo[1,2-α]pyrimidin-3-yl]biphenyl-2-carbonitrile;
2'-fluoro-5'-[7-(thien-3-yl)imidazo[1,2-α]pyrimidin-3-yl]biphenyl-2-carbonitrile;
2'-fluoro-5'-[7-(pyridin-2-yl)imidazo[1,2-α]pyrimidin-3-yl]biphenyl-2-carbonitrile;
2'-fluoro-5'-(6-fluoro-7-methylimidazo[1,2-α]pyrimidin-3-yl)biphenyl-2-carbonitrile;
7-(1,1-difluoroethyl)-3-[4-fluoro-3-(pyridin-3-yl)phenyl]imidazo[1,2-α]pyrimidine;
2-[3-(4-fluoro-3-(pyridin-3-yl)phenyl)imidazo[1,2-α]pyrimidin-7-yl]propan-2-ol;
3'-fluoro-5'-(7-trifluoromethylimidazo[1,2-α]pyrimidin-3-yl)biphenyl-2-carbonitrile;
3'-fluoro-5'-(7-hydroxymethylimidazo[1,2-α]pyrimidin-3-yl)biphenyl-2-carbonitrile;
2'-fluoro-3'-(7-trifluoromethylimidazo[1,2-α]pyrimidin-3-yl)biphenyl-2-carbonitrile;
3-[4-fluoro-3-(pyridin-2-yl)phenyl]-7-trifluoromethylimidazo[1,2-α]pyrimidine;
3-[4-fluoro-3-(pyridin-3-yl)phenyl]-7-trifluoromethylimidazo[1,2-α]pyrimidine;
2'-fluoro-5'-[7-([1,2,4]triazol-1-ylmethyl)imidazo[1,2-α]pyrimidin-3-yl]biphenyl-2-carbonitrile;
2'-fluoro-5'-[7-(imidazol-1-ylmethyl)imidazo[1,2-α]pyrimidin-3-yl]biphenyl-2-carbonitrile;
2'-fluoro-5'-[7-([1,2,3]triazol-1-ylmethyl)imidazo[1,2-α]pyrimidin-3-yl]biphenyl-2-carbonitrile;
2'-fluoro-5'-[7-([1,2,3]triazol-2-ylmethyl)imidazo[1,2-α]pyrimidin-3-yl]biphenyl-2-carbonitrile;
3-[4-fluoro-3-(pyridin-4-yl)phenyl]-7-trifluoromethylimidazo[1,2-α]pyrimidine;

3-[2,4-difluoro-3-(pyridin-3-yl)phenyl]-7-trifluoromethylimidazo[1,2-α]pyrimidine;
3-[2,4-difluoro-3-(pyridin-2-yl)phenyl]-7-trifluoromethylimidazo[1,2-α]pyrimidine;
2-[3-(4-fluoro-3-(pyridin-4-yl)phenyl)imidazo[1,2-α]pyrimidin-7-yl]propan-2-ol;
3-[2-fluoro-3-(pyridin-3-yl)phenyl]-7-trifluoromethylimidazo[1,2-α]pyrimidine;
2-[3-(2-fluoro-3-(pyridin-3-yl)phenyl)imidazo[1,2-α]pyrimidin-7-yl]propan-2-ol;
3-[2-fluoro-3-(pyridin-4-yl)phenyl]-7-trifluoromethylimidazo[1,2-α]pyrimidine;
2-[3-(2-fluoro-3-(pyridin-4-yl)phenyl)imidazo[1,2-α]pyrimidin-7-yl]propan-2-ol;
3-[2-fluoro-3-(pyridin-2-yl)phenyl]-7-trifluoromethylimidazo[1,2-α]pyrimidine;
2-[3-(2-fluoro-3-(pyridin-2-yl)phenyl)imidazo[1,2-α]pyrimidin-7-yl]propan-2-ol;
3-[4-fluoro-3-(4-methylpyridin-2-yl)phenyl]-7-trifluoromethylimidazo[1,2-α]pyrimidine;
3-[4-fluoro-3-(pyridazin-3-yl)phenyl]-7-trifluoromethylimidazo[1,2-α]pyrimidine;
2-[2-fluoro-5-(7-trifluoromethylimidazo[1,2-α]pyrimidin-3-yl)phenyl]nicotinonitrile;
3-[4-fluoro-3-(pyridin-2-yl)phenyl]imidazo[1,2-α]pyrimidine;
3,2'-difluoro-5'-(7-trifluoromethylimidazo[1,2-α]pyrimidin-3-yl)biphenyl-2-carbonitrile;
6,2'-difluoro-5'-(7-trifluoromethylimidazo[1,2-α]pyrimidin-3-yl)biphenyl-2-carbonitrile;
5,2'-difluoro-5'-(7-trifluoromethylimidazo[1,2-α]pyrimidin-3-yl)biphenyl-2-carbonitrile;
4,2'-difluoro-5'-(7-trifluoromethylimidazo[1,2-α]pyrimidin-3-yl)biphenyl-2-carbonitrile;
2',6'-difluoro-3'-(7-trifluoromethylimidazo[1,2-α]pyrimidin-3-yl)biphenyl-2-carbonitrile;
3-[4-fluoro-3-(pyrazin-2-yl)phenyl]-7-trifluoromethylimidazo[1,2-α]pyrimidine;
3-[4-fluoro-3-(pyrimidin-2-yl)phenyl]-7-trifluoromethylimidazo[1,2-α]pyrimidine;
3-[2-fluoro-5-(7-trifluoromethylimidazo[1,2-α]pyrimidin-3-yl)phenyl]pyridine-2-carbonitrile;
3-[4-fluoro-3-(5-fluoropyridin-2-yl)phenyl]-7-trifluoromethylimidazo[1,2-α]pyrimidine;
7-(1,1-difluoroethyl)-3-[4-fluoro-3-(pyridin-4-yl)phenyl]imidazo[1,2-α]pyrimidine;
7-(1,1-difluoroethyl)-3-[2,4-difluoro-3-(pyridin-3-yl)phenyl]imidazo[1,2-α]pyrimidine;
3-[4-chloro-3-(pyridin-3-yl)phenyl]-7-trifluoromethylimidazo[1,2-α]pyrimidine;
3-[4-methoxy-3-(pyridin-3-yl)phenyl]-7-trifluoromethylimidazo[1,2-α]pyrimidine;
and pharmaceutically acceptable salts thereof.
16. A compound selected from:
2-[3-(2,4-difluoro-3-(pyridin-3-yl)phenyl)imidazo[1,2-α]pyrimidin-7-yl]propan-2-ol;
1-[3-(4-fluoro-3-(pyridin-3-yl)phenyl)imidazo[1,2-α]pyrimidin-7-yl]ethanone;
3'-[7-(1-hydroxy-1-methylethyl)imidazo[1,2-α]pyrimidin-3-yl]-4,2',6'-trifluorobiphenyl-2-carbonitrile;
2-[3-(4-fluoro-3-(pyridin-3-yl)phenyl)imidazo[1,2-α]pyrimidin-7-yl]propane-1,2-diol;
3-[2-fluoro-5-(7-trifluoromethylimidazo[1,2-α]pyrimidin-3-yl)phenyl]thiophene-2-carbonitrile;
3-{2-fluoro-5-[7-(1-hydroxy-1-methylethyl)imidazo[1,2-α]pyrimidin-3-yl]phenyl}thiophene-2-carbonitrile;
2-{3-[4-fluoro-3-(1-oxypyridin-3-yl)phenyl]imidazo[1,2-α]pyrimidin-7-yl}propan-2-ol;
3-{2,6-difluoro-3-[7-(1-hydroxy-1-methylethyl)imidazo[1,2-α]pyrimidin-3-yl]phenyl}thiophene-2-carbonitrile;
3-{2,6-difluoro-3-[7-(1-hydroxy-1-methylethyl)imidazo[1,2-α]pyrimidin-3-yl]phenyl}thiophene-2-carboxylic acid amide;
3-[4-fluoro-3-(3-fluoropyridin-4-yl)phenyl]-7-trifluoromethylimidazo[1,2-α]pyrimidine;
4-chloro-2'-fluoro-5'-(7-trifluoromethylimidazo[1,2-α]pyrimidin-3-yl)biphenyl-2-carbonitrile;
3-[4-fluoro-3-(5-methylpyridin-3-yl)phenyl]-7-trifluoromethylimidazo[1,2-α]pyrimidine;
3-[2-fluoro-2'-(methanesulfonyl)biphenyl-5-yl]-7-trifluoromethylimidazo[1,2-α]pyrimidine;
2-[3-(4-fluoro-3-(pyrazin-2-yl)phenyl)imidazo[1,2-α]pyrimidin-7-yl]propan-2-ol;
2-[3-(4-fluoro-3-(5-fluoropyridin-2-yl)phenyl)imidazo[1,2-α]pyrimidin-7-yl]propan-2-ol;
3-[4-fluoro-3-(3-fluoropyridin-2-yl)phenyl]-7-trifluoromethylimidazo[1,2-α]pyrimidine;
2-[3-(4-fluoro-3-(3-fluoropyridin-2-yl)phenyl)imidazo[1,2-α]pyrimidin-7-yl]propan-2-ol;
3-[3-(3,5-difluoropyridin-2-yl)-4-fluorophenyl]-7-trifluoromethylimidazo[1,2-α]pyrimidine;
2-[3-(3-(3,5-difluoropyridin-2-yl)-4-fluorophenyl)imidazo[1,2-α]pyrimidin-7-yl]propan-2-ol;
3-[2,4-difluoro-3-(pyridin-4-yl)phenyl]-7-trifluoromethylimidazo[1,2-α]pyrimidine;
2-[3-(2,4-difluoro-3-(pyridin-4-yl)phenyl)imidazo[1,2-α]pyrimidin-7-yl]propan-2-ol;
4,2'-difluoro-5'-[7-(1-hydroxy-1-methylethyl)imidazo[1,2-α]pyrimidin-3-yl]biphenyl-2-carbonitrile;
2'-fluoro-5'-(7-trifluoromethylimidazo[1,2-α]pyrimidin-3-yl)biphenyl-3-carbonitrile;
2'-fluoro-5'-(7-trifluoromethylimidazo[1,2-α]pyrimidin-3-yl)biphenyl-4-carbonitrile;
3-[2,4-difluoro-3-(pyridin-3-yl)phenyl]-7-(1-fluoro-1-methylethyl)imidazo[1,2-α]pyrimidine;
7-(1-fluoro-1-methylethyl)-3-[4-fluoro-3-(pyridin-3-yl)phenyl]imidazo[1,2-α]pyrimidine;
2-[3-(2,4-difluoro-3-(pyridin-3-yl)phenyl)imidazo[1,2-α]pyrimidin-7-yl]-2-methylpropionic acid methyl ester;
2-[3-(4-fluoro-3-(pyridin-3-yl)phenyl)imidazo[1,2-α]pyrimidin-7-yl]-2-methylpropionitrile;
2-[3-(4-fluoro-3-(pyridin-3-yl)phenyl)imidazo[1,2-α]pyrimidin-7-yl]-2-methylpropan-1-ol;
3-[4-fluoro-3-(6-methoxypyridin-3-yl)phenyl]-7-trifluoromethylimidazo[1,2-α]pyrimidine;
5-[2-fluoro-5-(7-trifluoromethylimidazo[1,2-α]pyrimidin-3-yl)phenyl]pyridin-2-ol;
3-[4-fluoro-3-(4-fluoropyridin-3-yl)phenyl]-7-trifluoromethylimidazo[1,2-α]pyrimidine;
3-[4-fluoro-3-(pyrrol-1-yl)phenyl]-7-trifluoromethylimidazo[1,2-α]pyrimidine;
3-[4-fluoro-3-(pyridin-3-yl)phenyl]imidazo[1,2-α]pyrimidine;

3-[4-fluoro-3-(5-fluoropyridin-2-yl)phenyl]imidazo[1,2-α]pyrimidine;
3-[2,4-difluoro-3-(pyridin-3-yl)phenyl]imidazo[1,2-α]pyrimidine;
3-[4-chloro-3-(pyridin-3-yl)phenyl]imidazo[1,2-α]pyrimidine;
3-[5-fluoro-3-(pyridin-3-yl)phenyl]-7-trifluoromethylimidazo[1,2-α]pyrimidine;
3-[4-fluoro-3-(4-methylpyridin-3-yl)phenyl]-7-trifluoromethylimidazo[1,2-α]pyrimidine;
3-[2-fluoro-5-(pyridin-3-yl)phenyl]-7-trifluoromethylimidazo[1,2-α]pyrimidine;
3-[4-fluoro-3-(pyridazin-4-yl)phenyl]-7-trifluoromethylimidazo[1,2-α]pyrimidine;
3-[4-fluoro-3-(imidazol-1-yl)phenyl]-7-trifluoromethylimidazo[1,2-α]pyrimidine;
3-[4-fluoro-3-(isothiazol-4-yl)phenyl]-7-trifluoromethylimidazo[1,2-α]pyrimidine;
3-[4-fluoro-3-(pyrimidin-5-yl)phenyl]-7-trifluoromethylimidazo[1,2-α]pyrimidine;
3-[4-fluoro-3-(5-methoxypyridin-3-yl)phenyl]-7-trifluoromethylimidazo[1,2-α]pyrimidine;
3-[4-fluoro-3-(2-methylpyridin-3-yl)phenyl]-7-trifluoromethylimidazo[1,2-α]pyrimidine;
3-[4-fluoro-3-(2-methyltetrazol-5-yl)phenyl]-7-trifluoromethylimidazo[1,2-α]pyrimidine;
3-[4-fluoro-3-(1-methyltetrazol-5-yl)phenyl]-7-trifluoromethylimidazo[1,2-α]pyrimidine;
and pharmaceutically acceptable salts thereof.

17. A compound selected from:
3-[4-fluoro-3-(6-methoxypyridin-2-yl)phenyl]-7-trifluoromethylimidazo[1,2-α]pyrimidine;
3-[4-fluoro-3-(4-methoxypyridin-2-yl)phenyl]-7-trifluoromethylimidazo[1,2-α]pyrimidine;
3-[4-fluoro-3-(thiazol-2-yl)phenyl]-7-trifluoromethylimidazo[1,2-α]pyrimidine;
2-{2-fluoro-5-[7-(1-hydroxy-1-methylethyl)imidazo[1,2-α]pyrimidin-3-yl]phenyl}nicotinonitrile;
4-[2-fluoro-5-(7-trifluoromethylimidazo[1,2-α]pyrimidin-3-yl)phenyl]nicotinonitrile;
4-{2-fluoro-5-[7-(1-hydroxy-1-methylethyl)imidazo[1,2-α]pyrimidin-3-yl]phenyl}nicotinonitrile;
3-[2-fluoro-5-(7-trifluoromethylimidazo[1,2-α]pyrimidin-3-yl)phenyl]isonicotinonitrile;
3-[2-fluoro-5-(7-trifluoromethylimidazo[1,2-α]pyrimidin-3-yl)phenyl]isonicotinamide;
3-{2-fluoro-5-[7-(1-hydroxy-1-methylethyl)imidazo[1,2-α]pyrimidin-3-yl]phenyl}isonicotinamide;
2-[3-(4-fluoro-3-(pyridazin-3-yl)phenyl)imidazo[1,2-α]pyrimidin-7-yl]propan-2-ol;
2-[3-(4-fluoro-3-(pyridazin-4-yl)phenyl)imidazo[1,2-α]pyrimidin-7-yl]propan-2-ol;
3-[4-fluoro-3-(pyrazol-1-yl)phenyl]-7-trifluoromethylimidazo[1,2-α]pyrimidine;
2-[3-(4-fluoro-3-(pyrazol-1-yl)phenyl)imidazo[1,2-α]pyrimidin-7-yl]propan-2-ol;
3-[4-fluoro-3-([1,2,4]triazol-1-yl)phenyl]-7-trifluoromethylimidazo[1,2-α]pyrimidine;
2-[3-(4-fluoro-3-([1,2,4]triazol-1-yl)phenyl)imidazo[1,2-α]pyrimidin-7-yl]propan-2-ol;
2-[2-fluoro-5-(7-trifluoromethylimidazo[1,2-α]pyrimidin-3-yl)phenyl]nicotinamide;
2-{3-[4-fluoro-3-(5-fluoropyridin-3-yl)phenyl]imidazo[1,2-α]pyrimidin-7-yl}propan-2-ol;
and pharmaceutically acceptable salts thereof.

18. A pharmaceutical composition comprising an effective amount of a compound of formula I as defined in claim 1, or a pharmaceutically acceptable salt thereof, in association with a pharmaceutically acceptable carrier.

19. A method for the treatment and/or prevention of adverse neurological conditions which comprises administering to a patient in need of such treatment an effective amount of a compound of formula I as defined in claim 1 or a pharmaceutically acceptable salt thereof.

20. 2-[3-(4-Fluoro-3-(pyridin-3-yl)phenyl)imidazo[1,2-α]pyrimidin-7-yl]propan-2-ol, or a pharmaceutically acceptable salt thereof.

21. The bis-hydrochloride salt of 2-[3-(4-fluoro-3-(pyridin-3-yl)phenyl)imidazo[1,2-α]pyrimidin-7-yl]propan-2-ol.

22. A pharmaceutical composition comprising an effective amount of 2-[3-(4-fluoro-3-(pyridin-3-yl)phenyl)imidazo[1,2-α]pyrimidin-7-yl]propan-2-ol, or a pharmaceutically acceptable salt thereof, in association with a pharmaceutically acceptable carrier.

23. A pharmaceutical composition comprising an effective amount of the bis-hydrochloride salt of 2-[3-(4-fluoro-3-(pyridin-3-yl)phenyl)imidazo[1,2-α]pyrimidin-7-yl]propan-2-ol in association with a pharmaceutically acceptable carrier.

24. A method for the treatment of anxiety which comprises administering to a patient in need of such treatment an effective amount of 2-[3-(4-fluoro-3-(pyridin-3-yl)phenyl)imidazo[1,2-α]pyrimidin-7-yl]propan-2-ol, or a pharmaceutically acceptable salt thereof.

25. A method for the treatment of anxiety which comprises administering to a patient in need of such treatment an effective amount of the bis-hydrochloride salt of 2-[3-(4-fluoro-3-(pyridin-3-yl)phenyl)imidazo[1,2-α]pyrimidin-7-yl]propan-2-ol.

26. 4,2'-Difluoro-5'-(7-trifluoromethylimidazo[1,2-α]pyrimidin-3-yl)biphenyl-2-carbonitrile.

27. A pharmaceutical composition comprising an effective amount of 4,2'-difluoro-5'-(7-trifluoromethylimidazo[1,2-α]pyrimidin-3-yl)biphenyl-2-carbonitrile in association with a pharmaceutically acceptable carrier.

28. A method for the treatment of anxiety which comprises administering to a patient in need of such treatment an effective amount of 4,2'-difluoro-5'-(7-trifluoromethylimidazo[1,2-α]pyrimidin-3-yl)biphenyl-2-carbonitrile.

* * * * *